(12) United States Patent
Saha

(10) Patent No.: US 8,673,630 B2
(45) Date of Patent: Mar. 18, 2014

(54) βGI-IGG INTRON FOR ENHANCED ANTI-IGF1R EXPRESSION

(75) Inventor: Deba P. Saha, Nutley, NJ (US)

(73) Assignee: Merck, Sharp & Dohme Corp., Rahway, NJ (US)

( * ) Notice: Subject to any disclaimer, the term of this patent is extended or adjusted under 35 U.S.C. 154(b) by 111 days.

(21) Appl. No.: 13/128,774

(22) PCT Filed: Nov. 12, 2009

(86) PCT No.: PCT/US2009/064147
§ 371 (c)(1),
(2), (4) Date: May 11, 2011

(87) PCT Pub. No.: WO2010/056816
PCT Pub. Date: May 20, 2010

(65) Prior Publication Data
US 2011/0217695 A1 Sep. 8, 2011

Related U.S. Application Data

(60) Provisional application No. 61/113,807, filed on Nov. 12, 2008.

(51) Int. Cl.
C12N 15/63 (2006.01)
C12N 15/85 (2006.01)

(52) U.S. Cl.
USPC ........................................ 435/320.1; 435/325

(58) Field of Classification Search
None
See application file for complete search history.

(56) References Cited

U.S. PATENT DOCUMENTS

| 8,354,509 | B2 | 1/2013 | Carven et al. |
| 2005/0176099 | A1* | 8/2005 | Saha ........................... 435/69.1 |
| 2013/0108651 | A1 | 5/2013 | Carven et al. |
| 2013/0109843 | A1 | 5/2013 | Carven et al. |

FOREIGN PATENT DOCUMENTS

| WO | WO2008/156712 | 12/2008 |
| WO | WO2010/056816 | 5/2010 |

OTHER PUBLICATIONS

Sequence alignment (Seq ID No. 3), 2012, 2 pages.*
Sequence alignment (Seq ID Nos. 11, 12), 2012, 2 pages.*
Brondyk Bill; "pCI and pSI Mammalian Expression Vectors"; Promega Notes Magazine; 49:7-12 (1994).
Brondyk, W.H.; "Cloning Vector pCI-neo"; Embl. Syn. Host-Embl. Syn.; XP002219165:1-3; (1996).
Brondyk; William H.; "The pCI-neo Mammalian Expression Vector"; Promega Notes Magazine; 51:10-14; (1995).
Hesse, Friedemann, et al.; "Developments and improvements in the manufacturing of human therapeutics with mammalian cell cultures"; Trends in Biotechnology; 18(4):173-180; (2000).
Werner, Rolf. G, et al.; "Safety and economic aspects of continuous mammalian cell culture"; Journal of Biotechnology; 22:51-68 (1992).
Hermening S., et al.; "Increased protein expression from adenoviral shuttle plasmids and vectors by insertion of a small chimeric intron sequence"; Journal of Virological Methods; 122(1):73-77; (2004).
Rasmussen, Brian, et al.; "Isolation, characterization and recombinant protein expression in Veggie-CHO: a serum-free CHO host cell line"; Cytotechnology; 28(1-3):31-42; (1998).

* cited by examiner

*Primary Examiner* — Ilia Ouspenski

(57) ABSTRACT

The present invention provides polynucleotides for enhanced expression of a target gene such as an immunoglobulin. Methods of expressing a target gene using the polynucleotides of the invention are also covered.

7 Claims, 30 Drawing Sheets

Figure 6A

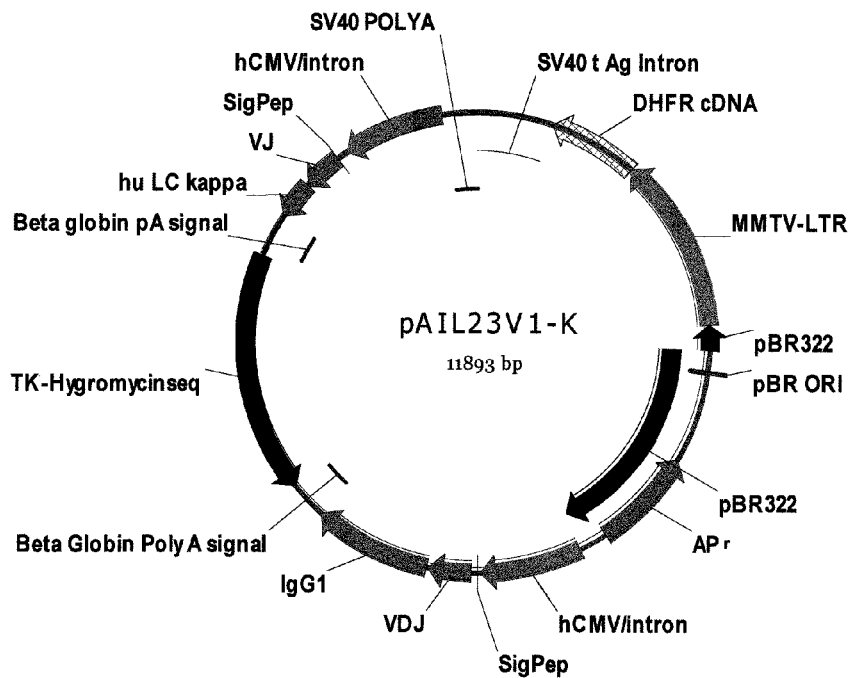

```
  1   GGCACTATAC ATCAAATATT CCTTATTAAC CCCTTTACAA ATTAAAAAGC TAAAGGTACA
 61   CAATTTTTGA GCATAGTTAT TAATAGCAGA CACTCTATGC CTGTGTGGAG TAAGAAAAAA
121   CAGTATGTTA TGATTATAAC TGTTATGCCT ACTTATAAAG GTTACAGAAT ATTTTTCCAT
181   AATTTTCTTG TATAGCAGTG CAGCTTTTTC CTTTGTGGTG TAAATAGCAA AGCAAGCAAG
241   AGTTCTATTA CTAAACACAG CATGACTCAA AAAACTTAGC AATTCTGAAG GAAAGTCCTT
301   GGGGTCTTCT ACCTTTCTCT TCTTTTTTGG AGGAGTAGAA TGTTGAGAGT CAGCAGTAGC
361   CTCATCATCA CTAGATGGCA TTTCTTCTGA GCAAAACAGG TTTTCCTCAT TAAAGGCATT
421   CCACCACTGC TCCCATTCAT CAGTTCCATA GGTTGGAATC TAAAATACAC AAACAATTAG
481   AATCAGTAGT TTAACACATT ATACACTTAA AAATTTTATA TTTACCTTAG AGCTTTAAAT
541   CTCTGTAGGT AGTTTGTCCA ATTATGTCAC ACCACAGAAG TAAGGTTCCT TCACAAAGAT
601   CGATCTAAAG CCAGCAAAAG TCCCATGGTC TTATAAAAAT GCATAGCTTT AGGAGGGGAG
661   CAGAGAACTT GAAAGCATCT TCCTGTTAGT CTTTCTTCTC GTAGACTTCA AACTTATACT
721   TGATGCCTTT TTCCTCCTGG ACCTCAGAGA GGACGCCTGG GTATTCTGGG AGAAGTTTAT
781   ATTTCCCCAA ATCAATTTCT GGGAAAAACG TGTCACTTTC AAATTCCTGC ATGATCCTTG
841   TCACAAAGAG TCTGAGGTGG CCTGGTTGAT TCATGGCTTC CTGGTAAACA GAACTGCCTC
901   CGACTATCCA AACCATGTCT ACTTTACTTG CCAATTCCGG TTGTTCAATA AGTCTTAAGG
961   CATCATCCAA ACTTTTGGCA AGAAAATGAG CTCCTCGTGG TGGTTCTTTG AGTTCTCTAC
```

Figure 6B

| | | | | | |
|---|---|---|---|---|---|
| 1021 | TGAGAACTAT | ATTAATTCTG | TCCTTTAAAG | GTCGATTCTT | CTCAGGAATG | GAGAACCAGG |
| 1081 | TTTTCCTACC | CATAATCACC | AGATTCTGTT | TACCTTCCAC | TGAAGAGGTT | GTGGTCATTC |
| 1141 | TTTGGAAGTA | CTTGAACTCG | TTCCTGAGCG | GAGGCCAGGG | TAGGTCTCCG | TTCTTGCCAA |
| 1201 | TCCCCATATT | TTGGGACACG | GCGACGATGC | AGTTCAATGG | TCGAACCATG | ATGGCAGCGG |
| 1261 | GGATAAAATC | CTACCAGCCT | TCACGCTAGG | ATTGCCGTCA | AGTTTGGCGC | GAAATCGCAG |
| 1321 | CCCTGAGCTG | TCCCCCCCCC | CAAGCTCAGA | TCTGAGCTTG | GTCCCTATGG | TGAGTCCGTT |
| 1381 | CCGCTCTTGT | GATGATAGCC | AGACAAGAAA | GAGACAATAC | AAGACAAACA | CCAAATAGTA |
| 1441 | GAAATAGAGA | CAAGGGTCAC | TTATCCGAGG | GTCCCTGTTC | GGGCGCCAGC | TGCCGCAGTC |
| 1501 | GGCCGACCTG | AGGGTCGCCG | GGGTCTGCGG | GGGGACCCTC | TGGAAAGTGA | AGGATAAGTG |
| 1561 | ACGAGCGGAG | ACGGGATGGC | GAACAGACAC | AAACACACAA | GAGGTGAATG | TTAGGACTGT |
| 1621 | TGCAAGTTTA | CTCAAAAAAT | CAGCACTCTT | TTATATCTTG | GTTTACATAA | GCATTTACAT |
| 1681 | AAGATTTGGA | TAAATTCCAA | AGAACATAG | GAAAATAGAA | CACTCAGAGC | TCAGATCAGA |
| 1741 | ACCTTTGATA | CCAAACCAAG | TCAGGAAACC | ACTTGTCTCA | CATCCTCGTT | TTAAGAACAG |
| 1801 | TTTGTAACCA | AAAACTTACT | TAAGCCCTGG | GAACCGCAAG | GTTGGGCCAA | TAAAGGCTAT |
| 1861 | TCATAATAAC | TCATGCCATG | AGTTTTTGCA | GAATAATGTT | CTATTAGTCC | AGCCACTGTC |
| 1921 | CCCTCCTTGG | TATGGAAAAT | CTTTCCCCAA | AAGTGCATTC | CTGTTCCTAG | ATAAATATAA |
| 1981 | TCATGTACCT | GTTGTTTCAT | GTCGTCTTTT | TCTTCTTGAG | ACAACATACA | CCAAGGAGGT |
| 2041 | CTAGCTCTGG | CGAGTCTTTC | ACGAAAAGGG | AGGGATCTAT | ATAACACTTT | ATAGCCATTG |
| 2101 | ACTGTAACCC | ACCTATCCCA | ATTTAAGTCA | TATCTTCCTG | TATATGGTAA | GGGGGCATCT |
| 2161 | GTTGGTCTGT | AGATGTAAGG | TCCCCTATAA | GTCCCTGGTT | GCCACCACCT | GTCTCCTATT |
| 2221 | TTGACAAAAA | CACTCTTTTT | TCCCTTTTTT | ACTTCTAGGC | CTGTGGTCAA | TAGTCCTTGC |
| 2281 | ACCTGTTCTT | CAATTGAGGT | TGAGCGTCTC | TTTCTATTTT | CTATTCCCAT | TTCTAACTTC |
| 2341 | TGAATTTGAG | TAAAAATAGT | ACTAAAAGAT | AATGATTCAT | TTCTTAACAT | AGTAACTAAT |
| 2401 | AATCTACCTA | TTGGATTGGT | CTTATTGGTA | AAAATATAAT | TTTTAGCAAG | CATTCTTATT |
| 2461 | TCTATTTCTG | AAGGACAAAA | TCGATGCGGC | TTGTAAGAGG | AAGTTGGCTG | TGGTCCTTGC |
| 2521 | CTCAGGAGGA | AGGTCGAGTT | CTCCGAATTG | TTTAGATTGT | AATCTTGCAC | AGAAGAGCTA |
| 2581 | TTAAAAGAGT | CAAGGGTGAG | AGCCCTGCGA | GCACGAACCG | CAACTTCCCC | CAATAGCCCC |
| 2641 | AGGCAAAGCA | GAGCTATGCC | AAGTTTGCAG | CAGAGAATGA | ATATGTCTTT | GTCTGATGGG |
| 2701 | CTCATCCGTT | TGTGCGCAGA | CGGGTCGTCC | TTGGTGGGAA | ACAACCCCTT | GGCTGCTTCT |
| 2761 | CCCCTAGGTG | TAGGACACTC | TCGGGAGTTC | AACCATTTCT | GCCCAAGCTC | AGATCTGAGC |
| 2821 | TTTAATGCGG | TAGTTTATCA | CAGTTAAATT | GCTAACGCAG | TCAGGCACCG | TGTATGAAAT |
| 2881 | CTAACAATGC | GCTCATCGTC | ATCCTCGGCA | CCGTCACCCT | GGATGCTGTA | GGCATAGGCT |
| 2941 | TGGTTATGCC | GGTACTGCCG | GGCCTCTTGC | GGGATATCGT | CCATTCCGAC | AGCATCGCCA |
| 3001 | GTCACTATGG | CGTGCTGCTA | GCGCTCTTCC | GCTTCCTCGC | TCACTGACTC | GCTGCGCTCG |
| 3061 | GTCGTTCGGC | TGCGGCGAGC | GGTATCAGCT | CACTCAAAGG | CGGTAATACG | GTTATCCACA |
| 3121 | GAATCAGGGG | ATAACGCAGG | AAAGAACATG | TGAGCAAAAG | GCCAGCAAAA | GGCCAGGAAC |
| 3181 | CGTAAAAAGG | CCGCGTTGCT | GGCGTTTTTC | CATAGGCTCC | GCCCCCCTGA | CGAGCATCAC |
| 3241 | AAAAATCGAC | GCTCAAGTCA | GAGGTGGCGA | AACCCGACAG | GACTATAAAG | ATACCAGGCG |
| 3301 | TTTCCCCCTG | GAAGCTCCCT | CGTGCGCTCT | CCTGTTCCGA | CCCTGCCGCT | TACCGGATAC |
| 3361 | CTGTCCGCCT | TTCTCCCTTC | GGGAAGCGTG | GCGCTTTCTC | ATAGCTCACG | CTGTAGGTAT |
| 3421 | CTCAGTTCGG | TGTAGGTCGT | TCGCTCCAAG | CTGGGCTGTG | TGCACGAACC | CCCCGTTCAG |
| 3481 | CCCGACCGCT | GCGCCTTATC | CGGTAACTAT | CGTCTTGAGT | CCAACCCGGT | AAGACACGAC |
| 3541 | TTATCGCCAC | TGGCAGCAGC | CACTGGTAAC | AGGATTAGCA | GAGCGAGGTA | TGTAGGCGGT |
| 3601 | GCTACAGAGT | TCTTGAAGTG | GTGGCCTAAC | TACGGCTACA | CTAGAAGGAC | AGTATTTGGT |
| 3661 | ATCTGCGCTC | TGCTGAAGCC | AGTTACCTTC | GGAAAAAGAG | TTGGTAGCTC | TTGATCCGGC |
| 3721 | AAACAAACCA | CCGCTGGTAG | CGGTGGTTTT | TTTGTTTGCA | AGCAGCAGAT | TACGCGCAGA |
| 3781 | AAAAAAGGAT | CTCAAGAAGA | TCCTTTGATC | TTTTCTACGG | GTCTGACGC | TCAGTGGAAC |
| 3841 | GAAAACTCAC | GTTAAGGGAT | TTTGGTCATG | AGATTATCAA | AAAGGATCTT | CACCTAGATC |
| 3901 | CTTTTAAATT | AAAAATGAAG | TTTTAAATCA | ATCTAAAGTA | TATATGAGTA | AACTTGGTCT |
| 3961 | GACAGTTACC | AATGCTTAAT | CAGTGAGGCA | CCTATCTCAG | CGATCTGTCT | ATTTCGTTCA |

Figure 6C

```
4021    TCCATAGTTG CCTGACTCCC CGTCGTGTAG ATAACTACGA TACGGGAGGG CTTACCATCT
4081    GGCCCCAGTG CTGCAATGAT ACCGCGAGAC CCACGCTCAC CGGCTCCAGA TTTATCAGCA
4141    ATAAACCAGC CAGCCGGAAG GGCCGAGCGC AGAAGTGGTC CTGCAACTTT ATCCGCCTCC
4201    ATCCAGTCTA TTAATTGTTG CCGGGAAGCT AGAGTAAGTA GTTCGCCAGT TAATAGTTTG
4261    CGCAACGTTG TTGCCATTGC TACAGGCATC GTGGTGTCAC GCTCGTCGTT TGGTATGGCT
4321    TCATTCAGCT CCGGTTCCCA ACGATCAAGG CGAGTTACAT GATCCCCCAT GTTGTGCAAA
4381    AAAGCGGTTA GCTCCTTCGG TCCTCCGATC GTTGTCAGAA GTAAGTTGGC CGCAGTGTTA
4441    TCACTCATGG TTATGGCAGC ACTGCATAAT TCTCTTACTG TCATGCCATC CGTAAGATGC
4501    TTTTCTGTGA CTGGTGAGTA CTCAACCAAG TCATTCTGAG AATAGTGTAT GCGGCGACCG
4561    AGTTGCTCTT GCCCGGCGTC AACACGGGAT AATACCGCGC CACATAGCAG AACTTTAAAA
4621    GTGCTCATCA TTGGAAAACG TTCTTCGGGG CGAAAACTCT CAAGGATCTT ACCGCTGTTG
4681    AGATCCAGTT CGATGTAACC CACTCGTGCA CCCAACTGAT CTTCAGCATC TTTTACTTTC
4741    ACCAGCGTTT CTGGGTGAGC AAAAACAGGA AGGCAAATG CCGCAAAAAA GGGAATAAGG
4801    GCGACACGGA AATGTTGAAT ACTCATACTC TTCCTTTTTC AATATTATTG AAGCATTTAT
4861    CAGGGTTATT GTCTCATGAG CGGATACATA TTTGAATGTA TTTAGAAAAA TAAACAAATA
4921    GGGGTTCCGC GCACATTTCC CCGAAAAGTG CCACCTGACG TCTAAGAGAC CATTATTATC
4981    ATGACATTAA CCTATAAAAA TAGGCGTATC ACGAGGCCCT TTCGTCTTCA AGAATTGTCT
5041    AGAGGCGCGC CGTTTAAACC CTCAGCTACC GATGTACGGG CCAGATATAC GCGTTGACAT
5101    TGATTATTGA CTAGTTATTA ATAGTAATCA ATTACGGGGT CATTAGTTCA TAGCCCATAT
5161    ATGGAGTTCC GCGTTACATA ACTTACGGTA AATGGCCCGC CTGGCTGACC GCCCAACGAC
5221    CCCCGCCCAT TGACCTCCAAT AATGACGTAT GTTCCATAG TAACGCCAAT AGGGACTTTC
5281    CATTGACGTC AATGGGTGGA CTATTTACGG TAAACTGCCC ACTTGGCAGT ACATCAAGTG
5341    TATCATATGC CAAGTACGCC CCCTATTGAC GTCAATGACG GTAAATGGCC CGCCTGGCAT
5401    TATGCCCAGT ACATGACCTT ATGGGACTTT CCTACTTGGC AGTACATCTA CGTATTAGTC
5461    ATCGCTATTA CCATGGTGAT GCGGTTTTGG CAGTACATCA ATGGGCGTGG ATAGCGGTTT
5521    GACTCACGGG GATTTCCAAG TCTCCACCCC ATTGACGTCA ATGGGAGTTT GTTTTGGCAC
5581    CAAAATCAAC GGGACTTTCC AAAATGTCGT AACAACTCCG CCCCATTGAC GCAAATGGGC
5641    GGTAGGCGTG TACGGTGGGA GGTCTATATA AGCAGAGCTC TCTGGCTAAC TAGAGAACCC
5701    ACTGCTTACT GGCTTATCGA AATTAATACG ACTCACTATA GCAATTGCAC GTGTGGCCAC
5761    AGGTAAGTTT AAAGCTCAGG TCGAGACCGG CCTTTGTCC GGCGCTCCCT TGGAGCCTAC
5821    CTAGACTCAG CCGGCTCTCC ACGCTTTGCC TGACCCTGCT TGCTCAACTC TACGTCTTTG
5881    TTTCGTTTTC TGTTCCTTTC TCTCCACAGG CTTAAGCTCG AGGCCGCCAC CATGGCTGTG
5941    CTGGGGCTGC TGTTCTGCCT GGTGACATTC CCAAGCTGTG TGCTGTCCCA GGTGCAGCTG
6001    GTGCAGTCTG GCGCTGAGGT GAAGAAGCCT GGCGCCTCCG TGAAGGTCTC CTGCAAGGCT
6061    TCTGGCTACA TCTTCATCAC CTACTGGATG ACCTGGGTGC GGCAGGCCCC TGGCCAGGGG
6121    CTGGAGTGGA TGGGCCAGAT CTTCCCTGCC AGCGGCTCTG CAGACTACAA CGAGAAGTTC
6181    GAAGGCAGAG TCACCATGAC CACAGACACA TCCACCAGCA CAGCCTACAT GGAGCTGAGG
6241    AGCCTGAGAT CTGACGACAC CGCCGTGTAT TACTGTGCCA GAGGCGGTGG CGGATTCGCT
6301    TACTGGGGCC AGGGCACCCT GGTCACCGTC TCCAGCGCTA GCACCAAGGG CCCATCGGTC
6361    TTCCCCCTGG CACCCTCCTC CAAGAGCACC TCTGGGGGCA CAGCGGCCCT GGGCTGCCTG
6421    GTCAAGGACT ACTTCCCCGA ACCGGTGACG GTGTCGTGGA ACTCAGGCGC CCTGACCAGC
6481    GGCGTGCACA CCTTCCCGGC TGTCCTACAG TCCTCAGGAC TCTACTCCCT CAGCAGCGTG
6541    GTGACCGTGC CCTCCAGCAG CTTGGGCACC CAGACCTACA TCTGCAACGT GAATCACAAG
6601    CCCAGCAACA CCAAGGTGGA CAAGAAAGTT GAGCCCAAAT CTTGTGACAA AACTCACACA
6661    TGCCCACCGT GCCCAGCACC TGAACTCCTG GGGGGACCGT CAGTCTTCCT CTTCCCCCCA
6721    AAACCCAAGG ACACCCTCAT GATCTCCCGG ACCCCTGAGG TCACATGCGT GGTGGTGGAC
6781    GTGAGCCACG AAGACCCTGA GGTCAAGTTC AACTGGTACG TGGACGGCGT GGAGGTGCAT
6841    AATGCCAAGA CAAAGCCGCG GGAGGAGCAG TACAACAGCA CGTACCGTGT GGTCAGCGTC
6901    CTCACCGTCC TGCACCAGGA CTGGCTGAAT GGCAAGGAGT ACAAGTGCAA GGTCTCCAAC
6961    AAAGCCCTCC CAGCCCCCAT CGAGAAAACC ATCTCCAAAG CCAAAGGGCA GCCCCGAGAA
```

Figure 6D

```
7021    CCACAGGTGT ACACCCTGCC CCCATCCCGG GATGAGCTGA CCAAGAACCA GGTCAGCCTG
7081    ACCTGCCTGG TCAAAGGCTT CTATCCCAGC GACATCGCCG TGGAGTGGGA GAGCAATGGG
7141    CAGCCGGAGA ACAACTACAA GACCACGCCT CCCGTGCTGG ACTCCGACGG CTCCTTCTTC
7201    CTCTACAGCA AGCTCACCGT GGACAAGAGC AGGTGGCAGC AGGGGAACGT CTTCTCATGC
7261    TCCGTGATGC ATGAGGCTCT GCACAACCAC TACACGCAGA AGAGCCTCTC CCTGTCTCCG
7321    GGTAAATGAA TCGATGATTC TAGATACGGG TCCGGAGGAT CCAGATCCCC CTCGCTTTCT
7381    TGCTGTCCAA TTTCTATTAA AGGTTCCTTT GTTCCCTAAG TCCAACTACT AAACTGGGGG
7441    ATATTATGAA GGGCCTTGAG CATCTGGATT CTGCCTAATA AAAAACATTT ATTTTCATTG
7501    CAATGATGTA TTTAAATTAT TTCTGAATAT TTTACTAAAA AGGGAATGTG GGAGGTCAGT
7561    GCATTTAAAA CATAAAGAAA TGAAGAGGGG GATCTGTCGA CAAGCTCTAG AGAGCTCACG
7621    CGTTGATCAT GTACAGGCCG GCCAAGCTTT CGACTAGCTT GGCACGCCAG AAATCCGCGC
7681    GGTGGTTTTT GGGGGTCGGG GGTGTTTGGC AGCCACAGAC GCCCGGTGTT CGTGTCGCGC
7741    CAGTACATGC GGTCCATGCC CAGGCCATCC AAAAACCATG GGTCTGTCTG CTCAGTCCAG
7801    TCGTGGACCT GACCCCACGC AACGCCCAAA ATAATAACCC CCACGAACCA TAAACCATTC
7861    CCCATGGGGG ACCCCGTCCC TAACCCACGG GGCCAGTGGC TATGGCAGGG CCTGCCGCCC
7921    CGACGTTGGC TGCGAGCCCT GGGCCTTCAC CCGAACTTGG GGGGTGGGGT GGGGAAAAGG
7981    AAGAAACGCG GGCGTATTGG CCCCAATGGG GTCTCGGTGG GGTATCGACA GAGTGCCAGC
8041    CCTGGGACCG AACCCCGCGT TTATGAACAA ACGACCCAAC ACCCGTGCGT TTTATTCTGT
8101    CTTTTTATTG CCGTCATAGC GCGGGTTCCT TCCGGTATTG TCTCCTTCCG TGTTTCAGTT
8161    AGCCTCCCCC ATCTCCCGAT CCGGACGAGT GCTGGGGCGT CGGTTTCCAC TATCGGCGAG
8221    TACTTCTACA CAGCCATCGG TCCAGACGGC CGCGCTTCTG CGGGCGATTT GTGTACGCCC
8281    GACAGTCCCG GCTCCGGATC GGACGATTGC GTCGCATCGA CCCTGCGCCC AAGCTGCATC
8341    ATCGAAATTG CCGTCAACCA AGCTCTGATA GAGTTGGTCA AGACCAATGC GGAGCATATA
8401    CGCCCGGAGC CGCGGCGATC CTGCAAGCTC CGGATGCCTC CGCTCGAAGT AGCGCGTCTG
8461    CTGCTCCATA CAAGCCAACC ACGGCCTCCA GAAGAAGATG TTGGCGACCT CGTATTGGGA
8521    ATCCCCGAAC ATCGCCTCGC TCCAGTCAAT GACCGCTGTT ATGCGGCCAT TGTCCGTCAG
8581    GACATTGTTG GAGCCGAAAT CCGCGTGCAC GAGGTGCCGG ACTTCGGGGC AGTCCTCGGC
8641    CCAAAGCATC AGCTCATCGA GAGCCTGCGC GACGGACGCA CTGACGGTGT CGTCCATCAC
8701    AGTTTGCCAG TGATACACAT GGGGATCAGC AATCGCGCAT ATGAAATCAC GCCATGTAGT
8761    GTATTGACCG ATTCCTTGCG GTCCGAATGG GCCGAACCCG CTCGTCTGGC TAAGATCGGC
8821    CGCAGCGATC GCATCCATGG CCTCCGCGAC CGGCTGCAGA ACAGCGGGCA GTTCGGTTTC
8881    AGGCAGGTCT TGCAACGTGA CACCCTGTGC ACGGCGGGAG ATGCAATAGG TCAGGCTCTC
8941    GCTGAATTCC CCAATGTCAA GCACTTCCGG AATCGGGAGC GCGGCCGATG CAAAGTGCCG
9001    ATAAACATAA CGATCTTTGT AGAAACCATC GGCGCAGCTA TTTACCCGCA GGACATATCC
9061    ACGCCCTCCT ACATCGAAGC TGAAAGCACG AGATTCTTCG CCCTCCGAGA GCTGCATCAG
9121    GTCGGAGACG CTGTCGAACT TTTCGATCAG AAACTTCTCG ACAGACGTCG CGGTGAGTTC
9181    AGGCTTTTTC ATATCTCATT GCCCCCCGGG ATCTGCGGCA CGCTGTTGAC GCTGTTAAGC
9241    GGGTCGCTGC AGGGTCGCTC GGTGTTCGAG GCCACACGCG TCACCTTAAT ATGCGAAGTG
9301    GACCTCGGAC CGCGCCGCCC CGACTGCATC TGCGTGTTCG AATTCGCCAA TGACAAGACG
9361    CTGGGCGGGG TTTGTGTCAT CATAGAACTA AAGACATGCA AATATATTTC TTCCGGGGAC
9421    ACCGCCAGCA AACGCGAGCA ACGGGCCACG GGATGAAGC AGGGCGGCAC CTCGCTAACG
9481    GATTCACCAC TCCAAGAATT GGAGCCAATC AATTCTTGCG GAGAACTGTG AATGCGCAAA
9541    CCAACCCTTG GCAGAACATA TCCATCGCGT CCGCCATCTC CAGCAGCCGC ACGCGGCGCA
9601    TCTCGGGCC GACGCGCTGG GCTACGTCTT GCTGGCGTTC GCACAGGCCG GCCAGCGCGC
9661    GGCGGCCGG TACCACGCGT TGGCCACATA TGGCGGCCGC TCGCGATTAA TTAATCGCGA
9721    TGGCCACATA TGGAGCTCTC TAGAGCTTGT CGACAGATCC CCCTCTTCAT TTCTTTATGT
9781    TTTAAATGCA CTGACCTCCC ACATTCCCTT TTTAGTAAAA TATTCAGAAA TAATTTAAAT
9841    ACATCATTGC AATGAAAATA AATGTTTTTT ATTAGGCAGA ATCCAGATGC TCAAGGCCCT
9901    TCATAATATC CCCCAGTTTA GTAGTTGGAC TTAGGGAACA AAGGAACCTT TAATAGAAAT
9961    TGGACAGCAA GAAAGCGAGG GGGATCTGGA TCCTCCTACG TATCTAGAAT CATCGATTAA
```

Figure 6E

```
10021    CACTCTCCCC TGTTGAAGCT CTTTGTCACG GGGCTGCTCA GGCCCTGATG GGTCACCTCG
10081    CAGGCGTACA CCTTGTGTTT CTCGTAGTCT GCTTTGCTCA GGGTCAGGGT GCTGCTCAGG
10141    CTGTAGGTGC TGTCCTTGCT GTCCTGCTCT GTCACGCTCT CCTGGGAGTT GCCGCTCTGG
10201    AGGGCGTTAT CCACCTTCCA CTGCACCTTG GCCTCTCTGG GATAGAAGTT ATTCAGCAGG
10261    CACACCACGG AGGCAGTTCC AGACTTCAGC TGCTCATCAG ATGGAGGGAA GATGAACACA
10321    GATGGTGCAG CCACCGTACG CTTGATCTCC ACCTTGGTGC CCTGGCCGAA GGTGAATGGA
10381    ATTCCGTAGT GGTGCTGACA GTAGTAGGTG GCGAAGTCCT CAGGCTGCAG GCTGCTGATG
10441    GTCAGGGTGA AGTCTGTCCC AGAGCCGCTG CCGCTGAACC TGGATGGCAC CCCTTCAGCC
10501    AGGGTCTTGG CGTTATAGAT CAGCAGCTTA GGGGCCTTCC CTGGCTTCTG CTGATACCAG
10561    GCCAGGTAGC TGTAGATGTT CTCGCTGGTC CTGCAGGTGA TGGTCACTCT GTCGCCCACA
10621    GAGGCAGACA GGGAGGATGG AGACTGGGTC ATCTGGATAT CACATCTCAT GGCTGGCAGG
10681    AACAGCACCA GCAGCCCCAG CAGCTGCACT GGAGCCATGG TGGCGGCCTC GAGAAGCTTA
10741    AGTTTAATTC TTAAGCCTGT GGAGAGAAAG GAACAGAAAA CGAAACAAAG ACGTAGAGTT
10801    GAGCAAGCAG GGTCAGGCAA AGCGTGGAGA GCCGGCTGAG TCTAGGTAGG CTCCAAGGGA
10861    GCGCCGGACA AAGGCCCGGT CTCGACCTGA GCTTTAAACT TACCTGTGGC CACACGTGCA
10921    ATTGCTATAG TGAGTCGTAT TAATTTCGAT AAGCCAGTAA GCAGTGGGTT CTCTAGTTAG
10981    CCAGAGAGCT CTGCTTATAT AGACCTCCCA CCGTACACGC CTACCGCCCA TTTGCGTCAA
11041    TGGGGCGGAG TTGTTACGAC ATTTTGGAAA GTCCCGTTGA TTTTGGTGCC AAAACAAACT
11101    CCCATTGACG TCAATGGGGT GGAGACTTGG AAATCCCCGT GAGTCAAACC GCTATCCACG
11161    CCCATTGATG TACTGCCAAA ACCGCATCAC CATGGTAATA GCGATGACTA ATACGTAGAT
11221    GTACTGCCAA GTAGGAAAGT CCCATAAGGT CATGTACTGG GCATAATGCC AGGCGGGCCA
11281    TTTACCGTCA TTGACGTCAA TAGGGGGCGT ACTTGGCATA TGATACACTT GATGTACTGC
11341    CAAGTGGGCA GTTTACCGTA AATAGTCCAC CCATTGACGT CAATGGAAAG TCCCTATTGG
11401    CGTTACTATG GGAACATACG TCATTATTGA CGTCAATGGG CGGGGGTCGT TGGGCGGTCA
11461    GCCAGGCGGG CCATTTACCG TAAGTTATGT AACGCGGAAC TCCATATATG GCTATGAAC
11521    TAATGACCCC GTAATTGATT ACTATTAATA ACTAGTCAAT AATCAATGTC AACGCGTATA
11581    TCTGGCCCGT ACATCGGTAA CTAGTCGGAC CGGCCCGGGC CACCGGTGCT CGAAGCTTGG
11641    ATCGATCCAG ACATGATAAG ATACATTGAT GAGTTTGGAC AAACCACAAC TAGAATGCAG
11701    TGAAAAAAAT GCTTTATTTG TGAAATTTGT GATGCTATTG CTTTATTTGT AACCATTATA
11761    AGCTGCAATA AACAAGTTAA CAACAACAAT TGCATTCATT TTATGTTTCA GGTTCAGGGG
11821    GAGGTGTGGG AGGTTTTTTA AAGCAAGTAA AACCTCTACA AATGTGGTAT GGCTGATTAT
11881    GATCTCTAGT CAA
```

Figure 7A

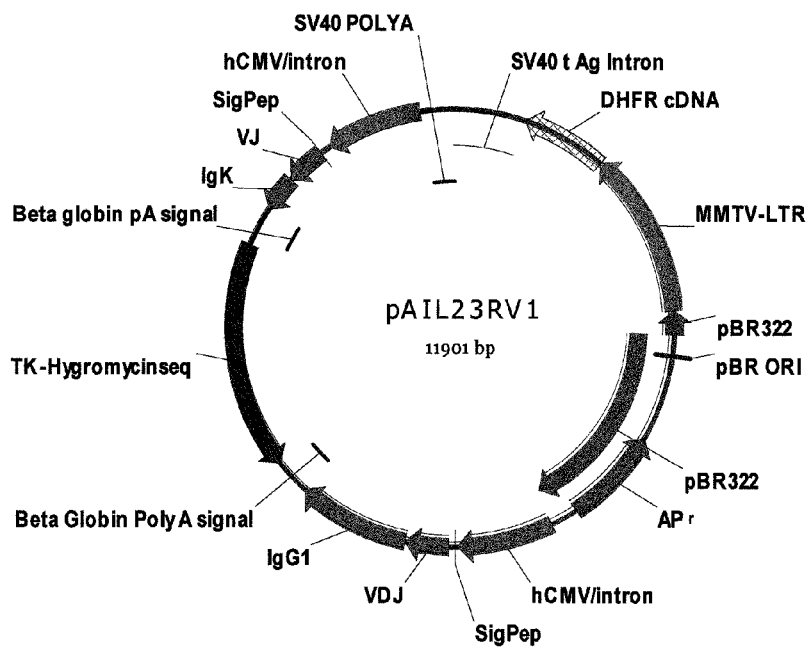

```
   1    GGCACTATAC ATCAAATATT CCTTATTAAC CCCTTTACAA ATTAAAAAGC TAAAGGTACA
  61    CAATTTTTGA GCATAGTTAT TAATAGCAGA CACTCTATGC CTGTGTGGAG TAAGAAAAAA
 121    CAGTATGTTA TGATTATAAC TGTTATGCCT ACTTATAAAG GTTACAGAAT ATTTTTCCAT
 181    AATTTTCTTG TATAGCAGTG CAGCTTTTTC CTTTGTGGTG TAAATAGCAA AGCAAGCAAG
 241    AGTTCTATTA CTAAACACAG CATGACTCAA AAAACTTAGC AATTCTGAAG GAAAGTCCTT
 301    GGGGTCTTCT ACCTTTCTCT TCTTTTTTGG AGGAGTAGAA TGTTGAGAGT CAGCAGTAGC
 361    CTCATCATCA CTAGATGGCA TTTCTTCTGA GCAAACAGG TTTTCCTCAT TAAAGGCATT
 421    CCACCACTGC TCCCATTCAT CAGTTCCATA GGTTGGAATC TAAAATACAC AAACAATTAG
 481    AATCAGTAGT TTAACACATT ATACACTTAA AAATTTTATA TTTACCTTAG AGCTTTAAAT
 541    CTCTGTAGGT AGTTTGTCCA ATTATGTCAC ACCACAGAAG TAAGGTTCCT TCACAAAGAT
 601    CGATCTAAAG CCAGCAAAAG TCCCATGGTC TTATAAAAAT GCATAGCTTT AGGAGGGGAG
 661    CAGAGAACTT GAAAGCATCT TCCTGTTAGT CTTTCTTCTC GTAGACTTCA AACTTATACT
 721    TGATGCCTTT TTCCTCCTGG ACCTCAGAGA GGACGCCTGG GTATTCTGGG AGAAGTTTAT
 781    ATTTCCCCAA ATCAATTTCT GGGAAAAACG TGTCACTTTC AAATTCCTGC ATGATCCTTG
 841    TCACAAAGAG TCTGAGGTGG CCTGGTTGAT TCATGGCTTC CTGGTAAACA GAACTGCCTC
 901    CGACTATCCA AACCATGTCT ACTTTACTTG CCAATTCCGG TTGTTCAATA AGTCTTAAGG
 961    CATCATCCAA ACTTTTGGCA AGAAAATGAG CTCCTCGTGG TGGTTCTTTG AGTTCTCTAC
1021    TGAGAACTAT ATTAATTCTG TCCTTTAAAG GTCGATTCTT CTCAGGAATG GAGAACCAGG
1081    TTTTCCTACC CATAATCACC AGATTCTGTT TACCTTCCAC TGAAGAGGTT GTGGTCATTC
```

Figure 7B

```
1141    TTTGGAAGTA CTTGAACTCG TTCCTGAGCG GAGGCCAGGG TAGGTCTCCG TTCTTGCCAA
1201    TCCCCATATT TTGGGACACG GCGACGATGC AGTTCAATGG TCGAACCATG ATGGCAGCGG
1261    GGATAAAATC CTACCAGCCT TCACGCTAGG ATTGCCGTCA AGTTTGGCGC GAAATCGCAG
1321    CCCTGAGCTG TCCCCCCCCC CAAGCTCAGA TCTGAGCTTG GTCCCTATGG TGAGTCCGTT
1381    CCGCTCTTGT GATGATAGCC AGACAAGAAA GAGACAATAC AAGACAAACA CCAAATAGTA
1441    GAAATAGAGA CAAGGGTCAC TTATCCGAGG GTCCCTGTTC GGGCGCCAGC TGCCGCAGTC
1501    GGCCGACCTG AGGGTCGCCG GGGTCTGCGG GGGGACCCTC TGGAAAGTGA AGGATAAGTG
1561    ACGAGCGGAG ACGGGATGGC GAACAGACAC AAACACACAA GAGGTGAATG TTAGGACTGT
1621    TGCAAGTTTA CTCAAAAAAT CAGCACTCTT TTATATCTTG GTTTACATAA GCATTTACAT
1681    AAGATTTGGA TAAATTCCAA AAGAACATAG GAAAATAGAA CACTCAGAGC TCAGATCAGA
1741    ACCTTTGATA CCAAACCAAG TCAGGAAACC ACTTGTCTCA CATCCTCGTT TTAAGAACAG
1801    TTTGTAACCA AAAACTTACT TAAGCCCTGG GAACCGCAAG GTTGGGCCAA TAAAGGCTAT
1861    TCATAATAAC TCATGCCATG AGTTTTTGCA GAATAATGTT CTATTAGTCC AGCCACTGTC
1921    CCCTCCTTGG TATGGAAAAT CTTTCCCCAA AAGTGCATTC CTGTTCCTAG ATAAATATAA
1981    TCATGTACCT GTTGTTTCAT GTCGTCTTTT TCTTCTTGAG ACAACATACA CCAAGGAGGT
2041    CTAGCTCTGG CGAGTCTTTC ACGAAAAGGG AGGGATCTAT ATAACACTTT ATAGCCATTG
2101    ACTGTAACCC ACCTATCCCA ATTTAAGTCA TATCTTCCTG TATATGGTAA GGGGGCATCT
2161    GTTGGTCTGT AGATGTAAGG TCCCCTATAA GTCCCTGGTT GCCACCACCT GTCTCCTATT
2221    TTGACAAAAA CACTCTTTTT TCCCTTTTTT ACTTCTAGGC CTGTGGTCAA TAGTCCTTGC
2281    ACCTGTTCTT CAATTGAGGT TGAGCGTCTC TTTCTATTTT CTATTCCCAT TTCTAACTTC
2341    TGAATTTGAG TAAAAATAGT ACTAAAGAT AATGATTCAT TTCTTAACAT AGTAACTAAT
2401    AATCTACCTA TTGGATTGGT CTTATTGGTA AAAATATAAT TTTTAGCAAG CATTCTTATT
2461    TCTATTTCTG AAGGACAAAA TCGATGCGGC TTGTAAGAGG AAGTTGGCTG TGGTCCTTGC
2521    CTCAGGAGGA AGGTCGAGTT CTCCGAATTG TTTAGATTGT AATCTTGCAC AGAAGAGCTA
2581    TTAAAAGAGT CAAGGGTGAG AGCCCTGCGA GCACGAACCG CAACTTCCCC CAATAGCCCC
2641    AGGCAAAGCA GAGCTATGCC AAGTTTGCAG CAGAGAATGA ATATGTCTTT GTCTGATGGG
2701    CTCATCCGTT TGTGCGCAGA CGGGTCGTCC TTGGTGGGAA ACAACCCCTT GGCTGCTTCT
2761    CCCCTAGGTG TAGGACACTC TCGGGAGTTC AACCATTTCT GCCCAAGCTC AGATCTGAGC
2821    TTTAATGCGG TAGTTTATCA CAGTTAAATT GCTAACGCAG TCAGGCACCG TGTATGAAAT
2881    CTAACAATGC GCTCATCGTC ATCCTCGGCA CCGTCACCCT GGATGCTGTA GGCATAGGCT
2941    TGGTTATGCC GGTACTGCCG GGCCTCTTGC GGGATATCGT CCATTCCGAC AGCATCGCCA
3001    GTCACTATGG CGTGCTGCTA GCGCTCTTCC GCTTCCTCGC TCACTGACTC GCTGCGCTCG
3061    GTCGTTCGGC TGCGGCGAGC GGTATCAGCT CACTCAAAGG CGGTAATACG GTTATCCACA
3121    GAATCAGGGG ATAACGCAGG AAAGAACATG TGAGCAAAAG GCCAGCAAAA GGCCAGGAAC
3181    CGTAAAAAGG CCGCGTTGCT GGCGTTTTTC CATAGGCTCC GCCCCCCTGA CGAGCATCAC
3241    AAAAATCGAC GCTCAAGTCA GAGGTGGCGA AACCCGACAG GACTATAAAG ATACCAGGCG
3301    TTTCCCCCTG GAAGCTCCCT CGTGCGCTCT CCTGTTCCGA CCCTGCCGCT TACCGGATAC
3361    CTGTCCGCCT TTCTCCCTTC GGGAAGCGTG GCGCTTTCTC ATAGCTCACG CTGTAGGTAT
3421    CTCAGTTCGG TGTAGGTCGT TCGCTCCAAG CTGGGCTGTG TGCACGAACC CCCCGTTCAG
3481    CCCGACCGCT GCGCCTTATC CGGTAACTAT CGTCTTGAGT CCAACCCGGT AAGACACGAC
3541    TTATCGCCAC TGGCAGCAGC CACTGGTAAC AGGATTAGCA GAGCGAGGTA TGTAGGCGGT
3601    GCTACAGAGT TCTTGAAGTG GTGGCCTAAC TACGGCTACA CTAGAAGGAC AGTATTTGGT
3661    ATCTGCGCTC TGCTGAAGCC AGTTACCTTC GGAAAAAGAG TTGGTAGCTC TTGATCCGGC
3721    AAACAAACCA CCGCTGGTAG CGGTGGTTTT TTTGTTTGCA AGCAGCAGAT TACGCGCAGA
3781    AAAAAAGGAT CTCAAGAAGA TCCTTTGATC TTTTCTACGG GGTCTGACGC TCAGTGGAAC
3841    GAAAACTCAC GTTAAGGGAT TTTGGTCATG AGATTATCAA AAAGGATCTT CACCTAGATC
3901    CTTTTAAATT AAAAATGAAG TTTTAAATCA ATCTAAAGTA TATATGAGTA AACTTGGTCT
3961    GACAGTTACC AATGCTTAAT CAGTGAGGCA CCTATCTCAG CGATCTGTCT ATTTCGTTCA
4021    TCCATAGTTG CCTGACTCCC CGTCGTGTAG ATAACTACGA TACGGGAGGG CTTACCATCT
4081    GGCCCCAGTG CTGCAATGAT ACCGCGAGAC CCACGCTCAC CGGCTCCAGA TTTATCAGCA
```

Figure 7C

```
4141  ATAAACCAGC CAGCCGGAAG GGCCGAGCGC AGAAGTGGTC CTGCAACTTT ATCCGCCTCC
4201  ATCCAGTCTA TTAATTGTTG CCGGGAAGCT AGAGTAAGTA GTTCGCCAGT TAATAGTTTG
4261  CGCAACGTTG TTGCCATTGC TACAGGCATC GTGGTGTCAC GCTCGTCGTT TGGTATGGCT
4321  TCATTCAGCT CCGGTTCCCA ACGATCAAGG CGAGTTACAT GATCCCCCAT GTTGTGCAAA
4381  AAAGCGGTTA GCTCCTTCGG TCCTCCGATC GTTGTCAGAA GTAAGTTGGC CGCAGTGTTA
4441  TCACTCATGG TTATGGCAGC ACTGCATAAT TCTCTTACTG TCATGCCATC CGTAAGATGC
4501  TTTTCTGTGA CTGGTGAGTA CTCAACCAAG TCATTCTGAG AATAGTGTAT GCGGCGACCG
4561  AGTTGCTCTT GCCCGGCGTC AACACGGGAT AATACCGCGC CACATAGCAG AACTTTAAAA
4621  GTGCTCATCA TTGGAAAACG TTCTTCGGGG CGAAAACTCT CAAGGATCTT ACCGCTGTTG
4681  AGATCCAGTT CGATGTAACC CACTCGTGCA CCCAACTGAT CTTCAGCATC TTTTACTTTC
4741  ACCAGCGTTT CTGGGTGAGC AAAAACAGGA AGGCAAAATG CCGCAAAAAA GGGAATAAGG
4801  GCGACACGGA AATGTTGAAT ACTCATACTC TTCCTTTTTC AATATTATTG AAGCATTTAT
4861  CAGGGTTATT GTCTCATGAG CGGATACATA TTTGAATGTA TTTAGAAAAA TAAACAAATA
4921  GGGGTTCCGC GCACATTTCC CCGAAAAGTG CCACCTGACG TCTAAGAGAC CATTATTATC
4981  ATGACATTAA CCTATAAAAA TAGGCGTATC ACGAGGCCCT TTCGTCTTCA AGAATTGTCT
5041  AGAGGCGCGC CGTTTAAACC CTCAGCTACC GATGTACGGG CCAGATATAC GCGTTGACAT
5101  TGATTATTGA CTAGTTATTA ATAGTAATCA ATTACGGGGT CATTAGTTCA TAGCCCATAT
5161  ATGGAGTTCC GCGTTACATA ACTTACGGTA AATGGCCCGC CTGGCTGACC GCCCAACGAC
5221  CCCCGCCCAT TGACGTCAAT AATGACGTAT GTTCCCATAG TAACGCCAAT AGGGACTTTC
5281  CATTGACGTC AATGGGTGGA CTATTTACGG TAAACTGCCC ACTTGGCAGT ACATCAAGTG
5341  TATCATATGC CAAGTACGCC CCCTATTGAC GTCAATGACG GTAAATGGCC CGCCTGGCAT
5401  TATGCCCAGT ACATGACCTT ATGGGACTTT CCTACTTGGC AGTACATCTA CGTATTAGTC
5461  ATCGCTATTA CCATGGTGAT GCGGTTTTGG CAGTACATCA ATGGGCGTGG ATAGCGGTTT
5521  GACTCACGGG GATTTCCAAG TCTCCACCCC ATTGACGTCA ATGGGAGTTT GTTTTGGCAC
5581  CAAAATCAAC GGGACTTTCC AAAATGTCGT AACAACTCCG CCCCATTGAC GCAAATGGGC
5641  GGTAGGCGTG TACGGTGGGA GGTCTATATA AGCAGAGCTC TCTGGCTAAC TAGAGAACCC
5701  ACTGCTTACT GGCTTATCGA AATTAATACG ACTCACTATA GCAATTGCAC GTGTGGCCAC
5761  AGGTAAGTTT AAAGCTCAGG TCGAGACCGG GCCTTTGTCC GGCGCTCCCT TGGAGCCTAC
5821  CTAGACTCAG CCGGCTCTCC ACGCTTTGCC TGACCCTGCT TGCTCAACTC TACGTCTTTG
5881  TTTCGTTTTC TGTTCCTTTC TCTCCACAGG CTTAAGCTCG AGGCCGCCAC CATGGCTGTG
5941  CTGGGGCTGC TGTTCTGCCT GGTGACATTC CCAAGCTGTG TGCTGTCCCA GGTGCAGCTG
6001  GTGCAGTCTG GCGCTGAGGT GAAGAAGCCT GGCGCCTCCG TGAAGGTCTC CTGCAAGGCT
6061  TCTGGCTACA CATTCACCAA CTACGCTATG AACTGGGTGC GGCAGGCCCC TGGCCAGGGG
6121  CTGGAGTGGA TGGGCTGGAT CAACACTTAC ACCGGTGAGC AACCTACAG CGACGACTTC
6181  AAGGGCAGAG TCACCTTCAC CCTGGACACA TCCACCAGCA CAGCCTACAT GGAGCTGAGG
6241  AGCCTGAGAT CTGACGACAC CGCCGTGTAT TACTGTGCCA GAGGTGGAGG CTACGATGAG
6301  GACTACTTCG ACTACTGGGG CCAGGGCACC CTGGTCACCG TCTCCAGCGC TAGCACCAAG
6361  GGCCCATCGG TCTTCCCCCT GGCACCCTCC TCCAAGAGCA CCTCTGGGGG CACAGCGGCC
6421  CTGGGCTGCC TGGTCAAGGA CTACTTCCCC GAACCGGTGA CGGTGTCGTG GAACTCAGGC
6481  GCCCTGACCA GCGGCGTGCA CACCTTCCCG GCTGTCCTAC AGTCCTCAGG ACTCTACTCC
6541  CTCAGCAGCG TGGTGACCGT GCCCTCCAGC AGCTTGGGCA CCCAGACCTA CATCTGCAAC
6601  GTGAATCACA AGCCCAGCAA CACCAAGGTG GACAAGAAAG TTGAGCCCAA ATCTTGTGAC
6661  AAAACTCACA CATGCCCACC GTGCCCAGCA CCTGAACTCC TGGGGGGACC GTCAGTCTTC
6721  CTCTTCCCCC CAAAACCCAA GGACACCCTC ATGATCTCCC GGACCCCTGA GGTCACATGC
6781  GTGGTGGTGG ACGTGAGCCA CGAAGACCCT GAGGTCAAGT TCAACTGGTA CGTGGACGGC
6841  GTGGAGGTGC ATAATGCCAA GACAAAGCCG CGGGAGGAGC AGTACAACAG CACGTACCGT
6901  GTGGTCAGCG TCCTCACCGT CCTGCACCAG GACTGGCTGA ATGGCAAGGA GTACAAGTGC
6961  AAGGTCTCCA ACAAAGCCCT CCCAGCCCCC ATCGAGAAAA CCATCTCCAA AGCCAAAGGG
7021  CAGCCCCGAG AACCACAGGT GTACACCCTG CCCCCATCCC GGGATGAGCT GACCAAGAAC
7081  CAGGTCAGCC TGACCTGCCT GGTCAAAGGC TTCTATCCCA GCGACATCGC CGTGGAGTGG
```

Figure 7D

```
 7141    GAGAGCAATG GGCAGCCGGA GAACAACTAC AAGACCACGC CTCCCGTGCT GGACTCCGAC
 7201    GGCTCCTTCT TCCTCTACAG CAAGCTCACC GTGGACAAGA GCAGGTGGCA GCAGGGGAAC
 7261    GTCTTCTCAT GCTCCGTGAT GCATGAGGCT CTGCACAACC ACTACACGCA GAAGAGCCTC
 7321    TCCCTGTCTC CGGGTAAATA AATCGATGAT TCTAGATACG GGTCCGGAGG ATCCAGATCC
 7381    CCCTCGCTTT CTTGCTGTCC AATTTCTATT AAAGGTTCCT TTGTTCCCTA AGTCCAACTA
 7441    CTAAACTGGG GGATATTATG AAGGGCTTG AGCATCTGGA TTCTGCCTAA TAAAAAACAT
 7501    TTATTTTCAT TGCAATGATG TATTTAAATT ATTTCTGAAT ATTTTACTAA AAAGGGAATG
 7561    TGGGAGGTCA GTGCATTTAA AACATAAAGA AATGAAGAGG GGGATCTGTC GACAAGCTCT
 7621    AGAGAGCTCA CGCGTTGATC ATGTACAGGC CGGCCAAGCT TTCGACTAGC TTGGCACGCC
 7681    AGAAATCCGC GCGGTGGTTT TTGGGGGTCG GGGGTGTTTG GCAGCCACAG ACGCCCGGTG
 7741    TTCGTGTCGC GCCAGTACAT GCGGTCCATG CCCAGGCCAT CCAAAAACCA TGGGTCTGTC
 7801    TGCTCAGTCC AGTCGTGGAC CTGACCCCAC GCAACGCCCA AATAATAAC CCCCACGAAC
 7861    CATAAACCAT TCCCCATGGG GGACCCCGTC CCTAACCCAC GGGGCCAGTG GCTATGGCAG
 7921    GGCCTGCCGC CCCGACGTTG GCTGCGAGCC CTGGGCCTTC ACCCGAACTT GGGGGGTGGG
 7981    GTGGGGAAAA GGAAGAAACG CGGGCGTATT GGCCCCAATG GGGTCTCGGT GGGGTATCGA
 8041    CAGAGTGCCA GCCCTGGGAC CGAACCCCGC GTTTATGAAC AAACGACCCA ACACCCGTGC
 8101    GTTTTATTCT GTCTTTTTAT TGCCGTCATA GCGCGGGTTC CTTCCGGTAT TGTCTCCTTC
 8161    CGTGTTTCAG TTAGCCTCCC CCATCTCCCG ATCCGGACGA GTGCTGGGGC GTCGGTTTCC
 8221    ACTATCGGCG AGTACTTCTA CACAGCCATC GGTCCAGACG GCCGCGCTTC TGCGGGCGAT
 8281    TTGTGTACGC CCGACAGTCC CGGCTCCGGA TCGGACGATT GCGTCGCATC GACCCTGCGC
 8341    CCAAGCTGCA TCATCGAAAT TGCCGTCAAC CAAGCTCTGA TAGAGTTGGT CAAGACCAAT
 8401    GCGGAGCATA TACGCCCGGA GCCGCGGCGA TCCTGCAAGC TCCGGATGCC TCCGCTCGAA
 8461    GTAGCGCGTC TGCTGCTCCA TACAAGCCAA CCACGGCCTC CAGAAGAAGA TGTTGGCGAC
 8521    CTCGTATTGG GAATCCCCGA ACATCGCCTC GCTCCAGTCA ATGACCGCTG TTATGCGGCC
 8581    ATTGTCCGTC AGGACATTGT TGGAGCCGAA ATCCGCGTGC ACGAGGTGCC GGACTTCGGG
 8641    GCAGTCCTCG GCCCAAAGCA TCAGCTCATC GAGAGCCTGC GCGACGGACG CACTGACGGT
 8701    GTCGTCCATC ACAGTTTGCC AGTGATACAC ATGGGGATCA GCAATCGCGC ATATGAAATC
 8761    ACGCCATGTA GTGTATTGAC CGATTCCTTG CGGTCCGAAT GGGCCGAACC CGCTCGTCTG
 8821    GCTAAGATCG GCCGCAGCGA TCGCATCCAT GGCCTCCGCG ACCGGCTGCA GAACAGCGGG
 8881    CAGTTCGGTT TCAGGCAGGT CTTGCAACGT GACACCCTGT GCACGGCGGG AGATGCAATA
 8941    GGTCAGGCTC TCGCTGAATT CCCCAATGTC AAGCACTTCC GGAATCGGGA GCGCGGCCGA
 9001    TGCAAAGTGC CGATAAACAT AACGATCTTT GTAGAAACCA TCGGCGCAGC TATTTACCCG
 9061    CAGGACATAT CCACGCCCTC CTACATCGAA GCTGAAAGCA CGAGATTCTT CGCCCTCCGA
 9121    GAGCTGCATC AGGTCGGAGA CGCTGTCGAA CTTTTCGATC AGAAACTTCT CGACAGACGT
 9181    CGCGGTGAGT TCAGGCTTTT TCATATCTCA TTGCCCCCCG GATCTGCGG CACGCTGTTG
 9241    ACGCTGTTAA GCGGGTCGCT GCAGGGTCGC TCGGTGTTCG AGGCCACACG CGTCACCTTA
 9301    ATATGCGAAG TGGACCTCGG ACCGCCGC CCCGACTGCA TCTGCGTGTT CGAATTCGCC
 9361    AATGACAAGA CGCTGGGCGG GGTTTGTGTC ATCATAGAAC TAAAGACATG CAAATATATT
 9421    TCTTCCGGGG ACACCGCCAG CAAACGCGAG CAACGGGCCA CGGGGATGAA GCAGGGCGGC
 9481    ACCTCGCTAA CGGATTCACC ACTCCAAGAA TTGGAGCCAA TCAATTCTTG CGGAGAACTG
 9541    TGAATGCGCA AACCAACCCT TGGCAGAACA TATCCATCGC GTCCGCCATC TCCAGCAGCC
 9601    GCACGCGGCG CATCTCGGGG CCGACGCGCT GGGCTACGTC TTGCTGGCGT TCGCACAGGC
 9661    CGGCCAGCGC GCGGCCGGCC GGTACCACGC GTTGGCCACA TATGGCGGCC GCTCGCGATT
 9721    AATTAATCGC GATGGCCACA TATGAGCTC TCTAGAGCTT GTCGACAGAT CCCCCTCTTC
 9781    ATTTCTTTAT GTTTTAAATG CACTGACCTC CCACATTCCC TTTTTAGTAA AATATTCAGA
 9841    AATAATTTAA ATACATCATT GCAATGAAAA TAAATGTTTT TTATTAGGCA GAATCAGAT
 9901    GCTCAAGGCC CTTCATAATA TCCCCCAGTT TAGTAGTTGG ACTTAGGGAA CAAAGGAACC
 9961    TTTAATAGAA ATTGGACAGC AAGAAAGCGA GGGGATCTG GATCCTTTAA CACTCTCCCC
10021    TGTTGAAGCT CTTTGTGACG GGCGAGCTCA GGCCCTGATG GGTGACTTCG CAGGCGTAGA
10081    CTTTGTGTTT CTCGTAGTCT GCTTTGCTCA GCGTCAGGGT GCTGCTGAGG CTGTAGGTGC
```

Figure 7E

```
10141      TGTCCTTGCT GTCCTGCTCT GTGACACTCT CCTGGGAGTT ACCCGATTGG AGGGCGTTAT
10201      CCACCTTCCA CTGTACTTTG GCCTCTCTGG GATAGAAGTT ATTCAGCAGG CACACAACAG
10261      AGGCAGTTCC AGATTTCAAC TGCTCATCAG ATGGCGGGAA GATGAAGACA GATGGTGCAG
10321      CCACCGTACG TTTGATTTCC ACCTTGGTCC CCTGTCCAAA GGTCCATGGT GTGTCATAGT
10381      GCTGCTGACA GTAGTACACG CCCACATCTT CGGCCTCCAC CCGGCTGATC TTCAGAGTGA
10441      AATCTGTCCC AGATCCGCTG CCGCTGAACC TGTCTGGCAC CCCGCTCTCG CGAGTGCTGG
10501      CGAAATAGAT CAGCAGCTGA GGGCTCTGCC CTGGTTTCTG CAGATACCAG GCCAGGTAGG
10561      TCTTCTGGTT GATGGTGTTG AACAGGCTCT GGCTGCTCTT GCAGCTGATG CTGGCTGGCT
10621      CTCCGGGTGT CACAGGCAGG GACAGTGGAG ACTGGGTCAT CACGATATCA CATCTCATGG
10681      CTGGCAGGAA CAGCACCAGC AGCCCCAGCA GCTGCACTGG AGCCATGGTG GCGGCCTCGA
10741      GAAGCTTAAG TTTAATTCTT AAGCCTGTGG AGAGAAAGGA ACAGAAAACG AAACAAAGAC
10801      GTAGAGTTGA GCAAGCAGGG TCAGGCAAAG CGTGGAGAGC CGGCTGAGTC TAGGTAGGCT
10861      CCAAGGGAGC GCCGGACAAA GGCCCGGTCT CGACCTGAGC TTTAAACTTA CCTGTGGCCA
10921      CACGTGCAAT TGCTATAGTG AGTCGTATTA ATTTCGATAA GCCAGTAAGC AGTGGGTTCT
10981      CTAGTTAGCC AGAGAGCTCT GCTTATATAG ACCTCCCACC GTACACGCCT ACCGCCCATT
11041      TGCGTCAATG GGGCGGAGTT GTTACGACAT TTTGGAAAGT CCCGTTGATT TTGGTGCCAA
11101      AACAAACTCC CATTGACGTC AATGGGGTGG AGACTTGGAA ATCCCCGTGA GTCAAACCGC
11161      TATCCACGCC CATTGATGTA CTGCCAAAAC CGCATCACCA TGGTAATAGC GATGACTAAT
11221      ACGTAGATGT ACTGCCAAGT AGGAAAGTCC CATAAGGTCA TGTACTGGGC ATAATGCCAG
11281      GCGGGCCATT TACCGTCATT GACGTCAATA GGGGGCGTAC TTGGCATATG ATACACTTGA
11341      TGTACTGCCA AGTGGGCAGT TTACCGTAAA TAGTCCACCC ATTGACGTCA ATGGAAAGTC
11401      CCTATTGGCG TTACTATGGG AACATACGTC ATTATTGACG TCAATGGGCG GGGTCGTTG
11461      GGCGGTCAGC CAGGCGGGCC ATTTACCGTA AGTTATGTAA CGCGGAACTC CATATATGGG
11521      CTATGAACTA ATGACCCCGT AATTGATTAC TATTAATAAC TAGTCAATAA TCAATGTCAA
11581      CGCGTATATC TGGCCCGTAC ATCGGTAACT AGTCGGACCG GCCCGGGCCA CCGGTGCTCG
11641      AAGCTTGGAT CGATCCAGAC ATGATAAGAT ACATTGATGA GTTTGGACAA ACCACAACTA
11701      GAATGCAGTG AAAAAAATGC TTTATTTGTG AAATTTGTGA TGCTATTGCT TTATTTGTAA
11761      CCATTATAAG CTGCAATAAA CAAGTTAACA ACAACAATTG CATTCATTTT ATGTTTCAGG
11821      TTCAGGGGGA GGTGTGGGAG GTTTTTTAAA GCAAGTAAAA CCTCTACAAA TGTGGTATGG
11881      CTGATTATGA TCTCTAGTCA A
```

Figure 8A

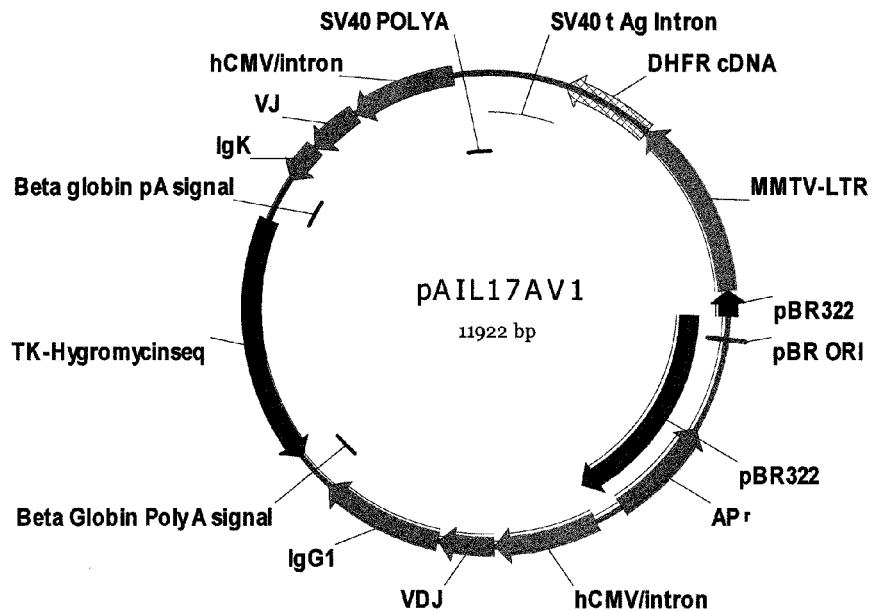

```
   1    GCACTATACA TCAAATATTC CTTATTAACC CCTTTACAAA TTAAAAAGCT AAAGGTACAC
  61    AATTTTTGAG CATAGTTATT AATAGCAGAC ACTCTATGCC TGTGTGGAGT AAGAAAAAAC
 121    AGTATGTTAT GATTATAACT GTTATGCCTA CTTATAAAGG TTACAGAATA TTTTTCCATA
 181    ATTTTCTTGT ATAGCAGTGC AGCTTTTTCC TTTGTGGTGT AAATAGCAAA GCAAGCAAGA
 241    GTTCTATTAC TAAACACAGC ATGACTCAAA AAACTTAGCA ATTCTGAAGG AAAGTCCTTG
 301    GGGTCTTCTA CCTTTCTCTT CTTTTTTGGA GGAGTAGAAT GTTGAGAGTC AGCAGTAGCC
 361    TCATCATCAC TAGATGGCAT TTCTTCTGAG CAAAACAGGT TTTCCTCATT AAAGGCATTC
 421    CACCACTGCT CCCATTCATC AGTTCCATAG GTTGGAATCT AAAATACACA AACAATTAGA
 481    ATCAGTAGTT TAACACATTA TACACTTAAA AATTTTATAT TTACCTTAGA GCTTTAAATC
 541    TCTGTAGGTA GTTTGTCCAA TTATGTCACA CCACAGAAGT AAGGTTCCTT CACAAAGATC
 601    GATCTAAAGC CAGCAAAAGT CCCATGGTCT TATAAAAATG CATAGCTTTA GGAGGGGAGC
 661    AGAGAACTTG AAAGCATCTT CCTGTTAGTC TTTCTTCTCG TAGACTTCAA ACTTATACTT
 721    GATGCCTTTT TCCTCCTGGA CCTCAGAGAG GACGCCTGGG TATTCTGGGA GAAGTTTATA
 781    TTTCCCCAAA TCAATTTCTG GGAAAAACGT GTCACTTTCA AATTCCTGCA TGATCCTTGT
 841    CACAAAGAGT CTGAGGTGGC CTGGTTGATT CATGGCTTCC TGGTAAACAG AACTGCCTCC
 901    GACTATCCAA ACCATGTCTA CTTTACTTGC CAATTCCGGT TGTTCAATAA GTCTTAAGGC
 961    ATCATCCAAA CTTTTGGCAA GAAAATGAGC TCCTCGTGGT GGTCTTTGA GTTCTCTACT
1021    GAGAACTATA TTAATTCTGT CCTTTAAAGG TCGATTCTTC TCAGGAATGG AGAACCAGGT
```

Figure 8B

```
1081    TTTCCTACCC ATAATCACCA GATTCTGTTT ACCTTCCACT GAAGAGGTTG TGGTCATTCT
1141    TTGGAAGTAC TTGAACTCGT TCCTGAGCGG AGGCCAGGGT AGGTCTCCGT TCTTGCCAAT
1201    CCCCATATTT TGGGACACGG CGACGATGCA GTTCAATGGT CGAACCATGA TGGCAGCGGG
1261    GATAAAATCC TACCAGCCTT CACGCTAGGA TTGCCGTCAA GTTTGGCGCG AAATCGCAGC
1321    CCTGAGCTGT CCCCCCCCCC AAGCTCAGAT CTGAGCTTGG TCCCTATGGT GAGTCCGTTC
1381    CGCTCTTGTG ATGATAGCCA GACAAGAAAG AGACAATACA AGACAAACAC CAAATAGTAG
1441    AAATAGAGAC AAGGGTCACT TATCCGAGGG TCCCTGTTCG GGCGCCAGCT GCCGCAGTCG
1501    GCCGACCTGA GGGTCGCCGG GGTCTGCGGG GGGACCCTCT GGAAAGTGAA GGATAAGTGA
1561    CGAGCGGAGA CGGGATGGCG AACAGACACA AACACACAAG AGGTGAATGT TAGGACTGTT
1621    GCAAGTTTAC TCAAAAAATC AGCACTCTTT TATATCTTGG TTTACATAAG CATTTACATA
1681    AGATTTGGAT AAATTCCAAA AGAACATAGG AAAATAGAAC ACTCAGAGCT CAGATCAGAA
1741    CCTTTGATAC CAAACCAAGT CAGGAAACCA CTTGTCTCAC ATCCTCGTTT TAAGAACAGT
1801    TTGTAACCAA AAACTTACTT AAGCCCTGGG AACCGCAAGG TTGGGCCAAT AAAGGCTATT
1861    CATAATAACT CATGCCATGA GTTTTTGCAG AATAATGTTC TATTAGTCCA GCCACTGTCC
1921    CCTCCTTGGT ATGGAAAATC TTTCCCCAAA AGTGCATTCC TGTTCCTAGA TAAATATAAT
1981    CATGTACCTG TTGTTTCATG TCGTCTTTTT CTTCTTGAGA CAACATACAC CAAGGAGGTC
2041    TAGCTCTGGC GAGTCTTTCA CGAAAAGGGA GGGATCTATA TAACACTTTA TAGCCATTGA
2101    CTGTAACCCA CCTATCCCAA TTTAAGTCAT ATCTTCCTGT ATATGGTAAG GGGGCATCTG
2161    TTGGTCTGTA GATGTAAGGT CCCCTATAAG TCCCTGGTTG CCACCACCTG TCTCCTATTT
2221    TGACAAAAAC ACTCTTTTTT CCCTTTTTTA CTTCTAGGCC TGTGGTCAAT AGTCCTTGCA
2281    CCTGTTCTTC AATTGAGGTT GAGCGTCTCT TTCTATTTTC TATTCCCATT TCTAACTTCT
2341    GAATTTGAGT AAAAATAGTA CTAAAGATA ATGATTCATT TCTTAACATA GTAACTAATA
2401    ATCTACCTAT TGGATTGGTC TTATTGGTAA AAATATAATT TTTAGCAAGC ATTCTTATTT
2461    CTATTTCTGA AGGACAAAAT CGATGCGGCT TGTAAGAGGA AGTTGGCTGT GGTCCTTGCC
2521    TCAGGAGGAA GGTCGAGTTC TCCGAATTGT TTAGATTGTA ATCTTGCACA GAAGAGCTAT
2581    TAAAAGAGTC AAGGGTGAGA GCCCTGCGAG CACGAACCGC AACTTCCCCC AATAGCCCCA
2641    GGCAAAGCAG AGCTATGCCA AGTTTGCAGC AGAGAATGAA TATGTCTTTG TCTGATGGGC
2701    TCATCCGTTT GTGCGCAGAC GGGTCGTCCT TGGTGGGAAA CAACCCCTTG GCTGCTTCTC
2761    CCCTAGGTGT AGGACACTCT CGGGAGTTCA ACCATTTCTG CCCAAGCTCA GATCTGAGCT
2821    TTAATGCGGT AGTTTATCAC AGTTAAATTG CTAACGCAGT CAGGCACCGT GTATGAAATC
2881    TAACAATGCG CTCATCGTCA TCCTCGGCAC CGTCACCCTG GATGCTGTAG GCATAGGCTT
2941    GGTTATGCCG GTACTGCCGG GCCTCTTGCG GGATATCGTC CATTCCGACA GCATCGCCAG
3001    TCACTATGGC GTGCTGCTAG CGCTCTTCCG CTTCCTCGCT CACTGACTCG CTGCGCTCGG
3061    TCGTTCGGCT GCGGCGAGCG GTATCAGCTC ACTCAAAGGC GGTAATACGG TTATCCACAG
3121    AATCAGGGGA TAACGCAGGA AGAACATGT GAGCAAAAGG CCAGCAAAAG GCCAGGAACC
3181    GTAAAAAGGC CGCGTTGCTG GCGTTTTTCC ATAGGCTCCG CCCCCCTGAC GAGCATCACA
3241    AAAATCGACG CTCAAGTCAG AGGTGGCGAA ACCCGACAGG ACTATAAAGA TACCAGGCGT
3301    TTCCCCCTGG AAGCTCCCTC GTGCGCTCTC CTGTTCCGAC CCTGCCGCTT ACCGGATACC
3361    TGTCCGCCTT TCTCCCTTCG GGAAGCGTGG CGCTTTCTCA TAGCTCACGC TGTAGGTATC
3421    TCAGTTCGGT GTAGGTCGTT CGCTCCAAGC TGGGCTGTGT GCACGAACCC CCCGTTCAGC
3481    CCGACCGCTG CGCCTTATCC GGTAACTATC GTCTTGAGTC AACCCGGTA AGACACGACT
3541    TATCGCCACT GGCAGCAGCC ACTGGTAACA GGATTAGCAG AGCGAGGTAT GTAGGCGGTG
3601    CTACAGAGTT CTTGAAGTGG TGGCCTAACT ACGGCTACAC TAGAAGGACA GTATTTGGTA
3661    TCTGCGCTCT GCTGAAGCCA GTTACCTTCG GAAAAGAGT TGGTAGCTCT TGATCCGGCA
3721    AACAAACCAC CGCTGGTAGC GGTGGTTTTT TTGTTTGCAA GCAGCAGATT ACGCGCAGAA
3781    AAAAAGGATC TCAAGAAGAT CCTTTGATCT TTTCTACGGG GTCTGACGCT CAGTGGAACG
3841    AAAACTCACG TTAAGGGATT TTGGTCATGA GATTATCAAA AAGGATCTTC ACCTAGATCC
3901    TTTTAAATTA AAAATGAAGT TTAAATCAA TCTAAAGTAT ATATGAGTAA ACTTGGTCTG
3961    ACAGTTACCA ATGCTTAATC AGTGAGGCAC CTATCTCAGC GATCTGTCTA TTTCGTTCAT
4021    CCATAGTTGC CTGACTCCCC GTCGTGTAGA TAACTACGAT ACGGGAGGGC TTACCATCTG
```

Figure 8C

```
4081   GCCCCAGTGC TGCAATGATA CCGCGAGACC CACGCTCACC GGCTCCAGAT TTATCAGCAA
4141   TAAACCAGCC AGCCGGAAGG GCCGAGCGCA GAAGTGGTCC TGCAACTTTA TCCGCCTCCA
4201   TCCAGTCTAT TAATTGTTGC CGGGAAGCTA GAGTAAGTAG TTCGCCAGTT AATAGTTTGC
4261   GCAACGTTGT TGCCATTGCT ACAGGCATCG TGGTGTCACG CTCGTCGTTT GGTATGGCTT
4321   CATTCAGCTC CGGTTCCCAA CGATCAAGGC GAGTTACATG ATCCCCCATG TTGTGCAAAA
4381   AAGCGGTTAG CTCCTTCGGT CCTCCGATCG TTGTCAGAAG TAAGTTGGCC GCAGTGTTAT
4441   CACTCATGGT TATGGCAGCA CTGCATAATT CTCTTACTGT CATGCCATCC GTAAGATGCT
4501   TTTCTGTGAC TGGTGAGTAC TCAACCAAGT CATTCTGAGA ATAGTGTATG CGGCGACCGA
4561   GTTGCTCTTG CCCGGCGTCA ACACGGGATA ATACCGCGCC ACATAGCAGA ACTTTAAAAG
4621   TGCTCATCAT TGGAAAACGT TCTTCGGGGC GAAAACTCTC AAGGATCTTA CCGCTGTTGA
4681   GATCCAGTTC GATGTAACCC ACTCGTGCAC CCAACTGATC TTCAGCATCT TTTACTTTCA
4741   CCAGCGTTTC TGGGTGAGCA AAAACAGGAA GGCAAAATGC CGCAAAAAAG GGAATAAGGG
4801   CGACACGGAA ATGTTGAATA CTCATACTCT TCCTTTTTCA ATATTATTGA AGCATTTATC
4861   AGGGTTATTG TCTCATGAGC GGATACATAT TTGAATGTAT TTAGAAAAAT AAACAAATAG
4921   GGGTTCCGCG CACATTTCCC CGAAAAGTGC CACCTGACGT CTAAGAGACC ATTATTATCA
4981   TGACATTAAC CTATAAAAAT AGGCGTATCA CGAGGCCCTT TCGTCTTCAA GAATTGTCTA
5041   GAGGCGCGCC GTTTAAACCC TCAGCTACCG ATGTACGGGC CAGATATACG CGTTGACATT
5101   GATTATTGAC TAGTTATTAA TAGTAATCAA TTACGGGTC ATTAGTTCAT AGCCCATATA
5161   TGGAGTTCCG CGTTACATAA CTTACGGTAA ATGGCCCGCC TGGCTGACCG CCCAACGACC
5221   CCCGCCCATT GACGTCAATA ATGACGTATG TTCCCATAGT AACGCCAATA GGGACTTTCC
5281   ATTGACGTCA ATGGGTGGAC TATTTACGGT AAACTGCCCA CTTGGCAGTA CATCAAGTGT
5341   ATCATATGCC AAGTACGCCC CCTATTGACG TCAATGACGG TAAATGGCCC GCCTGGCATT
5401   ATGCCCAGTA CATGACCTTA TGGGACTTTC CTACTTGGCA GTACATCTAC GTATTAGTCA
5461   TCGCTATTAC CATGGTGATG CGGTTTTGGC AGTACATCAA TGGGCGTGGA TAGCGGTTTG
5521   ACTCACGGGG ATTTCCAAGT CTCCACCCCA TTGACGTCAA TGGGAGTTTG TTTTGGCACC
5581   AAAATCAACG GGACTTTCCA AAATGTCGTA ACAACTCCGC CCCATTGACG CAAATGGGCG
5641   GTAGGCGTGT ACGGTGGGAG GTCTATATAA GCAGAGCTCT CTGGCTAACT AGAGAACCCA
5701   CTGCTTACTG GCTTATCGAA ATTAATACGA CTCACTATAG CAATTGCACG TGTGGCCACA
5761   GGTAAGTTTA AAGCTCAGGT CGAGACCGGG CCTTTGTCCG GCGCTCCCTT GGAGCCTACC
5821   TAGACTCAGC CGGCTCTCCA CGCTTTGCCT GACCCTGCTT GCTCAACTCT ACGTCTTTGT
5881   TTCGTTTTCT GTTCCTTTCT CTCCACAGGC TTAAGAGTAC TGCCGCCACC ATGGCTGTGC
5941   TGGGGCTGCT GTTCTGCCTG GTGACATTCC CAAGCTGTGT GCTGTCCCAG GTGCAGCTGC
6001   AGGAGTCTGG ACCAGGCCTG GTGAAGCCTA GCGAGACCCT GAGCCTGACC TGTACCGTGT
6061   CTGGATTCAG CCTGCCCAGC CACAGCGTGA GCTGGATCAG ACAGCCTCCA GGCAAGGGAC
6121   TGGAGTGGAT CGGCATCATT TGGAATCAAG GCGGCACTGA CTATAACAGC GCCTTCAAGA
6181   GCCGCGTGAC CATCTCCGTG GACACCTCCA AGAACCAGTT CAGCCTGAAG CTGAGCAGCG
6241   TGACCGCTGC CGACACCGCT GTGTATTACT GTGCCAGAAA TGCATACATC ACCGACTACT
6301   ATTACGAGAA CTACTTCATG GATGCCTGGG ACAGGGCAC CCTGGTGACC GTGAGCTCCG
6361   CTAGCACCAA GGGCCCATCG GTCTTCCCCC TGGCACCCTC CTCCAAGAGC ACCTCTGGGG
6421   GCACAGCGGC CCTGGGCTGC CTGGTCAAGG ACTACTTCCC CGAACCGGTG ACGGTGTCGT
6481   GGAACTCAGG CGCCCTGACC AGCGGCGTGC ACACCTTCCC GGCTGTCCTA CAGTCCTCAG
6541   GACTCTACTC CCTCAGCAGC GTGGTGACCG TGCCCTCCAG CAGCTTGGGC ACCCAGACCT
6601   ACATCTGCAA CGTGAATCAC AAGCCCAGCA ACACCAAGGT GGACAAGAAA GTTGAGCCCA
6661   AATCTTGTGA CAAAACTCAC ACATGCCCAC CGTGCCCAGC ACCTGAACTC CTGGGGGGAC
6721   CGTCAGTCTT CCTCTTCCCC CCAAAACCCA AGGACACCCT CATGATCTCC CGGACCCCTG
6781   AGGTCACATG CGTGGTGGTG GACGTGAGCC ACGAAGACCC TGAGGTCAAG TTCAACTGGT
6841   ACGTGGACGG CGTGGAGGTG CATAATGCCA AGACAAAGCC GCGGGAGGAG CAGTACAACA
6901   GCACGTACCG TGTGGTCAGC GTCCTCACCG TCCTGCACCA GGACTGGCTG AATGGCAAGG
6961   AGTACAAGTG CAAGGTCTCC AACAAAGCCC TCCCAGCCCC CATCGAGAAA ACCATCTCCA
7021   AAGCCAAAGG GCAGCCCCGA GAACCACAGG TGTACACCCT GCCCCATCC CGGGATGAGC
```

Figure 8D

```
7081   TGACCAAGAA CCAGGTCAGC CTGACCTGCC TGGTCAAAGG CTTCTATCCC AGCGACATCG
7141   CCGTGGAGTG GGAGAGCAAT GGGCAGCCGG AGAACAACTA CAAGACCACG CCTCCCGTGC
7201   TGGACTCCGA CGGCTCCTTC TTCCTCTACA GCAAGCTCAC CGTGGACAAG AGCAGGTGGC
7261   AGCAGGGGAA CGTCTTCTCA TGCTCCGTGA TGCATGAGGC TCTGCACAAC CACTACACGC
7321   AGAAGAGCCT CTCCCTGTCT CCGGGTAAAT GAATCGATGA TTCTAGATAC GGGTCCGGAG
7381   GATCCAGATC CCCCTCGCTT TCTTGCTGTC CAATTTCTAT TAAAGGTTCC TTTGTTCCCT
7441   AAGTCCAACT ACTAAACTGG GGGATATTAT GAAGGGCCTT GAGCATCTGG ATTCTGCCTA
7501   ATAAAAAACA TTTATTTTCA TTGCAATGAT GTATTTAAAT TATTTCTGAA TATTTTACTA
7561   AAAAGGGAAT GTGGGAGGTC AGTGCATTTA AAACATAAAG AAATGAAGAG GGGGATCTGT
7621   CGACAAGCTC TAGAGAGCTC ACGCGTTGAT CATGTACAGG CCGGCCAAGC TTTCGACTAG
7681   CTTGGCACGC CAGAAATCCG CGCGGTGGTT TTTGGGGGTC GGGGGTGTTT GGCAGCCACA
7741   GACGCCCGGT GTTCGTGTCG CGCCAGTACA TGCGGTCCAT GCCCAGGCCA TCCAAAAACC
7801   ATGGGTCTGT CTGCTCAGTC CAGTCGTGGA CCTGACCCCA CGCAACGCCC AAAATAATAA
7861   CCCCCACGAA CCATAAACCA TTCCCCATGG GGGACCCCGT CCCTAACCCA CGGGGCCAGT
7921   GGCTATGGCA GGGCCTGCCG CCCCGACGTT GGCTGCGAGC CCTGGGCCTT CACCCGAACT
7981   TGGGGGGTGG GGTGGGGAAA AGGAAGAAAC GCGGGCGTAT TGGCCCCAAT GGGGTCTCGG
8041   TGGGGTATCG ACAGAGTGCC AGCCCTGGGA CCGAACCCCG CGTTTATGAA CAAACGACCC
8101   AACACCCGTG CGTTTTATTC TGTCTTTTTA TTGCCGTCAT AGCGCGGGTT CCTTCCGGTA
8161   TTGTCTCCTT CCGTGTTTCA GTTAGCCTCC CCCATCTCCC GATCCGGACG AGTGCTGGGG
8221   CGTCGGTTTC CACTATCGGC GAGTACTTCT ACACAGCCAT CGGTCCAGAC GGCCGCGCTT
8281   CTGCGGGCGA TTTGTGTACG CCCGACAGTC CCGGCTCCGG ATCGGACGAT TGCGTCGCAT
8341   CGACCCTGCG CCCAAGCTGC ATCATCGAAA TTGCCGTCAA CCAAGCTCTG ATAGAGTTGG
8401   TCAAGACCAA TGCGGAGCAT ATACGCCCGG AGCCGCGGCG ATCCTGCAAG CTCCGGATGC
8461   CTCCGCTCGA AGTAGCGCGT CTGCTGCTCC ATACAAGCCA ACCACGGCCT CCAGAAGAAG
8521   ATGTTGGCGA CCTCGTATTG GGAATCCCCG AACATCGCCT CGCTCCAGTC AATGACCGCT
8581   GTTATGCGGC CATTGTCCGT CAGGACATTG TTGGAGCCGA AATCCGCGTG CACGAGGTGC
8641   CGGACTTCGG GGCAGTCCTC GGCCCAAAGC ATCAGCTCAT CGAGAGCCTG CGCGACGGAC
8701   GCACTGACGG TGTCGTCCAT CACAGTTTGC CAGTGATACA CATGGGGATC AGCAATCGCG
8761   CATATGAAAT CACGCCATGT AGTGTATTGA CCGATTCCTT GCGGTCCGAA TGGGCCGAAC
8821   CCGCTCGTCT GGCTAAGATC GGCCGCAGCG ATCGCATCCA TGGCCTCCGC GACCGGCTGC
8881   AGAACAGCGG GCAGTTCGGT TTCAGGCAGG TCTTGCAACG TGACACCCTG TGCACGGCGG
8941   GAGATGCAAT AGGTCAGGCT CTCGCTGAAT TCCCCAATGT CAAGCACTTC CGGAATCGGG
9001   AGCGCGGCCG ATGCAAAGTG CCGATAAACA TAACGATCTT TGTAGAAACC ATCGGCGCAG
9061   CTATTTACCC GCAGGACATA TCCACGCCCT CCTACATCGA AGCTGAAAGC ACGAGATTCT
9121   TCGCCCTCCG AGAGCTGCAT CAGGTCGGAG ACGCTGTCGA ACTTTTCGAT CAGAAACTTC
9181   TCGACAGACG TCGCGGTGAG TTCAGGCTTT TCATATCTC ATTGCCCCCC GGGATCTGCG
9241   GCACGCTGTT GACGCTGTTA AGCGGGTCGC TGCAGGGTCG CTCGGTGTTC GAGGCCACAC
9301   GCGTCACCTT AATATGCGAA GTGGACCTCG GACCGCGCCG CCCCGACTGC ATCTGCGTGT
9361   TCGAATTCGC CAATGACAAG ACGCTGGGCG GGGTTTGTGT CATCATAGAA CTAAAGACAT
9421   GCAAATATAT TTCTTCCGGG ACACCGCCA GCAAACGCGA GCAACGGGCC ACGGGGATGA
9481   AGCAGGGCGG CACCTCGCTA ACGGATTCAC CACTCCAAGA ATTGGAGCCA ATCAATTCTT
9541   GCGGAGAACT GTGAATGCGC AAACCAACCC TTGGCAGAAC ATATCCATCG CGTCCGCCAT
9601   CTCCAGCAGC CGCACGCGGC GCATCTCGGG GCCGACGCGC TGGGCTACGT CTTGCTGGCG
9661   TTCGCACAGG CCGGCCAGCG CGCGGCCGGC CGGTACCACG CGTTGCCAC ATATGGCGGC
9721   CGCTCGCGAT TAATTAATCG CGATGGCCAC ATATGGAGCT CTCTAGAGCT TGTCGACAGA
9781   TCCCCCTCTT CATTTCTTTA TGTTTTAAAT GCACTGACCT CCCACATTCC CTTTTTAGTA
9841   AAATATTCGA AAATAATTTA AATACATCAT TGCAATGAAA ATAAATGTTT TTTATTAGGC
9901   AGAATCCAGA TGCTCAAGGC CCTTCATAAT ATCCCCCAGT TTAGTAGTTG GACTTAGGGA
9961   ACAAAGGAAC CTTTAATAGA AATTGGACAG CAAGAAAGCG AGGGGATCT GGATCCTCCG
10021  GAGGGCCCCT TCTCCCTCTA ACACTCTCCC CTGTTGAAGC TCTTTGTGAC GGGCGAGCTC
```

Figure 8E

```
10081    AGGCCCTGAT GGGTGACTTC GCAGGCGTAG ACTTTGTGTT TCTCGTAGTC TGCTTTGCTC
10141    AGCGTCAGGG TGCTGCTGAG GCTGTAGGTG CTGTCCTTGC TGTCCTGCTC TGTGACACTC
10201    TCCTGGGAGT TACCCGATTG GAGGGCGTTA TCCACCTTCC ACTGTACTTT GGCCTCTCTG
10261    GGATAGAAGT TATTCAGCAG GCACACAACA GAGGCAGTTC CAGATTTCAA CTGCTCATCA
10321    GATGGCGGGA AGATGAAGAC AGATGGTGCA GCCACCGTAC GTTTGATTTC CACCTTGGTC
10381    CCCTGTCCAA AGGTGTAGGG TGTGTAATAG CTCTGCTGAC AGTAGTACAC GCCCACATCT
10441    TCGGCCTCCA CCCGGCTGAT CTTCAGAGTG AAATCTGTCC CAGATCCGCT GCCGCTGAAC
10501    CTGTCTGGCA CCCCGCTCTG CCGGGTGCTG GTCCAATAGA TCAGCAGCTG AGGGCTCTGC
10561    CCTGGTTTCT GCAGATACCA GGCCAGGTAG TTCTTCTGGT TCTCGCTGAA CAGCAGGCTC
10621    TGGCTGCTCT TGCAGCTGAT GCTGGCTGGC TCTCCGGGTG TCACAGGCAG GGACAGTGGA
10681    GACTGGGTCA TCACGATATC ACATCTCATG GCTGGCAGGA ACAGCACCAG CAGCCCCAGC
10741    AGCTGCACTG GAGCCATGGT GGCGGCGCTA GCGAATTCTT AAGCCTGTGG AGAGAAAGGA
10801    ACAGAAAACG AAACAAAGAC GTAGAGTTGA GCAAGCAGGG TCAGGCAAAG CGTGGAGAGC
10861    CGGCTGAGTC TAGGTAGGCT CCAAGGGAGC GCCGGACAAA GGCCCGGTCT CGACCTGAGC
10921    TTTAAACTTA CCTGTGGCCA CACGTGCAAT TGCTATAGTG AGTCGTATTA ATTTCGATAA
10981    GCCAGTAAGC AGTGGGTTCT CTAGTTAGCC AGAGAGCTCT GCTTATATAG ACCTCCCACC
11041    GTACACGCCT ACCGCCCATT TGCGTCAATG GGGCGGAGTT GTTACGACAT TTTGGAAAGT
11101    CCCGTTGATT TTGGTGCCAA AACAAACTCC CATTGACGTC AATGGGGTGG AGACTTGGAA
11161    ATCCCCGTGA GTCAAACCGC TATCCACGCC CATTGATGTA CTGCCAAAAC CGCATCACCA
11221    TGGTAATAGC GATGACTAAT ACGTAGATGT ACTGCCAAGT AGGAAAGTCC CATAAGGTCA
11281    TGTACTGGGC ATAATGCCAG GCGGGCCATT TACCGTCATT GACGTCAATA GGGGGCGTAC
11341    TTGGCATATG ATACACTTGA TGTACTGCCA AGTGGGCAGT TTACCGTAAA TAGTCCACCC
11401    ATTGACGTCA ATGGAAAGTC CCTATTGGCG TTACTATGGG AACATACGTC ATTATTGACG
11461    TCAATGGGCG GGGGTCGTTG GGCGGTCAGC CAGGCGGGCC ATTTACCGTA AGTTATGTAA
11521    CGCGGAACTC CATATATGGG CTATGAACTA ATGACCCCGT AATTGATTAC TATTAATAAC
11581    TAGTCAATAA TCAATGTCAA CGCGTATATC TGGCCCGTAC ATCGGTAACT AGTCGGACCG
11641    GCCCGGGCCA CCGGTGCTCG AAGCTTGGAT CGATCCAGAC ATGATAAGAT ACATTGATGA
11701    GTTTGGACAA ACCACAACTA GAATGCAGTG AAAAAAATGC TTTATTTGTG AAATTTGTGA
11761    TGCTATTGCT TTATTTGTAA CCATTATAAG CTGCAATAAA CAAGTTAACA ACAACAATTG
11821    CATTCATTTT ATGTTTCAGG TTCAGGGGGA GGTGTGGGAG GTTTTTTAAA GCAAGTAAAA
11881    CCTCTACAAA TGTGGTATGG CTGATTATGA TCTCTAGTCA AG
```

Figure 9A

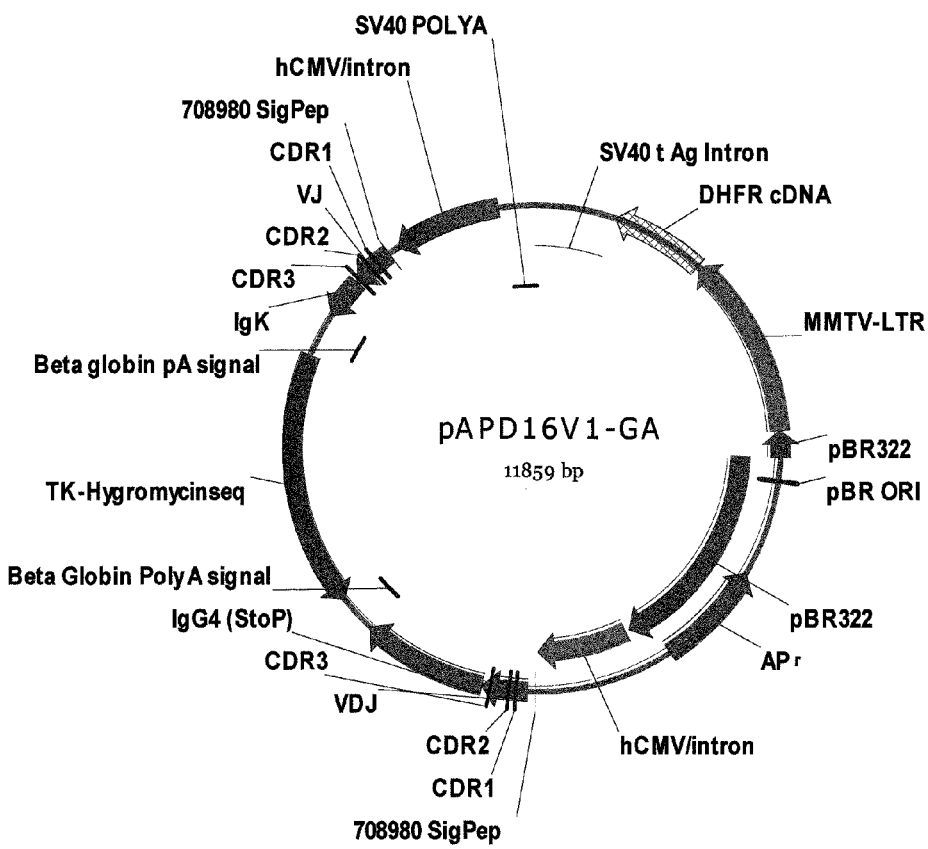

```
  1   GCACTATACA TCAAATATTC CTTATTAACC CCTTTACAAA TTAAAAAGCT AAAGGTACAC
 61   AATTTTTGAG CATAGTTATT AATAGCAGAC ACTCTATGCC TGTGTGGAGT AAGAAAAAAC
121   AGTATGTTAT GATTATAACT GTTATGCCTA CTTATAAAGG TTACAGAATA TTTTTCCATA
181   ATTTTCTTGT ATAGCAGTGC AGCTTTTTCC TTTGTGGTGT AAATAGCAAA GCAAGCAAGA
241   GTTCTATTAC TAAACACAGC ATGACTCAAA AAACTTAGCA ATTCTGAAGG AAAGTCCTTG
301   GGGTCTTCTA CCTTTCTCTT CTTTTTTGGA GGAGTAGAAT GTTGAGAGTC AGCAGTAGCC
361   TCATCATCAC TAGATGGCAT TTCTTCTGAG CAAAACAGGT TTTCCTCATT AAAGGCATTC
421   CACCACTGCT CCCATTCATC AGTTCCATAG GTTGGAATCT AAAATACACA AACAATTAGA
481   ATCAGTAGTT TAACACATTA TACACTTAAA AATTTTATAT TTACCTTAGA GCTTTAAATC
541   TCTGTAGGTA GTTTGTCCAA TTATGTCACA CCACAGAAGT AAGGTTCCTT CACAAAGATC
601   GATCTAAAGC CAGCAAAAGT CCCATGGTCT TATAAAAATG CATAGCTTTA GGAGGGGAGC
```

Figure 9B

```
 661   AGAGAACTTG AAAGCATCTT CCTGTTAGTC TTTCTTCTCG TAGACTTCAA ACTTATACTT
 721   GATGCCTTTT TCCTCCTGGA CCTCAGAGAG GACGCCTGGG TATTCTGGGA GAAGTTTATA
 781   TTTCCCCAAA TCAATTTCTG GGAAAAACGT GTCACTTTCA AATTCCTGCA TGATCCTTGT
 841   CACAAAGAGT CTGAGGTGGC CTGGTTGATT CATGGCTTCC TGGTAAACAG AACTGCCTCC
 901   GACTATCCAA ACCATGTCTA CTTTACTTGC CAATTCCGGT TGTTCAATAA GTCTTAAGGC
 961   ATCATCCAAA CTTTTGGCAA GAAAATGAGC TCCTCGTGGT GGTTCTTTGA GTTCTCTACT
1021   GAGAACTATA TTAATTCTGT CCTTTAAAGG TCGATTCTTC TCAGGAATGG AGAACCAGGT
1081   TTTCCTACCC ATAATCACCA GATTCTGTTT ACCTTCCACT GAAGAGGTTG TGGTCATTCT
1141   TTGGAAGTAC TTGAACTCGT TCCTGAGCGG AGGCCAGGGT AGGTCTCCGT TCTTGCCAAT
1201   CCCCATATTT TGGGACACGG CGACGATGCA GTTCAATGGT CGAACCATGA TGGCAGCGGG
1261   GATAAAATCC TACCAGCCTT CACGCTAGGA TTGCCGTCAA GTTTGGCGCG AAATCGCAGC
1321   CCTGAGCTGT CCCCCCCCCC AAGCTCAGAT CTGAGCTTGG TCCCTATGGT GAGTCCGTTC
1381   CGCTCTTGTG ATGATAGCCA GACAAGAAAG AGACAATACA AGACAAACAC CAAATAGTAG
1441   AAATAGAGAC AAGGGTCACT TATCCGAGGG TCCCTGTTCG GGCGCCAGCT GCCGCAGTCG
1501   GCCGACCTGA GGGTCGCCGG GGTCTGCGGG GGGACCCTCT GGAAAGTGAA GGATAAGTGA
1561   CGAGCGGAGA CGGGATGGCG AACAGACACA AACACACAAG AGGTGAATGT TAGGACTGTT
1621   GCAAGTTTAC TCAAAAAATC AGCACTCTTT TATATCTTGG TTTACATAAG CATTTACATA
1681   AGATTTGGAT AAATTCCAAA AGAACATAGG AAAATAGAAC ACTCAGAGCT CAGATCAGAA
1741   CCTTTGATAC CAAACCAAGT CAGGAAACCA CTTGTCTCAC ATCCTCGTTT TAAGAACAGT
1801   TTGTAACCAA AAACTTACTT AAGCCCTGGG AACCGCAAGG TTGGGCCAAT AAAGGCTATT
1861   CATAATAACT CATGCCATGA GTTTTTGCAG AATAATGTTC TATTAGTCCA GCCACTGTCC
1921   CCTCCTTGGT ATGGAAAATC TTTCCCCAAA AGTGCATTCC TGTTCCTAGA TAAATATAAT
1981   CATGTACCTG TTGTTTCATG TCGTCTTTTT CTTCTTGAGA CAACATACAC CAAGGAGGTC
2041   TAGCTCTGGC GAGTCTTTCA CGAAAAGGGA GGGATCTATA TAACACTTTA TAGCCATTGA
2101   CTGTAACCCA CCTATCCCAA TTTAAGTCAT ATCTTCCTGT ATATGGTAAG GGGGCATCTG
2161   TTGGTCTGTA GATGTAAGGT CCCCTATAAG TCCCTGGTTG CCACCACCTG TCTCCTATTT
2221   TGACAAAAAC ACTCTTTTTT CCCTTTTTTA CTTCTAGGCC TGTGGTCAAT AGTCCTTGCA
2281   CCTGTTCTTC AATTGAGGTT GAGCGTCTCT TTCTATTTTC TATTCCCATT TCTAACTTCT
2341   GAATTTGAGT AAAAATAGTA CTAAAGATA ATGATTCATT TCTTAACATA GTAACTAATA
2401   ATCTACCTAT TGGATTGGTC TTATTGGTAA AAATATAATT TTTAGCAAGC ATTCTTATTT
2461   CTATTTCTGA AGGACAAAAT CGATGCGGCT TGTAAGAGGA AGTTGGCTGT GGTCCTTGCC
2521   TCAGGAGGAA GGTCGAGTTC TCCGAATTGT TTAGATTGTA ATCTTGCACA GAAGAGCTAT
2581   TAAAAGAGTC AAGGGTGAGA GCCCTGCGAG CACGAACCGC AACTTCCCCC AATAGCCCCA
2641   GGCAAAGCAG AGCTATGCCA AGTTTGCAGC AGAGAATGAA TATGTCTTTG TCTGATGGGC
2701   TCATCCGTTT GTGCGCAGAC GGGTCGTCCT TGGTGGGAAA CAACCCCTTG GCTGCTTCTC
2761   CCCTAGGTGT AGGACACTCT CGGGAGTTCA ACCATTTCTG CCCAAGCTCA GATCTGAGCT
2821   TTAATGCGGT AGTTTATCAC AGTTAAATTG CTAACGCAGT CAGGCACCGT GTATGAAATC
2881   TAACAATGCG CTCATCGTCA TCCTCGGCAC CGTCACCCTG GATGCTGTAG GCATAGGCTT
2941   GGTTATGCCG GTACTGCCGG GCCTCTTGCG GGATATCGTC CATTCCGACA GCATCGCCAG
3001   TCACTATGGC GTGCTGCTAG CGCTCTTCCG CTTCCTCGCT CACTGACTCG CTGCGCTCGG
3061   TCGTTCGGCT GCGGCGAGCG GTATCAGCTC ACTCAAAGGC GGTAATACGG TTATCCACAG
3121   AATCAGGGGA TAACGCAGGA AAGAACATGT GAGCAAAAGG CCAGCAAAAG GCCAGGAACC
3181   GTAAAAAGGC CGCGTTGCTG GCGTTTTTCC ATAGGCTCCG CCCCCCTGAC GAGCATCACA
3241   AAAATCGACG CTCAAGTCAG AGGTGGCGAA ACCCGACAGG ACTATAAAGA TACCAGGCGT
3301   TTCCCCCTGG AAGCTCCCTC GTGCGCTCTC CTGTTCCGAC CCTGCCGCTT ACCGGATACC
3361   TGTCCGCCTT TCTCCCTTCG GGAAGCGTGG CGCTTTCTCA TAGCTCACGC TGTAGGTATC
3421   TCAGTTCGGT GTAGGTCGTT CGCTCCAAGC TGGGCTGTGT GCACGAACCC CCCGTTCAGC
3481   CCGACCGCTG CGCCTTATCC GGTAACTATC GTCTTGAGTC CAACCCGGTA AGACACGACT
3541   TATCGCCACT GGCAGCAGCC ACTGGTAACA GGATTAGCAG AGCGAGGTAT GTAGGCGGTG
3601   CTACAGAGTT CTTGAAGTGG TGGCCTAACT ACGGCTACAC TAGAAGGACA GTATTTGGTA
```

Figure 9C

```
3661    TCTGCGCTCT GCTGAAGCCA GTTACCTTCG GAAAAAGAGT TGGTAGCTCT TGATCCGGCA
3721    AACAAACCAC CGCTGGTAGC GGTGGTTTTT TTGTTTGCAA GCAGCAGATT ACGCGCAGAA
3781    AAAAAGGATC TCAAGAAGAT CCTTTGATCT TTTCTACGGG GTCTGACGCT CAGTGGAACG
3841    AAAACTCACG TTAAGGGATT TTGGTCATGA GATTATCAAA AAGGATCTTC ACCTAGATCC
3901    TTTTAAATTA AAAATGAAGT TTTAAATCAA TCTAAAGTAT ATATGAGTAA ACTTGGTCTG
3961    ACAGTTACCA ATGCTTAATC AGTGAGGCAC CTATCTCAGC GATCTGTCTA TTTCGTTCAT
4021    CCATAGTTGC CTGACTCCCC GTCGTGTAGA TAACTACGAT ACGGGAGGGC TTACCATCTG
4081    GCCCCAGTGC TGCAATGATA CCGCGAGACC CACGCTCACC GGCTCCAGAT TTATCAGCAA
4141    TAAACCAGCC AGCCGGAAGG GCCGAGCGCA GAAGTGGTCC TGCAACTTTA TCCGCCTCCA
4201    TCCAGTCTAT TAATTGTTGC CGGGAAGCTA GAGTAAGTAG TTCGCCAGTT AATAGTTTGC
4261    GCAACGTTGT TGCCATTGCT ACAGGCATCG TGGTGTCACG CTCGTCGTTT GGTATGGCTT
4321    CATTCAGCTC CGGTTCCCAA CGATCAAGGC GAGTTACATG ATCCCCCATG TTGTGCAAAA
4381    AAGCGGTTAG CTCCTTCGGT CCTCCGATCG TTGTCAGAAG TAAGTTGGCC GCAGTGTTAT
4441    CACTCATGGT TATGGCAGCA CTGCATAATT CTCTTACTGT CATGCCATCC GTAAGATGCT
4501    TTTCTGTGAC TGGTGAGTAC TCAACCAAGT CATTCTGAGA ATAGTGTATG CGGCGACCGA
4561    GTTGCTCTTG CCCGGCGTCA ACACGGGATA ATACCGCGCC ACATAGCAGA ACTTTAAAAG
4621    TGCTCATCAT TGGAAAACGT TCTTCGGGGC GAAAACTCTC AAGGATCTTA CCGCTGTTGA
4681    GATCCAGTTC GATGTAACCC ACTCGTGCAC CCAACTGATC TTCAGCATCT TTTACTTTCA
4741    CCAGCGTTTC TGGGTGAGCA AAAACAGGAA GGCAAAATGC CGCAAAAAAG GGAATAAGGG
4801    CGACACGGAA ATGTTGAATA CTCATACTCT TCCTTTTTCA ATATTATTGA AGCATTTATC
4861    AGGGTTATTG TCTCATGAGC GGATACATAT TTGAATGTAT TTAGAAAAAT AAACAAATAG
4921    GGGTTCCGCG CACATTTCCC CGAAAAGTGC CACCTGACGT CTAAGAGACC ATTATTATCA
4981    TGACATTAAC CTATAAAAAT AGGCGTATCA CGAGGCCCTT TCGTCTTCAA GAATTGTCTA
5041    GAGGCGCGCC GTTTAAACCC TCAGCTACCG ATGTACGGGC CAGATATACG CGTTGACATT
5101    GATTATTGAC TAGTTATTAA TAGTAATCAA TTACGGGGTC ATTAGTTCAT AGCCCATATA
5161    TGGAGTTCCG CGTTACATAA CTTACGGTAA ATGGCCCGCC TGGCTGACCG CCCAACGACC
5221    CCCGCCCATT GACGTCAATA ATGACGTATG TTCCCATAGT AACGCCAATA GGGACTTTCC
5281    ATTGACGTCA ATGGGTGGAC TATTTACGGT AAACTGCCCA CTTGGCAGTA CATCAAGTGT
5341    ATCATATGCC AAGTACGCCC CCTATTGACG TCAATGACGG TAAATGGCCC GCCTGGCATT
5401    ATGCCCAGTA CATGACCTTA TGGGACTTTC CTACTTGGCA GTACATCTAC GTATTAGTCA
5461    TCGCTATTAC CATGGTGATG CGGTTTTGGC AGTACATCAA TGGGCGTGGA TAGCGGTTTG
5521    ACTCACGGGG ATTTCCAAGT CTCCACCCCA TTGACGTCAA TGGGAGTTTG TTTTGGCACC
5581    AAAATCAACG GGACTTTCCA AAATGTCGTA ACAACTCCGC CCCATTGACG CAAATGGGCG
5641    GTAGGCGTGT ACGGTGGGAG GTCTATATAA GCAGAGCTCT CTGGCTAACT AGAGAACCCA
5701    CTGCTTACTG GCTTATCGAA ATTAATACGA CTCACTATAG CAATTGCACG TGTGGCCACA
5761    GGTAAGTTTA AAGCTCAGGT CGAGACCGGG CCTTTGTCCG GCGCTCCCTT GGAGCCTACC
5821    TAGACTCAGC CGGCTCTCCA CGCTTTGCCT GACCCTGCTT GCTCAACTCT ACGTCTTTGT
5881    TTCGTTTTCT GTTCCTTTCT CTCCACAGGC TTAAGCTCGA GGCCGCCACC ATGGCCGTGC
5941    TGGGCCTGCT GTTCTGCCTG GTGACCTTCC CTTCCTGCGT GCTGTCCCAG GTGCAGCTGG
6001    TGCAGTCCGG CGTGGAGGTG AAGAAGCCTG GCGCCTCCGT CAAGGTGTCC TGTAAGGCCT
6061    CCGGCTACAC CTTCACCAAC TACTACATGT ACTGGGTGCG GCAGGCCCCA GGCCAGGGAC
6121    TGGAGTGGAT GGGCGGCATC AACCCTTCCA ACGGCGGCAC CAACTTCAAC GAGAAGTTCA
6181    AGAACCGGGT GACCCTGACC ACCGACTCCT CCACCACAAC CGCCTACATG GAACTGAAGT
6241    CCCTGCAGTT CGACGACACC GCCGTGTACT ACTGCGCCAG GCGGGACTAC CGGTTCGACA
6301    TGGGCTTCGA CTACTGGGGC CAGGGCACCA CCGTGACCGT GTCCTCCGCT AGCACCAAGG
6361    GCCCTTCCGT GTTCCCTCTG GCCCCTTGCT CCCGGTCCAC CTCCGAGTCC ACCGCCGCTC
6421    TGGGCTGTCT GGTGAAGGAC TACTTCCCTG AGCCTGTGAC CGTGAGCTGG AACTCTGGCG
6481    CCCTGACCTC CGGCGTGCAC ACCTTCCCTG CCGTGCTGCA GTCCTCCGGC CTGTACTCCC
6541    TGTCCTCCGT GGTGACCGTG CCTTCCTCCT CCCTGGGCAC CAAGACCTAC ACCTGCAACG
6601    TGGACCACAA GCCTTCCAAC ACCAAGGTGG ACAAGCGGGT GGAGTCCAAG TACGGCCCTC
```

Figure 9D

```
6661    CTTGCCCTCC CTGCCCTGCC CCTGAGTTCC TGGGCGGACC CTCCGTGTTC CTGTTCCCTC
6721    CTAAGCCTAA GGACACCCTG ATGATCTCCC GGACCCCTGA GGTGACCTGC GTGGTGGTGG
6781    ACGTGTCCCA GGAAGATCCT GAGGTCCAGT TCAATTGGTA CGTGGATGGC GTGGAGGTGC
6841    ACAACGCCAA GACCAAGCCT CGGGAGGAAC AGTTCAACTC CACCTACCGG GTGGTGTCTG
6901    TGCTGACCGT GCTGCACCAG GACTGGCTGA ACGGCAAGGA ATACAAGTGC AAGGTCAGCA
6961    ACAAGGGCCT GCCCTCCTCC ATCGAGAAAA CCATCTCCAA GGCCAAGGGC CAGCCTCGCG
7021    AGCCTCAGGT GTACACCCTG CCTCCTAGCC AGGAAGAGAT GACCAAGAAT CAGGTGTCCC
7081    TGACATGCCT GGTGAAGGGC TTCTACCCTT CCGATATCGC CGTGGAGTGG GAGAGCAACG
7141    GCCAGCCAGA GAACAACTAC AAGACCACCC CTCCTGTGCT GGACTCCGAC GGCTCCTTCT
7201    TCCTGTACTC CAGGCTGACC GTGGACAAGT CCCGGTGGCA GGAAGGCAAC GTCTTTTCCT
7261    GCTCCGTGAT GCACGAGGCC CTGCACAACC ACTACACCCA GAAGTCCCTG TCCCTGTCTC
7321    TGGGCAAGTG AATCGATGGA TCCAGATCCC CCTCGCTTTC TTGCTGTCCA ATTTCTATTA
7381    AAGGTTCCTT TGTTCCCTAA GTCCAACTAC TAAACTGGGG GATATTATGA AGGGCCTTGA
7441    GCATCTGGAT TCTGCCTAAT AAAAAACATT TATTTTCATT GCAATGATGT ATTTAAATTA
7501    TTTCTGAATA TTTTACTAAA AAGGGAATGT GGGAGGTCAG TGCATTTAAA ACATAAAGAA
7561    ATGAAGAGGG GGATCTGTCG ACAAGCTCTA GAGAGCTCAC GCGTTGATCA TGTACAGGCC
7621    GGCCAAGCTT TCGACTAGCT TGGCACGCCA GAAATCCGCG CGGTGGTTTT TGGGGGTCGG
7681    GGGTGTTTGG CAGCCACAGA CGCCCGGTGT TCGTGTCGCG CCAGTACATG CGGTCCATGC
7741    CCAGGCCATC CAAAAACCAT GGGTCTGTCT GCTCAGTCCA GTCGTGGACC TGACCCCACG
7801    CAACGCCCAA AATAATAACC CCCACGAACC ATAAACCATT CCCCATGGGG GACCCCGTCC
7861    CTAACCCACG GGGCCAGTGG CTATGGCAGG GCCTGCCGCC CCGACGTTGG CTGCGAGCCC
7921    TGGGCCTTCA CCCGAACTTG GGGGGTGGGG TGGGGAAAAG GAAGAAACGC GGGCGTATTG
7981    GCCCCAATGG GGTCTCGGTG GGGTATCGAC AGAGTGCCAG CCCTGGGACC GAACCCCGCG
8041    TTTATGAACA AACGACCCAA CACCCGTGCG TTTTATTCTG TCTTTTTATT GCCGTCATAG
8101    CGCGGGTTCC TTCCGGTATT GTCTCCTTCC GTGTTTCAGT TAGCCTCCCC CATCTCCCGA
8161    TCCGGACGAG TGCTGGGGCG TCGGTTTCCA CTATCGGCGA GTACTTCTAC ACAGCCATCG
8221    GTCCAGACGG CCGCGCTTCT GCGGGCGATT TGTGTACGCC CGACAGTCCC GGCTCCGGAT
8281    CGGACGATTG CGTCGCATCG ACCCTGCGCC CAAGCTGCAT CATCGAAATT GCCGTCAACC
8341    AAGCTCTGAT AGAGTTGGTC AAGACCAATG CGGAGCATAT ACGCCCGGAG CCGCGGCGAT
8401    CCTGCAAGCT CCGGATGCCT CCGCTCGAAG TAGCGCGTCT GCTGCTCCAT ACAAGCCAAC
8461    CACGGCCTCC AGAAGAAGAT GTTGGCGACC TCGTATTGGG AATCCCCGAA CATCGCCTCG
8521    CTCCAGTCAA TGACCGCTGT TATGCGGCCA TTGTCCGTCA GGACATTGTT GGAGCCGAAA
8581    TCCGCGTGCA CGAGGTGCCG GACTTCGGGG CAGTCCTCGG CCCAAAGCAT CAGCTCATCG
8641    AGAGCCTGCG CGACGGACGC ACTGACGGTG TCGTCCATCA CAGTTTGCCA GTGATACACA
8701    TGGGGATCAG CAATCGCGCA TATGAAATCA CGCCATGTAG TGTATTGACC GATTCCTTGC
8761    GGTCCGAATG GGCCGAACCC GCTCGTCTGG CTAAGATCGG CCGCAGCGAT CGCATCCATG
8821    GCCTCCGCGA CCGGCTGCAG AACAGCGGGC AGTTCGGTTT CAGGCAGGTC TTGCAACGTG
8881    ACACCCTGTG CACGGCGGGA GATGCAATAG GTCAGGCTCT CGCTGAATTC CCCAATGTCA
8941    AGCACTTCCG GAATCGGGAG CGCGGCCGAT GCAAAGTGCC GATAAACATA ACGATCTTTG
9001    TAGAAACCAT CGGCGCAGCT ATTTACCCGC AGGACATATC CACGCCCTCC TACATCGAAG
9061    CTGAAAGCAC GAGATTCTTC GCCCTCCGAG AGCTGCATCA GGTCGGAGAC GCTGTCGAAC
9121    TTTTCGATCA GAAACTTCTC GACAGACGTC GCGGTGAGTT CAGGCTTTTT CATATCTCAT
9181    TGCCCCCGG GATCTGCGGC ACGCTGTTGA CGCTGTTAAG CGGGTCGCTG CAGGGTCGCT
9241    CGGTGTTCGA GGCCACACGC GTCACCTTAA TATGCGAAGT GGACCTCGGA CCGCGCCGCC
9301    CCGACTGCAT CTGCGTGTTC GAATTCGCCA ATGACAAGAC GCTGGGCGGG GTTTGTGTCA
9361    TCATAGAACT AAAGACATGC AAATATATTT CTTCCGGGGA CACCGCCAGC AAACGCGAGC
9421    AACGGGCCAC GGGGATGAAG CAGGGCGGCA CCTCGCTAAC GGATTCACCA CTCCAAGAAT
9481    TGGAGCCAAT CAATTCTTGC GGAGAACTGT GAATGCGCAA ACCAACCCTT GGCAGAACAT
9541    ATCCATCGCG TCCGCCATCT CCAGCAGCCG CACGCGGCGC ATCTCGGGGC CGACGCGCTG
9601    GGCTACGTCT TGCTGGCGTT CGCACAGGCC GGCCAGCGCG CGGCCGGCCG GTACCACGCG
```

Figure 9E

```
 9661    TTGGCCACAT ATGGCGGCCG CTCGCGATTA ATTAATCGCG ATGGCCACAT ATGGAGCTCT
 9721    CTAGAGCTTG TCGACAGATC CCCCTCTTCA TTTCTTTATG TTTTAAATGC ACTGACCTCC
 9781    CACATTCCCT TTTTAGTAAA ATATTCAGAA ATAATTTAAA TACATCATTG CAATGAAAAT
 9841    AAATGTTTTT TATTAGGCAG AATCCAGATG CTCAAGGCCC TTCATAATAT CCCCCAGTTT
 9901    AGTAGTTGGA CTTAGGGAAC AAAGGAACCT TTAATAGAAA TTGGACAGCA AGAAAGCGAG
 9961    GGGGATCTGG ATCCCTCCCT TCAGCACTCG CCCCGGTTGA AGGACTTGGT CACAGGGCTG
10021    GACAGGCCCT GGTGGGTCAC CTCGCAGGCG TACACCTTGT GCTTCTCGTA GTCGGCCTTG
10081    GACAGGGTCA GGGTGGAGGA CAGGGAGTAG GTGCTGTCCT TGGAGTCCTG CTCGGTGACG
10141    GATTCCTGGG AGTTGCCGGA CTGCAGGGCA TTGTCCACCT TCCACTGCAC CTTGGCCTCC
10201    CGAGGGTAGA AGTTGTTCAG CAGGCACACC ACGGAGGCGG TGCCGGACTT CAGCTGCTCG
10261    TCGGAGGGAG GGAAGATGAA CACGGAAGGA GCGGCCACCG TACGCTTGAT CTCCAGCTTG
10321    GTGCCCTGGC CGAAGGTCAG AGGCAGGTCC CGGGAGTGCT GGCAGTAGTA CACGCCCACG
10381    TCCTCGGCCT CCACCCGGGA GATCTTCAGG GTGAAGTCGG TGCCGCTGCC GGAGCCGGAG
10441    AACCGGTCAG GCACGCCGGA CTCCAGGTAG GAGGCCAGGT AGATCAGCAG CTGGGGGGAC
10501    TGGCCAGGCT TCTGCAGATA CCAGTGCAGG TAGGAGTAGC CGGAGGTGGA CACGCCCTTG
10561    GAGGCCCGGC AGGAGATGGA GGCAGGCTCG CCAGGGGTCA CAGGCAGGGA CAGAGGGGAC
10621    TGGGTCAGCA CGATCTCGCA CCGCATGGCA GGCAGGAACA GCACCAGCAG GCCCAGCAGC
10681    TGCACAGGGG CCATGGTGGC GGCCTCGAGG AATTCTTAAG CCTGTGGAGA GAAAGGAACA
10741    GAAAACGAAA CAAAGACGTA GAGTTGAGCA AGCAGGGTCA GGCAAAGCGT GGAGAGCCGG
10801    CTGAGTCTAG GTAGGCTCCA AGGGAGCGCC GGACAAAGGC CCGGTCTCGA CCTGAGCTTT
10861    AAACTTACCT GTGGCCACAC GTGCAATTGC TATAGTGAGT CGTATTAATT TCGATAAGCC
10921    AGTAAGCAGT GGGTTCTCTA GTTAGCCAGA GAGCTCTGCT TATATAGACC TCCCACCGTA
10981    CACGCCTACC GCCCATTTGC GTCAATGGGG CGGAGTTGTT ACGACATTTT GGAAAGTCCC
11041    GTTGATTTTG GTGCCAAAAC AAACTCCCAT TGACGTCAAT GGGGTGGAGA CTTGGAAATC
11101    CCCGTGAGTC AAACCGCTAT CCACGCCCAT TGATGTACTG CCAAAACCGC ATCACCATGG
11161    TAATAGCGAT GACTAATACG TAGATGTACT GCCAAGTAGG AAAGTCCCAT AAGGTCATGT
11221    ACTGGGCATA ATGCCAGGCG GGCCATTTAC CGTCATTGAC GTCAATAGGG GGCGTACTTG
11281    GCATATGATA CACTTGATGT ACTGCCAAGT GGGCAGTTTA CCGTAAATAG TCCACCCATT
11341    GACGTCAATG GAAAGTCCCT ATTGGCGTTA CTATGGGAAC ATACGTCATT ATTGACGTCA
11401    ATGGGCGGGG GTCGTTGGGC GGTCAGCCAG GCGGGCCATT TACCGTAAGT TATGTAACGC
11461    GGAACTCCAT ATATGGGCTA TGAACTAATG ACCCCGTAAT TGATTACTAT TAATAACTAG
11521    TCAATAATCA ATGTCAACGC GTATATCTGG CCCGTACATC GGTAACTAGT CGGACCGGCC
11581    CGGGCCACCG GTGCTCGAAG CTTGGATCGA TCCAGACATG ATAAGATACA TTGATGAGTT
11641    TGGACAAACC ACAACTAGAA TGCAGTGAAA AAAATGCTTT ATTTGTGAAA TTTGTGATGC
11701    TATTGCTTTA TTTGTAACCA TTATAAGCTG CAATAAACAA GTTAACAACA ACAATTGCAT
11761    TCATTTTATG TTTCAGGTTC AGGGGGAGGT GTGGGAGGTT TTTTAAAGCA AGTAAAACCT
11821    CTACAAATGT GGTATGGCTG ATTATGATCT CTAGTCAAG
```

Figure 10A

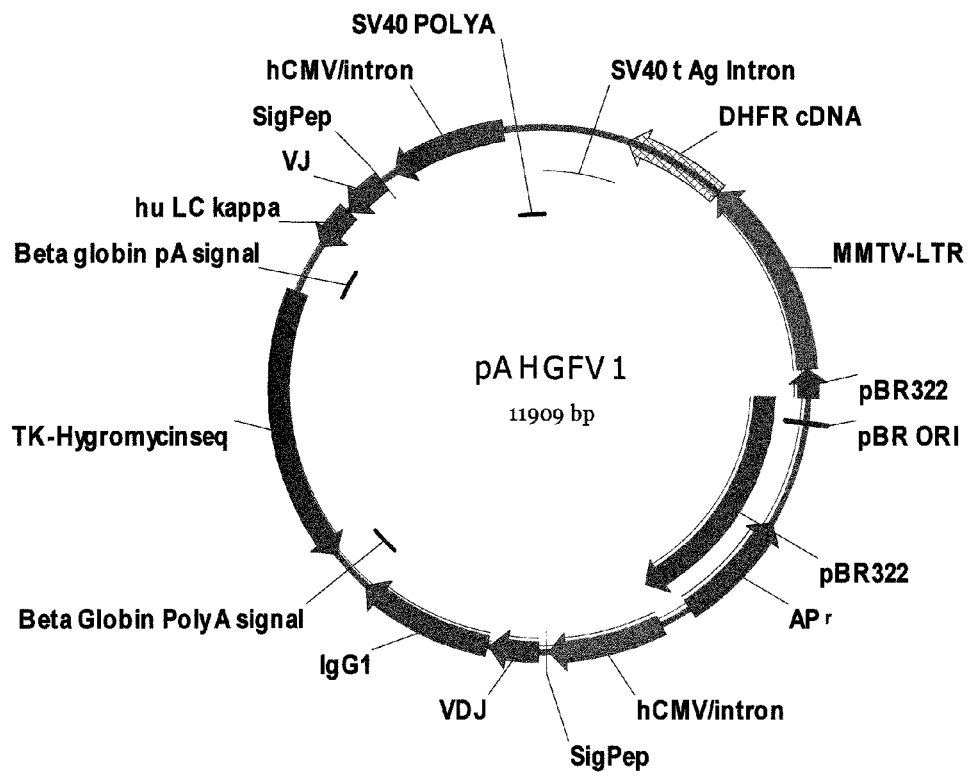

```
  1    GGCACTATAC ATCAAATATT CCTTATTAAC CCCTTTACAA ATTAAAAAGC TAAAGGTACA
 61    CAATTTTTGA GCATAGTTAT TAATAGCAGA CACTCTATGC CTGTGTGGAG TAAGAAAAAA
121    CAGTATGTTA TGATTATAAC TGTTATGCCT ACTTATAAAG GTTACAGAAT ATTTTTCCAT
181    AATTTTCTTG TATAGCAGTG CAGCTTTTTC CTTTGTGGTG TAAATAGCAA AGCAAGCAAG
241    AGTTCTATTA CTAAACACAG CATGACTCAA AAAACTTAGC AATTCTGAAG GAAAGTCCTT
301    GGGGTCTTCT ACCTTTCTCT TCTTTTTTGG AGGAGTAGAA TGTTGAGAGT CAGCAGTAGC
361    CTCATCATCA CTAGATGGCA TTTCTTCTGA GCAAAACAGG TTTTCCTCAT TAAAGGCATT
421    CCACCACTGC TCCCATTCAT CAGTTCCATA GGTTGGAATC TAAAATACAC AAACAATTAG
481    AATCAGTAGT TTAACACATT ATACACTTAA AAATTTTATA TTTACCTTAG AGCTTTAAAT
541    CTCTGTAGGT AGTTTGTCCA ATTATGTCAC ACCACAGAAG TAAGGTTCCT TCACAAAGAT
601    CGATCTAAAG CCAGCAAAAG TCCCATGGTC TTATAAAAAT GCATAGCTTT AGGAGGGGAG
661    CAGAGAACTT GAAAGCATCT TCCTGTTAGT CTTTCTTCTC GTAGACTTCA AACTTATACT
721    TGATGCCTTT TTCCTCCTGG ACCTCAGAGA GGACGCCTGG GTATTCTGGG AGAAGTTTAT
781    ATTTCCCCAA ATCAATTTCT GGGAAAAACG TGTCACTTTC AAATTCCTGC ATGATCCTTG
```

Figure 10B

```
 841    TCACAAAGAG TCTGAGGTGG CCTGGTTGAT TCATGGCTTC CTGGTAAACA GAACTGCCTC
 901    CGACTATCCA AACCATGTCT ACTTTACTTG CCAATTCCGG TTGTTCAATA AGTCTTAAGG
 961    CATCATCCAA ACTTTTGGCA AGAAAATGAG CTCCTCGTGG TGGTTCTTTG AGTTCTCTAC
1021    TGAGAACTAT ATTAATTCTG TCCTTTAAAG GTCGATTCTT CTCAGGAATG GAGAACCAGG
1081    TTTTCCTACC CATAATCACC AGATTCTGTT TACCTTCCAC TGAAGAGGTT GTGGTCATTC
1141    TTTGGAAGTA CTTGAACTCG TTCCTGAGCG GAGGCCAGGG TAGGTCTCCG TTCTTGCCAA
1201    TCCCCATATT TTGGGACACG GCGACGATGC AGTTCAATGG TCGAACCATG ATGGCAGCGG
1261    GGATAAAATC CTACCAGCCT TCACGCTAGG ATTGCCGTCA AGTTTGGCGC GAAATCGCAG
1321    CCCTGAGCTG TCCCCCCCCC CAAGCTCAGA TCTGAGCTTG GTCCCTATGG TGAGTCCGTT
1381    CCGCTCTTGT GATGATAGCC AGACAAGAAA GAGACAATAC AAGACAAACA CCAAATAGTA
1441    GAAATAGAGA CAAGGGTCAC TTATCCGAGG GTCCCTGTTC GGGCGCCAGC TGCCGCAGTC
1501    GGCCGACCTG AGGGTCGCCG GGTCTGCGG GGGGACCCTC TGGAAAGTGA AGGATAAGTG
1561    ACGAGCGGAG ACGGGATGGC GAACAGACAC AAACACACAA GAGGTGAATG TTAGGACTGT
1621    TGCAAGTTTA CTCAAAAAAT CAGCACTCTT TTATATCTTG GTTTACATAA GCATTTACAT
1681    AAGATTTGGA TAAATTCCAA AAGAACATAG GAAAATAGAA CACTCAGAGC TCAGATCAGA
1741    ACCTTTGATA CCAAACCAAG TCAGGAAACC ACTTGTCTCA CATCCTCGTT TTAAGAACAG
1801    TTTGTAACCA AAAACTTACT TAAGCCCTGG GAACCGCAAG GTTGGGCCAA TAAAGGCTAT
1861    TCATAATAAC TCATGCCATG AGTTTTTGCA GAATAATGTT CTATTAGTCC AGCCACTGTC
1921    CCCTCCTTGG TATGGAAAAT CTTTCCCCAA AAGTGCATTC CTGTTCCTAG ATAAATATAA
1981    TCATGTACCT GTTGTTTCAT GTCGTCTTTT TCTTCTTGAG ACAACATACA CCAAGGAGGT
2041    CTAGCTCTGG CGAGTCTTTC ACGAAAAGGG AGGGATCTAT ATAACACTTT ATAGCCATTG
2101    ACTGTAACCC ACCTATCCCA ATTTAAGTCA TATCTTCCTG TATATGGTAA GGGGGCATCT
2161    GTTGGTCTGT AGATGTAAGG TCCCCTATAA GTCCCTGGTT GCCACCACCT GTCTCCTATT
2221    TTGACAAAAA CACTCTTTTT TCCCTTTTTT ACTTCTAGGC CTGTGGTCAA TAGTCCTTGC
2281    ACCTGTTCTT CAATTGAGGT TGAGCGTCTC TTTCTATTTT CTATTCCCAT TTCTAACTTC
2341    TGAATTTGAG TAAAAATAGT ACTAAAAGAT AATGATTCAT TTCTTAACAT AGTAACTAAT
2401    AATCTACCTA TTGGATTGGT CTTATTGGTA AAAATATAAT TTTTAGCAAG CATTCTTATT
2461    TCTATTTCTG AAGGACAAAA TCGATGCGGC TTGTAAGAGG AAGTTGGCTG TGGTCCTTGC
2521    CTCAGGAGGA AGGTCGAGTT CTCCGAATTG TTTAGATTGT AATCTTGCAC AGAAGAGCTA
2581    TTAAAAGAGT CAAGGGTGAG AGCCCTGCGA GCACGAACCG CAACTTCCCC CAATAGCCCC
2641    AGGCAAAGCA GAGCTATGCC AAGTTTGCAG CAGAGAATGA ATATGTCTTT GTCTGATGGG
2701    CTCATCCGTT TGTGCGCAGA CGGGTCGTCC TTGGTGGGAA ACAACCCCTT GGCTGCTTCT
2761    CCCCTAGGTG TAGGACACTC TCGGGAGTTC AACCATTTCT GCCCAAGCTC AGATCTGAGC
2821    TTTAATGCGG TAGTTTATCA CAGTTAAATT GCTAACGCAG TCAGGCACCG TGTATGAAAT
2881    CTAACAATGC GCTCATCGTC ATCCTCGGCA CCGTCACCCT GGATGCTGTA GGCATAGGCT
2941    TGGTTATGCC GGTACTGCCG GCCTCTTGC GGGATATCGT CCATTCCGAC AGCATCGCCA
3001    GTCACTATGG CGTGCTGCTA GCGCTCTTCC GCTTCCTCGC TCACTGACTC GCTGCGCTCG
3061    GTCGTTCGGC TGCGGCGAGC GGTATCAGCT CACTCAAAGG CGGTAATACG GTTATCCACA
3121    GAATCAGGGG ATAACGCAGG AAAGAACATG TGAGCAAAAG GCCAGCAAAA GGCCAGGAAC
3181    CGTAAAAAGG CCGCGTTGCT GGCGTTTTTC CATAGGCTCC GCCCCCTGA CGAGCATCAC
3241    AAAAATCGAC GCTCAAGTCA GAGGTGGCGA AACCCGACAG GACTATAAAG ATACCAGGCG
3301    TTTCCCCCTG GAAGCTCCCT CGTGCGCTCT CCTGTTCCGA CCCTGCCGCT TACCGGATAC
3361    CTGTCCGCCT TTCTCCCTTC GGGAAGCGTG GCGCTTTCTC ATAGCTCACG CTGTAGGTAT
3421    CTCAGTTCGG TGTAGGTCGT TCGCTCCAAG CTGGGCTGTG TGCACGAACC CCCCGTTCAG
3481    CCCGACCGCT GCGCCTTATC CGGTAACTAT CGTCTTGAGT CCAACCCGGT AAGACACGAC
3541    TTATCGCCAC TGGCAGCAGC CACTGGTAAC AGGATTAGCA GAGCGAGGTA TGTAGGCGGT
3601    GCTACAGAGT TCTTGAAGTG GTGGCCTAAC TACGGCTACA CTAGAAGGAC AGTATTTGGT
3661    ATCTGCGCTC TGCTGAAGCC AGTTACCTTC GGAAAAAGAG TTGGTAGCTC TTGATCCGGC
3721    AAACAAACCA CCGCTGGTAG CGGTGGTTTT TTTGTTTGCA AGCAGCAGAT TACGCGCAGA
3781    AAAAAGGAT CTCAAGAAGA TCCTTTGATC TTTTCTACGG GTCTGACGC TCAGTGGAAC
```

Figure 10C

```
3841   GAAAACTCAC GTTAAGGGAT TTTGGTCATG AGATTATCAA AAAGGATCTT CACCTAGATC
3901   CTTTTAAATT AAAAATGAAG TTTTAAATCA ATCTAAAGTA TATATGAGTA AACTTGGTCT
3961   GACAGTTACC AATGCTTAAT CAGTGAGGCA CCTATCTCAG CGATCTGTCT ATTTCGTTCA
4021   TCCATAGTTG CCTGACTCCC CGTCGTGTAG ATAACTACGA TACGGGAGGG CTTACCATCT
4081   GGCCCCAGTG CTGCAATGAT ACCGCGAGAC CCACGCTCAC CGGCTCCAGA TTTATCAGCA
4141   ATAAACCAGC CAGCCGGAAG GGCCGAGCGC AGAAGTGGTC CTGCAACTTT ATCCGCCTCC
4201   ATCCAGTCTA TTAATTGTTG CCGGGAAGCT AGAGTAAGTA GTTCGCCAGT TAATAGTTTG
4261   CGCAACGTTG TTGCCATTGC TACAGGCATC GTGGTGTCAC GCTCGTCGTT TGGTATGGCT
4321   TCATTCAGCT CCGGTTCCCA ACGATCAAGG CGAGTTACAT GATCCCCCAT GTTGTGCAAA
4381   AAAGCGGTTA GCTCCTTCGG TCCTCCGATC GTTGTCAGAA GTAAGTTGGC CGCAGTGTTA
4441   TCACTCATGG TTATGGCAGC ACTGCATAAT TCTCTTACTG TCATGCCATC CGTAAGATGC
4501   TTTTCTGTGA CTGGTGAGTA CTCAACCAAG TCATTCTGAG AATAGTGTAT GCGGCGACCG
4561   AGTTGCTCTT GCCCGGCGTC AACACGGGAT AATACCGCGC CACATAGCAG AACTTTAAAA
4621   GTGCTCATCA TTGGAAAACG TTCTTCGGGG CGAAAACTCT CAAGGATCTT ACCGCTGTTG
4681   AGATCCAGTT CGATGTAACC CACTCGTGCA CCCAACTGAT CTTCAGCATC TTTTACTTTC
4741   ACCAGCGTTT CTGGGTGAGC AAAAACAGGA AGGCAAAATG CCGCAAAAAA GGGAATAAGG
4801   GCGACACGGA AATGTTGAAT ACTCATACTC TTCCTTTTTC AATATTATTG AAGCATTTAT
4861   CAGGGTTATT GTCTCATGAG CGGATACATA TTTGAATGTA TTTAGAAAAA TAAACAAATA
4921   GGGGTTCCGC GCACATTTCC CCGAAAAGTG CCACCTGACG TCTAAGAGAC CATTATTATC
4981   ATGACATTAA CCTATAAAAA TAGGCGTATC ACGAGGCCCT TTCGTCTTCA AGAATTGTCT
5041   AGAGGCGCGC CGTTTAAACC CTCAGCTACC GATGTACGGG CCAGATATAC GCGTTGACAT
5101   TGATTATTGA CTAGTTATTA ATAGTAATCA ATTACGGGGT CATTAGTTCA TAGCCCATAT
5161   ATGGAGTTCC GCGTTACATA ACTTACGGTA AATGGCCCGC CTGGCTGACC GCCCAACGAC
5221   CCCCGCCCAT TGACGTCAAT AATGACGTAT GTTCCCATAG TAACGCCAAT AGGGACTTTC
5281   CATTGACGTC AATGGGTGGA CTATTTACGG TAAACTGCCC ACTTGGCAGT ACATCAAGTG
5341   TATCATATGC CAAGTACGCC CCCTATTGAC GTCAATGACG GTAAATGGCC CGCCTGGCAT
5401   TATGCCCAGT ACATGACCTT ATGGGACTTT CCTACTTGGC AGTACATCTA CGTATTAGTC
5461   ATCGCTATTA CCATGGTGAT GCGGTTTTGG CAGTACATCA ATGGGCGTGG ATAGCGGTTT
5521   GACTCACGGG GATTTCCAAG TCTCCACCCC ATTGACGTCA ATGGGAGTTT GTTTTGGCAC
5581   CAAAATCAAC GGGACTTTCC AAAATGTCGT AACAACTCCG CCCCATTGAC GCAAATGGGC
5641   GGTAGGCGTG TACGGTGGGA GGTCTATATA AGCAGAGCTC TCTGGCTAAC TAGAGAACCC
5701   ACTGCTTACT GGCTTATCGA AATTAATACG ACTCACTATA GCAATTGCAC GTGTGGCCAC
5761   AGGTAAGTTT AAAGCTCAGG TCGAGACCGG GCCTTTGTCC GGCGCTCCCT TGGAGCCTAC
5821   CTAGACTCAG CCGGCTCTCC ACGCTTTGCC TGACCCTGCT TGCTCAACTC TACGTCTTTG
5881   TTTCGTTTTC TGTTCCTTTC TCTCCACAGG CTTAAAACGC CGCCACCATG GGTCAACCG
5941   CCATCCTCGC CCTCCTCCTG GCTGTTCTCC AAGGAGTCTG TGCCGAAGTG CAGCTGGTGC
6001   AGTCTGGAGC AGAGGTGAAA AAGCCCGGGG AGTCTCTGAA GATCTCCTGT AAGGGTTCTG
6061   GATACAGCTT TACCACCTAC TGGATGCACT GGGTGCGCCA GATGCCCGGG AAAGGCCTGG
6121   AGTGGATGGG GGAGATTAAT CCTACCAACG GTCATACTAA CTACAATCCG TCCTTCCAAG
6181   GCCAGGTCAC CATCTCAGCT GACAAGTCCA TCAGCACTGC CTACCTGCAG TGGAGCAGCC
6241   TGAAGGCCTC GGACACCGCC ATGTATTACT GTGCGAGAAA CTATGTTGGT AGCATCTTTG
6301   ACTACTGGGG CCAAGGAACC CTGGTCACCG TCTCCTCAGC TAGCACCAAG GGCCCATCGG
6361   TCTTCCCCCT GGCACCCTCC TCCAAGAGCA CCTCTGGGGG CACAGCGGCC CTGGGCTGCC
6421   TGGTCAAGGA CTACTTCCCC GAACCGGTGA CGGTGTCGTG GAACTCAGGC GCCCTGACCA
6481   GCGGCGTGCA CACCTTCCCG GCTGTCCTAC AGTCCTCAGG ACTCTACTCC CTCAGCAGCG
6541   TGGTGACCGT GCCCTCCAGC AGCTTGGGCA CCCAGACCTA CATCTGCAAC GTGAATCACA
6601   AGCCCAGCAA CACCAAGGTG GACAAGAAAG TTGAGCCCAA ATCTTGTGAC AAAACTCACA
6661   CATGCCCACC GTGCCCAGCA CCTGAACTCC TGGGGGGACC GTCAGTCTTC CTCTTCCCCC
6721   CAAAACCCAA GGACACCCTC ATGATCTCCC GGACCCCTGA GGTCACATGC GTGGTGGTGG
6781   ACGTGAGCCA CGAAGACCCT GAGGTCAAGT TCAACTGGTA CGTGGACGGC GTGGAGGTGC
```

Figure 10D

```
6841    ATAATGCCAA GACAAAGCCG CGGGAGGAGC AGTACAACAG CACGTACCGT GTGGTCAGCG
6901    TCCTCACCGT CCTGCACCAG GACTGGCTGA ATGGCAAGGA GTACAAGTGC AAGGTCTCCA
6961    ACAAAGCCCT CCCAGCCCCC ATCGAGAAAA CCATCTCCAA AGCCAAAGGG CAGCCCCGAG
7021    AACCACAGGT GTACACCCTG CCCCCATCCC GGGATGAGCT GACCAAGAAC CAGGTCAGCC
7081    TGACCTGCCT GGTCAAAGGC TTCTATCCCA GCGACATCGC CGTGGAGTGG GAGAGCAATG
7141    GGCAGCCGGA GAACAACTAC AAGACCACGC CTCCCGTGCT GGACTCCGAC GGCTCCTTCT
7201    TCCTCTACAG CAAGCTCACC GTGGACAAGA GCAGGTGGCA GCAGGGGAAC GTCTTCTCAT
7261    GCTCCGTGAT GCATGAGGCT CTGCACAACC ACTACACGCA GAAGAGCCTC TCCCTGTCTC
7321    CGGGTAAATG AATCGATGAT TCTAGATACG GGTCCGAGG ATCCAGATCC CCCTCGCTTT
7381    CTTGCTGTCC AATTTCTATT AAAGGTTCCT TTGTTCCCTA AGTCCAACTA CTAAACTGGG
7441    GGATATTATG AAGGGCCTTG AGCATCTGGA TTCTGCCTAA TAAAAAACAT TTATTTTCAT
7501    TGCAATGATG TATTTAAATT ATTTCTGAAT ATTTTACTAA AAAGGGAATG TGGGAGGTCA
7561    GTGCATTTAA AACATAAAGA AATGAAGAGG GGGATCTGTC GACAAGCTCT AGAGAGCTCA
7621    CGCGTTGATC ATGTACAGGC CGGCCAAGCT TTCGACTAGC TTGGCACGCC AGAAATCCGC
7681    GCGGTGGTTT TTGGGGGTCG GGGGTGTTTG GCAGCCACAG ACGCCCGGTG TTCGTGTCGC
7741    GCCAGTACAT GCGGTCCATG CCCAGGCCAT CCAAAAACCA TGGGTCTGTC TGCTCAGTCC
7801    AGTCGTGGAC CTGACCCCAC GCAACGCCCA AAATAATAAC CCCCACGAAC CATAAACCAT
7861    TCCCCATGGG GGACCCCGTC CCTAACCCAC GGGGCCAGTG GCTATGGCAG GGCCTGCCGC
7921    CCCGACGTTG GCTGCGAGCC CTGGGCCTTC ACCCGAACTT GGGGGGTGGG GTGGGGAAAA
7981    GGAAGAAACG CGGGCGTATT GGCCCCAATG GGGTCTCGGT GGGGTATCGA CAGAGTGCCA
8041    GCCCTGGGAC CGAACCCCGC GTTTATGAAC AAACGACCCA ACACCCGTGC GTTTATTCT
8101    GTCTTTTTAT TGCCGTCATA GCGCGGGTTC CTTCCGGTAT TGTCTCCTTC CGTGTTTCAG
8161    TTAGCCTCCC CCATCTCCCG ATCCGGACGA GTGCTGGGGC GTCGGTTTCC ACTATCGGCG
8221    AGTACTTCTA CACAGCCATC GGTCCAGACG GCCGCGCTTC TGCGGGCGAT TTGTGTACGC
8281    CCGACAGTCC CGGCTCCGGA TCGGACGATT GCGTCGCATC GACCCTGCGC CCAAGCTGCA
8341    TCATCGAAAT TGCCGTCAAC CAAGCTCTGA TAGAGTTGGT CAAGACCAAT GCGGAGCATA
8401    TACGCCCGGA GCCGCGGCGA TCCTGCAAGC TCCGGATGCC TCCGCTCGAA GTAGCGCGTC
8461    TGCTGCTCCA TACAAGCCAA CCACGGCCTC CAGAAGAAGA TGTTGGCGAC CTCGTATTGG
8521    GAATCCCCGA ACATCGCCTC GCTCCAGTCA ATGACCGCTG TTATGCGGCC ATTGTCCGTC
8581    AGGACATTGT TGGAGCCGAA ATCCGCGTGC ACGAGGTGCC GGACTTCGGG GCAGTCCTCG
8641    GCCCAAAGCA TCAGCTCATC GAGAGCCTGC GCGACGACG CACTGACGGT GTCGTCCATC
8701    ACAGTTTGCC AGTGATACAC ATGGGGATCA GCAATCGCGC ATATGAAATC ACGCCATGTA
8761    GTGTATTGAC CGATTCCTTG CGGTCCGAAT GGGCCGAACC CGCTCGTCTG GCTAAGATCG
8821    GCCGCAGCGA TCGCATCCAT GGCCTCCGCG ACCGGCTGCA GAACAGCGGG CAGTTCGGTT
8881    TCAGGCAGGT CTTGCAACGT GACACCCTGT GCACGGCGGG AGATGCAATA GGTCAGGCTC
8941    TCGCTGAATT CCCCAATGTC AAGCACTTCC GGAATCGGGA GCGCGGCCGA TGCAAAGTGC
9001    CGATAAACAT AACGATCTTT GTAGAAACCA TCGGCGCAGC TATTTACCCG CAGGACATAT
9061    CCACGCCCTC CTACATCGAA GCTGAAAGCA CGAGATTCTT CGCCCTCCGA GAGCTGCATC
9121    AGGTCGGAGA CGCTGTCGAA CTTTTCGATC AGAAACTTCT CGACAGACGT CGCGGTGAGT
9181    TCAGGCTTTT TCATATCTCA TTGCCCCCCG GGATCTGCGG CACGCTGTTG ACGCTGTTAA
9241    GCGGGTCGCT GCAGGGTCGC TCGGTGTTCG AGGCCACACG CGTCACCTTA ATATGCGAAG
9301    TGGACCTCGG ACCGCGCCGC CCCGACTGCA TCTGCGTGTT CGAATTCGCC AATGACAAGA
9361    CGCTGGGCGG GGTTTGTGTC ATCATAGAAC TAAAGACATG CAAATATATT TCTTCCGGGG
9421    ACACCGCCAG CAAACGCGAG CAACGGGCCA CGGGGATGAA GCAGGCGGC ACCTCGCTAA
9481    CGGATTCACC ACTCCAAGAA TTGGAGCCAA TCAATTCTTG CGGAGAACTG TGAATGCGCA
9541    AACCAACCCT TGGCAGAACA TATCCATCGC GTCCGCCATC TCCAGCAGCC GCACGCGGCG
9601    CATCTCGGGG CCGACGCGCT GGGCTACGTC TTGCTGGCGT TCGCACAGGC CGGCCAGCGC
9661    GCGGCCGGCC GGTACCACGC GTTGGCCACA TATGGCGGCC GCTCGCGATT AATTAATCGC
9721    GATGGCCACA TATGGAGCTC TCTAGAGCTT GTCGACAGAT CCCCCTCTTC ATTTCTTTAT
9781    GTTTTAAATG CACTGACCTC CCACATTCCC TTTTTAGTAA AATATTCAGA ATAATTTAA
```

Figure 10E

```
 9841   ATACATCATT GCAATGAAAA TAAATGTTTT TTATTAGGCA GAATCCAGAT GCTCAAGGCC
 9901   CTTCATAATA TCCCCCAGTT TAGTAGTTGG ACTTAGGGAA CAAAGGAACC TTTAATAGAA
 9961   ATTGGACAGC AAGAAAGCGA GGGGGATCTG GATCCTCCTA CGTATCTAGA ATCATCGATT
10021   AACACTCTCC CCTGTTGAAG CTCTTTGTCA CGGGGCTGCT CAGGCCCTGA TGGGTCACCT
10081   CGCAGGCGTA CACCTTGTGT TTCTCGTAGT CTGCTTTGCT CAGGGTCAGG GTGCTGCTCA
10141   GGCTGTAGGT GCTGTCCTTG CTGTCCTGCT CTGTCACGCT CTCCTGGGAG TTGCCGCTCT
10201   GGAGGGCGTT ATCCACCTTC CACTGCACCT TGGCCTCTCT GGGATAGAAG TTATTCAGCA
10261   GGCACACCAC GGAGGCAGTT CCAGACTTCA GCTGCTCATC AGATGGAGGG AAGATGAACA
10321   CAGATGGTGC AGCCACCGTA CGTTTGATCT CCAGCTTGGT CCCCTGGCCA AACGTGTACG
10381   GATAGTTGTA ACTCTGCCCA CAGTAGTAAG TTGCAAAATC TTCAGGTTGC AGACTGCTGA
10441   TGGTGAGAGT GAAATCTGTC CCAGATCCAC TGCCACTGAA CCTTGATGGG ACCCCAGTGT
10501   TCCGGTTGGA TGCCCCATAG ATCAGGAGCT TAGGGGCTTT CCCTGGTTTC TGCTGATACC
10561   AGGATACATA AGAAACCACA TTCTCACTGG CCTTGCAAGT GATGGTGACT CTGTCTCCTA
10621   CAGATGCAGA CAGGGAGGAT GGAGACTGGG TCATCTGGAT GTCACATCTG GCACCTCGGA
10681   GCCAGAGTAG CAGGAGCCCC AGGAGCTGAG CGGGACCCT CATGTCCATG GTGGCGGCGA
10741   ATTCTCGAGA AGCTTAAGTT TAATTCTTAA GCCTGTGGAG AGAAAGGAAC AGAAAACGAA
10801   ACAAAGACGT AGAGTTGAGC AAGCAGGGTC AGGCAAAGCG TGGAGAGCCG GCTGAGTCTA
10861   GGTAGGCTCC AAGGGAGCGC CGGACAAAGG CCCGGTCTCG ACCTGAGCTT TAAACTTACC
10921   TGTGGCCACA CGTGCAATTG CTATAGTGGA TCGTATTAAT TTCGATAAGC CAGTAAGCAG
10981   TGGGTTCTCT AGTTAGCCAG AGAGCTCTGC TTATATAGAC CTCCCACCGT ACACGCCTAC
11041   CGCCCATTTG CGTCAATGGG GCGGAGTTGT TACGACATTT TGGAAAGTCC CGTTGATTTT
11101   GGTGCCAAAA CAAACTCCCA TTGACGTCAA TGGGGTGGAG ACTTGGAAAT CCCCGTGAGT
11161   CAAACCGCTA TCCACGCCCA TTGATGTACT GCCAAAACCG CATCACCATG GTAATAGCGA
11221   TGACTAATAC GTAGATGTAC TGCCAAGTAG GAAAGTCCCA TAAGGTCATG TACTGGGCAT
11281   AATGCCAGGC GGGCCATTTA CCGTCATTGA CGTCAATAGG GGGCGTACTT GGCATATGAT
11341   ACACTTGATG TACTGCCAAG TGGGCAGTTT ACCGTAAATA GTCCACCCAT TGACGTCAAT
11401   GGAAAGTCCC TATTGGCGTT ACTATGGGAA CATACGTCAT TATTGACGTC AATGGGCGGG
11461   GGTCGTTGGG CGGTCAGCCA GGCGGGCCAT TTACCGTAAG TTATGTAACG CGGAACTCCA
11521   TATATGGGCT ATGAACTAAT GACCCCGTAA TTGATTACTA TTAATAACTA GTCAATAATC
11581   AATGTCAACG CGTATATCTG GCCCGTACAT CGGTAACTAG TCGGACCGGC CCGGGCCACC
11641   GGTGCTCGAA GCTTGGATCG ATCCAGACAT GATAAGATAC ATTGATGAGT TTGGACAAAC
11701   CACAACTAGA ATGCAGTGAA AAAAATGCTT TATTTGTGAA ATTTGTGATG CTATTGCTTT
11761   ATTTGTAACC ATTATAAGCT GCAATAAACA AGTTAACAAC AACAATTGCA TTCATTTTAT
11821   GTTTCAGGTT CAGGGGGAGG TGTGGGAGGT TTTTTAAAGC AAGTAAAACC TCTACAAATG
11881   TGGTATGGCT GATTATGATC TCTAGTCAA
```

βGI-IGG INTRON FOR ENHANCED ANTI-IGF1R EXPRESSION

This application claims the benefit of U.S. provisional patent application No. 61/113,807; filed Nov. 12, 2008; which is herein incorporated by reference in its entirety.

FIELD OF THE INVENTION

The present invention relates to polynucleotides comprising a target gene operably linked to a promoter/beta-globin-immunoglobin gamma (βGI-IgG) intron construct and methods of expressing such a target gene.

BACKGROUND OF THE INVENTION

The clinical and commercial success of antibodies, antibody fragments and other therapeutic proteins has led to the need for very large-scale production in mammalian cell culture. This has resulted in rapid expansion of global manufacturing capacity, an increase in size of reactors (up to 20,000 L) and a greatly increased effort to improve process efficiency with concomitant manufacturing cost reduction.

For example, most antibody therapies require high doses over a long period of time, which requires large amounts of purified product per patient. Therefore, manufacturing capacity to meet the demands of antibody production is a real challenge; it is desirable to have highly productive manufacturing processes.

One means by which to improve in vivo production levels of an antibody or other protein is to generate novel polynucleotide expression constructs which cause enhanced levels of protein production as compared to that of standard constructs. The present invention addresses this need in the art.

SUMMARY OF THE INVENTION

The present invention provides, in part, an isolated δGl-IgG intron polynucleotide comprising a beta-globin splice donor site and an immunoglobulin gamma splice acceptor site wherein said sites are separated by about 125 nucleotides. In addition to the βGI-IgG introns, the present invention includes methods of use for expressing target polypeptides at high levels. Plasmids, host cells, master cell banks and working cell banks also form part of the present invention.

For example, in an embodiment of the invention, the polynucleotides comprises a beta-globin splice donor site comprising the nucleotide sequence CAGGTAAGTTTA (SEQ ID NO: 4) and an immunoglobulin gamma splice acceptor site comprising the nucleotide sequence TTTCTCTCCACAGGC (SEQ ID NO: 5) wherein said sites are separated by about 125 nucleotides; e.g., wherein the splice donor site and the splice acceptor site are separated by the sequence

```
AAGCTCAGGT CGAGACCGGG CCTTTGTCCG GCGCTCCCTT
GGAGCCTACC TAGACTCAGC CGGCTCTCCA CGCTTTGCCT
GACCCTGCTT GCTCAACTCT ACGTCTTTGT TTCGTTTTCT
GTTCC
```

(nucleotides 51-175 of SEQ ID NO: 3). In an embodiment of the invention, the βGI-IgG intron is upstream of a gene and downstream of a promoter that is operably associated with said gene. The gene can be of any type, for example, an immunoglobulin, for example, wherein the immunoglobulin is a light chain variable region (optionally including a signal peptide) or heavy chain variable region (optionally including a signal peptide), or both, of an antibody or antigen-binding fragment thereof which binds specifically to IGF1R, IL-23 p19, IL23 receptor (any subunit thereof, e.g., IL-12β1 or IL-23R), IL-17A, PD1 or HGF, e.g., wherein the gene encodes CDR-L1, CDR-L2 and CDR-L3 of a light chain immunoglobulin comprising amino acids 20-128 of SEQ ID NO: 6, 8-11, 18 or 26 or SEQ ID NO 31; and/or wherein the gene encodes CDR-H1, CDR-H2 and CDR-H3 of a heavy chain immunoglobulin comprising amino acids 20-137 of SEQ ID NO: 7, 12, 13, 14 or 22 or SEQ ID NO: 30. The βGI-IgG intron can be placed in any polynucleotide, for example, a vector such as a plasmid vector or viral vector.

The present invention includes within its scope, an isolated plasmid that includes a βGI-IgG intron characterized by the plasmid vector map of any of FIGS. 1-10, for example, wherein the plasmid comprises βGI-IgG intron nucleotides 39-190 of the nucleotide sequence of SEQ ID NO: 3.

Host cells including a βGI-IgG intron of the present invention are also within the scope of the present invention. For example, in the host cell, the βGI-IgG intron polynucleotide can be integrated into the chromosomal DNA of the host cell or not integrated. Furthermore, the host cell can contain a high copy number of the polynucleotide, for example, 2 or more copies per cell.

Master cell banks (MCBs) also form part of the present invention. Accordingly, the present invention includes a method for making a master cell bank comprising introducing a βGI-IgG intron polynucleotide of the invention (e.g., plasmid vector shown in any of FIGS. 1-10) into a host cell (e.g., a mammalian cell, e.g., a CHO cell, such as a CHO-DG44, CHO-K1 or CHO-DXB11), selecting a single clonal population of host cells comprising said polynucleotide, culturing said clonal population, determining if cells from said culture contain bacteria, viruses, fungi and/or mycoplasma and, if none are detected, storing cells from said culture in one or more containers under refrigeration. In an embodiment of the invention, the master cell bank is free of biological contaminants, such as bacteria, viruses, fungi and/or mycoplasma. The master cell bank can be stored under refrigeration. A master cell bank, for example, produced by the described method of making a MCB is also part of the present invention is also part of the present invention. The present invention further provides a method for making a working cell bank (WCB) by culturing cells from a master cell bank of the present invention and storing cells from said culture in one or more containers under refrigeration. Similar to the method for making a MCB, this method can include a step for testing the WCB for bacteria, viruses, fungi and/or mycoplasma and, if none are detected, storing cells from said culture under refrigeration. A working cell bank, for example, produced by the described method of making a WCB is also part of the present. For example, in an embodiment of the invention, in the MCB or WCB, the cells are in vials (e.g., about 200 or more) comprising about $10^7$ cells per vial and are free of detectable levels of bacteria, viruses, mycoplasma and fungi.

The present invention also provides a method for expressing a target polypeptide encoded by a gene which is operably associated with a promoter, in a host cell (e.g., a mammalian cell, e.g., a CHO cell, such as a CHO-K1, CHO-DXB11 or CHO-DG44 cell), comprising introducing a βGI-IgG intron polynucleotide comprising a beta-globin splice donor site and an immunoglobulin gamma splice acceptor wherein said sites are separated by about 125 nucleotides, between the promoter and the polynucleotide encoding the target polypeptide (e.g., plasmid pAIG1FRLCb2V1, e.g., that comprises the nucleotide sequence of SEQ ID NO: 35) into the host cell under conditions whereby the target polypeptide is expressed; and, optionally, purifying said target polypeptide. In an embodiment of the invention, the beta-globin splice donor site comprises the nucleotide sequence CAGGTAAGTTTA (SEQ ID NO: 4) and the immunoglobulin splice acceptor site comprises the nucleotide sequence TTTCTCTCCACAGGC (SEQ ID NO: 5), e.g., wherein the splice donor site and the splice acceptor site are separated by the sequence

```
AAGCTCAGGT CGAGACCGGG CCTTTGTCCG GCGCTCCCTT

GGAGCCTACC TAGACTCAGC CGGCTCTCCA CGCTTTGCCT

GACCCTGCTT GCTCAACTCT ACGTCTTTGT TTCGTTTTCT

GTTCC
```

(nucleotides 51-175 or SEQ ID NO: 3). In an embodiment of the invention, the gene is an immunoglobulin, for example, wherein the immunoglobulin is a light chain variable region or heavy chain variable region of an antibody which binds specifically to IGF1R, e.g., wherein the gene encodes CDR-L1, CDR-L2 and CDR-L3 of a light chain immunoglobulin comprising amino acids 20-128 of SEQ ID NO: 6, 8-11, 18 or 26 or SEQ ID NO 31; or wherein the gene encodes CDR-H1, CDR-H2 and CDR-H3 of a heavy chain immunoglobulin comprising amino acids 20-137 of SEQ ID NO: 7, 12, 13, 14 or 22 or SEQ ID NO: 30.

Figure 1:
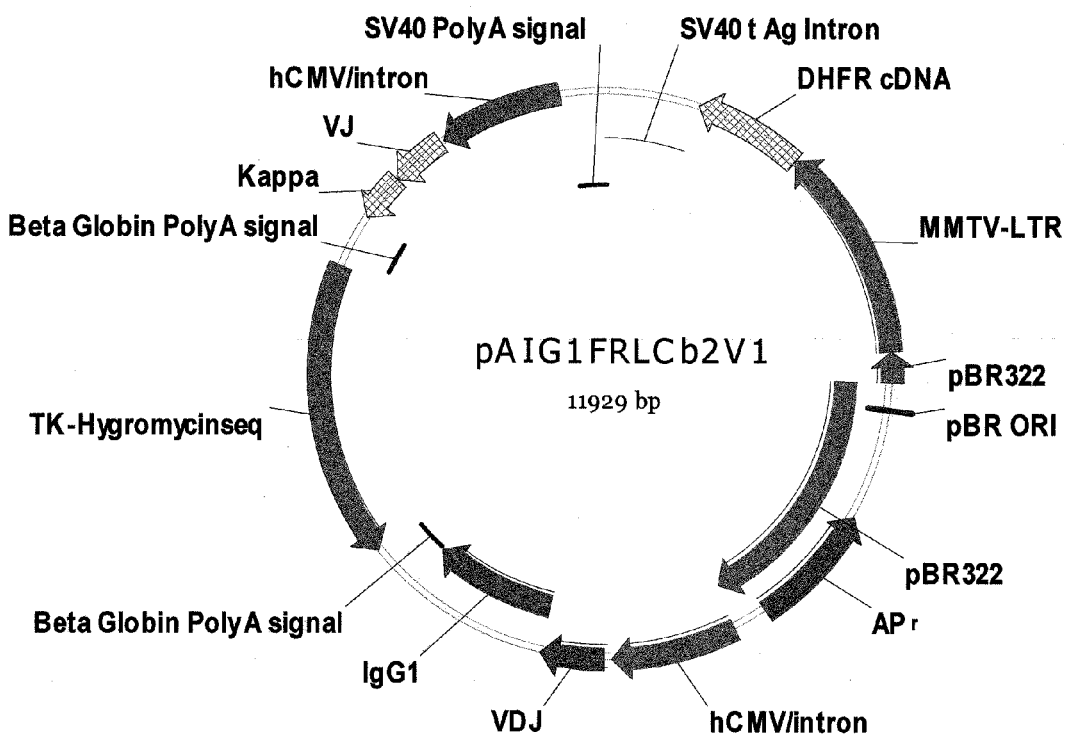
FIG. 1. Plasmid map for pAIG1FRLCb2V1. The feature map for this plasmid is set forth below:
AP(R)
Start: 3965 End: 4828
(Complementary)
VDJ
Start: 5966 End: 6393
IgG1
Start: 6393 End: 7373
IgG1 non genomic region
DHFR cDNA
Start: 601 End: 1347
(Complementary)
SV40 t Ag Intron
Start: 11916 End: 600
Kappa
Start: 10055 End: 10378
(Complementary)
Kappa Chain
VJ
Start: 10379 End: 10756
(Complementary)
VJ of IGF-1R (LCb, human germline sequence)
pBR322
Start: 2811 End: 3019
(Complementary)
pBR322
Start: 3020 End: 5033
TK-Hygromycinseq
Start: 7682 End: 9691
(Complementary)
Beta Globin Poly A signal
Start: 7398 End: 7636
Beta Globin Poly A signal
Start: 9784 End: 10032
(Complementary)
SV40 Poly A signal
Start: 11669 End: 11917
MMTV-LTR
Start: 1348 End: 2810
(Complementary)
hCMV/βGI-IgG intron
Start: 5069 End: 5910
Human CMV promoter/βGI-IgG intron
hCMV/βGI-IgG intron
Start: 10778 End: 11619
(Complementary)
Human CMV promoter/βGI-IgG intron
pBR ORI
Start: 3207 End: 3207

light chain and hCMV promoter-(βGI-IgG intron)-anti-IL-23 Ig. heavy chain constructs. βGI-IgG intron is at nt. 10906-10755 and 5760-5911.

FIG. 7A-7E. Plasmid map for pAIL23RV1 and nucleotide sequence of plasmid (SEQ ID NO: 45). Plasmid vector comprising hCMV promoter-(βGI-IgG intron)-anti-IL-23R Ig. light chain and hCMV promoter-(βGI-IgG intron)-anti-IL-23R Ig. heavy chain constructs. βGI-IgG intron is at nt. 10914-10763 and 5760-5911.

FIG. 8A-8E. Plasmid map for pAIL17AV1 and nucleotide sequence of plasmid (SEQ ID NO: 46). Plasmid vector comprising hCMV promoter-(βGI-IgG intron)-anti-IL-17 Ig. light chain and hCMV promoter-(βGI-IgG intron)-anti-IL-17 Ig. heavy chain constructs. βGI-IgG intron is at nt. 10934-10783 and 5759-5910.

FIG. 9A-9E. Plasmid map for pAPD16V1-GA and nucleotide sequence of plasmid (SEQ ID NO: 47). Plasmid vector comprising hCMV promoter(βGI-IgG intron)-anti-PD1 Ig. light chain and hCMV promoter-(βGI-IgG intron)-anti-PD1 Ig. heavy chain constructs. βGI-IgG intron is at nt.10871-10720 and 5759-5910.

FIG. 10A-10E. Plasmid map for pAHGFV1 and nucleotide sequence of plasmid (SEQ ID NO: 48). Plasmid vector comprising hCMV promoter-(βGI-IgG intron)-anti-HGF Ig. light chain and hCMV promoter-(βGI-IgG intron)-anti-HGF Ig. heavy chain constructs. βGI-IgG intron is at nt. 10922-10771 and 5760-5911.

DETAILED DESCRIPTION OF THE INVENTION

The present invention provides, in part, expression constructs from which target genes, such as immunoglobulin light or heavy chains, can be expressed at particularly high levels, relative to conventional expression constructs. For example, the present invention includes polynucleotides (e.g., plasmid vectors) which include a target gene to be expressed (e.g., an immunoglobulin light and/or heavy chain gene), operably linked to a promoter wherein, between the gene and promoter there is a construct comprising a beta-globin intron splice donor site, followed by about 125 nucleotides, followed, then, by an immunoglobulin-gamma intron acceptor site. The present invention also includes methods for expressing the target genes using the expression constructs of the present invention.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A "polynucleotide", "nucleic acid" or "nucleic acid molecule" includes DNA and RNA.

A "polynucleotide sequence", "nucleic acid sequence" or "nucleotide sequence" is a series of nucleotides in a nucleic acid, such as DNA or RNA, and means any chain of two or more nucleotides.

A "coding sequence" or a sequence "encoding" an expression product, such as a RNA, polypeptide, protein, or enzyme, is a nucleotide sequence that, when expressed, results in production of the product.

The term "gene" includes DNA that codes for or corresponds to a particular sequence of ribonucleotides or amino acids which comprise all or part of one or more RNA molecules or proteins. Genes may be transcribed from DNA to RNA which may or may not be translated into an amino acid sequence. A "target gene" or a "target polynucleotide" is a polynucleotide, e.g., that encodes a target polypeptide, which a practitioner intends to express or is expressing, for example, by introducing the polynucleotide into an expression construct for expression in e.g., a host cell.

The terms "isolated polynucleotide" or "isolated polypeptide" or the like include a polynucleotide (e.g., RNA or DNA molecule) or a polypeptide, respectively, which are partially or fully separated from other components that are normally found in cells or in recombinant DNA expression systems. These components include, but are not limited to, cell membranes, cell walls, ribosomes, polymerases, serum components and extraneous genomic sequences. An isolated polynucleotide or polypeptide will, in an embodiment of the invention, be an essentially homogeneous composition of molecules but may contain some heterogeneity.

"Amplification" of DNA as used herein includes the use of polymerase chain reaction (PCR) to increase the concentration of a particular DNA sequence within a mixture of DNA sequences. For a description of PCR see Saiki, et al., Science (1988) 239: 487.

As used herein, the term "oligonucleotide" includes a nucleic acid, generally of at least 10 (e.g., 10, 11, 12, 13 or 14), preferably at least 15 (e.g., 15, 16, 17, 18 or 19), and more preferably at least 20 nucleotides (e.g., 20, 21, 22, 23, 24, 25, 26, 27, 28, 29 or 30), preferably no more than 100 nucleotides (e.g., 40, 50, 60, 70, 80 or 90), that may be hybridizable to a genomic DNA molecule, a cDNA molecule, or an mRNA molecule encoding a gene, mRNA, cDNA, or other nucleic acid of interest. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment of the invention, a labeled oligonucleotide can be used as a probe to detect the presence of a nucleic acid. In another embodiment, oligonucleotides (one or both of which may be labeled) can be used as PCR primers, either for cloning full length or a fragment of a gene, or to detect the presence of nucleic acids. Generally, oligonucleotides are prepared synthetically, e.g., on a nucleic acid synthesizer.

The sequence of any nucleic acid may be sequenced by any method known in the art (e.g., chemical sequencing or enzymatic sequencing). "Chemical sequencing" of DNA includes methods such as that of Maxam and Gilbert (1977) (Proc. Natl. Acad. Sci. USA 74:560), in which DNA is randomly cleaved using individual base-specific reactions. "Enzymatic sequencing" of DNA may includes methods such as that of Sanger (Sanger, et al., (1977) Proc. Natl. Acad. Sci. USA 74:5463).

The nucleic acids of the invention may, in an embodiment of the invention, be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

A "promoter" or "promoter sequence" is, in an embodiment of the invention, a DNA regulatory region capable of binding an RNA polymerase in a cell (e.g., directly or through other promoter-bound proteins or substances) and initiating transcription of a coding sequence (e.g., an immunoglobulin such as an anti-IGF1R immunoglobulin). A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the β-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

A coding sequence is "under the control of", "functionally associated with" or "operably linked to" or "operably associated with" transcriptional or translational control sequences in a cell when the sequences direct RNA polymerase mediated transcription of the coding sequence into RNA, e.g., mRNA, which then may be trans-RNA spliced (if it contains introns) and, optionally, translated into a protein encoded by the coding sequence. A promoter is operably linked to a βGI-IgG intron if the intron causes increased levels of expression from the promoter relative to the promoter without the βGI-IgG intron.

The terms "express" and "expression" mean allowing or causing the information in a gene, e.g., an RNA or DNA, to become manifest; for example, producing a protein by activating the cellular functions involved in transcription and translation of a corresponding gene. A DNA sequence can be expressed in or by a cell to form an "expression product" such as an RNA (e.g., mRNA) or a protein. The expression product itself may also be said to be "expressed" by the cell.

The terms "vector", "cloning vector" and "expression vector" include a vehicle (e.g., a plasmid) by which a nucleic acid can be introduced into a host cell, so as to transform the host and, optionally, promote expression of a gene encoded by the nucleic acid and/or replication of the introduced nucleic acid. In an embodiment of the invention, the vector is an autonomously replicating nucleic acid such as a circular plasmid.

The term "transformation" means the introduction of a nucleic acid into a cell. The term includes the introduction of a nucleic acid encoding an anti-IGF1R, anti-IL23, anti-IL23R, anti-IL17, anti-PD1 or anti-HGF antibody or antigen-binding fragment thereof into a cell. The introduced gene or sequence may be called a "clone". A host cell that receives the introduced DNA or RNA has been "transformed" and is a "transformant" or a "clone". The DNA or RNA introduced to a host cell can come from any source, including cells of the same genus or species as the host cell, or cells of a different genus or species. Plasmids may be introduced into a cell by any of the many methods which are commonly known in the art. For example, a plasmid of the invention can be used to transform a cell by the calcium phosphate method, electroporation, the DEAE-dextran method or the liposome method.

The term "host cell" includes any cell of any organism that is selected, modified, transfected, transformed, grown, or used or manipulated in any way, for the production of a substance by the cell, for example the expression or replication, by the cell, of a gene, a DNA or RNA sequence, a protein or an enzyme. Host cells include Chinese hamster ovary cells such as CHO-K1 cells (ATCC accession no. CRL-9618), CHO-DG44 cells, and CHO-DXB-11 cells.

An "expression construct" is a polynucleotide which is capable of driving expression of a target gene encoded within the polynucleotide. For example, wherein the gene is operably linked to a promoter (e.g., CMV promoter) between which is located βGI-IgG intron.

A "promoter/βGI-IgG intron" is a promoter operably linked to a βGI-IgG intron. The βGI-IgG intron cause higher levels of expression from the promoter than in the absence of the βGI-IgG intron.

A "βGI-IgG intron" is an intron comprising splice donor (e.g., beta-globin) and splice acceptor sites (e.g., IgG).

In an embodiment of the invention, an expression construct comprises a Kozak consensus sequence, e.g., gccgccaccatgg (SEQ ID NO: 1) or gccgccaccatg (SEQ ID NO: 2).

The term "expression system" means a host cell and compatible vector which, under suitable conditions, can express a protein or nucleic acid which is carried by the vector and introduced to the host cell. Common expression systems include E. coli host cells and plasmid vectors, insect host cells and Baculovirus vectors, and mammalian host cells and vectors. As mentioned above, host cells include CHO (Chinese hamster ovary) cells, such as CHO-K1 or DXB-11; and also HeLa cells and NIH 3T3 cells and NS0 cells (non-Ig-producing murine myeloma cell line).

Plasmid vectors of the present invention may include any of several amplifiable markers known in the art. Use of amplifiable markers is discussed in Maniatis, Molecular Biology: A Laboratory Manual, Cold Spring Harbor Laboratory, NY (1989)). Useful selectable markers for gene amplification in drug-resistant mammalian cells include DHFR (MTX (methotrexate) resistance) (Alt et al., J. Biol. Chem. 253:1357 (1978); Wigler et al., Proc. Natl. Acad. Sci. USA 77:3567 (1980)); metallothionein (cadmium resistance) (Beach et al., Proc Natl. Acad. Sci. USA 78:210 (1981)); CAD (N-(phosphonoacetyl)-l-aspartate (PALA) resistance) (Wahl et al., J. Biol. Chem. 254: 8679 (1979)); adenylate deaminase (coformycin resistance) (Debatisse et al., Mol. Cell. Biol. 6:1776 (1986)); IMP 5'-dehydrogenase (mycophenolic acid resistance) (Huberman et al., Proc. Natl. Acad. Sci. USA 78:3151 (1981)) and other markers known in the art (as reviewed, for example, in Kaufman et al., Meth. Enzymology 185:537-566 (1988)).

The present invention contemplates any superficial or slight modification to the amino acid or nucleotide sequences which encode the target genes encoded by the plasmids of the present invention, e.g., antibodies or antigen-binding fragments thereof of the invention. "Sequence-conservative variants" of a polynucleotide sequence are those in which a change of one or more nucleotides in a given codon results in no alteration in the amino acid encoded at that position. Function-conservative variants of the target genes of the invention are also contemplated by the present invention. "Function-conservative variants" are those in which one or more amino acid residues in a protein have been changed without altering the overall conformation and function of the polypeptide, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine. Conservative substitutions of an amino acid sequence refer to those wherein an amino acid of one subtype (e.g., polar/hydrophilic) is replaced with another amino acid of the same subtype; and, in an embodiment of the invention, wherein the conservatively substituted polypeptide retains essentially the same level of biological activity.

The present invention includes plasmids including nucleic acids encoding target genes as well as nucleic acids which hybridize thereto. In an embodiment of the invention, the nucleic acids hybridize under low stringency conditions, more preferably under moderate stringency conditions and most preferably under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical low stringency hybridization conditions include, in an embodiment of the invention, 55° C., 5×SSC, 0.1% SDS, 0.25% milk, and no formamide; or 30% formamide, 5×SSC, 0.5% SDS. Typical, moderate stringency hybridization conditions are similar to the low stringency conditions except the hybridization is carried out in 40% formamide, with 5× or 6×SSC. High stringency hybridization conditions are similar to low stringency conditions except the hybridization conditions are carried out in 50% formamide, 5× or 6×SSC and, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra, 11.7-11.8).

Also included in the present invention are plasmids including target nucleotide sequences which encode target polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to the reference nucleotide and amino acid sequences (e.g., any of SEQ ID NOs: 6-31) of the present invention when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference amino acid sequences of the present invention (e.g., any of SEQ ID NOs: 6-31) when the comparison is performed with a BLAST algorithm wherein the parameters of the algorithm are selected to give the largest match between the respective sequences over the entire length of the respective reference sequences, are also included in the present invention.

Sequence identity refers to exact matches between the nucleotides or amino acids of two sequences which are being compared. Sequence similarity refers to both exact matches between the amino acids of two polypeptides which are being compared in addition to matches between nonidentical, biochemically related amino acids. Biochemically related amino acids which share similar properties and may be interchangeable are discussed above.

The following references regarding the BLAST algorithm are herein incorporated by reference: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., at al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, N.Y.

Introns

The present invention comprises polynucleotides, such as vectors (e.g., plasmids), comprising a promoter (e.g., human cytomegalovirus (CMV) promoter, e.g., immediate-early promoter-regulatory region of human cytomegalovirus) operably linked with a βGI-IgG intron that comprises a beta-globin splice donor and an immunoglobulin splice acceptor, which promoter/intron combination is operably linked with a target gene, such as an immunoglobulin. Methods of expressing such target genes using the polynucleotides of the present invention are also part of the present invention. As is discussed herein, it has been discovered that expression of a gene such as an anti-IGF1R immunoglobulin, from a human CMV promoter is greatly increased when the CMV promoter is linked with a βGI-IgG intron (beta-globin splice donor/Ig. splice acceptor).

For example, in an embodiment of the invention, the promoter/intron construct is upstream of the target gene to which it is operably linked. Methods for increasing expression of a target gene comprising operably linking the target gene to the promoter/intron are also within the scope of the present invention.

In an embodiment of the invention, the βGI-IgG intron, comprising the beta-globin splice donor and the IgG. splice acceptor, comprises the following nucleotide sequence:

```
ATTAATACGA CTCACTATAG CAATTGCACG

TGTGGCCACA GGTAAGTTTA AAGCTCAGGT

CGAGACCGGG CCTTTGTCCG GCGCTCCCTT

GGAGCCTACC TAGACTCAGC CGGCTCTCCA

CGCTTTGCCT GACCCTGCTT GCTCAACTCT

ACGTCTTTGT TTCGTTTTCT GTTCCTTTCT CTCCACAGGC

TTAA
```

(SEQ ID NO: 3). The beta-globin splice donor site is underscored with a solid line and the immunoglobulin splice acceptor is underscored with a broken line. In an embodiment of the invention, the beta-globin spice donor site comprises the nucleotide sequence CAGGTAAGTTTA (SEQ ID NO: 4). In an embodiment of the invention, the immunoglobulin splice acceptor site is derived from an IgG variable region, for example, comprising the nucleotide sequence TTTCTCTCCACAGGC (SEQ ID NO: 5).

In an embodiment of the invention, the βGI-IgG intron comprises

```
CA GGTAAGTTTA AAGCTCAGGT CGAGACCGGG CCTTTGTCCG

GCGCTCCCTT GGAGCCTACC TAGACTCAGC CGGCTCTCCA

CGCTTTGCCT GACCCTGCTT GCTCAACTCT ACGTCTTTGT

TTCGTTTTCT GTTCCTTTCT CTCCACAGGC
```

(nucleotides 39-190 of SEQ ID NO: 3).

Immunoglobulins

The present invention includes embodiments comprising polynucleotides (e.g., plasmids) comprising a promoter/intron construct operably associated with a target gene such as an immunoglobulin. In an embodiment of the invention, the immunoglobulin comprises an anti-IGF1R immunoglobulin light or heavy chain variable region, optionally linked with an immunoglobulin constant region.

In an embodiment of the invention, the immunoglobulin chain encodes any of those set forth below; for example, any of the following immunoglobulin light or heavy chains or any of the CDRs thereof. Dotted, underscored type encodes the signal peptide. Solid underscored type encodes the CDRs. Plain type encodes the framework regions. In an embodiment of the invention, the antibody chains are mature fragments which lack the signal peptide. In an embodiment of the invention, non-processed immunoglobulin chains are expressed, including the signal peptide, secreted from the host cell whereby the signal peptide is processed and removed to generate a mature immunoglobulin chain. Such compositions and methods of expression form part of the present invention.

Polynucleotides encoding any of the following target immunoglobulin amino acid sequences form part of the present invention.

19D12/15H12 Light Chain (SEQ ID NO: 6)

MSPSQLIGFLLLWVPASRGEIVLTQVPDFQSVTPKEKVTITCRASQSIG
SSLHWYQQKPDQSPKLLIKYASQSLSGVPSRFSGSGSGTDFTLTINSLE
AEDAAAYYCHQSSRLPHTFGGGTKVEIKRT

19D12/15H12 Heavy Chain (SEQ ID NO: 7)

MEFGLSWVFLVAILKGVQCEVQLVQSGGGLVHPGGSLRLSCAASGFTFS
SFAMHWVRQAPGKGLEWISVIDTRGATYYADSVKGRFTISRDNAKNSLY
LQMNSLRAEDMAVYYCARLGNFYYGMDVWGQGTTVTVSS

19D12/15H12 Light Chain-C (LLC) (SEQ ID NO: 8)

M S P S Q L I G F L L L W V P A S

R G E I V L T Q S P D S L S V T P

G E R V T I T C R A S Q S I G S S

L H W Y Q Q K P G Q S P K L L I K

Y A S Q S L S G V P S R F S G S G

S G T D F T L T I S S L E A E D A

A A Y Y C H Q S S R L P H T F G Q

G T K V E I K R T

19D12/15H12 Light Chain-D (LCD) (SEQ ID NO: 9)

M S P S Q L I G F L L L W V P A S

R G E I V L T Q S P D S L S V T P

G E R V T I T C R A S Q S I G S S

L H W Y Q Q K P G Q S P K L L I K

Y A S Q S L S G V P S R F S G S G

S G T D F T L T I S S L E A E D F

A V Y Y C H Q S S R L P H T F G Q

G T K V E I K R T

19D12/15H12 Light Chain-E (LCE) (SEQ ID NO: 10)

M S P S Q L I G F L L L W V P A S

R G E I V L T Q S P G T L S V S P

G E R A T L S C R A S Q S I G S S

L H W Y Q Q K P G Q A P R L L I K

Y A S Q S L S G I P D R F S G S G

S G T D F T L T I S R L E P E D A

A A Y Y C H Q S S R L P H T F G Q

G T K V E I K R T

19D12/15H12 Light Chain-F (LCF) (SEQ ID NO: 11)

M S P S Q L I G F L L L W V P A S

R G E I V L T Q S P G T L S V S P

G E R A T L S C R A S Q S I G S S

L H W Y Q Q K P G Q A P R L L I K

Y A S Q S L S G I P D R F S G S G

S G T D F T L T I S R L E P E D F

A V Y Y C H Q S S R L P H T F G Q

G T K V E I K R T

19D12/15H12 heavy chain-A (HCA) (SEQ ID NO: 12)

Met Glu Phe Gly Leu Ser Trp Val Phe Leu Val Ala
Ile Leu Lys Gly Val Gln Cys Glu Val Gln Leu Val
Gln Ser Gly Gly Gly Leu Val Lys Pro Gly Gly Ser
Leu Arg Leu Ser Cys Ala Ala Ser Gly Phe Thr Phe
Ser Ser Phe Ala Met His Trp Val Arg Gln Ala Pro
Gly Lys Gly Leu Glu Trp Ile Ser Val Ile Asp Thr
Arg Gly Ala Thr Tyr Tyr Ala Asp Ser Val Lys Gly
Arg Phe Thr Ile Ser Arg Asp Asn Ala Lys Asn Ser
Leu Tyr Leu Gln Met Asn Ser Leu Arg Ala Glu Asp
Thr Ala Val Tyr Tyr Cys Ala Arg Leu Gly Asn Phe
Tyr Tyr Gly Met Asp Val Trp Gly Gln Gly Thr Thr
Val Thr Val Ser Ser

19D12/15H12 heavy chain-B (HCB) (SEQ ID NO: 13)

Met Glu Phe Gly Leu Ser Trp Val Phe Leu Val Ala
Ile Leu Lys Gly Val Gln Cys Glu Val Gln Leu Val
Gln Ser Gly Gly Gly Leu Val Gln Pro Gly Gly Ser
Leu Arg Leu Ser Cys Ala Ala Ser Gly Phe Thr Phe
Ser Ser Phe Ala Met His Trp Val Arg Gln Ala Pro
Gly Lys Gly Leu Glu Trp Ile Ser Val Ile Asp Thr
Arg Gly Ala Thr Tyr Tyr Ala Asp Ser Val Lys Gly
Arg Phe Thr Ile Ser Arg Asp Asn Ala Lys Asn Ser
Leu Tyr Leu Gln Met Asn Ser Leu Arg Ala Glu Asp
Thr Ala Val Tyr Tyr Cys Ala Arg Leu Gly Asn Phe
Tyr Tyr Gly Met Asp Val Trp Gly Gln Gly Thr Thr
Val Thr Val Ser Ser

See international application publication no. WO2003/100008, wherein each sequence is disclosed; which is incorporated herein by reference in its entirety.

2C6 heavy chain
(SEQ ID NO: 14)
MELGLSWIFLLAILKGVQCEVQLVESGGGLVQPGRSLRLSCAAS**GFTFD
DYAMHWVRQAPGKGLEWVSGISWNSGSKGYVDSVKG**RFTISRDNAKNSL
YLQMNSLRAEDTALYYCAKDIRIGVAASYYFGMDVWGHGTTVTVSS

2C6 CDR-H1:
(SEQ ID NO: 15)
GFTFDDYAMH

2C6 CDR-H2:
(SEQ ID NO: 16)
GISWNSGSKGYVDSVKG

2C6 CDR-H3:
(SEQ ID NO: 17)
DIRIGVAASYYFGMDV

2C6 Light chain
(SEQ ID NO: 18)
MDMRVPAQLLGLLLLWLPGARCAIQLTQSPSSLSASVGDRVTITC**RASQ
GISSVLAWYQQKPGKAPKLLIYDASSLES**GVPSRFSGSGSGTDFTLTIS
SLQPEDFATYYCQQFNSYPYTFGQGTKLEIK

2C6 CDR-L1:
(SEQ ID NO: 19)
RASQGISSVLA

2C6 CDR-L2:
(SEQ ID NO: 20)
DASSLES

2C6 CDR-L3:
(SEQ ID NO: 21)
QQFNSYPYT

9H2 Heavy chain
(SEQ ID NO: 22)
MDWTWRILFLVAAATGAHSQVQLVQSGAEVKKPGASVKVSCKAS**GYTFT
SYVMHWVRQAPGQRLEWMGWINAGNGMTKYSQKFQG**RVTITRDTSASTV
YMELSSLRSEDTAVYYCARGGMPVAGPGYFYYYGMDVWGQGTTVTVSS

9H2 CDR-H1:
(SEQ ID NO: 23)
GYTFTSYVMH

9H2 CDR-H2:
(SEQ ID NO: 24)
WINAGNGNTKYSQKFQG

9H2 CDR-H3:
(SEQ ID NO: 25)
GGMPVAGPGYFYYYGMDV

9H2 Light chain
(SEQ ID NO: 26)
METPAQLLFLLLLWLPDTTGEIVLTQSPGTLSLSPGERATLSC**RASQSV
SRSYLAWYQQKPGQAPRLLIYGASSRAT**GIPDRFSGSGSGTDFTLTISR
LEPEDFAVYCCQQYGSSPWTFGQGTKVEIKRT

9H2 CDR-L1:
(SEQ ID NO: 27)
RASQSVSRSYLA

9H2 CDR-L2:
(SEQ ID NO: 28)
GASSRAT

9H2 CDR-L3:
(SEQ ID NO: 29)
QQYGSSPWT

Heavy chain immunoglobulin variable
region # 1.0 sequence
(SEQ ID NO: 30)
E VQLLESGGGL VQPGGSLRLS CTASGFTFSS YAMNWVRQAP
GKGLEWVSAI SGSGGTTFYA DSVKGRFTIS RDNSRTTLYL

```
QMNSLRAEDT AVYYCAKDLG WSDSYYYYG MDVWGQGTTV

TVSS;

Light chain immunoglobulin variable
region # 1.0 sequence
                                    (SEQ ID NO: 31)
DIQMTQFP SSLSASVGDR VTITCRASQG IRNDLGWYQQ

KPGKAPKRLI YAASRLHRGV PSRFSGSGSG TEFTLTISSL

QPEDFATYYC LQHNSYPCSF GQGTKLEIKR;
```

Embodiments of the invention include those wherein the polynucleotide (e.g., plasmid) includes a promoter/βGI-IgG intron construct operably linked to more than one immunoglobulin, for example, a combination of any of those set forth herein (e.g., heavy chain Ig. #1.0 and light chain Ig. #1.0; or LCC and HCA; or LCF and HCA; or LCC and HCB).

Plasmids

The present invention provides, in part, isolated plasmids which exhibit high levels of expression of anti-IGF1R heavy and light chains. These plasmids are pAIG1FRLCb2V1 and pAIG1FRLCb2V3. These plasmid encode and direct expression of antibodies including the LCF and the HCA. The sequences of the plasmids are set forth below:

```
pAIG1FRLCB2V1:
                                                            (SEQ ID NO: 35)
   1 GCACTATACA TCAAATATTC CTTATTAACC CCTTTACAAA TTAAAAAGCT AAAGGTACAC

61 AATTTTTGAG CATAGTTATT AATAGCAGAC ACTCTATGCC TGTGTGGAGT AAGAAAAAAC

121 AGTATGTTAT GATTATAACT GTTATGCCTA CTTATAAAGG TTACAGAATA TTTTTCCATA

181 ATTTTCTTGT ATAGCAGTGC AGCTTTTTCC TTTGTGGTGT AAATAGCAAA GCAAGCAAGA

241 GTTCTATTAC TAAACACAGC ATGACTCAAA AAACTTAGCA ATTCTGAAGG AAAGTCCTTG

301 GCGTCTTCTA CCTTTCTCTT CTTTTTTGGA GGAGTAGAAT GTTGAGAGTC AGCAGTAGCC

361 TCATCATCAC TAGATGGCAT TTCTTCTGAG CAAAACAGGT TTTCCTCATT AAAGGCATTC

421 CACCACTGCT CCCATTCATC AGTTCCATAG GTTGGAATCT AAAATACACA AACAATTAGA

481 ATCAGTAGTT TAACACATTA TACACTTAAA AATTTTATAT TTACCTTAGA GCTTTAAATC

541 TCTGTAGGTA GTTTGTCCAA TTATGTCACA CCACAGAAGT AAGGTTCCTT CACAAAGATC

601 GATCTAAAGC CAGCAAAAGT CCCATGGTCT TATAAAAATG CATAGCTTTA GGAGGGGAGC

661 AGAGAACTTG AAAGCATCTT CCTGTTAGTC TTTCTTCTCG TAGACTTCAA ACTTATACTT

721 GATGCCTTTT TCCTCCTGGA CCTCAGAGAG GACGCCTGGG TATTCTGGGA GAAGTTTATA

781 TTTCCCCAAA TCAATTTCTG GGAAAAACGT GTCACTTTCA AATTCCTGCA TGATCCTTGT

841 CACAAAGAGT CTGAGGTGGC CTGGTTGATT CATGGCTTCC TGGTAAACAG AACTGCCTCC

901 GACTATCCAA ACCATGTCTA CTTTACTTGC CAATTCCGGT TGTTCAATAA GTCTTAAGGC

961 ATCATCCAAA CTTTTGGCAA GAAAATGAGC TCCTCGTGGT GGTTCTTTGA GTTCTCTACT

1021 GAGAACTATA TTAATTCTGT CCTTTAAAGG TCGATTCTTC TCAGGAATGG AGAACCAGGT

1081 TTTCCTACCC ATAATCACCA GATTCTGTTT ACCTTCCACT GAAGAGGTTG TGGTCATTCT

1141 TTGGAAGTAC TTGAACTCGT TCCTGAGCGG AGGCCAGGGT AGGTCTCCGT TCTTGCCAAT

1201 CCCCATATTT TGGGACACGG CGACGATGCA GTTCAATGGT CGAACCATGA TGGCAGCGGG

1261 GATAAAATCC TACCAGCCTT CACGCTAGGA TTGCCGTCAA GTTTGGCGCG AAATCGCAGC

1321 CCTGAGCTGT CCCCCCCCCC AAGCTCAGAT CTGAGCTTGG TCCCTATGGT GAGTCCGTTC

1381 CGCTCTTGTG ATGATAGCCA GACAAGAAAG AGACAATACA AGACAAACAC CAAATAGTAG

1441 AAATAGAGAC AAGGGTCACT TATCCGAGGG TCCCTGTTCG GGCGCCAGCT GCCGCAGTCG

1501 GCCGACCTGA GGGTCGCCGG GGTCTGCGGG GGGACCCTCT GGAAAGTGAA GGATAAGTGA

1561 CGAGCGGAGA CGGGATGGCG AACAGACACA AACACACAAG AGGTGAATGT TAGGACTGTT

1621 GCAAGTTTAC TCAAAAAATC AGCACTCTTT TATATCTTGG TTTACATAAG CATTTACATA

1681 AGATTTGGAT AAATTCCAAA AGAACATAGG AAAATAGAAC ACTCAGAGCT CAGATCAGAA

1741 CCTTTGATAC CAAACCAAGT CAGGAAACCA CTTGTCTCAC ATCCTCGTTT TAAGAACAGT
```

-continued

```
1801  TTGTAACCAA AAACTTACTT AAGCCCTGGG AACCGCAAGG TTGGGCCAAT AAAGGCTATT

1861  CATAATAACT CATGCCATGA GTTTTTGCAG AATAATGTTC TATTAGTCCA GCCACTGTCC

1921  CCTCCTTGGT ATGGAAAATC TTTCCCCAAA AGTGCATTCC TGTTCCTAGA TAAATATAAT

1981  CATGTACCTG TTGTTTCATG TCGTCTTTTT CTTCTTGAGA CAACATACAC CAAGGAGGTC

2041  TAGCTCTGGC GAGTCTTTCA CGAAAAGGGA GGGATCTATA TAACACTTTA TAGCCATTGA

2101  CTGTAACCCA CCTATCCCAA TTTAAGTCAT ATCTTCCTGT ATATGGTAAG GGGCATCTG

2161  TTGGTCTGTA GATGTAAGGT CCCCTATAAG TCCCTGGTTG CCACCACCTG TCTCCTATTT

2221  TGACAAAAAC ACTCTTTTTT CCCTTTTTTA CTTCTAGGCC TGTGGTCAAT AGTCCTTGCA

2281  CCTGTTCTTC AATTGAGGTT GAGCGTCTCT TTCTATTTTC TATTCCCATT TCTAACTTCT

2341  GAATTTGAGT AAAAATAGTA CTAAAAGATA ATGATTCATT TCTTAACATA GTAACTAATA

2401  ATCTACCTAT TGGATTGGTC TTATTGGTAA AAATATAATT TTTAGCAAGC ATTCTTATTT

2461  CTATTTCTGA AGGACAAAAT CGATGCGGCT TGTAAGAGGA AGTTGGCTGT GGTCCTTGCC

2521  TCAGGAGGAA GGTCGAGTTC TCCGAATTGT TTAGATTGTA ATCTTGCACA GAAGAGCTAT

2581  TAAAAGAGTC AAGGGTGAGA GCCCTGCGAG CACGAACCGC AACTTCCCCC AATAGCCCCA

2641  GGCAAAGCAG AGCTATGCCA AGTTTGCAGC AGAGAATGAA TATGTCTTTG TCTGATGGGC

2701  TCATCCGTTT GTGCGCAGAC GGGTCGTCCT TGGTGGGAAA CAACCCCTTG GCTGCTTCTC

2761  CCCTAGGTGT AGGACACTCT CGGGAGTTCA ACCATTTCTG CCCAAGCTCA GATCTGAGCT

2821  TTAATGCGGT AGTTTATCAC AGTTAAATTG CTAACGCAGT CAGGCACCGT GTATGAAATC

2881  TAACAATGCG CTCATCGTCA TCCTCGGCAC CGTCACCCTG GATGCTGTAG CATAGGCTT

2941  GGTTATGCCG GTACTGCCGG GCCTCTTGCG GGATATCGTC CATTCCGACA GCATCGCCAG

3001  TCACTATGGC GTGCTGCTAG CGCTCTTCCG CTTCCTCGCT CACTGACTCG CTGCGCTCGG

3061  TCGTTCGGCT GCGGCGAGCG GTATCAGCTC ACTCAAAGGC GGTAATACGG TTATCCACAG

3121  AATCAGGGGA TAACGCAGGA AAGAACATGT GAGCAAAAGG CCAGCAAAAG GCCAGGAACC

3181  GTAAAAAGGC CGCGTTGCTG GCGTTTTTCC ATAGGCTCCG CCCCCCTGAC GAGCATCACA

3241  AAAATCGACG CTCAAGTCAG AGGTGGCGAA ACCCGACAGG ACTATAAAGA TACCAGGCGT

3301  TTCCCCCTGG AAGCTCCCTC GTGCGCTCTC CTGTTCCGAC CCTGCCGCTT ACCGGATACC

3361  TGTCCGCCTT TCTCCCTTCG GGAAGCGTGG CGCTTTCTCA TAGCTCACGC TGTAGGTATC

3421  TCAGTTCGGT GTAGGTCGTT CGCTCCAAGC TGGGCTGTGT GCACGAACCC CCCGTTCAGC

3481  CCGACCGCTG CGCCTTATCC GGTAACTATC GTCTTGAGTC AACCCGGTA AGACACGACT

3541  TATCGCCACT GGCAGCAGCC ACTGGTAACA GGATTAGCAG AGCGAGGTAT GTAGGCGGTG

3601  CTACAGAGTT CTTGAAGTGG TGGCCTAACT ACGGCTACAC TAGAAGGACA GTATTTGGTA

3661  TCTGCGCTCT GCTGAAGCCA GTTACCTTCG GAAAAAGAGT TGGTAGCTCT TGATCCGGCA

3721  AACAAACCAC CGCTGGTAGC GGTGGTTTTT TTGTTTGCAA GCAGCAGATT ACGCGCAGAA

3781  AAAAAGGATC TCAAGAAGAT CCTTTGATCT TTTCTACGGG GTCTGACGCT CAGTGGAACG

3841  AAAACTCACG TTAAGGGATT TTGGTCATGA GATTATCAAA AAGGATCTTC ACCTAGATCC

3901  TTTTAAATTA AAAATGAAGT TTTAAATCAA TCTAAAGTAT ATATGAGTAA ACTTGGTCTG

3961  ACAGTTACCA ATGCTTAATC AGTGAGGCAC CTATCTCAGC GATCTGTCTA TTTCGTTCAT

4021  CCATAGTTGC CTGACTCCCC GTCGTGTAGA TAACTACGAT ACGGGAGGGC TTACCATCTG

4081  GCCCCAGTGC TGCAATGATA CCGCGAGACC CACGCTCACC GGCTCCAGAT TTATCAGCAA

4141  TAAACCAGCC AGCCGGAAGG GCCGAGCGCA GAAGTGGTCC TGCAACTTTA TCCGCCTCCA

4201  TCCAGTCTAT TAATTGTTGC CGGGAAGCTA GAGTAAGTAG TTCGCCAGTT AATAGTTTGC
```

-continued

```
4261  GCAACGTTGT TGCCATTGCT ACAGGCATCG TGGTGTCACG CTCGTCGTTT GGTATGGCTT

4321  CATTCAGCTC CGGTTCCCAA CGATCAAGGC GAGTTACATG ATCCCCCATG TTGTGCAAAA

4381  AAGCGGTTAG CTCCTTCGGT CCTCCGATCG TTGTCAGAAG TAAGTTGGCC GCAGTGTTAT

4441  CACTCATGGT TATGGCAGCA CTGCATAATT CTCTTACTGT CATGCCATCC GTAAGATGCT

4501  TTTCTGTGAC TGGTGAGTAC TCAACCAAGT CATTCTGAGA ATAGTGTATG CGGCGACCGA

4561  GTTGCTCTTG CCCGGCGTCA ACACGGGATA ATACCGCGCC ACATAGCAGA ACTTTAAAAG

4621  TGCTCATCAT TGGAAAACGT TCTTCGGGGC GAAAACTCTC AAGGATCTTA CCGCTGTTGA

4681  GATCCAGTTC GATGTAACCC ACTCGTGCAC CCAACTGATC TTCAGCATCT TTTACTTTCA

4741  CCAGCGTTTC TGGGTGAGCA AAAACAGGAA GGCAAAATGC CGCAAAAAAG GGAATAAGGG

4801  CGACACGGAA ATGTTGAATA CTCATACTCT TCCTTTTTCA ATATTATTGA AGCATTTATC

4861  AGGGTTATTG TCTCATGAGC GGATACATAT TTGAATGTAT TTAGAAAAAT AAACAAATAG

4921  GGGTTCCGCG CACATTTCCC CGAAAAGTGC CACCTGACGT CTAAGAAACC ATTATTATCA

4981  TGACATTAAC CTATAAAAAT AGGCGTATCA CGAGGCCCTT TCGTCTTCAA GAATTGTCTA

5041  GAGGCGCGCC GTTTAAACCC TCAGCTACCG ATGTACGGGC CAGATATACG CGTTGACATT

5101  GATTATTGAC TAGTTATTAA TAGTAATCAA TTACGGGGTC ATTAGTTCAT AGCCCATATA

5161  TGGAGTTCCG CGTTACATAA CTTACGGTAA ATGGCCCGCC TGGCTGACCG CCCAACGACC

5221  CCCGCCCATT GACGTCAATA ATGACGTATG TTCCCATAGT AACGCCAATA GGGACTTTCC

5281  ATTGACGTCA ATGGGTGGAG TATTTACGGT AAACTGCCCA CTTGGCAGTA CATCAAGTGT

5341  ATCATATGCC AAGTACGCCC CCTATTGACG TCAATGACGG TAAATGGCCC GCCTGGCATT

5401  ATGCCCAGTA CATGACCTTA TGGGACTTTC CTACTTGGCA GTACATCTAC GTATTAGTCA

5461  TCGCTATTAC CATGGTGATG CGGTTTTGGC AGTACATCAA TGGGCGTGGA TAGCGGTTTG

5521  ACTCACGGGG ATTTCCAAGT CTCCACCCCA TTGACGTCAA TGGGAGTTTG TTTTGGCACC

5581  AAAATCAACG GGACTTTCCA AAATGTCGTA ACAACTCCGC CCTATTGACG CAAATGGGCG

5641  GTAGGCGTGT ACGGTGGGAG GTCTATATAA GCAGAGCTCT CTGGCTAACT AGAGAACCCA

5701  CTGCTTACTG GCTTATCGAA ATTAATACGA CTCACTATAG CAATTGCACG TGTGGCCACA

5761  GGTAAGTTTA AAGCTCAGGT CGAGACCGGG CCTTTGTCCG GCGCTCCCTT GGAGCCTACC

5821  TAGACTCAGC CGGCTCTCCA CGCTTTGCCT GACCCTGCTT GCTCAACTCT ACGTCTTTGT

5881  TTCGTTTTCT GTTCCTTTCT CTCCACAGGC TTAAGCTTGG TACCGAGCTC GGATCCACTA

5941  GTCCAGTGTG GTGGAATTCG CCCTTATGGA GTTTGGGCTG AGCTGGGTTT TCCTTGTTGC

6001  TATATTAAAA GGTGTCCAGT GTGAGGTTCA GCTGGTGCAG TCTGGGGGAG GCTTGGTAAA

6061  GCCTGGGGGG TCCCTGAGAC TCTCCTGTGC AGCCTCTGGA TTCACCTTCA GTAGCTTTGC

6121  TATGCACTGG GTTCGCCAGG CTCCAGGAAA AGGTCTGGAG TGGATATCAG TTATTGATAC

6181  TCGTGGTGCC ACATACTATG CAGACTCCGT GAAGGGCCGA TTCACCATCT CCAGAGACAA

6241  TGCCAAGAAC TCCTTGTATC TTCAAATGAA CAGCCTGAGA GCCGAGGACA CTGCTGTGTA

6301  TTACTGTGCA AGACTGGGGA ACTTCTACTA CGGTATGGAC GTCTGGGGCC AAGGGACCAC

6361  GGTCACCGTC TCCTCAGCTT CCACCAAGGG CCCATCGGTC TTCCCCCTGG CACCCTCCTC

6421  CAAGAGCACC TCTGGGGGCA CAGCGGCCCT GGGCTGCCTG GTCAAGGACT ACTTCCCCGA

6481  ACCGGTGACG GTGTCGTGGA ACTCAGGCGC CCTGACCAGC GGCGTGCACA CCTTCCCGGC

6541  TGTCCTACAG TCCTCAGGAC TCTACTCCCT CAGCAGCGTG GTGACCGTGC CCTCCAGCAG

6601  CTTGGGCACC CAGACCTACA TCTGCAACGT GAATCACAAG CCCAGCAACA CCAAGGTGGA
```

```
-continued
6661  CAAGAAAGTT GAGCCCAAAT CTTGTGACAA AACTCACACA TGCCCACCGT GCCCAGCACC

6721  TGAACTCCTG GGGGGACCGT CAGTCTTCCT CTTCCCCCCA AAACCCAAGG ACACCCTCAT

6781  GATCTCCCGG ACCCCTGAGG TCACATGCGT GGTGGTGGAC GTGAGCCACG AAGACCCTGA

6841  GGTCAAGTTC AACTGGTACG TGGACGGCGT GGAGGTGCAT AATGCCAAGA CAAAGCCGCG

6901  GGAGGAGCAG TACAACAGCA CGTACCGTGT GGTCAGCGTC CTCACCGTCC TGCACCAGGA

6961  CTGGCTGAAT GGCAAGGAGT ACAAGTGCAA GGTCTCCAAC AAAGCCCTCC CAGCCCCCAT

7021  CGAGAAAACC ATCTCCAAAG CCAAAGGGCA GCCCCGAGAA CCACAGGTGT ACACCCTGCC

7081  CCCATCCCGG GATGAGCTGA CCAAGAACCA GGTCAGCCTG ACCTGCCTGG TCAAAGGCTT

7141  CTATCCCAGC GACATCGCCG TGGAGTGGGA GAGCAATGGG CAGCCGGAGA ACAACTACAA

7201  GACCACGCCT CCCGTGCTGG ACTCCGACGG CTCCTTCTTC CTCTACAGCA AGCTCACCGT

7261  GGACAAGAGC AGGTGGCAGC AGGGGAACGT CTTCTCATGC TCCGTGATGC ATGAGGCTCT

7321  GCACAACCAC TACACGCAGA AGAGCCTCTC CCTGTCTCCG GGTAAATGAA TCGATGATTC

7381  TAGATACGGG TCCGGAGGAT CCAGATCCCC CTCGCTTTCT TGCTGTCCAA TTTCTATTAA

7441  AGGTTCCTTT GTTCCCTAAG TCCAACTACT AAACTGGGGG ATATTATGAA GGGCCTTGAG

7501  CATCTGGATT CTGCCTAATA AAAAACATTT ATTTTCATTG CAATGATGTA TTTAAATTAT

7561  TTCTGAATAT TTTACTAAAA AGGGAATGTG GGAGGTCAGT GCATTTAAAA CATAAAGAAA

7621  TCAAGAGGGG GATCTGTCGA CAAGCTCTAG AGAGCTCACG CGTTGATCAT GTACAGGCCG

7681  GCCAAGCTTT CGACTAGCTT GGCACGCCAG AAATCCGCGC GGTGGTTTTT GGGGGTCGGG

7741  GGTGTTTGGC AGCCACAGAC GCCCGGTGTT CGTGTCGCGC CAGTACATGC GGTCCATGCC

7801  CAGGCCATCC AAAAACCATG GGTCTGTCTG CTCAGTCCAG TCGTGGACCT GACCCCACGC

7861  AACGCCCAAA ATAATAACCC CCACGAACCA TAAACCATTC CCATGGGGG ACCCCGTCCC

7921  TAACCCACGG GGCCAGTGGC TATGGCAGGG CCTGCCGCCC GACGTTGGC TGCGAGCCCT

7981  GGGCCTTCAC CCGAACTTGG GGGGTGGGGG GGGGAAAAGG AAGAAACGCG GGCGTATTGG

8041  CCCCAATGGG GTCTCGGTGG GGTATCGACA GAGTGCCAGC CCTGGGACCG AACCCCGCGT

8101  TTATGAACAA ACGACCCAAC ACCCGTGCGT TTTATTCTGT CTTTTTATTG CCGTCATAGC

8161  GCGGGTTCCT TCCGGTATTG TCTCCTTCCG TGTTTCAGTT AGCCTCCCCC ATCTCCCGAT

8221  CCGGACGAGT GCTGGGGCGT CGGTTTCCAC TATCGGCGAG TACTTCTACA CAGCCATCGG

8281  TCCAGACGGC CGCGCTTCTG CGGGCGATTT GTGTACGCCC GACAGTCCCG GCTCCGGATC

8341  GGACGATTGC GTCGCATCGA CCCTGCGCCC AAGCTGCATC ATCGAAATTG CCGTCAACCA

8401  AGCTCTGATA GAGTTGGTCA AGACCAATGC GGAGCATATA CGCCCGGAGC CGCGGCGATC

8461  CTGCAAGCTC CGGATGCCTC CGCTCGAAGT AGCGCGTCTG CTGCTCCATA CAAGCCAACC

8521  ACGGCCTCCA GAAGAAGATG TTGGCGACCT CGTATTGGGA ATCCCCGAAC ATCGCCTCGC

8581  TCCAGTCAAT GACCGCTGTT ATGCGGCCAT TGTCCGTCAG GACATTGTTG GAGCCGAAAT

8641  CCGCGTGCAC GAGGTGCCGG ACTTCGGGGC AGTCCTCGGC CCAAAGCATC AGCTCATCGA

8701  GAGCCTGCGC GACGGACGCA CTGACGGTGT CGTCCATCAC AGTTTGCCAG TGATACACAT

8761  GGGGATCAGC AATCGCGCAT ATGAAATCAC GCCATGTAGT GTATTGACCG ATTCCTTGCG

8821  GTCCGAATGG GCCGAACCCG CTCGTCTGGC TAAGATCGGC CGCAGCGATC GCATCCATGG

8881  CCTCCGCGAC CGGCTGCAGA ACAGCGGGCA GTTCGGTTTC AGGCAGGTCT TGCAACGTGA

8941  CACCCTGTGC ACGGCGGGAG ATGCAATAGG TCAGGCTCTC GCTGAATTCC CCAATGTCAA

9001  GCACTTCCGG AATCGGGAGC GCGGCCGATG CAAAGTGCCG ATAAACATAA CGATCTTTGT

9061  AGAAACCATC GGCGCAGCTA TTTACCCGCA GGACATATCC ACGCCCTCCT ACATCGAAGC
```

-continued

```
 9121  TGAAAGCACG AGATTCTTCG CCCTCCGAGA GCTGCATCAG GTCGGAGACG CTGTCGAACT
 9181  TTTCGATCAG AAACTTCTCG ACAGACGTCG CGGTGAGTTC AGGCTTTTTC ATATCTCATT
 9241  GCCCCCCGGG ATCTGCGGCA CGCTGTTGAC GCTGTTAAGC GGGTCGCTGC AGGGTCGCTC
 9301  GGTGTTCGAG GCCACACGCG TCACCTTAAT ATGCGAAGTG GACCTCGGAC CGCGCCGCCC
 9361  CGACTGCATC TGCGTGTTCG AATTCGCCAA TGACAAGACG CTGGGCGGGG TTTGTGTCAT
 9421  CATAGAACTA AAGACATGCA AATATATTTC TTCCGGGGAC ACCGCCAGCA ACGCGAGCA
 9481  ACGGGCCACG GGGATGAAGC AGGGCGGCAC CTCGCTAACG GATTCACCAC TCCAAGAATT
 9541  GGAGCCAATC AATTCTTGCG GAGAACTGTG AATGCGCAAA CCAACCCTTG GCAGAACATA
 9601  TCCATCGCGT CCGCCATCTC CAGCAGCCGC ACGCGGCGCA TCTCGGGGCC GACGCGCTGG
 9661  GCTACGTCTT GCTGGCGTTC GCACAGGCCG GCCAGCGCGC GGCCGGCCGG TACCACGCGT
 9721  TGGCCACATA TGGCGGCCGC TCGCGATTAA TTAATCGCGA TGGCCACATA TGGAGCTCTC
 9781  TAGAGCTTGT CGACAGATCC CCCTCTTCAT TTCTTTATGT TTTAAATGCA CTGACCTCCC
 9841  ACATTCCCTT TTTAGTAAAA TATTCAGAAA TAATTTAAAT ACATCATTGC AATGAAAATA
 9901  AATGTTTTTT ATTAGGCAGA ATCCAGATGC TCAAGGCCCT TCATAATATC CCCCAGTTTA
 9961  GTAGTTGGAC TTAGGGAACA AAGGAACCTT TAATAGAAAT TGGACAGCAA GAAAGCGAGG
10021  GGGATCTGGA TCCTCCGGAG GGCCCCTTCT CCCTCTAACA CTCTCCCCTG TTGAAGCTCT
10081  TTGTGACGGG CGAGCTCAGG CCCTGATGGG TGACTTCGCA GGCGTAGACT TTGTGTTTCT
10141  CGTAGTCTGC TTTGCTCAGC GTCAGGGTGC TGCTGAGGCT GTAGGTGCTG TCCTTGCTGT
10201  CCTGCTCTGT GACACTCTCC TGGGAGTTAC CCGATTGGAG GGCGTTATCC ACCTTCCACT
10261  GTACTTTGGC CTCTCTGGGA TAGAAGTTAT TCAGCAGGCA CACAACAGAG GCAGTTCCAG
10321  ATTTCAACTG CTCATCAGAT GGCGGGAAGA TGAAGACAGA TGGTGCAGCC ACTGTACGTT
10381  TGATCTCCAC CTTGGTCCCT TGGCCGAAAG TGTGAGGTAA ACGACTACTC TGATGACAGT
10441  AATACACTGC GAAATCTTCA GGCTCCAGTC TACTGATGGT GAGGGTGAAA TCTGTCCCAG
10501  ATCCACTGCC ACTGAACCTA TCGGGGATCC CTGAGAGGGA CTGGGATGCA TACTTGATGA
10561  GAAGCCTTGG AGCCTGACCT GGTTTCTGCT GGTACCAGTG TAAGCTACTA CCAATGCTCT
10621  GACTGGCCCG GCAGGAGAGG GTGGCTCTCT CGCCTGGAGA CACAGACAGG GTACCTGGGC
10681  TCTGAGTCAG CACAATTTCA CCCCTGGAGG CTGGAACCCA GAGCAGCAGA ACCCAATGA
10741  GTTGTGATGG CGACATGTTA AACGCTAGAA TTCTTAAGCC TGTGGAGAGA AAGGAACAGA
10801  AAACGAAACA AAGACGTAGA GTTGAGCAAG CAGGGTCAGG CAAAGCGTGG AGAGCCGGCT
10861  GAGTCTAGGT AGGCTCCAAG GGAGCGCCGG ACAAAGGCCC GGTCTCGACC TGAGCTTTAA
10921  ACTTACCTGT GGCCACACGT GCAATTGCTA TAGTGAGTCG TATTAATTTC GATAAGCCAG
10981  TAAGCAGTGG GTTCTCTAGT TAGCCAGAGA GCTCTGCTTA TATAGACCTC CCACCGTACA
11041  CGCCTACCGC CCATTTGCGT CAATGGGGCG GAGTTGTTAC GACATTTTGG AAAGTCCCGT
11101  TGATTTTGGT GCCAAAACAA ACTCCCATTG ACGTCAATGG GGTGGAGACT TGGAAATCCC
11161  CGTGAGTCAA ACCGCTATCC ACGCCCATTG ATGTACTGCC AAAACCGCAT CACCATGGTA
11221  ATAGCGATGA CTAATACGTA GATGTACTGC CAAGTAGGAA AGTCCCATAA GGTCATGTAC
11281  TGGGCATAAT GCCAGGCGGG CCATTTACCG TCATTGACGT CAATAGGGGG CGTACTTGGC
11341  ATATGATACA CTTGATGTAC TGCCAAGTGG GCAGTTTACC GTAAATACTC CACCCATTGA
11401  CGTCAATGGA AAGTCCCTAT TGGCGTTACT ATGGGAACAT ACGTCATTAT TGACGTCAAT
11461  GGGCGGGGGT CGTTGGGCGG TCAGCCAGGC GGGCCATTTA CCGTAAGTTA TGTAACGCGG
```

-continued

```
11521  AACTCCATAT ATGGGCTATG AACTAATGAC CCCGTAATTG ATTACTATTA ATAACTAGTC

11581  AATAATCAAT GTCAACGCGT ATATCTGGCC CGTACATCG TAACTAGTCG ACCGCCGCG

11641  GACTAGTGCC CGGGCCACCG GTGCTCGAAG CTTGGATCGA TCCAGACATG ATAAGATACA

11701  TTGATGAGTT TGGACAAACC ACAACTAGAA TGCAGTGAAA AAAATGCTTT ATTTGTGAAA

11761  TTTGTGATGC TATTGCTTTA TTTGTAACCA TTATAAGCTG CAATAAACAA GTTAACAACA

11821  ACAATTGCAT TCATTTTATG TTTCAGGTTC AGGGGAGGT GTGGGAGGTT TTTTAAAGCA

11881  AGTAAAACCT CTACAAATGT GGTATGGCTG ATTATGATCT CTAGTCAAG
``` pAIG1FRLCB2V3:
(SEQ ID NO: 36)

```
   1  GCACTATACA TCAAATATTC CTTATTAACC CCTTTACAAA TTAAAAAGCT AAAGGTACAC

61  AATTTTTGAG CATAGTTATT AATAGCAGAC ACTCTATGCC TGTGTGGAGT AAGAAAAAAC

121  AGTATGTTAT GATTATAACT GTTATGCCTA CTTATAAAGG TTACAGAATA TTTTTCCATA

181  ATTTTCTTGT ATAGCAGTGC AGCTTTTTCC TTTGTGGTGT AAATAGCAAA GCAAGCAAGA

241  GTTCTATTAC TAAACACAGC ATGACTCAAA AAACTTAGCA ATTCTGAAGG AAAGTCCTTG

301  GGGTCTTCTA CCTTTCTCTT CTTTTTTGGA GGAGTAGAAT GTTGAGAGTC AGCAGTAGCC

361  TCATCATCAC TAGATGGCAT TTCTTCTGAG CAAAACAGGT TTCCTCATT AAAGGCATTC

421  CACCACTGCT CCCATTCATC AGTTCCATAG GTTGGAATCT AAAATACACA AACAATTAGA

481  ATCAGTAGTT TAACACATTA TACACTTAAA AATTTTATAT TTACCTTAGA GCTTTAAATC

541  TCTGTAGGTA GTTTGTCCAA TTATGTCACA CCACAGAAGT AAGGTTCCTT CACAAAGATC

601  GATCTAAAGC CAGCAAAAGT CCCATGGTCT TATAAAAATG CATAGCTTTA GGAGGGGAGC

661  AGAGAACTTG AAAGCATCTT CCTGTTAGTC TTTCTTCTCG TAGACTTCAA ACTTATACTT

721  GATGCCTTTT TCCTCCTGGA CCTCAGAGAG GACGCCTGGG TATTCTGGGA GAAGTTTATA

781  TTTCCCCAAA TCAATTTCTG GGAAAAACGT GTCACTTTCA AATTCCTGCA TGATCCTTGT

841  CACAAAGAGT CTGAGGTGGC CTGGTTGATT CATGGCTTCC TGGTAAACAG AACTGCCTCC

901  GACTATCCAA ACCATGTCTA CTTTACTTGC CAATTCCGGT TGTTCAATAA GTCTTAAGGC

961  ATCATCCAAA CTTTTGGCAA GAAAATGAGC TCCTCGTGGT GGTTCTTTGA GTTCTCTACT

1021  GAGAACTATA TTAATTCTGT CCTTTAAAGG TCGATTCTTC TCAGGAATGG AGAACCAGGT

1081  TTTCCTACCC ATAATCACCA GATTCTGTTT ACCTTCCACT GAAGAGGTTG TGGTCATTCT

1141  TTGGAAGTAC TTGAACTCGT TCCTGAGCGG AGGCCAGGGT AGGTCTCCGT TCTTGCCAAT

1201  CCCCATATTT TGGGACACGG CGACGATGCA GTTCAATGGT CGAACCATGA TGGCAGCGGG

1261  GATAAAATCC TACCAGCCTT CACGCTAGGA TTGCCGTCAA GTTTGGCGCG AAATCGCAGC

1321  CCTGAGCTGT CCCCCCCCCC AAGCTCAGAT CTGAGCTTGG TCCCTATGGT GAGTCCGTTC

1381  CGCTCTTGTG ATGATAGCCA GACAAGAAAG AGACAATACA AGACAAACAC CAAATAGTAG

1441  AAATAGAGAC AAGGGTCACT TATCCGAGGG TCCCTGTTCG GGCGCCAGCT GCCGCAGTCG

1501  GCCGACCTGA GGGTCGCCGG GGTCTGCGGG GGACCCTCT GGAAAGTGAA GGATAAGTGA

1561  CGAGCGGAGA CGGGATGGCG AACAGACACA AACACACAAG AGGTGAATGT TAGGACTGTT

1621  GCAAGTTTAC TCAAAAAATC AGCACTCTTT TATATCTTGG TTTACATAAG CATTTACATA

1681  AGATTTGGAT AAATTCCAAA AGAACATAGG AAAATAGAAC ACTCAGAGCT CAGATCAGAA

1741  CCTTTGATAC CAAACCAAGT CAGGAAACCA CTTGTCTCAC ATCCTCGTTT TAAGAACAGT

1801  TTGTAACCAA AAACTTACTT AAGCCCTGGG AACCGCAAGG TTGGGCCAAT AAAGGCTATT

1861  CATAATAACT CATGCCATGA GTTTTTGCAG AATAATGTTC TATTAGTCCA GCCACTGTCC

1921  CCTCCTTGGT ATGGAAAATC TTTCCCCAAA AGTGCATTCC TGTTCCTAGA TAAATATAAT
```

-continued

```
1981  CATGTACCTG TTGTTTCATG TCGTCTTTTT CTTCTTGAGA CAACATACAC CAAGGAGGTC

2041  TAGCTCTGGC GAGTCTTTCA CGAAAAGGGA GGGATCTATA TAACACTTTA TAGCCATTGA

2101  CTGTAACCCA CCTATCCCAA TTTAAGTCAT ATCTTCCTGT ATATGGTAAG GGGGCATCTG

2161  TTGGTCTGTA GATGTAAGGT CCCCTATAAG TCCCTGGTTG CCACCACCTG TCTCCTATTT

2221  TGACAAAAAC ACTCTTTTTT CCCTTTTTTA CTTCTAGGCC TGTGGTCAAT AGTCCTTGCA

2281  CCTGTTCTTC AATTGAGGTT GAGCGTCTCT TTCTATTTTC TATTCCCATT TCTAACTTCT

2341  GAATTTGAGT AAAAATAGTA CTAAAAGATA ATGATTCATT TCTTAACATA GTAACTAATA

2401  ATCTACCTAT TGGATTGGTC TTATTGGTAA AAATATAATT TTTAGCAAGC ATTCTTATTT

2461  CTATTTCTGA AGGACAAAAT CCATGCGGCT TGTAAGAGGA AGTTGGCTGT GGTCCTTGCC

2521  TCAGGAGGAA GGTCGAGTTC TCCGAATTGT TTAGATTGTA ATCTTGCACA AAGAGCTAT

2581  TAAAAGAGTC AAGGGTGAGA GCCCTGCGAG CACGAACCGC AACTTCCCCC AATAGCCCCA

2641  GGCAAAGCAG AGCTATGCCA AGTTTGCAGC AGAGAATGAA TATGTCTTTG TCTGATGGGC

2701  TCATCCGTTT GTGCGCAGAC GGGTCGTCCT TGGTGGGAAA CAACCCCTTG GCTGCTTCTC

2761  CCCTAGGTGT AGGACACTCT CGGGAGTTCA ACCATTTCTG CCCAAGCTCA GATCTGAGCT

2821  TTAATGCGGT AGTTTATCAC AGTTAAATTG CTAACGCAGT CAGGCACCGT GTATGAAATC

2881  TAACAATGCG CTCATCGTCA TCCTCGGCAC CGTCACCCTG GATGCTGTAG GCATAGGCTT

2941  GGTTATGCCG GTACTGCCGG GCCTCTTGCG GGATATCGTC CATTCCGACA GCATCGCCAG

3001  TCACTATGGC GTGCTGCTAG CGCTCTTCCG CTTCCTCGCT CACTGACTCG CTGCGCTCGG

3061  TCGTTCGGCT GCGGCGAGCG GTATCAGCTC ACTCAAAGGC GGTAATACGG TTATCCACAG

3121  AATCAGGGGA TAACGCAGGA AAGAACATGT GAGCAAAAGG CCAGCAAAAG GCCAGGAACC

3181  GTAAAAAGGC CGCGTTGCTG GCGTTTTTCC ATAGGCTCCG CCCCCCTGAC GAGCATCACA

3241  AAAATCGACG CTCAAGTCAG AGGTGGCGAA ACCCGACAGG ACTATAAAGA TACCAGGCGT

3301  TTCCCCCTGG AAGCTCCCTC GTGCGCTCTC CTGTTCCGAC CCTGCCGCTT ACCGGATACC

3361  TGTCCGCCTT TCTCCCTTCG GGAAGCGTGG CGCTTTCTCA TAGCTCACGC TGTAGGTATC

3421  TCAGTTCGGT GTAGGTCGTT CGCTCCAAGC TGGGCTGTGT GCACGAACCC CCCGTTCAGC

3481  CCGACCGCTG CGCCTTATCC GGTAACTATC GTCTTGAGTC AACCCGGTA AGACACGACT

3541  TATCGCCACT GGCAGCAGCC ACTGGTAACA GGATTAGCAG AGCGAGGTAT GTAGGCGGTG

3601  CTACAGAGTT CTTGAAGTGG TGGCCTAACT ACGGCTACAC TAGAAGGACA GTATTTGGTA

3661  TCTGCGCTCT GCTGAAGCCA GTTACCTTCG GAAAAAGAGT TGGTAGCTCT TGATCCGGCA

3721  AACAAACCAC CGCTGGTAGC GGTGGTTTTT TTGTTTGCAA GCAGCAGATT ACGCGCAGAA

3781  AAAAAGGATC TCAAGAAGAT CCTTTGATCT TTTCTACGGG GTCTGACGCT CAGTGGAACG

3841  AAAACTCACG TTAAGGGATT TTGGTCATGA GATTATCAAA AAGGATCTTC ACCTAGATCC

3901  TTTTAAATTA AAAATGAAGT TTTAAATCAA TCTAAAGTAT ATATGAGTAA ACTTGGTCTG

3961  ACAGTTACCA ATGCTTAATC AGTGAGGCAC CTATCTCAGC GATCTGTCTA TTTCGTTCAT

4021  CCATAGTTGC CTGACTCCCC GTCGTGTAGA TAACTACGAT ACGGGAGGGC TTACCATCTG

4081  GCCCCAGTGC TGCAATGATA CCGCGAGACC CACGCTCACC GGCTCCAGAT TTATCAGCAA

4141  TAAACCAGCC AGCCGGAAGG GCCGAGCGCA GAAGTGGTCC TGCAACTTTA TCCGCCTCCA

4201  TCCAGTCTAT TAATTGTTGC CGGGAAGCTA GAGTAAGTAG TTCGCCAGTT AATAGTTTGC

4261  GCAACGTTGT TGCCATTGCT ACAGGCATCG TGGTGTCACG CTCGTCGTTT GGTATGGCTT

4321  CATTCAGCTC CGGTTCCCAA CGATCAAGGC GAGTTACATG ATCCCCCATG TTGTGCAAAA
```

-continued

```
4381  AAGCGGTTAG CTCCTTCGGT CCTCCGATCG TTGTCAGAAG TAAGTTGGCC GCAGTGTTAT
4441  CACTCATGGT TATGGCAGCA CTGCATAATT CTCTTACTGT CATGCCATCC GTAAGATGCT
4501  TTTCTGTGAC TGGTGAGTAC TCAACCAAGT CATTCTGAGA ATAGTGTATG CGGCGACCGA
4561  GTTGCTCTTG CCCGGCGTCA ACACGGGATA ATACCGCGCC ACATAGCAGA ACTTTAAAAG
4621  TGCTCATCAT TGGAAAACGT TCTTCGGGGC GAAAACTCTC AAGGATCTTA CCGCTGTTGA
4681  GATCCAGTTC GATGTAACCC ACTCGTGCAC CCAACTGATC TTCAGCATCT TTTACTTTCA
4741  CCAGCGTTTC TGGGTGAGCA AAAACAGGAA GGCAAAATGC CGCAAAAAAG GGAATAAGGG
4801  CGACACGGAA ATGTTGAATA CTCATACTCT TCCTTTTTCA ATATTATTGA AGCATTTATC
4861  AGGGTTATTG TCTCATGAGC GGATACATAT TTGAATGTAT TTAGAAAAAT AAACAAATAG
4921  GGGTTCCGCG CACATTTCCC CGAAAAGTGC CACCTGACGT CTAAGAAACC ATTATTATCA
4981  TGACATTAAC CTATAAAAAT AGGCGTATCA CGAGGCCCTT TCGTCTTCAA GAATTGTCTA
5041  GAGGCGCGCT GGCCGGCCTG TGCGAACGCC AGCAAGACGT AGCCCAGCGC GTCGGCCCCG
5101  AGATGCGCCG CGTGCGGCTG CTGGAGATGG CGGACGCGAT GGATATGTTC TGCCAAGGGT
5161  TGGTTTGCGC ATTCACAGTT CTCCGCAAGA ATTGATTGGC TCCAATTCTT GGAGTGGTGA
5221  ATCCGTTAGC GAGGTGCCGC CCTGCTTCAT CCCCGTGGCC CGTTGCTCGC GTTTGCTGGC
5281  GGTGTCCCCG GAAGAAATAT ATTTGCATGT CTTTAGTTCT ATGATGACAC AAACCCCGCC
5341  CAGCGTCTTG TCATTGGCGA ATTCGAACAC GCAGATGCAG TCGGGGCGGC GCGGTCCGAG
5401  GTCCACTTCG CATATTAAGG TGACGCGTGT GGCCTCGAAC ACCGAGCGAC CCTGCAGCGA
5461  CCCGCTTAAC AGCGTCAACA GCGTCCCGCA GATCCCGGGG GGCAATGAGA TATGAAAAAG
5521  CCTGAACTCA CCGCGACGTC TGTCGAGAAG TTTCTGATCG AAAAGTTCGA CAGCGTCTCC
5581  GACCTGATGC AGCTCTCGGA GGGCGAAGAA TCTCGTGCTT TCAGCTTCGA TGTAGGAGGG
5641  CGTGGATATG TCCTGCGGGT AAATAGCTGC GCCGATGGTT TCTACAAAGA TCGTTATGTT
5701  TATCGGCACT TTGCATCGGC CGCGCTCCCG ATTCCGGAAG TGCTTGACAT TGGGGAATTC
5761  AGCGAGAGCC TGACCTATTG CATCTCCCGC CGTGCACAGG GTGTCACGTT GCAAGACCTG
5821  CCTGAAACCG AACTGCCCGC TGTTCTGCAG CCGGTCGCGG AGGCCATGGA TGCGATCGCT
5881  GCGGCCGATC TTAGCCAGAC GAGCGGGTTC GGCCCATTCG GACCGCAAGG AATCGGTCAA
5941  TACACTACAT GGCGTGATTT CATATGCGCG ATTGCTGATC CCCATGTGTA TCACTGGCAA
6001  ACTGTGATGG ACGACACCGT CAGTGCGTCC GTCGCGCAGG CTCTCGATGA GCTGATGCTT
6061  TGGGCCGAGG ACTGCCCCGA AGTCCGGCAC CTCGTGCACG CGGATTTCGG CTCCAACAAT
6121  GTCCTGACGG ACAATGGCCG CATAACAGCG GTCATTGACT GGAGCGAGGC GATGTTCGGG
6181  GATTCCCAAT ACGAGGTCGC CAACATCTTC TTCTGGAGGC CGTGGTTGGC TTGTATGGAG
6241  CAGCAGACGC GCTACTTCGA GCGGAGGCAT CCGGAGCTTG CAGCATCGCC GCGGCTCCGG
6301  GCGTATATGC TCCGCATTGG TCTTGACCAA CTCTATCAGA GCTTGGTTGA CGGCAATTTC
6361  GATGATGCAG CTTGGGCGCA GGGTCGATGC GACGCAATCG TCCGATCCGG AGCCGGGACT
6421  GTCGGGCGTA CACAAATCGC CCGCAGAAGC GCGGCCGTCT GGACCGATGC CTGTGTAGAA
6481  GTACTCGCCG ATAGTGGAAA CCGACGCCCC AGCACTCGTC CGGATCGGGA GATGGGGGAG
6541  GCTAACTGAA ACACGGAAGG AGACAATACC GGAAGGAACC CGCGCTATGA CGGCAATAAA
6601  AAGACAGAAT AAAACGCACG GTGTTGGGT CGTTTGTTCA TAAACGCGGG GTTCGGTCCC
6661  AGGGCTGGCA CTCTGTCGAT ACCCCACCGA GACCCCATTG GGGCCAATAC GCCCGCGTTT
6721  CTTCCTTTTC CCCACCCCAC CCCCCAAGTT CGGGTGAAGG CCCAGGGCTC GCAGCCAACG
6781  TCGGGCGGC AGGCCCTGCC ATAGCCACTG GCCCCGTGGG TTAGGGACGG GGTCCCCCAT
```

-continued

```
6841  GGGGAATGGT TTATGGTTCG TGGGGGTTAT TATTTTGGGC GTTGCGTGGG GTCAGGTCCA
6901  CGACTGGACT GAGCAGACAG ACCCATGGTT TTTGGATGGC CTGGGCATGG ACCGCATGTA
6961  CTGGCGCGAC ACGAACACCG GGCGTCTGTG GCTGCCAAAC ACCCCGACC  CCCAAAAACC
7021  ACCGCGCGGA TTTCTGGCGT GCCAAGCTAG TCGAAAGCTT GGCCGGCCTG TACATGATCA
7081  ACGCGTGAGC TCTCTAGAGC TTGTCGACAG ATCCCCCTCT TCATTTCTTT ATGTTTTAAA
7141  TGCACTGACC TCCCACATTC CCTTTTTAGT AAAATATTCA GAATAATTT  AAATACATCA
7201  TTGCAATGAA ATAAATGTT  TTTTATTAGG CAGAATCCAG ATGCTCAAGG CCCTTCATAA
7261  TATCCCCCAG TTAGTAGTT  GGACTTAGGG AACAAAGGAA CCTTTAATAG AAATTGGACA
7321  GCAAGAAAGC GAGGGGGATC TGGATCCTCC GGACCCGTAT CTAGAATCAT CGATTCATTT
7381  ACCCGGAGAC AGGGAGAGGC TCTTCTGCGT GTAGTGGTTG TGCAGAGCCT CATGCATCAC
7441  GGAGCATGAG AAGACGTTCC CCTGCTGCCA CCTGCTCTTG TCCACGGTGA GCTTGCTGTA
7501  GAGGAAGAAG GAGCCGTCGG AGTCCAGCAC GGGAGGCGTG GTCTTGTAGT TGTTCTCCGG
7561  CTGCCCATTG CTCTCCCACT CCACGGCGAT GTCGCTGGGA TAGAAGCCTT TGACCAGGCA
7621  GGTCAGGCTG ACCTGGTTCT TGGTCAGCTC ATCCCGGGAT GGGGCAGGG  TGTACACCTG
7681  TGGTTCTCGG GGCTGCCCTT TGGCTTTGGA GATGGTTTTC TCGATGGGGG CTGGGAGGGC
7741  TTTGTTGGAG ACCTTGCACT TGTACTCCTT GCCATTCAGC CAGTCCTGGT GCAGGACGGT
7801  GAGGACGCTG ACCACACGGT ACGTGCTGTT GTACTGCTCC TCCCGCGGCT TTGTCTTGGC
7861  ATTATGCACC TCCACGCCGT CCACGTACCA GTTGAACTTG ACCTCAGGGT CTTCGTGGCT
7921  CACGTCCACC ACCACGCATG TGACCTCAGG GGTCCGGGAG ATCATGAGGG TGTCCTTGGG
7981  TTTTGGGGGG AAGAGGAAGA CTGACGGTCC CCCCAGGAGT TCAGGTGCTG GGCACGGTGG
8041  GCATGTGTGA GTTTTGTCAC AAGATTTGGG CTCAACTTTC TTGTCCACCT TGGTGTTGCT
8101  GGGCTTGTGA TTCACGTTGC AGATGTAGGT CTGGGTGCCC AAGCTGCTGG AGGGCACGGT
8161  CACCACGCTG CTGAGGGAGT AGAGTCCTGA GGACTGTAGG ACAGCCGGGA AGGTGTGCAC
8221  GCCGCTGGTC AGGGCGCCTG AGTTCCACGA CACCGTCACC GGTTCGGGGA AGTAGTCCTT
8281  GACCAGGCAG CCCAGGGCCG CTGTGCCCCC AGAGGTGCTC TTGGAGGAGG GTGCCAGGGG
8341  GAAGACCGAT GGGCCCTTGG TGGAAGCTGA GGAGACGGTG ACCGTGGTCC CTTGGCCCCA
8401  GACGTCCATA CCGTAGTAGA AGTTCCCCAG TCTTGCACAG TAATACACAG CAGTGTCCTC
8461  GGCTCTCAGG CTGTTCATTT GAAGATACAA GGAGTTCTTG GCATTGTCTC TGGAGATGGT
8521  GAATCGGCCC TTCACGGAGT CTGCATAGTA TGTGGCACCA CGAGTATCAA TAACTGATAT
8581  CCACTCCAGA CCTTTTCCTG GAGCCTGGCG AACCCAGTGC ATAGCAAAGC TACTGAAGGT
8641  GAATCCAGAG GCTGCACAGG AGAGTCTCAG GGACCCCCA  GGCTTTACCA AGCCTCCCCC
8701  AGACTGCACC AGCTGAACCT CACACTGGAC ACCTTTTAAT ATAGCAACAA GGAAAACCCA
8761  GCTCAGCCCA AACTCCATAA GGGCGAATTC CACCCACTG  GACTAGTGGA TCCGAGCTCG
8821  GTACCAAGCT TAAGCCTGTG AGAGAAAGG  AACAGAAAAC GAAACAAAGA CGTAGAGTTG
8881  AGCAAGCAGG GTCAGGCAAA GCGTGGAGAG CCGGCTGAGT CTAGGTAGGC TCCAAGGGAG
8941  CGCCGGACAA AGGCCCGGTC TCGACCTGAG CTTTAAACTT ACCTGTGGCC ACACGTGCAA
9001  TTGCTATAGT GAGTCGTATT AATTTCGATA AGCCAGTAAG CAGTGGGTTC TCTAGTTAGC
9061  CAGAGAGCTC TGCTTATATA GACCTCCCAC CGTACACGCC TACCGCCCAT TTGCGTCAAT
9121  GGGGCGGAGT TGTTACGACA TTTTGGAAAG TCCCGTTGAT TTTGGTGCCA AAACAAACTC
9181  CCATTGACGT CAATGGGGTG GAGACTTGGA AATCCCCGTG AGTCAAACCG CTATCCACGC
```

-continued

```
 9241 CCATTGATGT ACTGCCAAAA CCGCATCACC ATGGTAATAG CGATGACTAA TACGTAGATG
 9301 TACTGCCAAG TAGGAAAGTC CCATAAGGTC ATGTACTGGG CATAATGCCA GGCGGGCCAT
 9361 TTACCGTCAT TGACGTCAAT AGGGGGCGTA CTTGGCATAT GATACACTTG ATGTACTGCC
 9421 AAGTGGGCAG TTTACCGTAA ATACTCCACC CATTGACGTC AATGGAAAGT CCCTATTGGC
 9481 GTTACTATGG AACATACGT CATTATTGAC GTCAATGGGC GGGGGTCGTT GGGCGGTCAG
 9541 CCAGGCGGGC CATTTACCGT AAGTTATGTA ACGCGGAACT CCATATATGG GCTATGAACT
 9601 AATGACCCCG TAATTGATTA CTATTAATAA CTAGTCAATA ATCAATGTCA ACGCGTATAT
 9661 CTGGCCCGTA CATCGGTAGC TGAGGGTTTA AACGGCGCGC GGCCGGCCGG TACCACGCGT
 9721 TGGCCACATA TGGCGGCCGC TCGCGATTAA TTAATCGCGA TGGCCACATA TGGAGCTCTC
 9781 TAGAGCTTGT CGACAGATCC CCCTCTTCAT TTCTTTATGT TTTAAATGCA CTGACCTCCC
 9841 ACATTCCCTT TTTAGTAAAA TATTCAGAAA TAATTTAAAT ACATCATTGC AATGAAAATA
 9901 AATGTTTTTT ATTAGGCAGA ATCCAGATGC TCAAGGCCCT TCATAATATC CCCCAGTTTA
 9961 GTAGTTGGAC TTAGGGAACA AAGGAACCTT TAATAGAAAT TGGACAGCAA GAAAGCGAGG
10021 GGGATCTGGA TCCTCCGGAG GGCCCCTTCT CCCTCTAACA CTCTCCCCTG TTGAAGCTCT
10081 TTGTGACGGG CGAGCTCAGG CCCTGATGGG TGACTTCGCA GGCGTAGACT TTGTGTTTCT
10141 CGTAGTCTGC TTTGCTCAGC GTCAGGGTGC TGCTGAGGCT GTAGGTGCTG TCCTTGCTGT
10201 CCTGCTCTGT GACACTCTCC TGGGAGTTAC CCGATTGGAG GGCGTTATCC ACCTTCCACT
10261 GTACTTTGGC CTCTCTGGGA TAGAAGTTAT TCAGCAGGCA CACAACAGAG GCAGTTCCAG
10321 ATTTCAACTG CTCATCAGAT GGCGGGAAGA TGAAGACAGA TGGTGCAGCC ACTGTACGTT
10381 TGATCTCCAC CTTGGTCCCT TGGCCGAAAG TGTGAGGTAA ACGACTACTC TGATGACAGT
10441 AATACACTGC GAAATCTTCA GGCTCCAGTC TACTGATGGT GAGGGTGAAA TCTGTCCCAG
10501 ATCCACTGCC ACTGAACCTA TCGGGATCC CTGAGAGGGA CTGGGATGCA TACTTGATGA
10561 GAAGCCTTGG AGCCTGACCT GGTTTCTGCT GGTACCAGTG TAAGCTACTA CCAATGCTCT
10621 GACTGGCCCG GCAGGAGAGG GTGGCTCTCT CGCCTGGAGA CACAGACAGG GTACCTGGGC
10681 TCTGAGTCAG CACAATTTCA CCCCTGGAGG CTGGAACCCA GAGCAGCAGA AACCCAATGA
10741 GTTGTGATGG CGACATGTTA AACGCTAGAA TTCTTAAGCC TGTGGAGAGA AAGGAACAGA
10801 AAACGAAACA AAGACGTAGA GTTGAGCAAG CAGGGTCAGG CAAAGCGTGG AGAGCCGGCT
10861 GAGTCTAGGT AGGCTCCAAG GGAGCGCCGG ACAAAGGCCC GGTCTCGACC TGAGCTTTAA
10921 ACTTACCTGT GGCCACACGT GCAATTGCTA TAGTGAGTCG TATTAATTTC GATAAGCCAG
10981 TAAGCAGTGG GTTCTCTAGT TAGCCAGAGA GCTCTGCTTA TATAGACCTC CACCGTACA
11041 CGCCTACCGC CCATTTGCGT CAATGGGGCG GAGTTGTTAC GACATTTTGG AAAGTCCCGT
11101 TGATTTTGGT GCCAAAACAA ACTCCCATTG ACGTCAATGG GGTGGAGACT TGGAAATCCC
11161 CGTGAGTCAA ACCGCTATCC ACGCCCATTG ATGTACTGCC AAAACCGCAT CACCATGGTA
11221 ATAGCGATGA CTAATACGTA GATGTACTGC CAAGTAGGAA AGTCCCATAA GGTCATGTAC
11281 TGGGCATAAT GCCAGGCGGG CCATTTACCG TCATTGACGT CAATAGGGGG CGTACTTGGC
11341 ATATGATACA CTTGATGTAC TGCCAAGTGG GCAGTTTACC GTAAATACTC CACCCATTGA
11401 CGTCAATGGA AAGTCCCTAT TGGCGTTACT ATGGGAACAT ACGTCATTAT TGACGTCAAT
11461 GGGCGGGGGT CGTTGGGCGG TCAGCCAGGC GGGCCATTTA CCGTAAGTTA TGTAACGCGG
11521 AACTCCATAT ATGGGCTATG AACTAATGAC CCCGTAATTG ATTACTATTA TAACTAGTC
11581 AATAATCAAT GTCAACGCGT ATATCTGGCC CGTACATCG TAACTAGTCG GACCGCCGCG
11641 GACTAGTGCC CGGGCCACCG GTGCTCGAAG CTTGGATCGA TCCAGACATG ATAAGATACA
```

```
11701  TTGATGAGTT TGGACAAACC ACAACTAGAA TGCAGTGAAA AAAATGCTTT ATTTGTGAAA

11761  TTTGTGATGC TATTGCTTTA TTTGTAACCA TTATAAGCTG CAATAAACAA GTTAACAACA

11821  ACAATTGCAT TCATTTTATG TTTCAGGTTC AGGGGGAGGT GTGGGAGGTT TTTTAAAGCA

11881  AGTAAAACCT CTACAAATGT GGTATGGCTG ATTATGATCT CTAGTCAAG
```

The present invention further provides, in part, isolated plasmids which exhibit high levels of expression of anti-IL-23 p19 heavy and light chains. One plasmid is pAIL23V1-K. The sequence of the pAIL23V1-K plasmid is set forth below:

(SEQ ID NO: 44)
```
   1  GGCACTATAC ATCAAATATT CCTTATTAAC CCCTTTACAA ATTAAAAAGC TAAAGGTACA

61  CAATTTTTGA GCATAGTTAT TAATAGCAGA CACTCTATGC CTGTGTGGAG TAAGAAAAAA

121  CAGTATGTTA TGATTATAAC TGTTATGCCT ACTTATAAAG GTTACAGAAT ATTTTTCCAT

181  AATTTTCTTG TATAGCAGTG CAGCTTTTTC CTTTGTGGTG TAAATAGCAA AGCAAGCAAG

241  AGTTCTATTA CTAAACACAG CATGACTCAA AAAACTTAGC AATTCTGAAG GAAAGTCCTT

301  GGGGTCTTCT ACCTTTCTCT TCTTTTTTGG AGGAGTAGAA TGTTGAGAGT CAGCAGTAGC

361  CTCATCATCA CTAGATGGCA TTTCTTCTGA GCAAAACAGG TTTTCCTCAT TAAAGGCATT

421  CCACCACTGC TCCCATTCAT CAGTTCCATA GGTTGGAATC TAAAATACAC AAACAATTAG

481  AATCAGTAGT TAACACATT ATACACTTAA AAATTTTATA TTTACCTTAG AGCTTTAAAT

541  CTCTGTAGGT AGTTTGTCCA ATTATGTCAC ACCACAGAAG TAAGGTTCCT TCACAAAGAT

601  CGATCTAAAG CCAGCAAAAG TCCCATGGTC TTATAAAAAT GCATAGCTTT AGGAGGGGAG

661  CAGAGAACTT GAAAGCATCT TCCTGTTAGT CTTTCTTCTC GTAGACTTCA AACTTATACT

721  TGATGCCTTT TTCCTCCTGG ACCTCAGAGA GGACGCCTGG GTATTCTGGG AGAAGTTTAT

781  ATTTCCCCAA ATCAATTTCT GGGAAAAACG TGTCACTTTC AAATTCCTGC ATGATCCTTG

841  TCACAAGAG TCTGAGGTGG CCTGGTTGAT TCATGGCTTC CTGGTAAACA GAACTGCCTC

901  CGACTATCCA AACCATGTCT ACTTTACTTG CCAATTCCGG TTGTTCAATA AGTCTTAAGG

961  CATCATCCAA ACTTTTGGCA AGAAAATGAG CTCCTCGTGG TGGTTCTTTG AGTTCTCTAC

1021  TGAGAACTAT ATTAATTCTG TCCTTTAAAG GTCGATTCTT CTCAGGAATG GAGAACCAGG

1081  TTTTCCTACC CATAATCACC AGATTCTGTT TACCTTCCAC TGAAGAGGTT GTGGTCATTC

1141  TTTGGAAGTA CTTGAACTCG TTCCTGAGCG GAGGCCAGGG TAGGTCTCCG TTCTTGCCAA

1201  TCCCCATATT TTGGGACACG GCGACGATGC AGTTCAATGG TCGAACCATG ATGGCAGCGG

1261  GGATAAAATC CTACCAGCCT TCACGCTAGG ATTGCCGTCA AGTTTGGCGC GAAATCGCAG

1321  CCCTGAGCTG TCCCCCCCCC CAAGCTCAGA TCTGAGCTTG GTCCCTATGG TGAGTCCGTT

1381  CCGCTCTTGT GATGATAGCC AGACAAGAAA GAGACAATAC AAGACAAACA CCAAATAGTA

1441  GAAATAGAGA CAAGGGTCAC TTATCCGAGG GTCCCTGTTC GGGCGCCAGC TGCCGCAGTC

1501  GGCCGACCTG AGGGTCGCCG GGGTCTGCGG GGGGACCCTC TGGAAAGTGA AGGATAAGTG

1561  ACGAGCGGAG ACGGGATGGC GAACAGACAC AAACACACAA GAGGTGAATG TTAGGACTGT

1621  TGCAAGTTTA CTCAAAAAAT CAGCACTCTT TTATATCTTG GTTTACATAA GCATTTACAT

1681  AAGATTTGGA TAAATTCCAA AAGAACATAG GAAAATAGAA CACTCAGAGC TCAGATCAGA

1741  ACCTTTGATA CCAAACCAAG TCAGGAAACC ACTTGTCTCA CATCCTCGTT TTAAGAACAG

1801  TTTGTAACCA AAAACTTACT TAAGCCCTGG GAACCGCAAG GTTGGGCCAA TAAAGGCTAT

1861  TCATAATAAC TCATGCCATG AGTTTTTGCA GAATAATGTT CTATTAGTCC AGCCACTGTC

1921  CCCTCCTTGG TATGGAAAAT CTTTCCCCAA AAGTGCATTC CTGTTCCTAG ATAAATATAA
```

-continued

```
1981  TCATGTACCT GTTGTTTCAT GTCGTCTTTT TCTTCTTGAG ACAACATACA CCAAGGAGGT
2041  CTAGCTCTGG CGAGTCTTTC ACGAAAAGGG AGGGATCTAT ATAACACTTT ATAGCCATTG
2101  ACTGTAACCC ACCTATCCCA ATTTAAGTCA TATCTTCCTG TATATGGTAA GGGGGCATCT
2161  GTTGGTCTGT AGATGTAAGG TCCCCTATAA GTCCCTGGTT GCCACCACCT GTCTCCTATT
2221  TTGACAAAAA CACTCTTTTT TCCCTTTTTT ACTTCTAGGC CTGTGGTCAA TAGTCCTTGC
2281  ACCTGTTCTT CAATTGAGGT TGAGCGTCTC TTTCTATTTT CTATTCCCAT TTCTAACTTC
2341  TGAATTTGAG TAAAAATAGT ACTAAAAGAT AATGATTCAT TTCTTAACAT AGTAACTAAT
2401  AATCTACCTA TTGGATTGGT CTTATTGGTA AAAATATAAT TTTTAGCAAG CATTCTTATT
2461  TCTATTTCTG AAGGACAAAA TCGATGCGGC TTGTAAGAGG AAGTTGGCTG TGGTCCTTGC
2521  CTCAGGAGGA AGGTCGAGTT CTCCGAATTG TTTAGATTGT AATCTTGCAC AGAAGAGCTA
2581  TTAAAAGAGT CAAGGGTGAG AGCCCTGCGA GCACGAACCG CAACTTCCCC CAATAGCCCC
2641  AGGCAAAGCA GAGCTATGCC AAGTTTGCAG CAGAGAATGA ATATGTCTTT GTCTGATGGG
2701  CTCATCCGTT TGTGCGCAGA CGGGTCGTCC TTGGTGGGAA ACAACCCCTT GGCTGCTTCT
2761  CCCCTAGGTG TAGGACACTC TCGGGAGTTC AACCATTTCT GCCCAAGCTC AGATCTGAGC
2821  TTTAATGCGG TAGTTTATCA CAGTTAAATT GCTAACGCAG TCAGGCACCG TGTATGAAAT
2881  CTAACAATGC GCTCATCGTC ATCCTCGGCA CCGTCACCCT GGATGCTGTA GGCATAGGCT
2941  TGGTTATGCC GGTACTGCCG GGCCTCTTGC GGGATATCGT CCATTCCGAC AGCATCGCCA
3001  GTCACTATGG CGTGCTGCTA GCGCTCTTCC GCTTCCTCGC TCACTGACTC GCTGCGCTCG
3061  GTCGTTCGGC TGCGGCGAGC GGTATCAGCT CACTCAAAGG CGGTAATACG GTTATCCACA
3121  GAATCAGGGG ATAACGCAGG AAAGAACATG TGAGCAAAAG GCCAGCAAAA GGCCAGGAAC
3181  CGTAAAAAGG CCGCGTTGCT GGCGTTTTTC CATAGGCTCC GCCCCCCTGA CGAGCATCAC
3241  AAAAATCGAC GCTCAAGTCA GAGGTGGCGA AACCCGACAG GACTATAAAG ATACCAGGCG
3301  TTTCCCCCTG GAAGCTCCCT CGTGCGCTCT CCTGTTCCGA CCCTGCCGCT TACCGGATAC
3361  CCGTCACCCT TTCTCCCTTC GGGAAGCGTG GCGCTTTCTC ATAGCTCACG CTGTAGGTAT
3421  CTCAGTTCGG TGTAGGTCGT TCGCTCCAAG CTGGGCTGTG TGCACGAACC CCCCGTTCAG
3481  CCCGACCGCT GCGCCTTATC CGGTAACTAT CGTCTTGAGT CCAACCCGGT AAGACACGAC
3541  TTATCGCCAC TGGCAGCAGC CACTGGTAAC AGGATTAGCA GAGCGAGGTA TGTAGGCGGT
3601  GCTACAGAGT TCTTGAAGTG GTGGCCTAAC TACGGCTACA CTAGAAGGAC AGTATTTGGT
3661  ATCTGCGCTC TGCTGAAGCC AGTTACCTTC GGAAAAAGAG TTGGTAGCTC TTGATCCGGC
3721  AAACAAACCA CCGCTGGTAG CGGTGGTTTT TTTGTTTGCA AGCAGCAGAT TACGCGCAGA
3781  AAAAAGGAT CTCAAGAAGA TCCTTTGATC TTTTCTACGG GGTCTGACGC TCAGTGGAAC
3841  GAAAACTCAC GTTAAGGGAT TTTGGTCATG AGATTATCAA AAAGGATCTT CACCTAGATC
3901  CTTTTAAATT AAAAATGAAG TTTTAAATCA ATCTAAAGTA TATATGAGTA AACTTGGTCT
3961  GACAGTTACC AATGCTTAAT CAGTGAGGCA CCTATCTCAG CGATCTGTCT ATTTCGTTCA
4021  TCCATAGTTG CCTGACTCCC CGTCGTGTAG ATAACTACGA TACGGGAGGG CTTACCATCT
4081  GGCCCCAGTG CTGCAATGAT ACCGCGAGAC CCACGCTCAC CGGCTCCAGA TTTATCAGCA
4141  ATAAACCAGC CAGCCGGAAG GGCCGAGCGC AGAAGTGGTC CTGCAACTTT ATCCGCCTCC
4201  ATCCAGTCTA TTAATTGTTG CCGGGAAGCT AGAGTAAGTA GTTCGCCAGT TAATAGTTTG
4261  CGCAACGTTG TTGCCATTGC TACAGGCATC GTGGTGTCAC GCTCGTCGTT TGGTATGGCT
4321  TCATTCAGCT CCGGTTCCCA ACGATCAAGG CGAGTTACAT GATCCCCCAT GTTGTGCAAA
```

-continued

```
4381  AAAGCGGTTA GCTCCTTCGG TCCTCCGATC GTTGTCAGAA GTAAGTTGGC CGCAGTGTTA

4441  TCACTCATGG TTATGGCAGC ACTGCATAAT TCTCTTACTG TCATGCCATC CGTAAGATGC

4501  TTTTCTGTGA CTGGTGAGTA CTCAACCAAG TCATTCTGAG AATAGTGTAT GCGGCGACCG

4561  AGTTGCTCTT GCCCGGCGTC AACACGGGAT AATACCGCGC CACATAGCAG AACTTTAAAA

4621  GTGCTCATCA TTGGAAAACG TTCTTCGGGG CGAAAACTCT CAAGGATCTT ACCGCTGTTG

4631  AGATCCAGTT CGATGTAACC CACTCGTGCA CCCAACTGAT CTTCAGCATC TTTTACTTTC

4741  ACCAGCGTTT CTGGGTGAGC AAAAACAGGA AGGCAAAATG CCGCAAAAAA GGGAATAAGG

4801  GCGACACGGA AATGTTGAAT ACTCATACTC TTCCTTTTTC AATATTATTG AAGCATTTAT

4861  CAGGGTTATT GTCTCATGAG CGGATACATA TTTGAATGTA TTTAGAAAAA TAAACAAATA

4921  GGGGTTCCGC GCACATTTCC CCGAAAAGTG CCACCTGACG TCTAAGAGAC CATTATTATC

4981  ATGACATTAA CCTATAAAAA TAGGCGTATC ACGAGGCCCT TTCGTCTTCA AGAATTGTCT

5041  AGAGGCGCGC CGTTTAAACC CTCAGCTACC GATGTACGGG CCAGATATAC GCGTTGACAT

5101  TGATTATTGA CTAGTTATTA ATAGTAATCA ATTACGGGGT CATTAGTTCA TAGCCCATAT

5161  ATGGAGTTCC GCGTTACATA ACTTACGGTA AATGGCCCGC CTGGCTGACC GCCCAACGAC

5221  CCCCGCCCAT TGACGTCAAT AATGACGTAT GTTCCCATAG TAACGCCAAT AGGGACTTTC

5281  CATTGACGTC AATGGGTGGA CTATTTACGG TAAACTGCCC ACTTGGCAGT ACATCAAGTG

5341  TATCATATGC CAAGTACGCC CCCTATTGAC GTCAATGACG GTAAATGGCC CGCCTGGCAT

5401  TATGCCCAGT ACATGACCTT ATGGGACTTT CCTACTTGGC AGTACATCTA CGTATTAGTC

5461  ATCGCTATTA CCATGGTGAT GCGGTTTTGG CAGTACATCA ATGGGCGTGG ATAGCGGTTT

5521  GACTCACGGG GATTTCCAAG TCTCCACCCC ATTGACGTCA ATGGGACTTT GTTTTGGCAC

5581  CAAAATCAAC GGGACTTTCC AAAATGTCGT AACAACTCCG CCCCATTGAC GCAAATGGGC

5641  GGTAGGCGTG TACGGTGGGA GGTCTATATA AGCAGAGCTC TCTGGCTAAC TAGAGAACCC

5701  ACTGCTTACT GGCTTATCGA AATTAATACG ACTCACTATA GCAATTGCAC GTGTGGCCAC

5761  AGGTAAGTTT AAAGCTCAGG TCGAGACCGG GCCTTTGTCC GGCGCTCCCT TGGAGCCTAC

5821  CTAGACTCAG CCGGCTCTCC ACGCTTTGCC TGACCCTGCT TGCTCAACTC TACGTCTTTG

5881  TTTCGTTTTC TGTTCCTTTC TCTCCACAGG CTTAAGCTCG AGGCCGCCAC CATGGCTGTG

5941  CTGGGGCTGC TGTTCTGCCT GGTGACATTC CCAAGCTGTG TGCTGTCCCA GGTGCAGCTG

6001  GTGCAGTCTG GCGCTGAGGT GAAGAAGCCT GGCGCCTCCG TGAAGGTCTC CTGCAAGGCT

6061  TCTGGCTACA TCTTCATCAC CTACTGGATG ACCTGGGTGC GGCAGGCCCC TGGCCAGGGG

6121  CTGGAGTGGA TGGGCCAGAT CTTCCCTGCC AGCGGCTCTG CAGACTACAA CGAGAAGTTC

5181  GAAGGCAGAG TCACCATGAC CACAGACACA TCCACCAGCA CAGCCTACAT GGAGCTGAGG

5241  AGCCTGAGAT CTGACGACAC CGCCGTGTAT TACTGTGCCA GAGGCGGTGG CGGATTCGCT

6301  TACTGGGGCC AGGGCACCCT GGTCACCGTC TCCAGCGCTA GCACCAAGGG CCCATCGGTC

6361  TTCCCCCTGG CACCCTCCTC CAAGAGCACC TCTGGGGGCA CAGCGGCCCT GGGCTGCCTG

6421  GTCAAGGACT ACTTCCCCGA ACCGGTGACG GTGTCGTGGA ACTCAGGCGC CCTGACCAGC

6481  GGCGTGCACA CCTTCCCGGC TGTCCTACAG TCCTCAGGAC TCTACTCCCT CAGCAGCGTG

6541  GTGACCGTGC CCTCCAGCAG CTTGGGCACC CAGACCTACA TCTGCAACGT GAATCACAAG

6601  CCCAGCAACA CCAAGGTGGA CAAGAAAGTT GAGCCCAAAT CTTGTGACAA AACTCACACA

6661  TGCCCACCGT GCCCAGCACC TGAACTCCTG GGGGGACCGT CAGTCTTCCT CTTCCCCCCA

6721  AAACCCAAGG ACACCCTCAT GATCTCCCGG ACCCCTGAGG TCACATGCGT GGTGGTGGAC

6781  GTGAGCCACG AAGACCCTGA GGTCAAGTTC AACTGGTACG TGGACGGCGT GGAGGTGCAT
```

```
-continued
6841  AATGCCAAGA CAAAGCCGCG GGAGGAGCAG TACAACAGCA CGTACCGTGT GGTCAGCGTC
6901  CTCACCGTCC TGCACCAGGA CTGGCTGAAT GGCAAGGAGT ACAAGTGCAA GGTCTCCAAC
6961  AAAGCCCTCC CAGCCCCCAT CGAGAAAACC ATCTCCAAAG CCAAGGGGCA GCCCCGAGAA
7021  CCACAGGTGT ACACCCTGCC CCCATCCCGG GATGAGCTGA CCAAGAACCA GGTCAGCCTG
7081  ACCTGCCTGG TCAAAGGCTT CTATCCCAGC GACATCGCCG TGGAGTGGGA GAGCAATGGG
7141  CAGCCGGAGA ACAACTACAA GACCACGCCT CCCGTGCTGG ACTCCGACGG CTCCTTCTTC
7201  CTCTACAGCA AGCTCACCGT GGACAAGAGC AGGTGGCAGC AGGGGAACGT CTTCTCATGC
7261  TCCGTGATGC ATGAGGCTCT GCACAACCAC TACACGCAGA AGAGCCTCTC CCTGTCTCCG
7321  GGTAAATGAA TCGATGATTC TAGATACGGG TCCGGAGGAT CCAGATCCCC CTCGCTTTCT
7381  TGCTGTCCAA TTTCTATTAA AGGTTCCTTT GTTCCCTAAG TCCAACTACT AAACTGGGGG
7441  ATATTATGAA GGGCCTTGAG CATCTGGATT CTGCCTAATA AAAAACATTT ATTTTCATTG
7501  CAATGATGTA TTTAAATTAT TTCTGAATAT TTTACTAAAA AGGGAATGTG GGAGGTCAGT
7561  GCATTTAAAA CATAAAGAAA TGAAGAGGGG GATCTGTCGA CAAGCTCTAG AGAGCTCACG
7621  CGTTGATCAT GTACAGGCCG GCCAAGCTTT CGACTAGCTT GGCACGCCAG AAATCCGCGC
7681  GGTGGTTTTT GGGGGTCGGG GGTGTTTGGC AGCCACAGAC GCCCGGTGTT CGTGTCGCGC
7741  CAGTACATGC GGTCCATGCC CAGGCCATCC AAAAACCATG GGTCTGTCTG CTCAGTCCAG
7801  TCGTGGACCT GACCCCACGC AACGCCCAAA ATAATAACCC CCACGAACCA TAAACCATTC
7861  CCCATGGGGG ACCCCGTCCC TAACCCACGG GGCCAGTGGC TATGGCAGGG CCTGCCGCCC
7921  CGACGTTGGC TGCGAGCCCT GGGCCTTCAC CCGAACTTGG GGGTGGGGT GGGGAAAAGG
7981  AAGAAACGCG GGCGTATTGG CCCCAATGGG GTCTCGGTGG GGTATCGACA GAGTGCCAGC
8041  CCTGGGACCG AACCCCGCGT TTATGAACAA ACCACCCAAC ACCCGTGCGT TTTATTCTGT
8101  CTTTTTATTG CCGTCATAGC GCGGGTTCCT TCCGGTATTG TCTCCTTCCG TGTTTCAGTT
8161  AGCCTCCCCC ATCTCCCGAT CCGGACGAGT GCTGGGCGT CGGTTTCCAC TATCGGCGAG
8221  TACTTCTACA CAGCCATCGG TCCAGACGGC CGCGCTTCTG CGGGCGATTT GTGTACGCCC
3281  GACAGTCCCG GCTCCGGATC GGACGATTGC GTCGCATCGA CCCTGCGCCC AAGCTGCATC
8341  ATCGAAATTG CCGTCAACCA AGCTCTGATA GAGTTGGTCA AGACCAATGC GGAGCATATA
3401  CGCCCGGAGC CGCGGCGATC CTGCAAGCTC CGGATGCCTC CGCTCGAAGT AGCGCGTCTG
8461  CTGCTCCATA CAAGCCAACC ACGGCCTCCA GAAGAAGATG TTGGCGACCT CGTATTGGGA
8521  ATCCCCGAAC ATCGCCTCGC TCCAGTCAAT GACCGCTGTT ATGCGGCCAT TGTCCGTCAG
8581  GACATTGTTG GAGCCGAAAT CCGCGTGCAC GAGGTGCCGG ACTTCGGGGC AGTCCTCGGC
8641  CCAAAGCATC AGCTCATCGA GAGCCTGCGC GACGGACGCA CTGACGGTGT CGTCCATCAC
8701  AGTTTGCCAG TGATACACAT GGGGATCAGC AATCGCGCAT ATGAAATCAC GCCATGTAGT
8761  GTATTGACCG ATTCCTTGCG GTCCGAATGG GCCGAACCCG CTCGTCTGGC TAAGATCGGC
3821  CGCAGCGATC GCATCCATGG CCTCCGCGAC CGGCTGCAGA ACAGCGGGCA GTTCGGTTTC
8881  AGGCAGGTCT TGCAACGTGA CACCCTGTGC ACGGCGGGAG ATGCAATAGG TCAGGCTCTC
8941  GCTGAATTCC CCAATGTCAA GCACTTCCGG AATCGGGAGC GCGGCCGATG CAAAGTGCCG
9001  ATAAACATAA CGATCTTTGT AGAAACCATC GGCGCAGCTA TTTACCCGCA GGACATATCC
9061  ACGCCCTCCT ACATCGAAGC TGAAAGCACG AGATTCTTCG CCCTCCGAGA GCTGCATCAG
9121  GTCGGAGACG CTGTCGAACT TTTCGATCAG AAACTTCTCG ACAGACGTCG CGGTGAGTTC
9181  AGGCTTTTTC ATATCTCATT GCCCCCCGGG ATCTGCGGCA CGCTGTTGAC GCTGTTAAGC
```

```
                          -continued
 9241  GGGTCGCTGC AGGGTCGCTC GGTGTTCGAG GCCACACGCG TCACCTTAAT ATGCGAAGTG
 9301  GACCTCGGAC CGCGCCGCCC CGACTGCATC TGCGTGTTCG AATTCGCCAA TGACAAGACG
 9361  CTGGGCGGGG TTTGTGTCAT CATAGAACTA AAGACATGCA AATATATTTC TTCCGGGGAC
 9421  ACCGCCAGCA AACGCGAGCA ACGGGCCACG GGGATGAAGC AGGGCGGCAC CTCGCTAACG
 9481  GATTCACCAC TCCAAGAATT GGAGCCAATC AATTCTTGCG GAGAACTGTG AATGCGCAAA
 9541  CCAACCCTTG GCAGAACATA TCCATCGCGT CCGCCATCTC CAGCAGCCGC ACGCGGCGCA
 9601  TCTCGGGGCC GACGCGCTGG GCTACGTCTT GCTGGCGTTC GCACAGGCCG GCCAGCGCGC
 9661  GGCCGGCCGG TACCACGCGT TGGCCACATA TGGCGGCCGC TCGCGATTAA TTAATCGCGA
 9721  TGGCCACATA TGGAGCTCTC TAGAGCTTGT CGACAGATCC CCCTCTTCAT TTCTTTATGT
 9781  TTTAAATGCA CTGACCTCCC ACATTCCCTT TTTAGTAAAA TATTCAGAAA TAATTTAAAT
 9841  ACATCATTGC AATGAAAATA AATGTTTTTT ATTAGGCAGA ATCCAGATGC TCAAGGCCCT
 9901  TCATAATATC CCCCAGTTTA GTAGTTGGAC TTAGGGAACA AAGGAACCTT AATAGAAAT
 9961  TGGACAGCAA GAAAGCGAGG GGGATCTGGA TCCTCCTACG TATCTAGAAT CATCGATTAA
10021  CACTCTCCCC TGTTGAAGCT CTTTGTCACG GGGCTGCTCA GGCCCTGATG GGTCACCTCG
10081  CAGGCGTACA CCTTGTGTTT CTCGTAGTCT GCTTTGCTCA GGGTCAGGGT GCTGCTCAGG
10141  CTGTAGGTGC TGTCCTTGCT GTCCTGCTCT GTCACGCTCT CCTGGGAGTT GCCGCTCTGG
10201  AGGGCGTTAT CCACCTTCCA CTGCACCTTG GCCTCTCTGG GATAGAAGTT ATTCAGCAGG
10261  CACACCACGG AGGCAGTTCC AGACTTCAGC TGCTCATCAG ATGGAGGGAA GATGAACACA
10321  GATGGTGCAG CCACCGTACG CTTGATCTCC ACCTTGGTGC CCTGGCCGAA GGTGAATGGA
10381  ATTCCGTAGT GGTGCTGACA GTAGTAGGTG GCGAAGTCCT CAGGCTGCAG GCTGCTGATG
10441  GTCAGGGTGA AGTCTGTCCC AGAGCCGCTG CCGCTGAACC TGGATGGCAC CCCTTCAGCC
10501  AGGGTCTTGG CGTTATAGAT CAGCAGCTTA GGGGCCTTCC CTGGCTTCTG CTGATACCAG
10561  GCCAGGTAGC TGTAGATGTT CTCGCTGGTC CTGCAGGTGA TGGTCACTCT GTCGCCCACA
10621  GAGGCAGACA GGGAGGATGG AGACTGGGTC ATCTGGATAT CACATCTCAT GGCTGGCAGG
10681  AACAGCACCA GCAGCCCCAG CAGCTGCACT GGAGCCATGG TGGCGGCCTC GAGAAGCTTA
10741  AGTTTAATTC TTAAGCCTGT GGAGAGAAAG GAACAGAAAA CGAAACAAAG ACGTAGAGTT
10801  GAGCAAGCAG GGTCAGGCAA AGCGTGGAGA GCCGGCTGAG TCTAGGTAGG CTCCAAGGGA
10861  GCGCCGGACA AAGGCCCGGT CTCGACCTGA GCTTTAAACT TACCTGTGGC CACACGTGCA
10921  ATTGCTATAG TGAGTCGTAT TAATTTCGAT AAGCCAGTAA GCAGTGGGTT CTCTAGTTAG
10981  CCAGAGAGCT CTGCTTATAT AGACCTCCCA CCGTACACGC CTACCGCCCA TTTGCGTCAA
11041  TGGGGCGGAG TTGTTACGAC ATTTTGGAAA GTCCCGTTGA TTTTGGTGCC AAAACAAACT
11101  CCCATTGACG TCAATGGGGT GGAGACTTGG AAATCCCCGT GAGTCAAACC GCTATCCACG
11161  CCCATTGATG TACTGCCAAA ACCGCATCAC CATGGTAATA GCGATGACTA ATACGTAGAT
11221  GTACTGCCAA GTAGGAAAGT CCCATAAGGT CATGTACTGG GCATAATGCC AGGCGGGCCA
11281  TTTACCGTCA TTGACGTCAA TAGGGGGCGT ACTTGGCATA TGATACACTT GATGTACTGC
11341  CAAGTGGGCA GTTTACCGTA AATAGTCCAC CCATTGACGT CAATGGAAAG TCCCTATTGG
11401  CGTTACTATG GGAACATACG TCATTATTGA CGTCAATGGG CGGGGGTCGT TGGGCGGTCA
11461  GCCAGGCGGG CCATTTACCG TAAGTTATGT AACGCGGAAC TCCATATATG GCTATGAAC
11521  TAATGACCCC GTAATTGATT ACTATTAATA ACTAGTCAAT AATCAATGTC AACGCGTATA
11581  TCTGGCCCGT ACATCGGTAA CTAGTCGGAC CGGCCCGGGC CACCGGTGCT CGAAGCTTGG
11441  ATCGATCCAG ACATGATAAG ATACATTGAT GAGTTTGGAC AAACCACAAC TAGAATGCAG
```

-continued

```
11701 TGAAAAAAT GCTTTATTTG TGAAATTTGT GATGCTATTG CTTTATTTGT AACCATTATA

11761 AGCTGCAATA AACAAGTTAA CAACAACAAT TGCATTCATT TTATGTTTCA GGTTCAGGGG

11821 GAGGTGTGGG AGGTTTTTTA AAGCAAGTAA AACCTCTACA AATGTGGTAT GGCTGATTAT

11881 GATCTCTAGT CAA
```

The present invention further provides, in part, isolated plasmids which exhibit high levels of expression of anti-IL-23R heavy and light chains. One plasmid is pAIL23RV1. The sequence of the pAIL23RV1 plasmid is set forth below:

(SEQ ID NO: 45)
```
   1 GGCACTATAC ATCAAATATT CCTTATTAAC CCCTTTACAA ATTAAAAAGC TAAAGGTACA

61 CAATTTTTGA GCATAGTTAT TAATAGCAGA CACTCTATGC CTGTGTGGAG TAAGAAAAAA

121 CAGTATGTTA TGATTATAAC TGTTATGCCT ACTTATAAAG GTTACAGAAT ATTTTTCCAT

181 AATTTTCTTG TATAGCAGTG CAGCTTTTTC CTTTGTGGTG TAAATAGCAA AGCAAGCAAG

241 AGTTCTATTA CTAAACACAG CATGACTCAA AAAACTTAGC AATTCTGAAG GAAAGTCCTT

301 GGGGTCTTCT ACCTTTCTCT TCTTTTTTGG AGGAGTAGAA TGTTGAGAGT CAGCAGTAGC

361 CTCATCATCA CTAGATGGCA TTTCTTCTGA GCAAAACAGG TTTTCCTCAT TAAAGGCATT

421 CCACCACTGC TCCCATTCAT CAGTTCCATA GGTTGGAATC TAAAATACAC AAACAATTAG

481 AATCAGTAGT TTAACACATT ATACACTTAA AAATTTTATA TTTACCTTAG AGCTTTAAAT

541 CTCTGTAGGT AGTTTGTCCA ATTATGTCAC ACCACAGAAG TAAGGTTCCT TCACAAAGAT

601 CGATCTAAAG CCAGCAAAAG TCCCATGGTC TTATAAAAAT GCATAGCTTT AGGAGGGGAG

661 CAGAGAACTT GAAAGCATCT TCCTGTTAGT CTTTCTTCTC GTAGACTTCA AACTTATACT

721 TGATGCCTTT TTCCTCCTGG ACCTCAGAGA GGACGCCTGG GTATTCTGGG AGAAGTTTAT

781 ATTTCCCCAA ATCAATTTCT GGGAAAAACG TGTCACTTTC AAATTCCTGC ATGATCCTTG

841 TCACAAAGAG TCTGAGGTGG CCTGGTTGAT TCATGGCTTC CTGGTAAACA GAACTGCCTC

901 CGACTATCCA AACCATGTCT ACTTTACTTG CCAATTCCGG TTGTTCAATA AGTCTTAAGG

961 CATCATCCAA ACTTTTGGCA AGAAAATGAG CTCCTCGTGG TGGTTCTTTG AGTTCTCTAC

1021 TGAGAACTAT ATTAATTCTG TCCTTTAAAG GTCGATTCTT CTCAGGAATG GAGAACCAGG

1081 TTTTCCTACC CATAATCACC AGATTCTGTT TACCTTCCAC TGAAGAGGTT GTGGTCATTC

1141 TTTGGAAGTA CTTGAACTCG TTCCTGAGCG GAGGCCAGGG TAGGTCTCCG TTCTTGCCAA

1201 TCCCCATATT TTGGGACACG GCGACGATGC AGTTCAATGG TCGAACCATG ATGGCAGCGG

1261 GGATAAAATC CTACCAGCCT TCACGCTAGG ATTGCCGTCA AGTTTGGCGC GAAATCGCAG

1321 CCCTGAGCTG TCCCCCCCCC CAAGCTCAGA TCTGAGCTTG GTCACTATGG TGAGTCCGTT

1381 CCGCTCTTGT GATGATAGCC AGACAAGAAA GAGACAATAC AAGACAAACA CCAAATAGTA

1441 GAAATAGAGA CAAGGGTCAC TTATCCGAGG GTCCCTGTTC GGGCGCCAGC TGCCGCAGTC

1501 GGCCGACCTG AGGGTCGCCG GGGTCTGCGG GGGACCCTC TGGAAAGTGA AGGATAAGTG

1561 ACGAGCGGAG ACGGGATGGC GAACAGACAC AAACACACAA GAGGTGAATG TTAGGACTGT

1621 TGCAAGTTTA CTCAAAAAAT CAGCACTCTT TTATATCTTG GTTTACATAA GCATTTACAT

1681 AAGATTTGGA TAAATTCCAA AAGAACATAG GAAAATAGAA CACTCAGAGC TCAGATCAGA

1741 ACCTTTGATA CCAAACCAAG TCAGGAAACC ACTTGTCTCA CATCCTCGTT TTAAGAACAG

1801 TTTGTAACCA AAAACTTACT TAAGCCCTGG GAACCGCAAG GTTGTGCAAA TAAAGGCTAT

1861 TCATAATAAC TCATGCCATG AGTTTTTGCA GAATAATGTT CTATTAGTCC AGCCACTGTC

1921 CCCTCCTTGG TATGGAAAAT CTTTCCCCAA AAGTGCATTC CTGTTCCTAG ATAAATATAA
```

-continued

```
1981  TCATGTACCT GTTGTTTCAT GTCGTCTTTT TCTTCTTGAG ACAACATACA CCAAGGAGGT
2041  CTAGCTCTGG CGAGTCTTTC ACGAAAAGGG AGGGATCTAT ATAACACTTT ATAGCCATTG
2101  ACTGTAACCC ACCTATCCCA ATTTAAGTCA TATCTTCCTG TATATGGTAA GGGGGCATCT
2161  GTTGGTCTGT AGATGTAAGG TCCCCTATAA GTCCCTGGTT GCCACCACCT GTCTCCTATT
2221  TTGACAAAAA CACTCTTTTT TCCCTTTTTT ACTTCTAGGC CTGTGGTCAA TAGTCCTTGC
2281  ACCTGTTCTT CAATTGAGGT TGAGCGTCTC TTTCTATTTT CTATTCCCAT TTCTAACTTC
2341  TGAATTTGAG TAAAAATAGT ACTAAAGAT AATGATTCAT TTCTTAACAT AGTAACTAAT
2401  AATCTACCTA TTGGATTGGT CTTATTGGTA AAATATAAT TTTTAGCAAG CATTCTTATT
2461  TCTATTTCTG AAGGACAAAA TCGATGCGGC TTGTAAGAGG AAGTTGGCTG TGGTCCTTGC
2521  CTCAGGAGGA AGGTCGAGTT CTCCGAATTG TTTAGATTGT AATCTTGCAC AGAAGAGCTA
2581  TTAAAAGAGT CAAGGGTGAG AGCCCTGCGA GCACGAACCG CAACTTCCCC CAATAGCCCC
2641  AGGCAAAGCA GAGCTATGCC AAGTTTGCAG CAGAGAATGA ATATGTCTTT GTCTGATGGG
2701  CTCATCCGTT TGTGCGCAGA CGGGTCGTCC TTGGTGGGAA ACAACCCCTT GGCTGCTTCT
2761  CCCCTAGGTG TAGGACACTC TCGGGAGTTC AACCATTTCT GCCCAAGCTC AGATCTGAGC
2821  TTTAATGCGG TAGTTTATCA CAGTTAAATT GCTAACGCAG TCAGGCACCG TGTATGAAAT
2881  CTAACAATGC GCTCATCGTC ATCCTCGGCA CCGTCACCCT GGATGCTGTA GGCATAGGCT
2941  TGGTTATGCC GGTACTGCCG GGCCTCTTGC GGGATATCGT CCATTCCGAC AGCATCGCCA
3001  GTCACTATGG CGTGCTGCTA GCGCTCTTCC GCTTCCTCGC TCACTGACTC GCTGCGCTCG
3061  GTCGTTCGGC TGCGGCGAGC GGTATCAGCT CACTCAAAGG CGGTAATACG GTTATCCACA
3121  GAATCAGGGG ATAACGCAGG AAAGAACATG TGAGCAAAAG GCCAGCAAAA GGCCAGGAAC
3181  CGTAAAAAGG CCGCGTTGCT GGCGTTTTTC CATAGGCTCC GCCCCCCTGA CGAGCATCAC
3241  AAAAATCGAC GCTCAAGTCA GAGGTGGCGA AACCCGACAG GACTATAAAG ATACCAGGCG
3301  TTTCCCCCTG GAAGCTCCCT CGTGCGCTCT CCTGTTCCGA CCCTGCCGCT TACCGGATAC
3361  CTGTCCGCCT TTCTCCCTTC GGGAAGCGTG GCGCTTTCTC ATAGCTCACG CTGTAGGTAT
3421  CTCAGTTCGG TGTAGGTCGT TCGCTCCAAG CTGGGCTGTG TGCACGAACC CCCCGTTCAG
3481  CCCGACCGCT GCGCCTTATC CGGTAACTAT CGTCTTGAGT CCAACCCGGT AAGACACGAC
3541  TTATCGCCAC TGGCAGCAGC CACTGGTAAC AGGATTAGCA GAGCGAGGTA TGTAGGCGGT
3601  GCTACAGAGT TCTTGAAGTG GTGGCCTAAC TACGGCTACA CTAGAAGGAC AGTATTTGGT
3661  ATCTGCGCTC TGCTGAAGCC AGTTACCTTC GGAAAAAGAG TTGGTAGCTC TTGATCCGGC
3721  AAACAAACCA CCGCTGGTAG CGGTGGTTTT TTTGTTTGCA AGCAGCAGAT TACGCGCAGA
3781  AAAAAGGAT CTCAAGAAGA TCCTTTGATC TTTTCTACGG GTCTGACGC TCAGTGGAAC
3841  GAAAACTCAC GTTAAGGGAT TTTGGTCATG AGATTATCAA AAAGGATCTT CACCTAGATC
3901  CTTTTAAATT AAAAATGAAG TTTTAAATCA ATCTAAAGTA TATATGAGTA AACTTGGTCT
3961  GACAGTTACC AATGCTTAAT CAGTGAGGCA CCTATCTCAG CGATCTGTCT ATTTCGTTCA
4021  TCCATAGTTG CCTGACTCCC CGTCGTGTAG ATAACTACGA TACGGGAGGG CTTACCATCT
4081  GGCCCCAGTG CTGCAATGAT ACCGCGAGAC CCACGCTCAC CGGCTCCAGA TTTATCAGCA
4141  ATAAACCAGC CAGCCGGAAG GGCCGAGCGC AGAAGTGGTC CTGCAACTTT ATCCGCCTCC
4201  ATCCAGTCTA TTAATTGTTG CCGGGAAGCT AGAGTAAGTA GTTCGCCAGT TAATAGTTTG
4261  CGCAACGTTG TTGCCATTGC TACAGGCATC GTGGTGTCAC GCTCGTCGTT TGGTATGGCT
4321  TCATTCAGCT CCGGTTCCCA ACGATCAAGG CGAGTTACAT GATCCCCCAT GTTGTGCAAA
```

-continued

```
4381  AAAGCGGTTA GCTCCTTCGG TCCTCCGATC GTTGTCAGAA GTAAGTTGGC CGCAGTGTTA
4441  TCACTCATGG TTATGGCAGC ACTGCATAAT TCTCTTACTG TCATGCCATC CGTAAGATGC
4501  TTTTCTGTGA CTGGTGAGTA CTCAACCAAG TCATTCTGAG AATAGTGTAT GCGGCGACCG
4561  AGTTGCTCTT GCCCGGCGTC AACACGGGAT AATACCGCGC CACATAGCAG AACTTTAAAA
4621  GTGCTCATCA TTGGAAAACG TTCTTCGGGG CGAAAACTCT CAAGGATCTT ACCGCTGTTG
4681  AGATCCAGTT CGATGTAACC CACTCGTGCA CCCAACTGAT CTTCAGCATC TTTTACTTTC
4741  ACCAGCGTTT CTGGGTGAGC AAAAACAGGA AGGCAAAATG CCGCAAAAAA GGGAATAAGG
4801  GCGACACGGA AATGTTGAAT ACTCATACTC TTCCTTTTTC AATATTATTG AAGCATTTAT
4861  CAGGGTTATT GTCTCATGAG CGGATACATA TTTGAATGTA TTTAGAAAAA TAAACAAATA
4921  GGGGTTCCGC GCACATTTCC CCGAAAAGTG CCACCTGACG TCTAAGAGAC CATTATTATC
4981  ATGACATTAA CCTATAAAAA TAGGCGTATC ACGAGGCCCT TTCGTCTTCA AGAATTGTCT
5041  AGAGGCGCGC CGTTTAAACC CTCAGCTACC GATGTACGGG CCAGATATAC GCGTTGACAT
5101  TGATTATTGA CTAGTTATTA ATAGTAATCA ATTACGGGGT CATTAGTTCA TAGCCCATAT
5161  ATGGAGTTCC GCGTTACATA ACTTACGGTA AATGGCCCGC CTGGCTGACC GCCCAACGAC
5221  CCCCGCCCAT TGACGTCAAT AATGACGTAT GTTCCCATAG TAACGCCAAT AGGGACTTTC
5281  CATTGACGTC AATGGGTGGA CTATTTACGG TAAACTGCCC ACTTGGCAGT ACATCAAGTG
5341  TATCATATGC CAAGTACGCC CCCTATTGAC GTCAATGACG GTAAATGGCC CGCCTGGCAT
5401  TATGCCCAGT ACATGACCTT ATGGGACTTT CCTACTTGGC AGTACATCTA CGTATTAGTC
5461  ATCGCTATTA CCATGGTGAT GCGGTTTTGG CAGTACATCA ATGGGCGTGG ATAGCGGTTT
5521  GACTCACGGG GATTTCCAAG TCTCCACCCC ATTGACGTCA ATGGGACTTT GTTTTGGCAC
5581  CAAAATCAAC GGGACTTTCC AAAATGTCGT AACAACTCCG CCCCATTGAC GCAAATGGGC
5641  GGTAGGCGTG TACGGTGGGA GGTCTATATA AGCAGAGCTC TCTGGCTAAC TAGAGAACCC
5701  ACTGCTTACT GGCTTATCGA AATTAATACG ACTCACTATA GCAATTGCAC GTGTGGCCAC
5761  AGGTAAGTTT AAAGCTCAGG TCGAGACCGG GCCTTTGTCC GGCGCTCCCT TGGAGCCTAC
5821  CTAGACTCAG CCGGCTCTCC ACGCTTTGCC TGACCCTGCT TGCTCAACTC TACGTCTTTG
5881  TTTCGTTTTC TGTTCCTTTC TCTCCACAGG CTTAAGCTCG AGGCCGCCAC CATGGCTGTG
5941  CTGGGGCTGC TGTTCTGCCT GGTGACATTC CCAAGCTGTG TGCTGTCCCA GGTGCAGCTG
6001  GTGCAGTCTG GCGCTGAGGT GAAGAAGCCT GGCGCCTCCG TGAAGGTCTC CTGCAAGGCT
6061  TCTGGCTACA CATTCACCAA CTACGCTATG AACTGGGTGC GGCACCCTCC TGGCCAGGGG
6121  CTGGAGTGGA TGGGCTGGAT CAACACTTAC ACCGGTGAGC AACCTACAG CGACGACTTC
6181  AAGGGCAGAG TCACCTTCAC CCTGGACACA TCCACCAGCA CAGCCTACAT GGAGCTGAGG
6241  AGCCTGAGAT CTGACGACAC CGCCGTGTAT TACTGTGCCA GAGGTGGAGG CTACGATGAG
6301  GACTACTTCG ACTACTGGGG CCAGGGCACC CTGGTCACCG TCTCCAGCGC TAGCACCAAG
6361  GGCCCATCGG TCTTCCCCCT GGCACCCTCC TCCAAGAGCA CCTCTGGGGG CACAGCGGCC
6421  CTGGGCTGCC TGGTCAAGGA CTACTTCCCC GAACCGGTGA CGGTGTCGTG GAACTCAGGC
6481  GCCCTGACCA GCGGCGTGCA CACCTTCCCG GCTGTCCTAC AGTCCTCAGG ACTCTACTCC
6541  CTCAGCAGCG TGGTGACCGT GCCCTCCAGC AGCTTGGGCA CCCAGACCTA CATCTGCAAC
6601  GTGAATCACA AGCCCAGCAA CACCAAGGTG GACAAGAAAG TTGAGCCCAA ATCTTGTGAC
6661  AAAACTCACA CATGCCCACC GTGCCCAGCA CCTGAACTCC TGGGGGGACC GTCAGTCTTC
6721  CTCTTCCCCC CAAAACCCAA GGACACCCTC ATGATCTCCC GGACCCCTGA GGTCACATGC
6781  GTGGTGGTGG ACGTGAGCCA CGAAGACCCT GAGGTCAAGT TCAACTGGTA CGTGGACGGC
```

-continued

```
6841   GTGGAGGTGC ATAATGCCAA GACAAAGCCG CGGGAGGAGC AGTACAACAG CACGTACCGT
6901   GTGGTCAGCG TCCTCACCGT CCTGCACCAG GACTGGCTGA ATGGCAAGGA GTACAAGTGC
6961   AAGGTCTCCA ACAAAGCCCT CCCAGCCCCC ATCGAGAAAA CCATCTCCAA AGCCAAAGGG
7021   CAGCCCCGAG AACCACAGGT GTACACCCTG CCCCCATCCC GGGATGAGCT GACCAAGAAC
7081   CAGGTCAGCC TGACCTGCCT GGTCAAAGGC TTCTATCCCA GCGACATCGC CGTGGAGTGG
7141   GAGAGCAATG GGCAGCCGGA GAACAACTAC AAGACCACGC CTCCCGTGCT GGACTCCGAC
7201   GGCTCCTTCT TCCTCTACAG CAAGCTCACC GTGGACAAGA GCAGGTGGCA GCAGGGGAAC
7261   GTCTTCTCAT GCTCCGTGAT GCATGAGGCT CTGCACAACC ACTACACGCA GAAGAGCCTC
7321   TCCCTGTCTC CGGATACATA AATCGATGAT TCTAGATACG GTCCGGAGG ATCCAGATCC
7381   CCCTCGCTTT CTTGCTGTCC AATTTCTATT AAAGGTTCCT TTGTTCCCTA AGTCCAACTA
7441   CTAAACTGGG GGATATTATG AAGGGCCTTG AGCATCTGGA TTCTGCCTAA TAAAAAACAT
7501   TTATTTTCAT TGCAATGATG TATTTAAATT ATTTCTGAAT ATTTTACTAA AAGGGAATG
7561   TGGGAGGTCA GTGCATTTAA AACATAAAGA AATGAAGAGG GGGATCTGTC GACAAGCTCT
7621   AGAGAGCTCA CGCGTTGATC ATGTACAGGC CGGCCAAGCT TTCGACTAGC TTGGCACGCC
7681   AGAAATCCGC GCGGTGGTTT TTGGGGGTCG GGGGTGTTTG GCAGCCACAG ACGCCCGGTG
7741   TTCGTGTCGC GCCAGTACAT GCGGTCCATG CCCAGGCCAT CCAAAAACCA TGGGTCTGTC
7801   TGCTCAGTCC AGTCGTGGAC CTGACCCCAC GCAACGCCCA AATAATAAC CCCCACGAAC
7861   CATAAACCAT TCCCCATGGG GGACCCCGTC CCTAACCCAC GGGGCCAGTG GCTATGGCAG
7921   GGCCTGCCGC CCCGACGTTG GCTGCGAGCC CTGGGCCTTC ACCCGAACTT GGGGGGTGGG
7981   GTGGGGAAAA GGAAGAAACG CGGGCGTATT GGCCCCAATG GGGTCTCGGT GGGGTATCGA
8041   CAGAGTGCCA GCCCTGGGAC CGAACCCCGC GTTTATGAAC AAACGACCCA ACACCCGTGC
8101   GTTTTATTCT GTCTTTTTAT TGCCGTCATA GCGCGGGTTC CTTCCGGTAT TGTCTCCTTC
8161   CGTGTTTCAG TTAGCCTCCC CCATCTCCCG ATCCGGACGA GTGCTGGGGC GTCGGTTTCC
8221   ACTATCGGCG AGTACTTCTA CACAGCCATC GGTCCAGACG GCCGCGCTTC TGCGGGCGAT
8281   TTGTGTACGC CCGACAGTCC CGGCTCCGGA TCGGACGATT GCGTCGCATC GACCCTGCGC
8341   CCAAGCTGCA TCATCGAAAT TGCCGTCAAC CAAGCTCTGA TAGAGTTGGT CAAGACCAAT
8401   GCGGAGCATA TACGCCCGGA GCCGCGGCGA TCCTGCAAGC TCCGGATGCC TCCGCTCGAA
8461   GTAGCGCGTC TGCTGCTCCA TACAAGCCAA CCACGGCCTC CAGAAGAAGA TGTTGGCGAC
8521   CTCGTATTGG GAATCCCCGA ACATCGCCTC GCTCCAGTCA ATGACCGCTG TTATGCGGCC
8581   ATTGTCCGTC AGGACATTGT TGGAGCCGAA ATCCGCGTGC ACGAGGTGCC GGACTTCGGG
8641   GCAGTCCTCG GCCCAAAGCA TCAGCTCATC GAGAGCCTGC GCGACGGACG CACTGACGGT
8701   GTCGTCCATC ACAGTTTGCC AGTGATACAC ATGGGGATCA GCAATCGCGC ATATGAAATC
8761   ACGCCATGTA GTGTATTGAC CGATTCCTTG CGGTCCGAAT GGGCCGAACC CGCTCGTCTG
8821   GCTAAGATCG GCCGCAGCGA TCGCATCCAT GGCCTCCGCG ACCGGCTGCA GAACAGCGGG
8881   CAGTTCGGTT TCAGGCAGGT CTTGCAACGT GACACCCTGT GCACGGCGGG AGATGCAATA
8941   GGTCAGGCTC TCGCTGAATT CCCCAATGTC AAGCACTTCC GGAATCGGGA GCGCGGCCGA
9001   TGCAAAGTGC CGATAAACAT AACGATCTTT GTAGAAACCA TCGGCGCAGC TATTTACCCG
9061   CAGGACATAT CCACGCCCTC CTACATCGAA GCTGAAAGCA CGAGATTCTT CGCCCTCCGA
9121   GAGCTGCATC AGGTCGGAGA CGCTGTCGAA CTTTTCGATC AGAAACTTCT CGACAGACGT
9181   CGCGGTGAGT TCAGGCTTTT TCATATCTCA TTGCCCCCCG GGATCTGCGG CACGCTGTTG
```

```
                               -continued
 9241   ACGCTGTTAA GCGGGTCGCT GCAGGGTCGC TCGGTGTTCG AGGCCACACG CGTCACCTTA
 9301   ATATGCGAAG TGGACCTCGG ACCGCGCCGC CCCGACTGCA TCTGCGTGTT CGAATTCGCC
 9361   AATGACAAGA CGCTGGGCGG GGTTTGTGTC ATCATAGAAC TAAAGACATG CAAATATATT
 9421   TCTTCCGGGG ACACCGCCAG CAAACGCGAG CAACGGGCCA CGGGGATGAA GCAGGGCGGC
 9481   ACCTCGCTAA CGGATTCACC ACTCCAAGAA TTGGAGCCAA TCAATTCTTG CGGAGAACTG
 9541   TGAATGCGCA AACCAACCCT TGGCAGAACA TATCCATCGC GTCCGCCATC TCCAGCAGCC
 9601   GCACGCGGCG CATCTCGGGG CCGACGCGCT GGGCTACGTC TTGCTGGCGT TCGCACAGGC
 9661   CGGCCAGCGC GCGGCCGGCC GGTACCACGC GTTGGCCACA TATGGCGGCC GCTCGCGATT
 9721   AATTAATCGC GATGGCCACA TATGGAGCTC TCTAGAGCTT GTCGACAGAT CCCCCTCTTC
 9781   ATTTCTTTAT GTTTTAAATG CACTGACCTC CCACATTCCC TTTTTAGTAA AATATTCAGA
 9841   AATAATTTAA ATACATCATT GCAATGAAAA TAAATGTTTT TTATTAGGCA GAATCCAGAT
 9901   GGTCAGGCTC CTTCATAATA TCCCCCAGTT TAGTAGTTGG ACTTAGGGAA CAAAGGAACC
 9961   TTTAATAGAA ATTGGACAGC AAGAAAGCGA GGGGGATCTG GATCCTTTAA CACTCTCCCC
10021   TGTTGAAGCT CTTTGTGACG GGCGAGCTCA GGCCCTGATG GGTGACTTCG CAGGCGTAGA
10081   CTTTGTGTTT CTCGTAGTCT GCTTTGCTCA GCGTCAGGGT GCTGCTGAGG CTGTAGGTGC
10141   TGTCCTTGCT GTCCTGCTCT GTGACACTCT CCTGGGAGTT ACCCGATTGG AGGGCGTTAT
10201   CCACCTTCCA CTGTACTTTG GCCTCTCTGG GATAGAAGTT ATTCAGCAGG CACACAACAG
10261   AGGCAGTTCC AGATTTCAAC TGCTCATCAG ATGGCGGGAA GATGAAGACA GATGGTGCAG
10321   CCACCGTACG TTTGATTTCC ACCTTGGTCC CCTGTCCAAA GGTCCATGGT GTGTCATAGT
10381   GCTGCTGACA GTAGTACACG CCCACATCTT CGGCCTCCAC CCGGCTGATC TTCAGAGTGA
10441   AATCTGTCCC AGATCCGCTG CCGCTGAACC TGTCTGGCAC CCCGCTCTCG CGAGTGCTGG
10501   CGAAATAGAT CAGCAGCTGA GGGCTCTGCC CTGGTTTCTG CAGATACCAG GCCAGGTAGG
10561   TCTTCTGGTT GATGGTGTTG AACAGGCTCT GGCTGCTCTT GCAGCTGATG CTGGCTGGCT
10621   CTCCGGGTGT CACAGGCAGG GACAGTGGAG ACTGGGTCAT CACGATATCA CATCTCATGG
10681   CTGGCAGGAA CAGCACCAGC AGCCCCAGCA GCTGCACTGG AGCCATGGTG GCGGCCTCGA
10741   GAAGCTTAAG TTTAATTCTT AAGCCTGTGG AGAGAAAGGA ACAGAAAACG AAACAAAGAC
10801   GTAGAGTTGA GCAAGCAGGG TCAGGCAAAG CGTGGAGAGC CGGCTGAGTC TAGGTAGGCT
10861   CCAAGGGAGC GCCGGACAAA GGCCCGGTCT CGACCTGAGC TTTAAACTTA CCTGTGGCCA
10921   CACGTGCAAT TGCTATAGTG AGTCGTATTA ATTTCGATAA GCCAGTAAGC AGTGGGTTCT
10981   CTAGTTAGCC AGAGAGCTCT GCTTATATAG ACCTCCCACC GTACACGCCT ACCGCCCATT
11041   TGCGTCAATG GGCGGAGTT GTTACGACAT TTTGGAAAGT CCCGTTGATT TTGGAGCCAA
11101   AACAAACTCC CATTGACGTC AATGGGGTGG AGACTTGGAA ATCCCCGTGA GTCAAACCGC
11161   TATCCACGCC CATTGATGTA CTGCCAAAAC CGCATCACCA TGGTAATAGC GATGACTAAT
11221   ACGTAGATGT ACTGCCAAGT AGGAAAGTCC CATAAGGTCA TGTACTGGGC ATAATGCCAG
11281   GCGGGCCATT TACCGTCATT GACGTCAATA GGGGCGTAC TTGGCATATG ATACACTTGA
11341   TGTACTGCCA AGTGGGCAGT TTACCGTAAA TAGTCCACCC ATTGACGTCA ATGGAAAGTC
11401   CCTATTGGCG TTACTATGGG AACATACGTC ATTATTGACG TCAATGGGCG GGGTCGTTG
11461   GGCGGTCAGC CAGGCGGGCC ATTTACCGTA AGTTATGTAA CGCGGAACTC CATATATGGG
11521   CTATGAACTA ATGACCCCGT AATTGATTAC TATTAATAAC TAGTCAATAA TCAATGTCAA
11581   CGCGTATATC TGGCCCGTAC ATCGGTAACT AGTCGGACCG GCCCGGGCCA CCGGTGCTCG
11641   AAGCTTGGAT CGATCCAGAC ATGATAAGAT ACATTGATGA GTTTGGACAA ACCACAACTA
```

```
11701  GAATGCAGTG AAAAAAATGC TTTATTTGTG AAATTTGTGA TGCTATTGCT TTATTTGTAA

11761  CCATTATAAG CTGCAATAAA CAAGTTAACA ACAACAATTG CATTCATTTT ATGTTTCAGG

11821  TTCAGGGGGA GGTGTGGGAG GTTTTTTAAA GCAAGTAAAA CCTCTACAAA TGTGGTATGG

11881  CTGATTATGA TCTCTAGTCA A
```

The present invention further provides, in part, isolated plasmids which exhibit high levels of expression of anti-IL-17 heavy and light chains. One plasmid is pAIL17AV1. The sequence of the pAIL17AV1 plasmid is set forth below:

(SEQ ID NO: 46)
```
   1  GCACTATACA TCAAATATTC CTTATTAACC CCTTTACAAA TTAAAAAGCT AAAGGTACAC

61  AATTTTTGAG CATAGTTATT AATAGCAGAC ACTCTATGCC TGTGTGGAGT AAGAAAAAAC

121  AGTATGTTAT GATTATAACT GTTATGCCTA CTTATAAAGG TTACAGAATA TTTTTCCATA

181  ATTTTCTTGT ATAGCAGTGC AGCTTTTTCC TTTGTGGTGT AAATAGCAAA GCAAGCAAGA

241  GTTCTATTAC TAAACACAGC ATGACTCAAA AAACTTAGCA ATTCTGAAGG AAAGTCCTTG

301  GGGTCTTCTA CCTTTCTCTT CTTTTTTGGA GGAGTAGAAT GTTGAGAGTC AGCAGTAGCC

361  TCATCATCAC TAGATGGCAT TTCTTCTGAG CAAAACAGGT TTTCCTCATT AAAGGCATTC

421  CACCACTGCT CCCATTCATC AGTTCCATAG GTTGGAATCT AAAATACACA AACAATTAGA

481  ATCAGTAGTT TAACACATTA TACACTTAAA AATTTTATAT TTACCTTAGA GCTTTAAATC

541  TCTGTAGGTA GTTTGTCCAA TTATGTCACA CCACAGAAGT AAGGTTCCTT CACAAAGATC

601  GATCTAAAGC CAGCAAAAGT CCCATGGTCT TATAAAAATG CATAGCTTTA GGAGGGGAGC

661  AGAGAACTTG AAAGCATCTT CCTGTTAGTC TTTCTTCTCG TAGACTTCAA ACTTATACTT

721  GATGCCTTTT TCCTCCTGGA CCTCAGAGAG GACGCCTGGG TATTCTGGGA GAAGTTTATA

781  TTTCCCCAAA TCAATTTCTG GGAAAAACGT GTCACTTTCA AATTCCTGCA TGATCCTTGT

441  CACAAAGAGT CTGAGGTGGC CTGGTTGATT CATGGCTTCC TGGTAAACAG AACTGCCTCC

901  GACTATCCAA ACCATGTCTA CTTTACTTGC CAATTCCGGT TGTTCAATAA GTCTTAAGGC

961  ATCATCCAAA CTTTTGGCAA GAAAATGAGC TCCTCGTGGT GGTTCTTTGA GTTCTCTACT

1021  GAGAACTATA TTAATTCTGT CCTTTAAAGG TCGATTCTTC TCAGGAATGG AGAACCAGGT

1081  TTTCCTACCC ATAATCACCA GATTCTGTTT ACCTTCCACT GAAGAGGTTG TGGTCATTCT

1141  TTGGAAGTAC TTGAACTCGT TCCTGAGCGG AGGCCAGGGT AGGTCTCCGT TCTTGCCAAT

1201  CCCCATATTT TGGGACACGG CGACGATGCA GTTCAATGGT CGAACCATGA TGGCAGCGGG

1261  GATAAAATCC TACCAGCCTT CACGCTAGGA TTGCCGTCAA GTTGGCGCG  AAATCGCAGC

1321  CCTGAGCTGT CCCCCCCCCC AAGCTCAGAT CTGAGCTTGG TCCCTATGGT GAGTCCGTTC

1381  CGCTCTTGTG ATGATAGCCA GACAAGAAAG AGACAATACA AGACAAACAC CAAATAGTAG

1441  AAATAGAGAC AAGGGTCACT TATCCGAGGG TCCCTGTTCG GGCGCCAGCT GCCGCAGTCG

1501  GCCGACCTGA GGGTCGCCGG GGTCTGCGGG GGACCCTCT  GGAAAGTGAA GGATAAGTGA

1561  CGAGCGGAGA CGGGATGGCG AACAGACACA AACACACAAG AGGTGAATGT TAGGACTGTT

1621  GCAAGTTTAC TCAAAAAATC AGCACTCTTT TATATCTTGG TTTACATAAG CATTTACATA

1681  AGATTTGGAT AAATTCCAAA AGAACATAGG AAAATAGAAC ACTCAGAGCT CAGATCAGAA

1741  CCTTTGATAC CAAACCAAGT CAGGAAACCA CTTGTCTCAC ATCCTCGTTT TAAGAACAGT

1801  TTGTAACCAA AAACTTACTT AAGCCCTGGG AACCGCAAGG TTGGGCCAAT AAAGGCTATT

1861  CATAATAACT CATGCCATGA GTTTTGCAG  AATAATGTTC TATTAGTCCA GCCACTGTCC

1921  CCTCCTTGGT ATGGAAAATC TTTCCCCAAA AGTGCATTCC TGTTCCTAGA TAAATATAAT
```

-continued

```
1981  CATGTACCTG TTGTTTCATG TCGTCTTTTT CTTCTTGAGA CAACATACAC CAAGGAGGTC
2041  TAGCTCTGGC GAGTCTTTCA CGAAAAGGGA GGGATCTATA TAACACTTTA TAGCCATTGA
2101  CTGTAACCCA CCTATCCCAA TTTAAGTCAT ATCTTCCTGT ATATGGTAAG GGGGCATCTG
2161  TTGGTCTGTA GATGTAAGGT CCCCTATAAG TCCCTGGTTG CCACCACCTG TCTCCTATTT
2221  TGACAAAAAC ACTCTTTTTT CCCTTTTTTA CTTCTAGGCC TGTGGTCAAT AGTCCTTGCA
2281  CCTGTTCTTC AATTGAGGTT GAGCGTCTCT TTCTATTTTC TATTCCCATT TCTAACTTCT
2341  GAATTTGAGT AAAAATAGTA CTAAAGATA ATGATTCATT TCTTAACATA GTAACTAATA
2401  ATCTACCTAT TGGATTGGTC TTATTGGTAA AAATATAATT TTTAGCAAGC ATTCTTATTT
2461  CTATTTCTGA AGGACAAAAT CGATGCGGCT TGTAAGAGGA AGTTGGCTGT GGTCCTTGCC
2521  TCAGGAGGAA GGTCGAGTTC TCCGAATTGT TTAGATTGTA ATCTTGCACA GAAGAGCTAT
2581  TAAAAGAGTC AAGGGTGAGA GCCCTGCGAG CACGAACCGC AACTTCCCCC AATAGCCCCA
2641  GGCAAAGCAG AGCTATGCCA AGTTTGCAGC AGAGAATGAA TATGTCTTTG TCTGATGGGC
2701  TCATCCGTTT GTGCGCAGAC GGGTCGTCCT TGGTGGGAAA CAACCCCTTG GCTGCTTCTC
2761  CCCTAGGTGT AGGACACTCT CGGGAGTTCA ACCATTTCTG CCCAAGCTCA GATCTGAGCT
2821  TTAATGCGGT AGTTTATCAC AGTTAAATTG CTAACGCAGT CAGGCACCGT GTATGAAATC
2881  TAACAATGCG CTCATCGTCA TCCTCGGCAC CGTCACCCTG GATGCTGTAG GCATAGGCTT
2941  GGTTATGCCG GTACTGCCGG GCCTCTTGCG GGATATCGTC CATTCCGACA GCATCGCCAG
3001  TCACTATGGC GTGCTGCTAG CGCTCTTCCG CTTCCTCGCT CACTGACTCG CTGCGCTCGG
3061  TCGTTCGGCT GCGGCGAGCG GTATCAGCTC ACTCAAAGGC GGTAATACGG TTATCCACAG
3121  AATCAGGGGA TAACGCAGGA AGAACATGT GAGCAAAAGG CCAGCAAAAG GCCAGGAACC
3181  GTAAAAAGGC CGCGTTGCTG GCGTTTTTCC ATAGGCTCCG CCCCCCTGAC GAGCATCACA
3241  AAAATCGACG CTCAAGTCAG AGGTGGCGAA ACCCGACAGG ACTATAAAGA TACCAGGCGT
3301  TTCCCCCTGG AAGCTCCCTC GTGCGCTCTC CTGTTCCGAC CCTGCCGCTT ACCGGATACC
3361  TGTCCGCCTT TCTCCCTTCG GGAAGCGTGG CGCTTTCTCA TAGCTCACGC TGTAGGTATC
3421  TCAGTTCGGT GTAGGTCGTT CGCTCCAAGC TGGGCTGTGT GCACGAACCC CCCGTTCAGC
3481  CCGACCGCTG CGCCTTATCC GGTAACTATC GTCTTGAGTC CAACCCGGTA AGACACGACT
3541  TATCGCCACT GGCAGCAGCC ACTGGTAACA GGATTAGCAG AGCGAGGTAT GTAGGCGGTG
3601  CTACAGAGTT CTTGAAGTGG TGGCCTAACT ACGGCTACAC TAGAAGGACA GTATTTGGTA
3661  TCTGCGCTCT GCTGAAGCCA GTTACCTTCG GAAAAAGAGT TGGTAGCTCT TGATCCGGCA
3721  AACAAACCAC CGCTGGTAGC GGTGGTTTTT TTGTTTGCAA GCAGCAGATT ACGCGCAGAA
3781  AAAAAGGATC TCAAGAAGAT CCTTTGATCT TTTCTACGGG GTCTGACGCT CAGTGGAACG
3841  AAAATCGACG TTAAGGGATT TTGGTCATGA GATTATCAAA AAGGATCTTC ACCTAGATCC
3901  TTTTAAATTA AAAATGAAGT TTTAAATCAA TCTAAAGTAT ATATGAGTAA ACTTGGTCTG
3961  ACAGTTACCA ATGCTTAATC AGTGAGGCAC CTATCTCAGC GATCTGTCTA TTTCGTTCAT
4021  CCATAGTTGC CTGACTCCCC GTCGTGTAGA TAACTACGAT ACGGGAGGGC TTACCATCTG
4081  GCCCCAGTGC TGCAATGATA CCGCGAGACC CACGCTCACC GGCTCCAGAT TTATCAGCAA
4141  TAAACCAGCC AGCCGGAAGG GCCGAGCGCA GAAGTGGTCC TGCAACTTTA TCCGCCTCCA
4201  TCCAGTCTAT TAATTGTTGC CGGGAAGCTA GAGTAAGTAG TTCGCCAGTT AATAGTTTGC
4261  GCAACGTTGT TGCCATTGCT ACAGGCATCG TGGTGTCACG CTCGTCGTTT GGTATGGCTT
4321  CATTCAGCTC CGGTTCCCAA CGATCAAGGC GAGTTACATG ATCCCCCATG TTGTGCAAAA
```

```
4381 AAGCGGTTAG CTCCTTCGGT CCTCCGATCG TTGTCAGAAG TAAGTTGGCC GCAGTGTTAT

4441 CACTCATGGT TATGGCAGCA CTGCATAATT CTCTTACTGT CATGCCATCC GTAAGATGCT

4501 TTTCTGTGAC TGGTGAGTAC TCAACCAAGT CATTCTGAGA ATAGTGTATG CGGCGACCGA

4561 GTTGCTCTTG CCCGGCGTCA ACACGGGATA ATACCGCGCC ACATAGCAGA ACTTTAAAAG

4621 TGCTCATCAT TGGAAAACGT TCTTCGGGGC GAAAACTCTC AAGGATCTTA CCGCTGTTGA

4681 GATCCAGTTC GATGTAACCC ACTCGTGCAC CCAACTGATC TTCAGCATCT TTTACTTTCA

4741 CCAGCGTTTC TGGGTGAGCA AAAACAGGAA GGCAAAATGC CGCAAAAAAG GGAATAAGGG

4801 CGACACGGAA ATGTTGAATA CTCATACTCT TCCTTTTTCA ATATTATTGA AGCATTTATC

4861 AGGGTTATTG TCTCATGAGC GGATACATAT TTGAATGTAT TTAGAAAAAT AAACAAATAG

4921 GGGTTCCGCG CACATTTCCC CGAAAAGTGC CACCTGACGT CTAAGAGACC ATTATTATCA

4981 TGACATTAAC CTATAAAAAT AGGCGTATCA CGAGGCCCTT TCGTCTTCAA GAATTGTCTA

5041 GAGGCGCGCC GTTTAAACCC TCAGCTACCG ATGTACGGGC CAGATATACG CGTTGACATT

5101 GATTATTGAC TAGTTATTAA TAGTAATCAA TTACGGGGTC ATTAGTTCAT AGCCCATATA

5161 TGGAGTTCCG CGTTACATAA CTTACGGTAA ATGGCCCGCC TGGCTGACCG CCCAACGACC

5221 CCTGCCGCTT GACGTCAATA ATGACGTATG TTCCCATAGT AACGCCAATA GGGACTTTCC

5281 ATTGACGTCA ATGGGTGGAC TATTTACGGT AAACTGCCCA CTTGGCAGTA CATCAAGTGT

5341 ATCATATGCC AAGTACGCCC CCTATTGACG TCAATGACGG TAAATGGCCC GCCTGGCATT

5401 ATGCCCAGTA CATGACCTTA TGGGACTTTC CTACTTGGCA GTACATCTAC GTATTAGTCA

5461 TCGCTATTAC CATGGTGATG CGGTTTTGGC AGTACATCAA TGGGCGTGGA TAGCGGTTTG

5521 ACTCACGGGG ATTTCCAAGT CTCCACCCCA TTGACGTCAA TGGGAGTTTG TTTTGGCACC

5581 AAAATCAACG GGACTTTCCA AAATGTCGTA ACAACTCCGC CCCATTGACG CAAATGGGCG

5641 GTAGGCGTGT ACGGTGGGAG GTCTATATAA GCAGAGCTCT CTGGCTAACT AGAGAACCCA

5701 CTGCTTACTG GCTTATCGAA ATTAATACGA CTCACTATAG CAATTGCACG TGTGGCCACA

5761 GGTAAGTTTA AAGCTCAGGT CGAGACCGGG CCTTTGTCCG GCGCTCCCTT GGAGCCTACC

5821 TAGACTCAGC CGGCTCTCCA CGCTTTGCCT GACCCTGCTT GCTCAACTCT ACGTCTTTGT

5881 TTCGTTTTCT GTTCCTTTCT CTCCACAGGC TTAAGAGTAC TGCCGCCACC ATGGCTGTGC

5941 TGGGGCTGCT GTTCTGCCTG GTGACATTCC CAAGCTGTGT GCTGTCCCAG GTGCAGCTGC

6001 AGGAGTCTGG ACCAGGCCTG GTGAAGCCTA GCGAGACCCT GAGCCTGACC TGTACCGTGT

6061 CTGGATTCAG CCTGCCCAGC CACAGCGTGA GCTGGATCAG ACAGCCTCCA GGCAAGGGAC

6121 TGGAGTGGAT CGGCATCATT TGGAATCAAG GCGGCACTGA CTATAACAGC GCCTTCAAGA

6181 GCCGCGTGAC CATCTCCGTG GACACCTCCA AGAACCAGTT CAGCCTGAAG CTGAGCAGCG

6241 TGACCGCTGC CGACACCGCT GTGTATTACT GTGCCAGAAA TGCATACATC ACCGACTACT

6301 ATTACGAGAA CTACTTCATG GATGCCTGGG ACAGGGCAC CCTGGTGACC GTGAGCTCCG

6361 CTAGCACCAA GGGCCCATCG GTCTTCCCCC TGGCACCCTC CTCCAAGAGC ACCTCTGGGG

6421 GCACAGCGGC CCTGGGCTGC CTGGTCAAGG ACTACTTCCC CGAACCGGTG ACGGTGTCGT

6481 GGAACTCAGG CGCCCTGACC AGCGGCGTGC ACACCTTCCC GGCTGTCCTA CAGTCCTCAG

6541 GACTCTACTC CCTCAGCAGC GTGGTGACCG TGCCCTCCAG CAGCTTGGGC ACCCAGACCT

6601 ACATCTGCAA CGTGAATCAC AAGCCCAGCA ACACCAAGGT GGACAAGAAA GTTGAGCCCA

6661 AATCTTGTGA CAAAACTCAC ACATGCCCAC CGTGCCCAGC ACCTGAACTC CTGGGGGGAC

6721 CGTCAGTCTT CCTCTTCCCC CCAAAACCCA AGGACACCCT CATGATCTCC CGGACCCCTG

6781 AGGTCACATG CGTGGTGGTG GACGTGAGCC ACGAAGACCC TGAGGTCAAG TTCAACTGGT
```

-continued

```
6841  ACGTGGACGG CGTGGAGGTG CATAATGCCA AGACAAAGCC GCGGGAGGAG CAGTACAACA
6901  GCACGTACCG TGTGGTCAGC GTCCTCACCG TCCTGCACCA GGACTGGCTG AATGGCAAGG
6961  AGTACAAGTG CAAGGTCTCC AACAAAGCCC TCCCAGCCCC CATCGAGAAA ACCATCTCCA
7021  AAGCCAAAGG GCAGCCCCGA GAACCACAGG TGTACACCCT GCCCCCATCC CGGGATGAGC
7081  TGACCAAGAA CCAGGTCAGC CTGACCTGCC TGGTCAAAGG CTTCTATCCC AGCGACATCG
7141  CCGTGGAGTG GGAGAGCAAT GGGCAGCCGG AGAACAACTA CAAGACCACG CCTCCCGTGC
7201  TGGACTCCGA CGGCTCCTTC TTCCTCTACA GCAAGCTCAC CGTGGACAAG AGCAGGTGGC
7261  AGCAGGGGAA CGTCTTCTCA TGCTCCGTGA TGCATGAGGC TCTGCACAAC CACTACACGC
7321  AGAAGAGCCT CTCCCTGTCT CCGGGTAAAT GAATCGATGA TTCTAGATAC GGGTCCGGAG
7381  GATCCAGATC CCCCTCGCTT TCTTGCTGTC CAATTTCTAT TAAAGGTTCC TTTGTTCCCT
7441  AAGTCCAACT ACTAAACTGG GGGATATTAT GAAGGGCCTT GAGCATCTGG ATTCTGCCTA
7501  ATAAAAAACA TTTATTTTCA TTGCAATGAT GTATTTAAAT TATTTCTGAA TATTTTACTA
7561  AAAAGGGAAT GTGGGAGGTC AGTGCATTTA AAACATAAAG AAATGAAGAG GGGGATCTGT
7621  CGACAAGCTC TAGAGAGCTC ACGCGTTGAT CATGTACAGG CCGGCCAAGC TTTCGACTAG
7681  CTTGGCACGC CAGAAATCCG CGCGGTGGTT TTTGGGGGTC GGGGGTGTTT GGCAGCCACA
7741  GACGCCCGGT GTTCGTGTCG CGCCAGTACA TGCGGTCCAT GCCCAGGCCA TCCAAAAACC
7801  ATGGGTCTGT CTGCTCAGTC CAGTCGTGGA CCTGACCCCA CGCAACGCCC AAAATAATAA
7861  CCCCCACGAA CCATAAACCA TTCCCCATGG GGACCCCGT CCCTAACCCA CGGGGCCAGT
7921  GGCTATGGCA GGGCCTGCCG CCCCGACGTT GGCTGCGAGC CCTGGGCCTT CACCCGAACT
7981  TGGGGGGTGG GGTGGGGAAA AGGAAGAAAC GCGGGCGTAT TGGCCCCAAT GGGGTCTCGG
8041  TGGGGTATCG ACAGAGTGCC AGCCCTGGGA CCGAACCCCG CGTTTATGAA CAAACGACCC
8101  AACACCCGTG CGTTTTATTC TGTCTTTTTA TTGCCGTCAT AGCGCGGGTT CCTTCCGGTA
8161  TTGTCTCCTT CCGTGTTTCA GTTAGCCTCC CCCATCTCCC GATCCGGACG AGTGCTGGGG
8221  CGTCGGTTTC CACTATCGGC GAGTACTTCT ACACAGCCAT CGGTCCAGAC GGCCGCGCTT
8281  CTGCGGGCGA TTTGTGTACG CCCGACAGTC CCGGCTCCGG ATCGGACGAT TGCGTCGCAT
8341  CGACCCTGCG CCCAAGCTGC ATCATCGAAA TTGCCGTCAA CCAAGCTCTG ATAGAGTTGG
8401  TCAAGACCAA TGCGGAGCAT ATACGCCCGG AGCCGCGGCG ATCCTGCAAG CTCCGGATGC
8461  CTCCGCTCGA AGTAGCGCGT CTGCTGCTCC ATACAAGCCA ACCACGGCCT CCAGAAGAAG
8521  ATGTTGGCGA CCTCGTATTG GGAATCCCCG AACATCGCCT CGCTCCAGTC AATGACCGCT
8581  GTTATGCGGC CATTGTCCGT CAGGACATTG TTGGAGCCGA ATCCGCGTG CACGAGGTGC
8641  CGGACTTCGG GGCAGTCCTC GGCCCAAAGC ATCAGCTCAT CGAGAGCCTG CGCGACGGAC
8701  GCACTGACGG TGTCGTCCAT CACAGTTTGC CAGTGATACA CATGGGGATC AGCAATCGCG
8761  CATATGAAAT CACGCCATGT AGTGTATTGA CCGATTCCTT GCGGTCCGAA TGGGCCGAAC
8821  CCGCTCGTCT GGCTAAGATC GGCCGCAGCG ATCGCATCCA TGGCCTCCGC GACCGGCTGC
8881  AGAACAGCGG GCAGTTCGGT TTCAGGCAGG TCTTGCAACG TGACACCCTG TGCACGGCGG
8941  GAGATGCAAT AGGTCAGGCT CTCGCTGAAT TCCCCAATGT CAAGCACTTC CGGAATCGGG
9001  AGCGCGGCCG ATGCAAAGTG CCGATAAACA TAACGATCTT TGTAGAAACC ATCGGCGCAG
9061  CTATTTACCC GCAGGACATA TCCACGCCCT CCTACATCGA AGCTGAAAGC ACGAGATTCT
9121  TCGCCCTCCG AGAGCTGCAT CAGGTCGGAG ACGCTGTCGA ACTTTTCGAT CAGAAACTTC
9181  TCGACAGACG TCGCGGTGAG TTCAGGCTTT TTCATATCTC ATTGCCCCCC GGGATCTGCG
```

```
                            -continued
 9241  GCACGCTGTT GACGCTGTTA AGCGGGTCGC TGCAGGGTCG CTCGGTGTTC GAGGCCACAC

9301  GCGTCACCTT AATATGCGAA GTGGACCTCG GACCGCGCCG CCCCGACTGC ATCTGCGTGT

9361  TCGAATTCGC CAATGACAAG ACGCTGGGCG GGGTTTGTGT CATCATAGAA CTAAAGACAT

9421  GCAAATATAT TTCTTCCGGG GACACCGCCA GCAAACGCGA GCAACGGGCC ACGGGGATGA

9481  AGCAGGGCGG CACCTCGCTA ACGGATTCAC CACTCCAAGA ATTGGAGCCA ATCAATTCTT

9541  GCGGAGAACT GTGAATGCGC AAACCAACCC TTGGCAGAAC ATATCCATCG CGTCCGCCAT

9601  CTCCAGCAGC CGCACGCGGC GCATCTCGGG GCCGACGCGC TGGGCTACGT CTTGCTGGCG

9661  TTCGCACAGG CCGGCCAGCG CGCGGCCGGC CGGTACCACG CGTTGGCCAC ATATGGCGGC

9721  CGCTCGCGAT TAATTAATCG CGATGGCCAC ATATGGAGCT CTCTAGAGCT TGTCGACAGA

9781  TCCCCCTCTT CATTTCTTTA TGTTTTAAAT GCACTGACCT CCCACATTCC CTTTTTAGTA

9841  AAATATTCAG AAATAATTTA AATACATCAT TGCAATGAAA ATAAATGTTT TTTATTAGGC

9901  AGAATCCAGA TGCTCAAGGC CCTTCATAAT ATCCCCCAGT TTAGTAGTTG GACTTAGGGA

9961  ACAAAGGAAC CTTTAATAGA AATTGGACAG CAAGAAAGCG AGGGGGATCG GATCCTCCG

10021  GAGGGCCCCT TCTCCCTCTA ACACTCTCCC CTGTTGAAGC TCTTTGTGAC GGGCGAGCTC

10081  AGGCCCTGAT GGGTGACTTC GCAGGCGTAG ACTTTGTGTT TCTCGTAGTC TGCTTTGCTC

10141  AGCGTCAGGG TGCTGCTGAG GCTGTAGGTG CTGTCCTTGC TGTCCTGCTC TGTGACACTC

10201  TCCTGGGAGT TACCCGATTG GAGGGCGTTA TCCACCTTCC ACTGTACTTT GGCCTCTCTG

10261  GGATAGAAGT TATTCAGCAG GCACACAACA GAGGCAGTTC CAGATTTCAA CTGCTCATCA

10321  GATGGCGGGA AGATGAAGAC AGATGGTGCA GCCACCGTAC GTTTGATTTC CACCTTGGTC

10381  CCCTGTCCAA AGGTGTAGGG TGTGTAATAG CTCTGCTGAC AGTAGTACAC GCCCACATCT

10441  TCGGCCTCCA CCCGGCTGAT CTTCAGAGTG AAATCTGTCC CAGATCCGCT GCCGCTGAAC

10501  CTGTCTGGCA CCCCGCTCTG CCGGGTGCTG GTCCAATAGA TCAGCAGCTG AGGGCTCTGC

10561  CCTGGTTTCT GCAGATACCA GGCCAGGTAG TTCTTCTGGT TCTCGCTGAA CAGCAGGCTC

10621  TGGCTGCTCT TGCAGCTGAT GCTGGCTGGC TCTCCGGGTG TCACAGGCAG GGACAGTGGA

10681  GACTGGGTCA TCACGATATC ACATCTCATG GCTGGCAGGA ACAGCACCAG CAGCCCCAGC

10741  AGCTGCACTG GAGCCATGGT GGCGGCGCTA GCGAATTCTT AAGCCTGTGG AGAGAAAGGA

10801  ACAGAAAACG AAACAAAGAC GTAGAGTTGA GCAAGCAGGG TCAGGCAAAG CGTGGAGAGC

10861  CGGCTGAGTC TAGGTAGGCT CCAAGGGAGC GCCGGACAAA GGCCCGGTCT CGACCTGAGC

10921  TTTAAACTTA CCTGTGGCCA CACGTGCAAT TGCTATAGTG AGTCGTATTA ATTTCGATAA

10981  GCCAGTAAGC AGTGGGTTCT CTAGTTAGCC AGAGAGCTCT GCTTATATAG ACCTCCCACC

11041  GTACACGCCT ACCGCCCATT TGCGTCAATG GGGCGGAGTT GTTACGACAT TTTGGAAAGT

11101  CCCGTTGATT TTGGTGCCAA AACAAACTCC CATTGACGTC AATGGGGTGG AGACTTGGAA

11161  ATCCCCGTGA GTCAAACCGC TATCCACGCC CATTGATGTA CTGCCAAAAC CGCATCACCA

11221  TGGTAATAGC GATGACTAAT ACGTAGATGT ACTGCCAAGT AGGAAAGTCC CATAAGGTCA

11281  TGTACTGGGC ATAATGCCAG GCGGGCCATT TACCGTCATT GACGTCAATA GGGGGCGTAC

11341  TTGGCATATG ATACACTTGA TGTACTGCCA AGTGGGCAGT TTACCGTAAA TAGTCCACCC

11401  ATTGACGTCA ATGGAAAGTC CTATTGGCG TTACTATGGG AACATACGTC ATTATTGACG

11461  TCAATGGGCG GGGTCGTTG GGCGGTCAGC CAGGCGGGCC ATTTACCGTA AGTTATGTAA

11521  CGCGGAACTC CATATATGGG CTATGAACTA ATGACCCCGT AATTGATTAC TATTAATAAC

11581  TAGTCAATAA TCAATGTCAA CGCGTATATC TGGCCCGTAC ATCGGTAACT AGTCGGACCG

11641  GCCCGGGCCA CCGGTGCTCG AAGCTTGGAT CGATCCAGAC ATGATAAGAT ACATTGATGA
```

-continued

```
11701  GTTTGGACAA ACCACAACTA GAATGCAGTG AAAAAAATGC TTTATTTGTG AAATTTGTGA

11761  TGCTATTGCT TTATTTGTAA CCATTATAAG CTGCAATAAA CAAGTTAACA ACAACAATTG

11821  CATTCATTTT ATGTTTCAGG TTCAGGGGGA GGTGTGGGAG GTTTTTTAAA GCAAGTAAAA

11881  CCTCTACAAA TGTGGTATGG CTGATTATGA TCTCTAGTCA AG
```

The present invention further provides, in part, isolated plasmids which exhibit high levels of expression of anti-PD1 (Programmed Death 1) heavy and light chains. One plasmid is pAPD16V1-GA. The sequence of the pAPD16V1-GA plasmid is set forth below:

(SEQ ID NO: 47)
```
   1  GCACTATACA TCAAATATTC CTTATTAACC CCTTTACAAA TTAAAAAGCT AAAGGTACAC

61  AATTTTTGAG CATAGTTATT AATAGCAGAC ACTCTATGCC TGTGTGGAGT AAGAAAAAAC

121  AGTATGTTAT GATTATAACT GTTATGCCTA CTTATAAAGG TTACAGAATA TTTTTCCATA

181  ATTTTCTTGT ATAGCAGTGC AGCTTTTTCC TTTGTGGTGT AAATAGCAAA GCAAGCAAGA

241  GTTCTATTAC TAAACACAGC ATGACTCAAA AAACTTAGCA ATTCTGAAGG AAAGTCCTTG

301  GGGTCTTCTA CCTTTCTCTT CTTTTTTGGA GGAGTAGAAT GTTGAGAGTC AGCAGTAGCC

361  TCATCATCAC TAGATGGCAT TTCTTCTGAG CAAAACAGGT TTTCCTCATT AAAGGCATTC

421  CACCACTGCT CCCATTCATC AGTTCCATAG GTTGGAATCT AAAATACACA AACAATTAGA

481  ATCAGTAGTT TAACACATTA TACACTTAAA AATTTTATAT TTACCTTAGA GCTTTAAATC

541  TCTGTAGGTA GTTTGTCCAA TTATGTCACA CCACAGAAGT AAGGTTCCTT CACAAAGATC

601  GATCTAAAGC CAGCAAAAGT CCCATGGTCT TATAAAAATG CATAGCTTTA GGAGGGGAGC

661  AGAGAACTTG AAAGCATCTT CCTGTTAGTC TTTCTTCTCG TAGACTTCAA ACTTATACTT

721  GATGCCTTTT TCCTCCTGGA CCTCAGAGAG GACGCCTGGG TATTCTGGGA GAAGTTTATA

781  TTTCCCCAAA TCAATTTCTG GGAAAAACGT GTCACTTTCA AATTCCTGCA TGATCCTTGT

841  CACAAAGAGT CTGAGGTGGC CTGGTTGATT CATGGCTTCC TGGTAAACAG AACTGCCTCC

901  GACTATCCAA ACCATGTCTA CTTTACTTGC CAATTCCGGT TGTTCAATAA GTCTTAAGGC

961  ATCATCCAAA CTTTTGGCAA GAAAATGAGC TCCTCGTGGT GGTTCTTTGA GTTCTCTACT

1021  GAGAACTATA TTAATTCTGT CCTTTAAAGG TCGATTCTTC TCAGGAATGG AGAACCAGGT

1081  TTTCCTACCC ATAATCACCA GATTCTGTTT ACCTTCCACT GAAGAGGTTG TGGTCATTCT

1141  TTGGAAGTAC TTGAACTCGT TCCTGAGCGG AGGCCAGGGT AGGTCTCCGT TCTTGCCAAT

1201  CCCCATATTT TGGGACACGG CGACGATGCA GTTCAATGGT CGAACCATGA TGGCAGCGGG

1261  GATAAAATCC TACCAGCCTT CACGCTAGGA TTGCCGTCAA GTTTGGCGCG AAATCGCAGC

1321  CCTGAGCTGT CCCCCCCCCC AAGCTCAGAT CTGAGCTTGG TCCCTATGGT GAGTCCGTTC

1381  CGCTCTTGTG ATGATAGCCA GACAAGAAAG AGACAATACA AGACAAACAC CAAATAGTAG

1441  AAATAGAGAC AAGGGTCACT TATCCGAGGG TCCCTGTTCG GGCGCCAGCT GCCGCAGTCG

1501  GCCGACCTGA GGGTCGCCGG GGTCTGCGGG GGGACCCTCT GGAAAGTGAA GGATAAGTGA

1561  CGAGCGGAGA CGGGATGGCG AACAGACACA AACACACAAG AGGTGAATGT TAGGACTGTT

1621  GCAAGTTTAC TCAAAAAATC AGCACTCTTT TATATCTTGG TTTACATAAG CATTTACATA

1681  AGATTTGGAT AAATTCCAAA AGAACATAGG AAAATAGAAC ACTCAGAGCT CAGATCAGAA

1741  CCTTTGATAC CAAACCAAGT CAGGAAACCA CTTGTCTCAC ATCCTCGTTT TAAGAACAGT

1801  TTGTAACCAA AAACTTACTT AAGCCCTGGG AACCGCAAGG TTGGGCCAAT AAAGGCTATT
```

-continued

```
1861 CATAATAACT CATGCCATGA GTTTTTGCAG AATAATGTTC TATTAGTCCA GCCACTGTCC
1921 CCTCCTTGGT ATGGAAAATC TTTCCCCAAA AGTGCATTCC TGTTCCTAGA TAAATATAAT
1981 CATGTACCTG TTGTTTCATG TCGTCTTTTT CTTCTTGAGA CAACATACAC CAAGGAGGTC
2041 TAGCTCTGGC GAGTCTTTCA CGAAAAGGGA GGGATCTATA TAACACTTTA TAGCCATTGA
2101 CTGTAACCCA CCTATCCCAA TTTAAGTCAT ATCTTCCTGT ATATGGTAAG GGGGCATCTG
2161 TTGGTCTGTA GATGTAAGGT CCCCTATAAG TCCCTGGTTG CCACCACCTG TCTCCTATTT
2221 TGACAAAAAC ACTCTTTTTT CCCTTTTTTA CTTCTAGGCC TGTGGTCAAT AGTCCTTGCA
2281 CCTGTTCTTC AATTGAGGTT GAGCGTCTCT TTCTATTTTC TATTCCCATT TCTAACTTCT
2341 GAATTTGAGT AAAAATAGTA CTAAAGATA ATGATTCATT TCTTAACATA GTAACTAATA
2401 ATCTACCTAT TGGATTGGTC TTATTGGTAA AAATATAATT TTTAGCAAGC ATTCTTATTT
2461 CTATTTCTGA AGGACAAAAT CGATGCGGCT TGTAAGAGGA AGTTGGCTGT GGTCCTTGCC
2521 TCAGGAGGAA GGTCGAGTTC TCCGAATTGT TTAGATTGTA ATCTTGCACA GAAGAGCTAT
2581 TAAAAGAGTC AAGGGTGAGA GCCCTGCGAG CACGAACCGC AACTTCCCCC AATAGCCCCA
2641 GGCAAAGCAG AGCTATGCCA AGTTTGCAGC AGAGAATGAA TATGTCTTTG TCTGATGGGC
2701 TCATCCGTTT GTGCGCAGAC GGGTCGTCCT TGGTGGGAAA CAACCCCTTG GCTGCTTCTC
2761 CCCTAGGTGT AGGACACTCT CGGGAGTTCA ACCATTTCTG CCCAAGCTCA GATCTGAGCT
2821 TTAATGCGGT AGTTTATCAC AGTTAAATTG CTAACGCAGT CAGGCACCGT GTATGAAATC
2881 TAACAATGCG CTCATCGTCA TCCTCGGCAC CGTCACCCTG GATGCTGTAG GCATAGGCTT
2941 GGTTATGCCG GTACTGCCGG GCCTCTTGCG GGATATCGTC CATTCCGACA GCATCGCCAG
3001 TCACTATGGC GTGCTGCTAG CGCTCTTCCG CTTCCTCGCT CACTGACTCG CTGCGCTCGG
3061 TCGTTCGGCT GCGGCGAGCG GTATCAGCTC ACTCAAAGGC GGTAATACGG TTATCCACAG
3121 AATCAGGGGA TAACGCAGGA AAGAACATGT GAGCAAAAGG CCAGCAAAAG GCCAGGAACC
3181 GTAAAAAGGC CGCGTTGCTG GCGTTTTTCC ATAGGCTCCG CCCCCCTGAC GAGCATCACA
3241 AAAATCGACG CTCAAGTCAG AGGTGGCGAA ACCCGACAGG ACTATAAAGA TACCAGGCGT
3301 TTCCCCCTGG AAGCTCCCTC GTGCGCTCTC CTGTTCCGAC CCTGCCGCTT ACCGGATACC
3361 TGTCCGCCTT TCTCCCTTCG GGAAGCGTGG CGCTTTCTCA TAGCTCACGC TGTAGGTATC
3421 TCAGTTCGGT GTAGGTCGTT CGCTCCAAGC TGGGCTGTGT GCACGAACCC CCCGTTCAGC
3481 CCGACCGCTG CGCCTTATCC GGTAACTATC GTCTTGAGTC AACCCGGTA AGACACGACT
3541 TATCGCCACT GGCAGCAGCC ACTGGTAACA GGATTAGCAG AGCGAGGTAT GTAGGCGGTG
3601 CTACAGAGTT CTTGAAGTGG TGGCCTAACT ACGGCTACAC TAGAAGGACA GTATTTGGTA
3661 TCTGCGCTCT GCTGAAGCCA GTTACCTTCG GAAAAAGAGT TGGTAGCTCT TGATCCGGCA
3721 AACAAACCAC CGCTGGTAGC GGTGGTTTTT TTGTTTGCAA GCAGCAGATT ACGCGCAGAA
3781 AAAAAGGATC TCAAGAAGAT CCTTTGATCT TTTCTACGGG GTCTGACGCT CAGTGGAACG
3841 AAAACTCACG TTAAGGGATT TTGGTCATGA GATTATCAAA AAGGATCTTC ACCTAGATCC
3901 TTTTAAATTA AAAATGAAGT TTTAAATCAA TCTAAAGTAT ATATGAGTAA ACTTGGTCTG
3961 ACAGTTACCA ATGCTTAATC AGTGAGGCAC CTATCTCAGC GATCTGTCTA TTTCGTTCAT
4021 CCATAGTTGC CTGACTCCCC GTCGTGTAGA TAACTACGAT ACGGGAGGGC TTACCATCTG
4081 GCCCCAGTGC TGCAATGATA CCGCGAGACC CACGCTCACC GGCTCCAGAT TTATCAGCAA
4141 TAAACCAGCC AGCCGGAAGG GCCGAGCGCA GAAGTGGTCC TGCAACTTTA TCCGCCTCCA
4201 TCCAGTCTAT TAATTGTTGC CGGGAAGCTA GAGTAAGTAG TTCGCCAGTT AATAGTTTGC
4261 GCAACGTTGT TGCCATTGCT ACAGGCATCG TGGTGTCACG CTCGTCGTTT GGTATGGCTT
```

-continued

```
4321  CATTCAGCTC CGGTTCCCAA CGATCAAGGC GAGTTACATG ATCCCCCATG TTGTGCAAAA
4381  AAGCGGTTAG CTCCTTCGGT CCTCCGATCG TTGTCAGAAG TAAGTTGGCC GCAGTGTTAT
4441  CACTCATGGT TATGGCAGCA CTGCATAATT CTCTTACTGT CATGCCATCC GTAAGATGCT
4501  TTTCTGTGAC TGGTGAGTAC TCAACCAAGT CATTCTGAGA ATAGTGTATG CGGCGACCGA
4561  GTTGCTCTTG CCCGGCGTCA ACACGGGATA ATACCGCGCC ACATAGCAGA ACTTTAAAAG
4621  TGCTCATCAT TGGAAAACGT TCTTCGGGGC GAAAACTCTC AAGGATCTTA CCGCTGTTGA
4681  GATCCAGTTC GATGTAACCC ACTCGTGCAC CCAACTGATC TTCAGCATCT TTTACTTTCA
4741  CCAGCGTTTC TGGGTGAGCA AAAACAGGAA GGCAAAATGC CGCAAAAAAG GGAATAAGGG
4801  CGACACGGAA ATGTTGAATA CTCATACTCT TCCTTTTTCA ATATTATTGA AGCATTTATC
4861  AGGGTTATTG TCTCATGAGC GGATACATAT TTGAATGTAT TTAGAAAAAT AAACAAATAG
4921  GGGTTCCGCG CACATTTCCC CGAAAAGTGC CACCTGACGT CTAAGAGACC ATTATTATCA
4981  TGACATTAAC CTATAAAAAT AGGCGTATCA CGAGGCCCTT TCGTCTTCAA GAATTGTCTA
5041  GAGGCGCGCC GTTTAAACCC TCAGCTACCG ATGTACGGGC CAGATATACG CGTTGACATT
5101  GATTATTGAC TAGTTATTAA TAGTTATTAA TTACGGGTC ATTAGTTCAT AGCCCATATA
5161  TGGAGTTCCG CGTTACATAA CTTACGGTAA ATGGCCCGCC TGGCTGACCG CCCAACGACC
5221  CCCGCCCATT GACGTCAATA ATGACGTATG TTCCCATAGT AACGCCAATA GGGACTTTCC
5281  ATTGACGTCA ATGGGTGGAC TATTTACGGT AAACTGCCCA CTTGGCAGTA CATCAAGTGT
5341  ATCATATGCC AAGTACGCCC CCTATTGACG TCAATGACGG TAAATGGCCC GCCTGGCATT
5401  ATGCCCAGTA CATGACCTTA TGGGACTTTC CTACTTGGCA GTACATCTAC GTATTAGTCA
5461  TCGCTATTAC CATGGTGATG CGGTTTTGGC AGTACATCAA TGGGCGTGGA TAGCGGTTTG
5521  ACTCACGGGG ATTTCCAAGT CTCCACCCCA TTGACGTCAA TGGGAGTTTG TTTTGGCACC
5581  AAAATCAACG GGACTTTCCA AAATGTCGTA ACAACTCCGC CCCATTGACG CAAATGGGCG
5641  GTAGGCGTGT ACGGTGGGAG GTCTATATAA GCAGAGCTCT CTGGCTAACT AGAGAACCCA
5701  CTGCTTACTG GCTTATCGAA ATTAATACGA CTCACTATAG CAATTGCACG TGTGGCCACA
5761  GGTAAGTTTA AAGCTCAGGT CGAGACCGGG CCTTTGTCCG GCGCTCCCTT GGAGCCTACC
5821  TAGACTCAGC CGGCTCTCCA CGCTTTGCCT GACCCTGCTT GCTCAACTCT ACGTCTTTGT
5881  TTCGTTTTCT GTTCCTTTCT CTCCACAGGC TTAAGCTCGA GGCCGCCACC ATGGCCGTGC
5941  TGGGCCTGCT GTTCTGCCTG GTGACCTTCC CTTCCTGCGT GCTGTCCCAG GTGCAGCTGG
6001  TGCAGTCCGG CGTGGAGGTG AAGAAGCCTG GCGCCTCCGT CAAGGTGTCC TGTAAGGCCT
6061  CCGGCTACAC CTTCACCAAC TACTACATGT ACTGGGTGCG GCAGGCCCCA GGCCAGGGAC
6121  TGGAGTGGAT GGGCGGCATC AACCCTTCCA ACGGCGGCAC CAACTTCAAC GAGAAGTTCA
6181  ACAAGCGGGT GACCCTGACC ACCGACTCCT CCACCACAAC CGCCTACATG GAACTGAAGT
6241  CCCTGCAGTT CGACGACACC GCCGTGTACT ACTGCGCCAG GCGGGACTAC CGGTTCGACA
6301  TGGGCTTCGA CTACTGGGGC CAGGGCACCA CCGTGACCGT GTCCTCCGCT AGCACCAAGG
6361  GCCCTTCCGT GTTCCCTCTG GCCCCTTGCT CCCGGTCCAC CTCCGAGTCC ACCGCCGCTC
6421  TGGGCTGTCT GGTGAAGGAC TACTTCCCTG AGCCTGTGAC CGTGAGCTGG AACTCTGGCG
6481  CCCTGACCTC CGGCGTGCAC ACCTTCCCTG CCGTGCTGCA GTCCTCCGGC CTGTACTCCC
6541  TGTCCTCCGT GGTGACCGTG CCTTCCTCCT CCCTGGGCAC CAAGACCTAC ACCTGCAACG
6601  TGGACCACAA GCCTTCCAAC ACCAAGGTGG ACAAGCGGGT GGAGTCCAAG TACGGCCCTC
6661  CTTGCCCTCC CTGCCCTGCC CCTGAGTTCC TGGGCGGACC CTCCGTGTTC CTGTTCCCTC
```

```
                         -continued
6721  CTAAGCCTAA GGACACCCTG ATGATCTCCC GGACCCCTGA GGTGACCTGC GTGGTGGTGG

6781  ACGTGTCCCA GGAAGATCCT GAGGTCCAGT TCAATTGGTA CGTGGATGGC GTGGAGGTGC

6841  ACAACGCCAA GACCAAGCCT CGGGAGGAAC AGTTCAACTC CACCTACCGG GTGGTGTCTG

6901  TGCTGACCGT GCTGCACCAG GACTGGCTGA ACGGCAAGGA ATACAAGTGC AAGGTCAGCA

6961  ACAAGGGCCT GCCCTCCTCC ATCGAGAAAA CCATCTCCAA GGCCAAGGGC CAGCCTCGCG

7021  AGCCTCAGGT GTACACCCTG CCTCCTAGCC AGGAAGAGAT GACCAAGAAT CAGGTGTCCC

7081  TGACATGCCT GGTGAAGGGC TTCTACCCTT CCGATATCGC CGTGGAGTGG GAGAGCAACG

7141  GCCAGCCAGA GAACAACTAC AAGACCACCC CTCCTGTGCT GGACTCCGAC GGCTCCTTCT

7201  TCCTGTACTC CAGGCTGACC GTGGACAAGT CCCGGTGGCA GGAAGGCAAC GTCTTTTCCT

7261  GCTCCGTGAT GCACGAGGCC CTGCACAACC ACTACACCCA GAAGTCCCTG TCCCTGTCTC

7321  TGGGCAAGTG AATCGATGGA TCCAGATCCC CCTCGCTTTC TTGCTGTCCA ATTTCTATTA

7381  AAGGTTCCTT TGTTCCCTAA GTCCAACTAC TAAACTGGGG GATATTATGA AGGGCCTTGA

7441  GCATCTGGAT TCTGCCTAAT AAAAAACATT TATTTTCATT GCAATGATGT ATTTAAATTA

7501  TTTCTGAATA TTTTACTAAA AAGGGAATGT GGGAGGTCAG TGCATTTAAA ACATAAAGAA

7561  ATGAAGAGGG GGATCTGTCG ACAAGCTCTA GAGAGCTCAC GCGTTGATCA TGTACAGGCC

7621  GGCCAAGCTT TCGACTAGCT TGGCACGCCA GAAATCCGCG CGGTGGTTTT TGGGGGTCGG

7681  GGGTGTTTGG CAGCCACAGA CGCCCGGTGT TCGTGTCGCG CCAGTACATG CGGTCCATGC

7741  CCAGGCCATC CAAAAACCAT GGGTCTGTCT GCTCAGTCCA GTCGTGGACC TGACCCCACG

7801  CAACGCCCAA AATAATAACC CCCACGAACC ATAAACCATT CCCCATGGGG GACCCCGTCC

7861  CTAACCCACG GGGCCAGTGG CTATGGCAGG GCCTGCCGCC CCGACGTTGG CTGCGAGCCC

7921  TGGGCCTTCA CCCGAACTTG GGGGGTGGGG TGGGGAAAAG GAAGAAACGC GGGCGTATTG

7981  GCCCCAATGG GGTCTCGGTG GGGTATCGAC AGAGTGCCAG CCCTGGGACC GAACCCCGCG

8041  TTTATGAACA AACGACCCAA CACCCGTGCG TTTTATTCTG TCTTTTTATT GCCGTCATAG

8101  CGCGGGTTCC TTCCGGTATT GTCTCCTTCC GTGTTTCAGT TAGCCTCCCC CATCTCCCGA

8161  TCCGGACGAG TGCTGGGGCG TCGGTTTCCA CTATCGGCGA GTACTTCTAC ACAGCCATCG

8221  GTCCAGACGG CCCGCGCTTCT GCGGGCGATT TGTGTACGCC CGACAGTCCC GGCTCCGGAT

8281  CGGACGATTG CGTCGCATCG ACCCTGCGCC CAAGCTGCAT CATCGAAATT GCCGTCAACC

8341  AAGCTCTGAT AGAGTTGGTC AAGACCAATG CGGAGCATAT ACGCCCGGAG CCGCGGCGAT

8401  CCTGCAAGCT CCGGATGCCT CCGCTCGAAG TAGCGCGTCT GCTGCTCCAT ACAAGCCAAC

8461  CACGGCCTCC AGAAGAAGAT GTTGGCGACC TCGTATTGGG AATCCCCGAA CATCGCCTCG

8521  CTCCAGTCAA TGACCGCTGT TATGCGGCCA TTGTCCGTCA GGACATTGTT GGAGCCGAAA

8581  TCCGCGTGCA CGAGGTGCCG GACTTCGGGG CAGTCCTCGG CCCAAAGCAT CAGCTCATCG

8641  AGAGCCTGCG CGACGGACGC ACTGACGGTG TCGTCCATCA CAGTTTGCCA GTGATACACA

8701  TGGGGATCAG CAATCGCGCA TATGAAATCA CGCCATGTAG TGTATTGACC GATTCCTTGC

8761  GGTCCGAATG GGCCGAACCC GCTCGTCTGG CTAAGATCGG CCGCAGCGAT CGCATCCATG

8821  GCCTCCGCGA CCGGCTGCAG AACAGCGGGC AGTTCGGTTT CAGGCAGGTC TTGCAACGTG

8881  ACACCCTGTG CACGGCGGGA GATGCAATAG GTCAGGCTCT CGCTGAATTC CCCAATGTCA

8941  AGCACTTCCG GAATCGGGAG CGCGGCCGAT GCAAAGTGCC GATAAACATA ACGATCTTTG

9001  TAGAAACCAT CGGCGCAGCT ATTTACCCGC AGGACATATC CACGCCCTCC TACATCGAAG

9061  CTGAAAGCAC GAGATTCTTC GCCCTCCGAG AGCTGCATCA GGTCGGAGAC GCTGTCGAAC

9121  TTTTCGATCA GAAACTTCTC GACAGACGTC GCGGTGAGTT CAGGCTTTTT CATATCTCAT
```

-continued

```
 9181  TGCCCCCCGG GATCTGCGGC ACGCTGTTGA CGCTGTTAAG CGGGTCGCTG CAGGGTCGCT

9241  CGGTGTTCGA GGCCACACGC GTCACCTTAA TATGCGAAGT GGACCTCGGA CCGCGCCGCC

9301  CCGACTGCAT CTGCGTGTTC GAATTCGCCA ATGACAAGAC GCTGGGCGGG GTTTGTGTCA

9361  TCATAGAACT AAAGACATGC AAATATATTT CTTCCGGGGA CACCGCCAGC AAACGCGAGC

9421  AACGGGCCAC GGGGATGAAG CAGGGCGGCA CCTCGCTAAC GGATTCACCA CTCCAAGAAT

9481  TGGAGCCAAT CAATTCTTGC GGAGAACTGT GAATGCGCAA ACCAACCCTT GGCAGAACAT

9541  ATCCATCGCG TCCGCCATCT CCAGCAGCCG CACGCGGCGC ATCTCGGGGC CGACGCGCTG

9601  GGCTACGTCT TGCTGGCGTT CGCACAGGCC GGCCAGCGCG CGGCCGGCCG GTACCACGCG

9661  TTGGCCACAT ATGGCGGCCG CTCGCGATTA ATTAATCGCG ATGGCCACAT ATGGAGCTCT

9721  CTAGAGCTTG TCGACAGATC CCCCTCTTCA TTTCTTTATG TTTTAAATGC ACTGACCTCC

9781  CACATTCCCT TTTTAGTAAA ATATTCAGAA ATAATTTAAA TACATCATTG CAATGAAAAT

9841  AAATGTTTTT TATTAGGCAG AATCCAGATG CTCAAGGCCC TTCATAATAT CCCCCAGTTT

9901  AGTAGTTGGA CTTAGGGAAC AAAGGAACCT TTAATAGAAA TTGGACAGCA AGAAAGCGAG

9961  GGGGATCTGG ATCCCTCCCT TCAGCACTCG CCCCGGTTGA AGGACTTGGT CACAGGGCTG

10021  GACAGGCCCT GGTGGGTCAC CTCGCAGGCG TACACCTTGT GCTTCTCGTA GTCGGCCTTG

10081  GACAGGGTCA GGGTGGAGGA CAGGGAGTAG GTGCTGTCCT TGGAGTCCTG CTCGGTGACG

10141  GATTCCTGGG AGTTGCCGGA CTGCAGGGCA TTGTCCACCT TCCACTGCAC CTTGGCCTCC

10201  CGAGGGTAGA AGTTGTTCAG CAGGCACACC ACGGAGGCGG TGCCGGACTT CAGCTGCTCG

10261  TCGGAGGGAG GGAAGATGAA CACGGAAGGA GCGGCCACCG TACGCTTGAT CTCCAGCTTG

10321  GTGCCCTGGC CGAAGGTCAG AGGCAGGTCC CGGGAGTGCT GGCAGTAGTA CACGCCCACG

10381  TCCTCGGCCT CCACCCGGGA GATCTTCAGG GTGAAGTCGG TGCCGCTGCC GGAGCCGGAG

10441  AACCGGTCAG GCACGCCGGA CTCCAGGTAG GAGGCCAGGT AGATCAGCAG CTGGGGGGAC

10501  TGGCCAGGCT TCTGCAGATA CCAGTGCAGG TAGGAGTAGC CGGAGGTGGA CACGCCCTTG

10561  GAGGCCCGGC AGGAGATGGA GGCAGGCTCG CCAGGGGTCA CAGGCAGGGA CAGAGGGGAC

10621  TGGGTCAGCA CGATCTCGCA CCGCATGGCA GGCAGGAACA GCACCAGCAG GCCCAGCAGC

10681  TGCACAGGGG CCATGGTGGC GGCCTCGAGG AATTCTTAAG CCTGTGGAGA GAAAGGAACA

10741  GAAAACGAAA CAAAGACGTA GAGTTGAGCA AGCAGGGTCA GGCAAAGCGT GGAGAGCCGG

10801  CTGAGTCTAG GTAGGCTCCA AGGGAGCGCC GGACAAAGGC CCGGTCTCGA CCTGAGCTTT

10861  AAACTTACCT GTGGCCACAC GTGCAATTGC TATAGTGAGT CGTATTAATT TCGATAAGCC

10921  AGTAAGCAGT GGGTTCTCTA GTTAGCCAGA GAGCTCTGCT TATATAGACC TCCCACCGTA

10981  CACGCCTACC GCCCATTTGC GTCAATGGGG CGGAGTTGTT ACGACATTTT GGAAAGTCCC

11041  GTTGATTTTG GTGCCAAAAC AAACTCCCAT TGACGTCAAT GGGGTGGAGA CTTGGAAATC

11101  CCCGTGAGTC AAACCGCTAT CCACGCCCAT TGATGTACTG CCAAAACCGC ATCACCATGG

11161  TAATAGCGAT GACTAATACG TAGATGTACT GCCAAGTAGG AAAGTCCCAT AAGGTCATGT

11221  ACTGGGCATA ATGCCAGGCG GGCCATTTAC CGTCATTGAC GTCAATAGGG GGCGTACTTG

11281  GCATATGATA CACTTGATGT ACTGCCAAGT GGGCAGTTTA CCGTAAATAG TCCACCCATT

11341  GACGTCAATG GAAAGTCCCT ATTGGCGTTA CTATGGGAAC ATACGTCATT ATTGACGTCA

11401  ATGGGCGGGG TCGTTGGGC GGTCAGCCAG GCGGGCCATT TACCGTAAGT TATGTAACGC

11461  GGAACTCCAT ATATGGGCTA TGAACTAATG ACCCCGTAAT TGATTACTAT TAATAACTAG

11521  TCAATAATCA ATGTCAACGC GTATATCTGG CCCGTACATC GGTAACTAGT CGGACCGGCC
```

-continued

```
11581  CGGGCCACCG GTGCTCGAAG CTTGGATCGA TCCAGACATG ATAAGATACA TTGATGAGTT

11641  TGGACAAACC ACAACTAGAA TGCAGTGAAA AAAATGCTTT ATTTGTGAAA TTTGTGATGC

11701  TATTGCTTTA TTTGTAACCA TTATAAGCTG CAATAAACAA GTTAACAACA ACAATTGCAT

11761  TCATTTTATG TTTCAGGTTC AGGGGGAGGT GTGGGAGGTT TTTTAAAGCA AGTAAAACCT

11821  CTACAAATGT GGTATGGCTG ATTATGATCT CTAGTCAAG
```

The present invention further provides, in part, isolated plasmids which exhibit high levels of expression of anti-HGF (hepatocyte growth factor) heavy and light chains. One plasmid is pAHGFV1. The sequence of the pAHGFV1 plasmid is set forth below:

(SEQ ID NO: 48)
```
   1  GGCACTATAC ATCAAATATT CCTTATTAAC CCCTTTACAA ATTAAAAAGC TAAAGGTACA

61  CAATTTTTGA GCATAGTTAT TAATAGCAGA CACTCTATGC CTGTGTGGAG TAAGAAAAAA

121  CAGTATGTTA TGATTATAAC TGTTATGCCT ACTTATAAAG GTTACAGAAT ATTTTTCCAT

181  AATTTTCTTG TATAGCAGTG CAGCTTTTTC CTTTGTGGTG TAAATAGCAA AGCAAGCAAG

241  AGTTCTATTA CTAAACACAG CATGACTCAA AAACTTAGC AATTCTGAAG GAAAGTCCTT

301  GGGGTCTTCT ACCTTTCTCT TCTTTTTTGG AGGAGTAGAA TGTTGAGAGT CAGCAGTAGC

361  CTCATCATCA CTAGATGGCA TTTCTTCTGA GCAAAACAGG TTTTCCTCAT TAAAGGCATT

421  CCACCACTGC TCCCATTCAT CAGTTCCATA GGTTGGAATC TAAAATACAC AAACAATTAG

481  AATCAGTAGT TTAACACATT ATACACTTAA AAATTTTATA TTTACCTTAG AGCTTTAAAT

541  CTCTGTAGGT AGTTTGTCCA ATTATGTCAC ACCACAGAAG TAAGGTTCCT TCACAAAGAT

601  CGATCTAAAG CCAGCAAAAG TCCCATGGTC TTATAAAAAT GCATAGCTTT AGGAGGGGAG

661  CAGAGAACTT GAAACCATCT TCCTGTTAGT CTTTCTTCTC GTAGACTTCA AACTTATACT

721  TGATGCCTTT TTCCTCCTGG ACCTCAGAGA GGACGCCTGG GTATTCTGGG AGAAGTTTAT

781  ATTTCCCCAA ATCAATTTCT GGGAAAAACG TGTCACTTTC AAATTCCTGC ATGATCCTTG

841  TCACAAAGAG TCTGAGGTGG CCTGGTTGAT TCATGCCTTC CTGGTAAACA GAACTGCCTC

901  CGACTATCCA AACCATGTCT ACTTTACTTG CCAATTCCGG TTGTTCAATA AGTCTTAAGG

961  CATCATCCAA ACTTTTGGCA AGAAAATGAG CTCCTCGTGG TGGTTCTTTG AGTTCTCTAC

1021  TGAGAACTAT ATTAATTCTG TCCTTTAAAG GTCGATTCTT CTCAGGAATG GAGAACCAGG

1081  TTTTCCTACC CATAATCACC AGATTCTGTT TACCTTCCAC TGAAGAGGTT GTGGTCATTC

1141  TTTGGAAGTA CTTGAACTCG TTCCTGAGCG GAGGCCAGGG TAGGTCTCCG TTCTTGCCAA

1201  TCCCCATATT TTGGGACACG GCGACGATGC AGTTCAATGG TCGAACCATG ATGGCAGCGG

1261  GGATAAAATC CTACCAGCCT TCACGCTAGG ATTGCCGTCA AGTTTGGCGC GAAATCGCAG

1321  CCCTGAGCTG TCCCCCCCCC CAAGCTCAGA TCTGAGCTTG GTCCCTATGG TGAGTCCGTT

1381  CCGCTCTTGT GATGATAGCC AGACAAGAAA GAGACAATAC AAGACAAACA CCAAATAGTA

1441  GAAATAGAGA CAAGGGTCAC TTATCCGAGG GTCCCTGTTC GGGCGCCAGC TGCCGCAGTC

1501  GGCCGACCTG AGGGTCGCCG GGGTCTGCGG GGGACCCTC TGGAAAGTGA AGGATAAGTG

1561  ACGAGCGGAG ACGGGATGGC GAACAGACAC AAACACACAA GAGGTGAATG TTAGGACTGT

1621  TGCAAGTTTA CTCAAAAAAT CAGCACTCTT TTATATCTTG GTTTACATAA GCATTTACAT

1681  AAGATTTGGA TAAATTCCAA AAGAACATAG GAAAATAGAA CACTCAGAGC TCAGATCAGA

1741  ACCTTTGATA CCAAACCAAG TCAGGAAACC ACTTGTCTCA CATCCTCGTT TTAAGAACAG

1801  TTTGTAACCA AAAACTTACT TAAGCCCTGG GAACCGCAAG GTTGGGCCAA TAAAGGCTAT
```

-continued

```
1861  TCATAATAAC TCATGCCATG AGTTTTTGCA GAATAATGTT CTATTAGTCC AGCCACTGTC
1921  CCCTCCTTGG TATGGAAAAT CTTTCCCCAA AAGTGCATTC CTGTTCCTAG ATAAATATAA
1981  TCATGTACCT GTTGTTTCAT GTCGTCTTTT TCTTCTTGAG ACAACATACA CCAAGGAGGT
2041  CTAGCTCTGG CGAGTCTTTC ACGAAAAGGG AGGGATCTAT ATAACACTTT ATAGCCATTG
2101  ACTGTAACCC ACCTATCCCA ATTTAAGTCA TATCTTCCTG TATATGGTAA GGGGGCATCT
2161  GTTGGTCTGT AGATGTAAGG TCCCCTATAA GTCCCTGGTT GCCACCACCT GTCTCCTATT
2221  TTGACAAAAA CACTCTTTTT TCCCTTTTTT ACTTCTAGGC CTGTGGTCAA TAGTCCTTGC
2281  ACCTGTTCTT CAATTGAGGT TGAGCGTCTC TTTCTATTTT CTATTCCCAT TTCTAACTTC
2341  TGAATTTGAG TAAAAATAGT ACTAAAGAT AATGATTCAT TTCTTAACAT AGTAACTAAT
2401  AATCTACCTA TTGGATTGGT CTTATTGGTA AAATATAAT TTTTAGCAAG CATTCTTATT
2461  TCTATTTCTG AAGGACAAAA TCGATGCGGC TTGTAAGAGG AAGTTGGCTG TAGTCCTTGC
2521  CTCAGGAGGA AGGTCGAGTT CTCCGAATTG TTTAGATTGT AATCTTGCAC AGAAGAGCTA
2581  TTAAAAGAGT CAAGGGTGAG AGCCCTGCGA GCACGAACCG CAACTTCCCC CAATAGCCCC
2641  AGGCAAAGCA GAGCTATGCC AAGTTTGCAG CAGAGAATGA ATATGTCTTT GTCTGATGGG
2701  CTCATCCGTT TGTGCGCAGA CGGGTCGTCC TTGGTGGGAA ACAACCCCTT GGCTGCTTCT
2761  CCCCTAGGTG TAGGACACTC TCGGGAGTTC AACCATTTCT GCCCAAGCTC AAAACTTAGC
2821  TTTAATGCGG TAGTTTATCA CAGTTAAATT GCTAACGCAG TCAGGCACCG TGTATGAAAT
2881  CTAACAATGC GCTCATCGTC ATCCTCGGCA CCGTCACCCT GGATGCTGTA GGCATAGGCT
2941  TGGTTATGCC GGTACTGCCG GGCCTCTTGC GGGATATCGT CCATTCCGAC AGCATCGCCA
3001  GTCACTATGG CGTGCTGCTA GCGCTCTTCC GCTTCCTCGC TCACTGACTC GCTGCGCTCG
3061  GTCGTTCGGC TGCGGCGAGC GGTATCAGCT CACTCAAAGG CGGTAATACG GTTATCCACA
3121  GAATCAGGGG ATAACGCAGG AAAGAACATG TGAGCAAAAG GCCAGCAAAA GGCCAGGAAC
3181  CGTAAAAAGG CCGCGTTGCT GGCGTTTTTC CATAGGCTCC GCCCCCCTGA CGAGCATCAC
3241  AAAAATCGAC GCTCAAGTCA GAGGTGGCGA AACCCGACAG GACTATAAAG ATACCAGGCG
3301  TTTCCCCCTG GAAGCTCCCT CGTGCGCTCT CCTGTTCCGA CCCTGCCGCT TACCGGATAC
3361  CTGTCCGCCT TTCTCCCTTC GGGAAGCGTG GCGCTTTCTC ATAGCTCACG CTGTAGGTAT
3421  CTCAGTTCGG TGTAGGTCGT TCGCTCCAAG CTGGGCTGTG TGCACGAACC CCCCGTTCAG
3481  CCCGACCGCT GCGCCTTATC CGGTAACTAT CGTCTTGAGT CCAACCCGGT AAGACACGAC
3541  TTATCGCCAC TGGCAGCAGC CACTGGTAAC AGGATTAGCA GAGCGAGGTA TGTAGGCGGT
3601  GCTACAGAGT TCTTGAAGTG GTGGCCTAAC TACGGCTACA CTAGAAGGAC AGTATTTGGT
3661  ATCTGCGCTC TGCTGAAGCC AGTTACCTTC GGAAAAAGAG TTGGTAGCTC TTGATCCGGC
3721  AAACAAACCA CCGCTGGTAG CGGTGGTTTT TTTGTTTGCA AGCAGCAGAT TACGCGCAGA
3781  AAAAAGGAT CTCAAGAAGA TCCTTTGATC TTTTCTACGG GTCTGACGC TCAGTGGAAC
3841  GAAAACTCAC GTTAAGGGAT TTTGGTCATG AGATTATCAA AAAGGATCTT CACCTAGATC
3901  CTTTTAAATT AAAAATGAAG TTTTAAATCA ATCTAAAGTA TATATGAGTA AACTTGGTCT
3961  GACAGTTACC AATGCTTAAT CAGTGAGGCA CCTATCTCAG CGATCTGTCT ATTTCGTTCA
4021  TCCATAGTTG CCTGACTCCC CGTCGTGTAG ATAACTACGA TACGGGAGGG CTTACCATCT
4081  GGCCCCAGTG CTGCAATGAT ACCGCGAGAC CCACGCTCAC CGGCTCCAGA TTTATCAGCA
4141  ATAAACCAGC CAGCCGGAAG GGCCGAGCGC AGAAGTGGTC CTGCAACTTT ATCCGCCTCC
4201  ATCCAGTCTA TTAATTGTTG CCGGGAAGCT AGAGTAAGTA GTTCGCCAGT TAATAGTTTG
```

```
4261  CGCAACGTTG TTGCCATTGC TACAGGCATC GTGGTGTCAC GCTCGTCGTT TGGTATGGCT
4321  TCATTCAGCT CCGGTTCCCA ACGATCAAGG CGAGTTACAT GATCCCCCAT GTTGTGCAAA
4381  AAAGCGGTTA GCTCCTTCGG TCCTCCGATC GTTGTCAGAA GTAAGTTGGC CGCAGTGTTA
4441  TCACTCATGG TTATGGCAGC ACTGCATAAT TCTCTTACTG TCATGCCATC CGTAAGATGC
4501  TTTTCTGTGA CTGGTGAGTA CTCAACCAAG TCATTCTGAG AATAGTGTAT GCGGCGACCG
4561  AGTTGCTCTT GCCCGGCGTC AACACGGGAT AATACCGCGC CACATAGCAG AACTTTAAAA
4621  GTGCTCATCA TTGGAAAACG TTCTTCGGGG CGAAAACTCT CAAGGATCTT ACCGCTGTTG
4681  AGATCCAGTT CGATGTAACC CACTCGTGCA CCCAACTGAT CTTCAGCATC TTTTACTTTC
4741  ACCAGCGTTT CTGGGTGAGC AAAAACAGGA AGGCAAAATG CCGCAAAAAA GGGAATAAGG
4801  GCGACACGGA AATGTTGAAT ACTCATACTC TTCCTTTTTC AATATTATTG AAGCATTTAT
4861  CAGGGTTATT GTCTCATGAG CGGATACATA TTTGAATGTA TTTAGAAAAA TAAACAAATA
4921  GGGGTTCCGC GCACATTTCC CCGAAAAGTG CCACCTGACG TCTAAGAGAC CATTATTATC
4981  ATGACATTAA CCTATAAAAA TAGGCGTATC ACGAGGCCCT TTCGTCTTCA AGAATTGTCT
5041  AGAGGCGCGC CGTTTAAACC CTCAGCTACC GATGTACGGG CCAGATATAC GCGTTGACAT
5101  TGATTATTGA CTAGTTATTA ATAGTAATCA ATTACGGGGT CATTAGTTCA TAGCCCATAT
5161  ATGGAGTTCC GCGTTACATA ACTTACGGTA AATGGCCCGC CTGGCTGACC GCCCAACGAC
5221  CCCCGCCCAT TGACGTCAAT AATGACGTAT GTTCCCATAG TAACGCCAAT AGGGACTTTC
5281  CATTGACGTC AATGGGTGGA CTATTTACGG TAAACTGCCC ACTTGGCAGT ACATCAAGTG
5341  TATCATATGC CAAGTACGCC CCCTATTGAC GTCAATGACG GTAAATGGCC CGCCTGGCAT
5401  TATGCCCAGT ACATGACCTT ATGGGACTTT CCTACTTGGC AGTACATCTA CGTATTAGTC
5461  ATCGCTATTA CCATGGTGAT GCGGTTTTGG CAGTACATCA ATGGGCGTGG ATAGCGGTTT
5521  GACTCACGGG GATTTCCAAG TCTCCACCCC ATTGACGTCA ATGGGAGTTT GTTTTGGCAC
5581  CAAAATCAAC GGGACTTTCC AAAATGTCGT AACAACTCCG CCCCATTGAC GCAAATGGGC
5641  GGTAGGCGTG TACGGTGGGA GGTCTATATA AGCAGAGCTC TCTGGCTAAC TAGAGAACCC
5701  ACTGCTTACT GGCTTATCGA AATTAATACG ACTCACTATA GCAATTGCAC GTGTGGCCAC
5761  AGGTAAGTTT AAAGCTCAGG TCGAGACCGG GCCTTTGTCC GGCGCTCCCT TGGAGCCTAC
5821  CTAGACTCAG CCGGCTCTCC ACGCTTTGCC TGACCCTGCT TGCTCAACTC TACGTCTTTG
5881  TTTCGTTTTC TGTTCCTTTC TCTCCACAGG CTTAAAACGC CGCCACCATG GGGTCAACCG
5941  CCATCCTCGC CCTCCTCCTG GCTGTTCTCC AAGGAGTCTG TGCCGAAGTG CAGCTGGTGC
6001  AGTCTGGAGC AGAGGTGAAA AAGCCCGGGG AGTCTCTGAA GATCTCCTGT AAGGGTTCTG
6061  GATACAGCTT TACCACCTAC TGGATGCACT GGGTGCGCCA GATGCCCGGG AAAGGCCTGG
6121  AGTGGATGGG GGAGATTAAT CCTACCAACG GTCATACTAA CTACAATCCG TCCTTCCAAG
6181  GCCAGGTCAC CATCTCAGCT GACAAGTCCA TCAGCACTGC CTACCTGCAG TGGAGCAGCC
6241  TGAAGGCCTC GGACACCGCC ATGTATTACT GTGCGAGAAA CTATGTTGGT AGCATCTTTG
6301  ACTACTGGGG CCAAGGAACC CTGGTCACCG TCTCCTCAGC TAGCACCAAG GGCCCATCGG
6361  TCTTCCCCCT GGCACCCTCC TCCAAGAGCA CCTCTGGGGG CACAGCGGCC CTGGGCTGCC
6421  TGGTCAAGGA CTACTTCCCC GAACCGGTGA CGGTGTCGTG GAACTCAGGC GCCCTGACCA
6481  GCGGCGTGCA CACCTTCCCG GCTGTCCTAC AGTCCTCAGG ACTCTACTCC CTCAGCAGCG
6541  TGGTGACCGT GCCCTCCAGC AGCTTGGGCA CCCAGACCTA CATCTGCAAC GTGAATCACA
6601  AGCCCAGCAA CACCAAGGTG GACAAGAAAG TTGAGCCCAA ATCTTGTGAC AAAACTCACA
6661  CATGCCCACC GTGCCCAGCA CCTGAACTCC TGGGGGGACC GTCAGTCTTC CTCTTCCCCC
```

-continued

```
6721 CAAAACCCAA GGACACCCTC ATGATCTCCC GGACCCCTGA GGTCACATGC GTGGTGGTGG

6781 ACGTGAGCCA CGAAGACCCT GAGGTCAAGT TCAACTGGTA CGTGGACGGC GTGGAGGTGC

6841 ATAATGCCAA GACAAAGCCG CGGGAGGAGC AGTACAACAG CACGTACCGT GTGGTCAGCG

6901 TCCTCACCGT CCTGCACCAG GACTGGCTGA ATGGCAAGGA GTACAAGTGC AAGGTCTCCA

6961 ACAAAGCCCT CCCAGCCCCC ATCGAGAAAA CCATCTCCAA AGCCAAGGG CAGCCCCGAG

7021 AACCACAGGT GTACACCCTG CCCCCATCCC GGGATGAGCT GACCAAGAAC CAGGTCAGCC

7081 TGACCTGCCT GGTCAAAGGC TTCTATCCCA GCGACATCGC CGTGGAGTGG GAGAGCAATG

7141 GGCAGCCGGA GAACAACTAC AAGACCACGC CTCCCGTGCT GGACTCCGAC GGCTCCTTCT

7201 TCCTCTACAG CAAGCTCACC GTGGACAAGA GCAGGTGGCA GCAGGGGAAC GTCTTCTCAT

7261 GCTCCGTGAT GCATGAGGCT CTGCACAACC ACTACACGCA GAAGAGCCTC TCCCTGTCTC

7321 CGGGTAAATG AATCGATGAT TCTAGATACG GGTCCGGAGG ATCCAGATCC CCCTCGCTTT

7381 CTTGCTGTCC AATTTCTATT AAAGGTTCCT TTGTTCCCTA AGTCCAACTA CTAAACTGGG

7441 GGATATTATG AAGGGCCTTG AGCATCTGGA TTCTGCCTAA TAAAAAACAT TTATTTTCAT

7501 TGCAATGATG TATTTAAATT ATTTCTGAAT ATTTTACTAA AAGGGAATG TGGGAGGTCA

7561 GTGCATTTAA AACATAAAGA AATGAAGAGG GGGATCTGTC GACAAGCTCT AGAGAGCTCA

7621 CGCGTTGATC ATGTACAGGC CGGCCAAGCT TTCGACTAGC TTGGCACGCC AGAAATCCGC

7681 GCGGTGGTTT TTGGGGGTCG GGGGTGTTTG CAGCCACAG ACGCCCGGTG TTCGTGTCGC

7741 GCCAGTACAT GCGGTCCATG CCCAGGCCAT CCAAAAACCA TGGGTCTGTC TGCTCAGTCC

7801 AGTCGTGGAC CTGACCCCAC GCAACGCCCA AAATAATAAC CCCCACGAAC CATAAACCAT

7861 TCCCCATGGG GGACCCCGTC CCTAACCCAC GGGGCCAGTG GCTATGGCAG GGCCTGCCGC

7921 CCCGACGTTG GCTGCGAGCC CTGGGCCTTC ACCCGAACTT GGGGGGTGGG GTGGGGAAAA

7981 GGAAGAAACG CGGGCGTATT GGCCCCAATG GGGTCTCGGT GGGGTATCGA CAGAGTGCCA

8041 GCCCTGGGAC CGAACCCCGC GTTTATGAAC AAACGACCCA ACACCCGTGC GTTTTATTCT

8101 GTCTTTTTAT TGCCGTCATA GCGCGGGTTC CTTCCGGTAT TGTCTCCTTC CGTGTTTCAG

8161 TTAGCCTCCC CCATCTCCCG ATCCGGACGA GTGCTGGGGC GTCGGTTTCC ACTATCGGCG

8221 AGTACTTCTA CACAGCCATC GGTCCAGACG GCCGCGCTTC TGCGGGCGAT TTGTGTACGC

8281 CCGACAGTCC CGGCTCCGGA TCGACGATT GCGTCGCATC GACCCTGCGC CCAAGCTGCA

8341 TCATCGAAAT TGCCGTCAAC CAAGCTCTGA TAGAGTTGGT CAAGACCAAT GCGGAGCATA

8401 TACGCCCGGA GCCGCGGCGA TCCTGCAAGC TCCGGATGCC TCCGCTCGAA GTAGCGCGTC

8461 TGCTGCTCCA TACAAGCCAA CCACGGCCTC CAGAAGAAGA TGTTGGCGAC CTCGTATTGG

8521 GAATCCCCGA ACATCGCCTC GCTCCAGTCA ATGACCGCTG TTATGCGGCC ATTGTCCGTC

8581 AGGACATTGT TGGAGCCGAA ATCCGCGTGC ACGAGGTGCC GGACTTCGGG GCAGTCCTCG

8641 GCCCAAAGCA TCAGCTCATC GAGAGCCTGC GCGACGGACG CACTGACGGT GTCGTCCATC

8701 ACAGTTTGCC AGTGATACAC ATGGGATCA GCAATCGCGC ATATGAAATC ACGCCATGTA

8761 GTGTATTGAC CGATTCCTTG CGGTCCGAAT GGGCCGAACC CGCTCGTCTG GCTAAGATCG

8821 GCCGCAGCGA TCGCATCCAT GGCCTCCGCG ACCGGCTGCA GAACAGCGGG CAGTTCGGTT

8881 TCAGGCAGGT CTTGCAACGT GACACCCTGT GCACGGCGGG AGATGCAATA GGTCAGGCTC

8941 TCGCTGAATT CCCCAATGTC AAGCACTTCC GGAATCGGGA GCGCGGCCGA TGCAAAGTGC

9001 CGATAAACAT AACGATCTTT GTAGAAACCA TCGGCGCAGC TATTTACCCG CAGGACATAT

9061 CCACGCCCTC CTACATCGAA GCTGAAAGCA CGAGATTCTT CGCCCTCCGA GAGCTGCATC
```

-continued

```
 9121 AGGTCGGAGA CGCTGTCGAA CTTTTCGATC AGAAACTTCT CGACAGACGT CGCGGTGAGT
 9181 TCAGGCTTTT TCATATCTCA TTGCCCCCCG GGATCTGCGG CACGCTGTTG ACGCTGTTAA
 9241 GCGGGTCGCT GCAGGGTCGC TCGGTGTTCG AGGCCACACG CGTCACCTTA ATATGCGAAG
 9301 TGGACCTCGG ACCGCGCCGC CCCGACTGCA TCTGCGTGTT CGAATTCGCC AATGACAAGA
 9361 CGCTGGGCGG GGTTTGTGTC ATCATAGAAC TAAAGACATG CAAATATATT TCTTCCGGGG
 9421 ACACCGCCAG CAAACGCGAG CAACGGGCCA CGGGGATGAA GCAGGGCGGC ACCTCGCTAA
 9481 CGGATTCACC ACTCCAAGAA TTGGAGCCAA TCAATTCTTG CGGAGAACTG TGAATGCGCA
 9541 AACCAACCCT TGGCAGAACA TATCCATCGC GTCCGCCATC TCCAGCAGCC GCACGCGGCG
 9601 CATCTCGGGG CCGACGCGCT GGGCTACGTC TTGCTGGCGT TCGCACAGGC CGGCCAGCGC
 9661 GCGGCCGGCC GGTACCACGC GTTGGCCACA TATGGCGGCC GCTCGCGATT AATTAATCGC
 9721 GATGGCCACA TATGGAGCTC TCTAGAGCTT GTCGACAGAT CCCCCTCTTC ATTTCTTTAT
 9781 GTTTTAAATG CACTGACCTC CCACATTCCC TTTTTAGTAA AATATTCAGA AATAATTTAA
 9841 ATACATCATT GCAATGAAAA TAAATGTTTT TTATTAGGCA GAATCCAGAT GCTCAAGGCC
 9901 CTTCATAATA TCCCCCAGTT TAGTAGTTGG ACTTAGGGAA CAAAGGAACC TTTAATAGAA
 9961 ATTGGACAGC AAGAAAGCGA GGGGGATCTG GATCCTCCTA CGTATCTAGA ATCATCGATT
10021 AACACTCTCC CCTGTTGAAG CTCTTTGTCA CGGGGCTGCT CAGGCCCTGA TGGGTCACCT
10081 CGCAGGCGTA CACCTTGTGT TTCTCGTAGT CTGCTTTGCT CAGGGTCAGG GTGCTGCTCA
10141 GGCTGTAGGT GCTGTCCTTG CTGTCCTGCT CTGTCACGCT CTCCTGGGAG TTGCCGCTCT
10201 GGAGGGCGTT ATCCACCTTC CACTGCACCT TGGCCTCTCT GGGATAGAAG TTATTCAGCA
10261 GGCACACCAC GGAGGCAGTT CCAGACTTCA GCTGCTCATC AGATGGAGGG AAGATGAACA
10321 CAGATGGTGC AGCCACCGTA CGTTTGATCT CCAGCTTGGT CCCCTGGCCA AACGTGTACG
10381 GATAGTTGTA ACTCTGCCCA CAGTAGTAAG TTGCAAAATC TTCAGGTTGC AGACTGCTGA
10441 TGGTGAGAGT GAAATCTGTC CCAGATCCAC TGCCACTGAA CCTTGATGGG ACCCCAGTGT
10501 TCCGGTTGGA TGCCCCATAG ATCAGGAGCT TAGGGGCTTT CCCTGGTTTC TGCTGATACC
10561 AGGATACATA AGAAACCACA TTCTCACTGG CCTTGCAAGT GATGGTGACT CTGTCTCCTA
10621 CAGATGCAGA CAGGGAGGAT GGAGACTGGG TCATCTGGAT GTCACATCTG GCACCTCGGA
10681 GCCAGAGTAG CAGGAGCCCC AGGAGCTGAG CGGGGACCCT CATGTCCATG GTGGCGGCGA
10741 ATTCTCGAGA AGCTTAAGTT TAATTCTTAA GCCTGTGGAG AGAAAGGAAC AGAAAACGAA
10801 ACAAAGACGT AGAGTTGAGC AAGCAGGGTC AGGCAAAGCG TGGAGAGCCG GCTGAGTCTA
10861 GGTAGGCTCC AAGGGAGCGC CGGACAAAGG CCCGGTCTCG ACCTGAGCTT TAAACTTACC
10921 TGTGGCCACA CGTGCAATTG CTATAGTGAG TCGTATTAAT TTCGATAAGC CAGTAAGCAG
10981 TGGGTTCTCT AGTTAGCCAG AGAGCTCTGC TTATATAGAC CTCCCACCGT ACACGCCTAC
11041 CGCCCATTTG CGTCAATGGG GCGGAGTTGT TACGACATTT TGGAAAGTCC CGTTGATTTT
11101 GGTGCCAAAA CAAACTCCCA TTGACGTCAA TGGGGTGGAG ACTTGGAAAT CCCCGTGAGT
11161 CAAACCGCTA TCCACGCCCA TTGATGTACT GCCAAAACCG CATCACCATG GTAATAGCGA
11221 TGACTAATAC GTAGATGTAC TGCCAAGTAG GAAAGTCCCA TAAGGTCATG TACTGGGCAT
11281 AATGCCAGGC GGGCCATTTA CCGTCATTGA CGTCAATAGG GGGCGTACTT GGCATATGAT
11341 ACACTTGATG TACTGCCAAG TGGGCAGTTT ACCGTAAATA GTCCACCCAT TGACGTCAAT
11401 GGAAAGTCCC TATTGGCGTT ACTATGGGAA CATACGTCAT TATTGACGTC AATGGGCGGG
11461 GGTCGTTGGG CGGTCAGCCA GGCGGGCCAT TTACCGTAAG TTATGTAACG CGGAACTCCA
11521 TATATGGGCT ATGAACTAAT GACCCCGTAA TTGATTACTA TTAATAACTA GTCAATAATC
```

```
11581  AATGTCAACG CGTATATCTG GCCCGTACAT CGGTAACTAG TCGGACCGGC CCGGGCCACC

11641  GGTGCTCGAA GCTTGGATCG ATCCAGACAT GATAAGATAC ATTGATGAGT TTGGACAAAC

11701  CACAACTAGA ATGCAGTGAA AAAAATGCTT TATTTGTGAA ATTTGTGATG CTATTGCTTT

11761  ATTTGTAACC ATTATAAGCT GCAATAAACA AGTTAACAAC AACAATTGCA TTCATTTTAT

11821  GTTTCAGGTT CAGGGGGAGG TGTGGGAGGT TTTTTAAAGC AAGTAAAACC TCTACAAATG

11881  TGGTATGGCT GATTATGATC TCTAGTCAA
```

Figure 2:
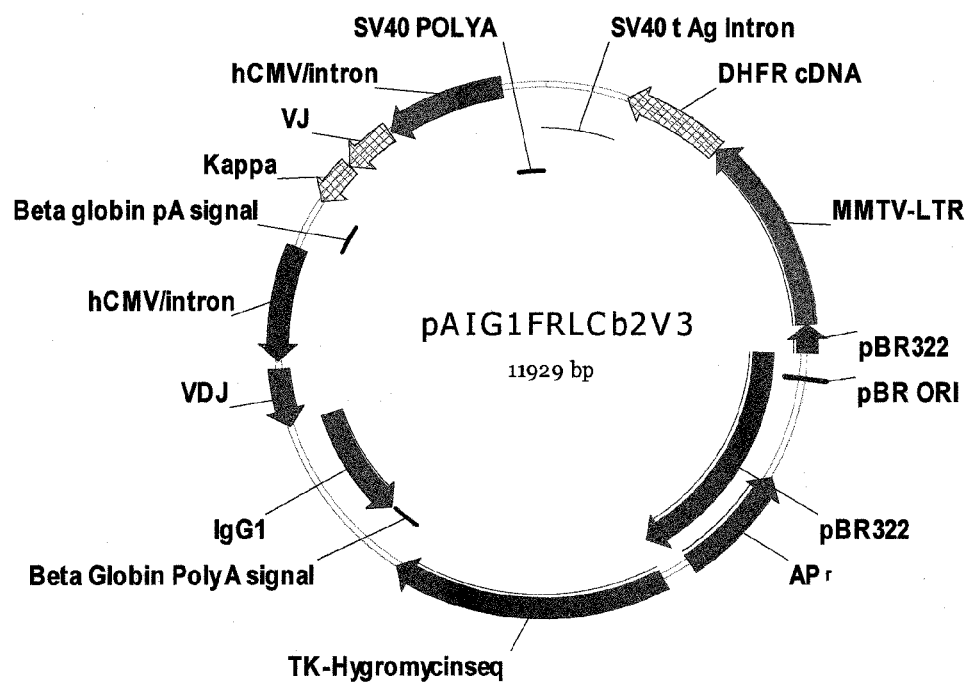
FIG. 2. Plasmid map for pAIG1FRLCb2V3. The feature map for this plasmid is set forth below:
AP(R)
Start: 3965 End: 4828
(Complementary)
IgG1
Start: 7371 End: 8351
(Complementary)
IgG1 non genomic region
VDJ
Start: 8351 End: 8778
(Complementary)
DHFR cDNA
Start: 601 End: 1347
(Complementary)
SV40 t Ag Intron
Start: 11916 End: 600
Kappa
Start: 10055 End: 10378
(Complementary)
Kappa Chain
VJ
Start: 10379 End: 10756
(Complementary)
VJ of IGF-1R (LCb, human germline sequence)
pBR322
Start: 2811 End: 3019
(Complementary)
pBR322
Start: 3020 End: 5033
TK-Hygromycinseq
Start: 5053 End: 7062
Beta Globin Poly A signal
Start: 7108 End: 7346
(Complementary)
Beta globin pA signal
Start: 9784 End: 10032
(Complementary)
SV40 POLYA
Start: 11669 End: 11917
MMTV-LTR
Start: 1348 End: 2810
(Complementary)
hCMV/βGI-IgG intron
Start: 8834 End: 9675
(Complementary)
Human CMV promoter with βGI-IgG intron
hCMV/βGI-IgG intron
Start: 10778 End: 11619
(Complementary)
Human CMV promoter and βGI-IgG intron
pBR ORI
Start: 3207 End: 3207
Figure 3:
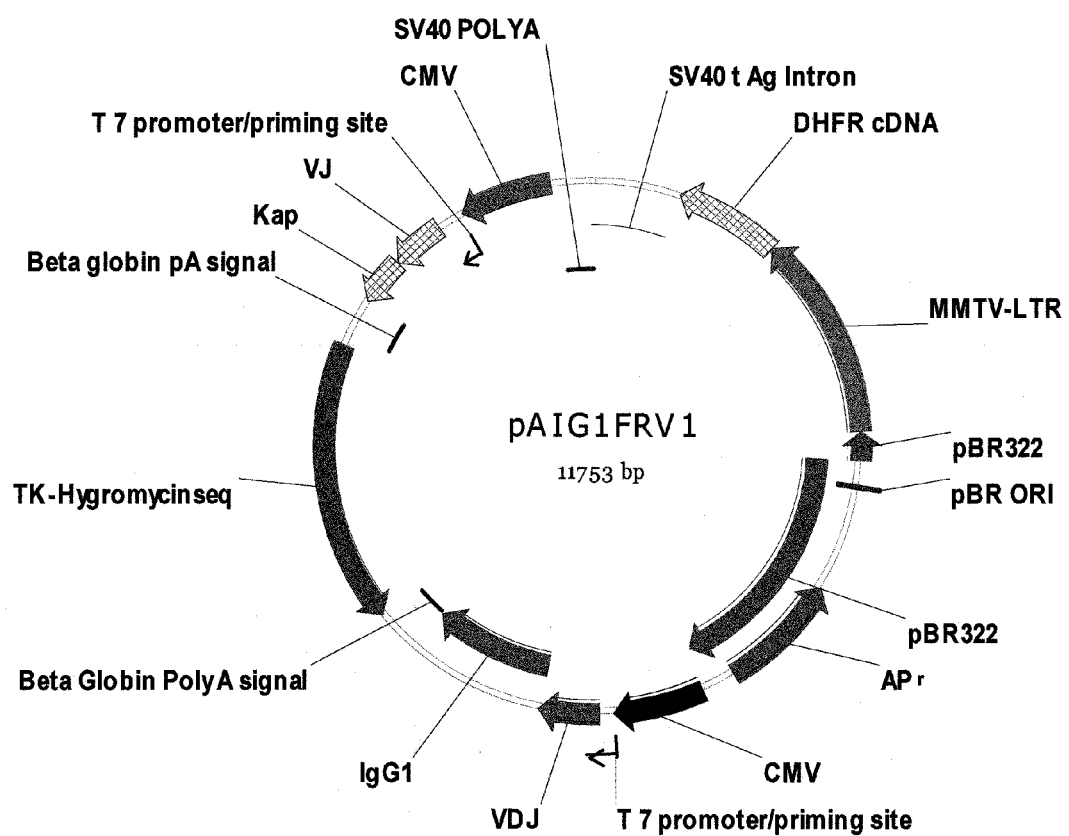
FIG. 3. Plasmid map for pAIG1FRV1.
AP(R)
  Start: 3965 End: 4828 (Complementary)
VDJ
  Start: 5824 End: 6251
  VDJ of IGFR1 of 19D12 hybridoma
IgG1
  Start: 6241 End: 7231
  IgG1 non genomic region
DHFR cDNA
  Start: 601 End: 1347 (Complementary)
SV40 t Ag Intron
  Start: 11740 End: 600
Kap
  Start: 9898 End: 10233 (Complementary)
  Kappa chain of hu-antiIGFR gene
VJ
  Start: 10234 End: 10614 (Complementary)
  VJ Domain of hu-anti IGFR gene for light chain
pBR322
  Start: 2811 End: 3019 (Complementary)
pBR322
  Start: 3020 End: 5033
TK-Hygromycinseq
  Start: 7540 End: 9549 (Complementary)
  TK-hygromycin sequenced in Union U-3
Beta Globin Poly A signal
  Start: 7256 End: 7494
Beta globin pA signal
  Start: 9642 End: 9890 (Complementary)
SV40 POLYA
  Start: 11493 End: 11741
MMTV-LTR
  Start: 1348 End: 2810 (Complementary)
CMV
  Start: 10801 End: 11455 (Complementary)
CMV
  Start: 5069 End: 5723
T 7 promoter/priming site
  Start: 5723 End: 5742
T 7 promoter/priming site
  Start: 10782 End: 10801 (Complementary)
pBR ORI
  Start: 3207 End: 3207
FIG. 4. Plasmid map for pAIG1FRV3.
AP(R)
  Start: 3965 End: 4828 (Complementary)
IgG1
  Start: 7371 End: 8361 (Complementary)
  IgG1 non genomic region
VDJ
  Start: 8351 End: 8778 (Complementary)
  VDJ of IGFR1 of 19D12 hybridoma
DHFR cDNA
  Start: 601 End: 1347 (Complementary)
SV40 t Ag Intron
  Start: 11740 End: 600
Kap
  Start: 9898 End: 10233 (Complementary)
  Kappa chain of hu-antiIGFR gene
VJ
  Start: 10234 End: 10614 (Complementary)
  VJ Domain of hu-anti IGFR gene for light chain
pBR322
  Start: 2811 End: 3019 (Complementary)
pBR322
  Start: 3020 End: 5033
TK-Hygromycinseq
  Start: 5053 End: 7062
  TK-hygromycin
Beta Globin Poly A signal
  Start: 7108 End: 7346 (Complementary)
Beta globin pA signal
  Start: 9642 End: 9890 (Complementary)
SV40 POLYA
  Start: 11493 End: 11741
MMTV-LTR
  Start: 1348 End: 2810 (Complementary)
CMV
  Start: 10801 End: 11455 (Complementary)
T 7 promoter/priming site
  Start: 8860 End: 8879 (Complementary)
CMV
  Start: 8879 End: 9533 (Complementary)
T 7 promoter/priming site
  Start: 10782 End: 10801 (Complementary)
pBR ORI
  Start: 3207 End: 3207
FIG. 5. Plasmid map for pAIG1FRLCB2-V1K.
AP(R)
  Start: 3965 End: 4828 (Complementary)
VDJ
  Start: 6356 End: 6356
  VDJ region of anti-IL10 (12G8)
IgG1
  Start: 6361 End: 7341
  IgG1 non genomic region
VJ
  Start: 10368 End: 10745 (Complementary)
IgK
  Start: 10013 End: 10367 (Complementary)
  VDJ-IgK for 12G8 light chain (anti-IL10)
DHFR cDNA
  Start: 601 End: 1347 (Complementary)
SV40 t Ag Intron
  Start: 11899 End: 600
pBR322
  Start: 2811 End: 3019 (Complementary)
pBR322
  Start: 3020 End: 5033
TK-Hygromycinseq
  Start: 7650 End: 9659 (Complementary)
  TK-hygromycin
Beta Globin Poly A signal
  Start: 7366 End: 7604
Beta Globin Poly A signal
  Start: 9763 End: 9996
SV40 POLYA
  Start: 11652 End: 11900
MMTV-LTR
  Start: 1348 End: 2810 (Complementary)
hCMV/βGI-IgG intron
  Start: 5069 End: 5910
  Human CMV promoter with hybrid intron
hCMV/βGI-IgG intron
  Start: 10773 End: 11614 (Complementary)
  Human CMV promoter and hybrid intron
pBR ORI
  Start: 3207 End: 3207
FIG. 6A-6E. Plasmid map for pAIL23V1K and nucleotide sequence of plasmid (SEQ ID NO: 44). Plasmid vector comprising hCMV promoter-(βGI-IgG intron)-anti-IL-23 Ig.
Figure 4:
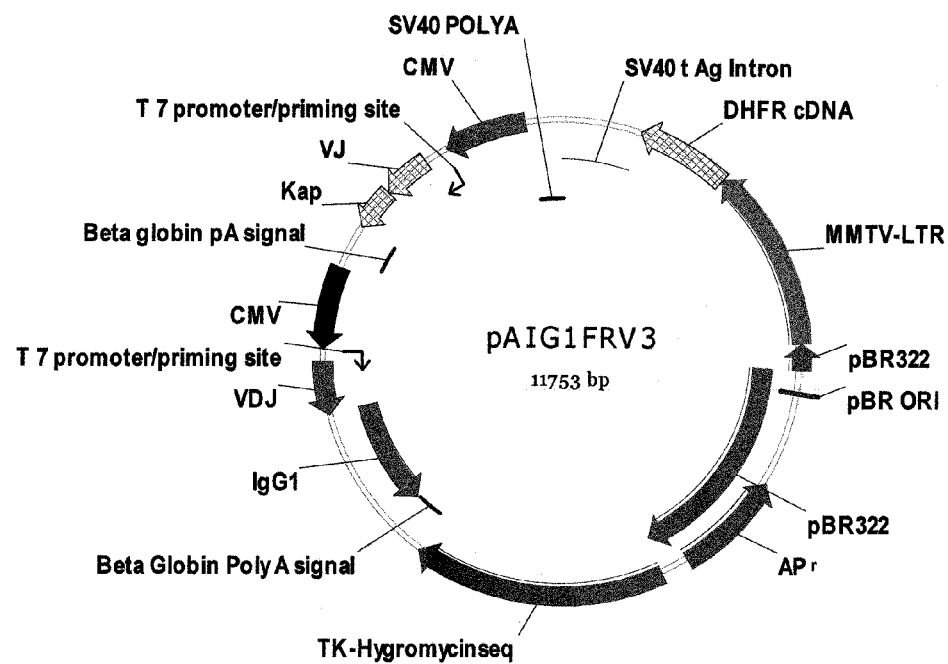
Figure 5:
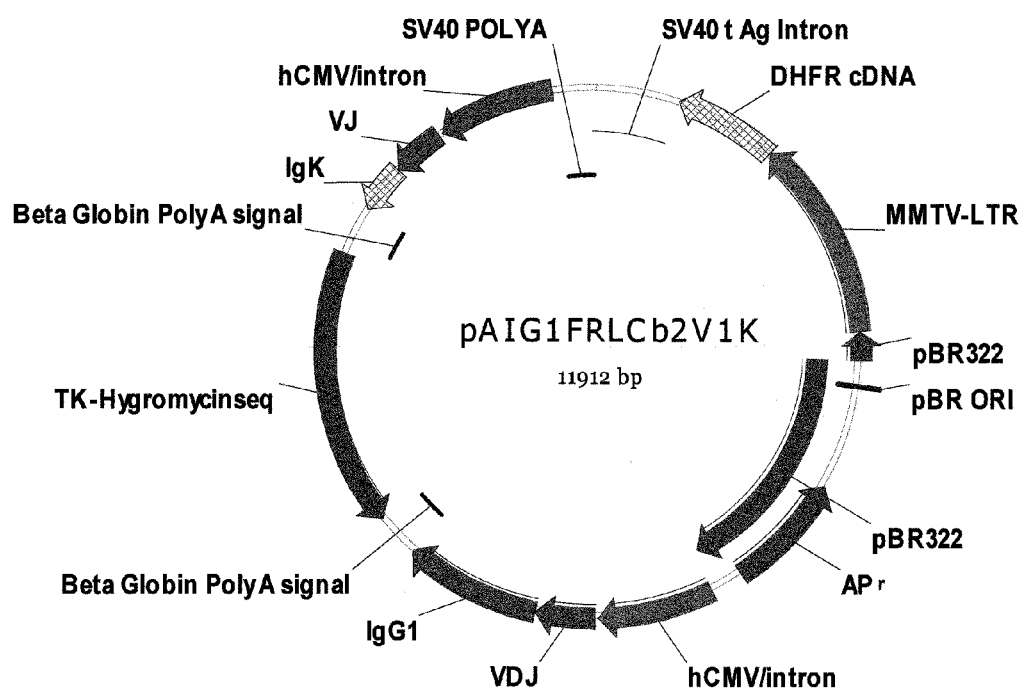

Plasmid maps for these plasmids are also provided herein in FIGS. 1-10.

Expression

Vectors, such as plasmids (e.g., FIGS. 1-10), including a target gene to be expressed may be introduced into a host cell by any of several methods known in the art. If cells without cell wall barriers are used as host cells, transformation can be carried out by the calcium phosphate precipitation method as described by Graham and Van der Eb, Virology, 52: 546 (1978). However, other methods for introducing DNA into cells such as by nuclear injection or by protoplast fusion may also be used. Other methods for transformation include electroporation, liposomal transformation and DEAE-Dextran transformation.

If prokaryotic cells (e.g., *E. coli* such as BL21 or BD21DE3 or HB101 or DH1 or DH5) or cells which contain substantial cell wall constructions (such as *S. cerevisiae*) are used, transformation can be by calcium treatment using calcium chloride as described by Cohen, F. N. et al. Proc. Natl. Acad. Sci. (USA) 69: 2110 (1972).

Host cells comprising a vector (e.g., FIGS. 1-10) of the present invention may be selected and screened to identify the clone with the requisite characteristics for expression of a target gene. In Chinese hamster ovary (CHO) cells, one common approach to achieve maximal expression involves the use of mutant cell lines and a gradual increase in the selection pressure over several months for a co-transfected selection marker such as dihydrofolate reductase (DHFR) (Kaufman et al. (1982) J. Mol. Biol. 159: 601-621; Schimke et al. (1982) Natl. Cancer Inst. Monogr. 60: 79-86). In order to achieve high production rates, a dihydrofolate reductase (DHFR) negative cell line (e.g., a CHO cell line) (Urlaub et al. (1980) Proc. Natl. Acad. Sci. USA 77: 4216-4220) is transformed with an expression vector containing a functional DHFR gene in combination with the target gene to be expressed. Amplification of the vector-inserted target genes occurs in response to addition of increasing amounts of the DHFR antagonist methotrexate (MTX) to the culture medium and clones or subpopulations carrying multiple copies of the recombinant genes are generated and can be selected (Wurm (1990) Biologicals 18:159-164). The gene amplification process typically takes several months until stable cell lines are obtained which show high target gene copy numbers and high production rates of the desired protein.

In an embodiment of the invention, a polynucleotide of the present invention is integrated into host cell (e.g., CHO, CHO-K1, CHO-D1 DXB11) DNA or is ectopic (non-integrated). In an embodiment of the invention, the polynucleotide of the present invention is present in the cell at several copies per cell (e.g., 2, 3, 4, 5, 6, 7, 8, 9, 10, 15, 20). Where an expression vector has been integrated into the genomic DNA of the host cell to improve stability, the copy number of the vector DNA, and, concomitantly, the amount of product which could be expressed, can be increased by selecting for cell lines in which the vector sequences have been amplified after integration into the DNA of the host cell.

Any of several cell culture mediums known in the art can be used to propagate cells expressing a target gene. Several commercially available culture mediums are available. If expressing a protein to be used therapeutically, animal-product-free media (e.g., serum-free media (SFM)) may be desirable. There are several methods known in the art by which to cells may be adapted to growth in serum-free medium. For example, direct adaption includes merely switching cells from serum supplemented media to serum-free media. Sequential adaptation or weaning includes switching cells from a serum-supplemented medium into a serum-free medium in several steps (e.g., 25% SFM, 50% SFM, 75% SFM, then, 90% SFM for about 3 passages, then 100% SFM). Sequential adaptation tends to be less harsh on cells than direct adaptation. Generally, to adapt cells to serum-free media, the culture should be in mid-logarithmic phase, >90% viable and seeded at a higher initial cell inoculum than during adaptation.

A cell line containing a host cell of the present invention may also be stored in a master cell bank (MCB) and working cell bank (WCB). Typically, when a cell line is to be used over many manufacturing cycles, a two-tiered cell banking system consisting of a master cell bank or master seed bank (MSB) and a working cell bank can be established. A cell line is established from a single host cell clone and this cell line is used to make-up the MCB. Generally, this MCB must be characterized and extensively tested for contaminants such as bacteria, fungi, viruses and mycoplasma. A sample of cells from the MCB can be expanded to form the WCB, which is characterized for cell viability prior to use in a manufacturing process. The cells in a MCB or WCB can be stored in vials, for example, at low temperature (e.g., 0° C. or lower, −20° C. or −80° C.).

Typically, the working cell bank includes cells from one vial of the master bank which have been grown for several passages before storage. In general, when future cells are needed, they are taken from the working cell bank; whereas, the master cell bank is used only when necessary, ensuring a stock of cells with a low passage number to avoid genetic variation within the cell culture.

Thus, the present invention includes a method for making a master cell bank comprising transforming a cell, e.g., a CHO cell, with a plasmid of the present invention, selecting a single clonal population of said transformed cells (e.g., a single colony growth on a culture plate), culturing said clonal population (e.g., in liquid growth media), determining if the cells from said culture contains bacteria, viruses, mycoplasma and/or fungi, and, if the cells of the culture are free of detectable levels of such agents, storing cells taken from such culture, e.g., in one or more separate containers, such as vials (e.g., comprising about 10⁷ cells per vial), under refrigeration (e.g., at −80° C.). The present invention also includes methods for preparing a working cell bank comprising selecting a sample of cells from a master cell bank, growing the cells and storing the cells in one or more containers, such as vials. Cells used to make a working cell bank can also be tested for bacteria, viruses, mycoplasma or fungi as with the master cell bank.

The present invention also includes a master cell bank and/or a working cell bank including any host cell of the present invention (e.g., as set forth herein) or one or more cells therefrom. Cells in a master cell bank or working cell bank can be stored in hundreds (e.g., 100, 200, 500, 700, 1000, or 2000 vials or more) of containers, such as vials (e.g., glass vials) under refrigeration (e.g., 0° C. or lower, −20° C. or −80° C.).

EXAMPLES

These examples are intended to further clarify the present invention and not to limit the invention. Any composition or method, in whole or in part, set forth in the examples form a part of the present invention.

Example 1

Evaluation of an Intron Element in the Antibody Expression Cassette

A βGI-IgG intron containing the β-globin splice donor that is present in plasmid pDSRG along with a part of the sequence of pDSRG and an immunoglobulin splice acceptor was synthesized by PCR:

```
                                              (SEQ ID NO: 3)
ATTAATACGA CTCACTATAG CAATTGCACG TGTGGCCACA

G/GTAAGTTTA AAGCTCAGGT CGAGACCGGG CCTTTGTCCG

GCGCTCCCTT GGAGCCTACC TAGACTCAGC CGGCTCTCCA

CGCTTTGCCT GACCCTGCTT GCTCAACTCT ACGTCTTTGT

TTCGTTTTCT GTTCCTTTCT CTCCACAG/GC TTAAGAATTC

ATAT
```

The sequence containing CAGGTAAGTTTA (SEQ ID NO: 4) is the β-globin splice donor, and the sequence containing TTTCTCTCCACAGGC (SEQ ID NO: 5) is immunoglobulin acceptor site. The slashes represent the predicted splice site between the donor and acceptor sequences.

The intron was inserted downstream of the human CMV promoter, within the 5' flanking region of the expression cassette in anticipation of expression enhancement. To do this, the 5' end of the βGI-IgG intron was extended by PCR to contain a partial sequence of the CMV promoter. The resulting extended PCR product was digested with EcoRI, filled in with Klenow polymerase and digested with NcoI. Simultaneously, the light chain expression plasmid, pUhCMVIGFR-LCb2, was also digested with NheI, filled in with Klenow polymerase, and digested with NcoI. The intron was then ligated to pUhCMVIGFRLCb2 to construct pUIGFRLCb2 (SEQ ID NO: 32). To insert the intron into the heavy chain expression plasmid, the PCR-extended, intron-containing fragment was digested with SnaBI and AflII. Simultaneously, pUhyg(−)IG1FRhuH was digested by SnaBI and AM, and the intron was inserted to construct pUIG1FRmodH (SEQ ID NO: 33). Subsequently, a single plasmid vector containing both the heavy and light chain expression cassettes was constructed as follows: pUIGFRLCb2 was digested by RsrII and PacI to transfer the light chain expression cassette. pXBLS was also digested by RsrII and PacI and the LCB2-containing light chain expression cassette was inserted to construct pAIGFRLCb2 (SEQ ID NO: 34). pUIG1FRmodH was then digested by BssHII to release the fragment carrying heavy chain and hygromycin-B phosphotransferase expression cassettes. pAIGFRLCb2 was also digested by BssHII and the heavy chain expression cassette was inserted at the site to construct pAIG1FRLCb2V1 (SEQ ID NO: 35) and pAIG1FRLCb2V3 (SEQ ID NO: 36).

The intron containing plasmids were evaluated for antibody expression in a transient transfection by ELISA. The results demonstrated that when the transfection was performed with plasmids carrying the intron in both the heavy and light chain expression cassettes, expression of anti-IGF1R was about two- to three-fold higher than that obtained from transfection by similar plasmids without the intron.

The two single expression plasmids, pAIG1FRLCb2V1 and pAIG1FRLCb2V3, were evaluated for bioactivity in the KIRA (kinase receptor activation) assay. The result suggests that both of the single expression plasmids show equivalent bioactivity to that shown by the purified antibody obtained from 19D12 hybridoma.

Some plasmid vectors were further modified through PCR to incorporate the Kozak consensus sequence (shown below in bold) at the 5' end of the heavy and light chain cDNA sequences. The restriction sites in the primers, noted below, are underlined, and the initiating methionine codons (atg) are in bold and italics.

The primer pair for the heavy chain is as follows:

5' primer:
(SEQ ID NO: 37)
5'- gcttggtaccgccgccaccatggagtttgggctgagctgggtttt-3'

3' primer:
(SEQ ID NO: 38)
5'- agaccgatgggcccttggtggaagctgagg -3'

The 5' primer has a KpnI (ggtacc) site along with the Kozak sequence and the 3' primer has an ApaI site (gggccc).

For the light chain the following primers were used:

5' primer:
(SEQ ID NO: 39)
5'-gaattcgtttaaacgccgccaccatgtcgccatcacaactcattgggt-3'

3' primer:
(SEQ ID NO: 40)
5'-ccaccgtacgtttgatctccaccttggtccctt-3'

The 5' primer for the light chain has an EcoRI (gaattc) and a PmeI (gtttaaac) site along with the Kozak sequence, and the 3' primer has a BsiWI site (cgtacg). The PmeI site was added to the 5' primer to serve as an indicator of successful ligation of the PCR product to the plasmid.

The amplified heavy chain sequence was cloned in pUIG1FRmodH/Kan at the KpnI and ApaI sites to construct pAIG1FRH-K (SEQ ID NO: 41), and the light chain sequence was cloned in pAIGFRLCb2 at the EcoRI and BsiWI sites to construct pAIGFRLCb2(−)L-K (SEQ ID NO: 42).

pAIG1FRH-K was then digested by BssHII to transfer the heavy chain expression cassette along with the hygromycin-B resistance gene expression cassette to pAIGFRLCb2(−)L-K. pAIGFRLCb2(−)L-K was also digested by BssHII, and the heavy chain expression cassette was inserted at the same site to construct pAIG1FRLCb2V1-K (SEQ ID NO: 43).

DXB11 cells were transfected with expression plasmids with and without introns. The presence of the βGI-IgG intron brought about a two- to three-fold increase in expression of anti-IGF1R in DXB11 cells. pAIG1FRV1 and pAIG1FRV3 were the plasmids carrying both heavy and light chain expression cassettes of anti-IGF1R without the intron. pAIG1FRLCB2V1 and pAIGFRLCB2V3 were the plasmids that carried both heavy and light chain expression cassettes of anti-IGF1R along with the intron. The supernatants from day 3 and 5 post-transfection were analyzed by ELISA. The data from the ELISA analyses are set forth below in table 1.

ELISA Procedure

Reagents

Anti-IGF1R 20.24 mg/mL concentrate

Human IgG-coated plates

HRP-conjugated goat anti-human IgG

ELISA Diluent—0.1% BSA (bovine serum albumin)/PBST (Phosphate buffer saline and Tween 20

TMB liquid substrate system: 1 step turbo system from Pierce

Stopping Reagent (~2M $H_2SO_4$)

Procedure

A. Preparation of Standard Curve

Diluted purified anti-IGF1R to 200 ng/mL in ELISA Diluent. 20,240,000 ng/mL÷200 ng/mL=1:101200 dilution Added 10 μL Human IgG1 standard to 990 μL ELISA diluent (I).

Diluted to 200 ng/mL by adding 49.4 μL of (I) to 49950.6 μL ELISA diluent.

Prepared 4 mL aliquots of the 200 ng/mL standard and stored at 4° C. On day of assay, prepared remainder of the standard curve by loading 200 μL of standard to row A and performed 1:2, serial dilutions from the top standard to the bottom (3.125 ng/mL). Used ELISA Diluent as the blank or 0 ng/mL standard.

B. Preparation of Control

Prepared control at 300 ng/mL.

Added 74.1 μL of (I), (see Preparation of Standard Curve) 49925.9 μL of ELISA diluent.

Prepared 2.5 mL aliquots and stored at 4° C.

C. Assay

Allowed all reagents to warm to room temperature before using them.

1. Set up a template denoting positions of standard curve and unknowns.
2. Washed plate 1× with EIA Wash Buffer
3. Added standards, controls, and samples to the appropriate wells as per the template.

Final volume in each well was 100 μL.

Covered the plate and incubated for 1 hour at room temperature.

4. Diluted the HRP-conjugated anti-huIgG 1:10,000 in ELISA diluent.

Performed an initial 1:100 dilution by adding 10 μL of anti-huIgG stock to 990 μL of 0.1% BSA-PBST, then performed an additional 1:100 dilution by adding 350 μL of the initial dilution to 34650 μL of 0.1% BSA-PBST. The final dilution of this solution was 1:10000.

5. Aspirated the liquid in the wells. Washed the wells 4 times with EIA Wash Buffer.
6. Added 100 μL of the HRP conjugate to all wells. Covered the plate and incubated for 30 minutes at room temperature.
7. Washed the wells as in Step 5.
8. Developed color in the wells by adding 100 μL of TMB substrate to each well.
9. Depending upon the amount of blue color in the wells, added 50 μL of Stopping Reagent to all the wells in the same order as dispensed in Step 8. This took approximately 2-4 minutes. Plate developed for 2 minutes.
10. Within 30 minutes of adding the Stopping Reagent, read the absorbance of each well using a microplate reader, setting the wavelengths at 450-650 nm.

D. Data Analysis

Analyzed data using a 4-parameter logistics curve fit.

Kinase Receptor Activation (KIRA) Assay Procedure

1) Prepared MCF-7 cells at 200,000 cells/well ($2.0 \times 10^6$ cells/mL-0.1 mL) in culture media without Bovine Insulin. Seeded cells in 96-well tissue culture plates (Falcon #35-3075). Prepared duplicate wells/sample. Incubated plates overnight in $CO_2$ incubator (5-6% $CO_2$, 35-37° C.).

2) Coated ELISA plate(s) (NUNC MAXI-SORP) with 100 μL/well anti-IGF1R capture antibody (a commercially available IgG1 specific antibody). Prepared purified hybridoma derived 19D12 to 1.0 μg/mL. Each batch was tested for use. Incubated ELISA plate at 4° C. overnight.

3) Removed tissue culture plate(s) from incubator. Withdrew media from all wells except the untreated (EMEM) control wells. Using a 12-channel multichannel pipet, removed the media one row at a time to prevent wells from drying prior to sample addition.

4) For dilution curves in a 96-well dilution plate, added 100 μl/mL EMEM to columns 1-10 and 12. Added 200 μL/well control Ab at 5.0 μg/mL to appropriate wells of column 11. Add 200 μl/well samples to appropriate wells of column 11. Using serial diluting apparatus transferred 100 μl (1:2) from column 11 to column 1 (column 12 is untreated cell control). Removed media from wells of cell plate. Transferred 50 μl/well from dilution plate to corresponding wells of cell plate. Incubated for 30 minutes in $CO_2$ incubator (5-6% $CO_2$, 35-37° C.).

5) Prepared IGF-I (R&D Systems; Minneapolis, Minn.) at 75 ng/mL in EMEM (no FBS). Removed tissue culture plates from incubator. Withdrew the contents from all the wells (1 plate at a time). Added 100 μL/well IGF-I to the sample wells, and the IGF-I control wells. Added 100 μl/well EMEM to column 12.

6) While cell plates were incubating, blocked the previously coated ELISA plate(s). Discarded the capture antibody (dumping into a container is acceptable) and blotted on paper towel. Added 150 μL/well blocking buffer (see reagent sheet). Gently shook plate(s) on a plate shaker at room temperature for 1 hour.

7) Following IGF-I incubation of cell plate(s), withdrew contents of all wells of tissue culture plate(s) (all wells can be withdrawn/96-well plate). Added 100 μL/well lyse buffer. Shook plate(s) on a plate shaker at room temperature for 1 hour.

8) Following blocking buffer incubation of ELISA plate(s), discarded block buffer (dump, blot). Washed plate 6× with 150 μL/well wash buffer (see reagent sheet). Dumped and blotted after each wash.

9) Following lyse buffer incubation of cell plate(s), transferred 85 μL from cell plate(s) wells to corresponding wells of ELISA plate(s). A whole row was transferred at one time using a 12 channel multichannel pipet. Prior to transfer, gently pipetted, up and down, the transfer volume in order to break up some of the remaining cell clumps. Avoided producing bubbles when pipeting the lysates. Shook plate(s) on a plate shaker at room temperature for 2 hours.

10) Prepared biotinylated anti-phosphotyrosine detection Ab-4G10 (Upstate USA; Lake Placid, N.Y.) at 0.2 µg/mL in dilution buffer (see reagent sheet). Brought to room temperature. Following incubation of lysates, discarded the lysates (dump, blot). Washed ELISA plate(s) 4× with 100 µL/well wash buffer. Dumped and blotted after each wash.

11) Added 100 µL/well 4G10 Ab (anti-phosphotyrosine antibody) to ELISA plate(s). Gently shook plate(s) on a plate shaker at room temperature for 2 hours.

12) Prepared HRP conjugated Streptavidin (Kirkegaard and Perry Laboratories Inc.; Gaithersburg, Md.) at 0.025 µg/mL in dilution buffer. Brought to room temperature. Following the 4G10 (anti-phosphotyrosine antibody) incubation, discarded the detection antibody (dump, blot). Washed ELISA plate(s) 4× with 100 µL/well wash buffer. Dumped and blotted after each wash.

13) Added 100 µL/well HRP conjugated Streptavidin. Gently shook plate(s) on a plate shaker at room temperature for 30 minutes.

14) Prepared TMB substrate (2 component system, R&D Systems) at a 1:1 mixture of component A to component B. Brought to room temperature. Following the Streptavidin incubation in ELISA plate(s), discarded the Streptavidin (dump, blot). Washed ELISA plate 4× with 100 µL/well wash buffer. Dumped and blotted after each wash.

15) Added 100 µL/well TMB substrate to ELISA plate(s). Shook plate(s) on a plate shaker at room temperature for 15 minutes.

16) Following TMB incubation, added 50 µL/well 1N $H_2SO_4$ stop agent. Read plate(s) on plate reader (Molecular Devices) at 450 nm/570 nm. Plate was read within 20 minutes of adding stop agent.

TABLE 1

Anti-IGF1R expression level from various plasmids.

|  | Day 3* | Day 5* |
| --- | --- | --- |
| pAIG1FRV1 (LC/HCA) | 1.04 | 1.09 |
| pAIG1FRV3 (LC/HCA) | 0.76 | 0.83 |
| pAIG1FRLCB2V1 (LCF/HCA) | 2.42 | 2.91 |
| pAIG1FRLCB2V3 (LCF/HCA) | 3.03 | 3.26 |
| pAIG1FRLCB2V1 (LCF/HCA) | 2.61 | 2.76 |
| pAIG1FRLCB2-V1K (LCF/HCA) | 3.23 | 4.06 |

*mAb production expressed in (ug/ml)

These data demonstrate the superior expression levels associated with βGI-IgG-containing plasmids, pAIG1FRLCB2V1 and pAIG1FRLCB2V3, compared to related plasmids lacking the βGI-IgG intron, pAIG1FRV1 and pAIG1FRV3. Even greater levels of expression were possible when a Kozak consensus sequence was operably associated with the immunoglobulin genes of plasmid pAIG1FRLCB2V1 to generate pAIG1FRLCB2-V1K.

The biological activity of the 19D12 antibodies from the 19D12 parental hybridoma and from the plasmids pAIG1FRLCB2V1 and pAIG1FRLCB2V3 were analyzed by KIRA assay. These data are set forth below in table 2.

TABLE 2

Evaluation of anti-IGF1R antibodies from a 19D12 hybridoma and from CHO-DXB11 cells containing plasmids pAIG1FRLCB2V1 and pAIG1FRLCB2V3.

| | % Inhibition | | |
| --- | --- | --- | --- |
| nM Ab | 19D12 | pAIG1FRLCb2V1 (LCF/HCA) | pAIG1FRLCb2V3 (LCF/HCA) |
| 0.01 | −3.26 | −4.68 | 1.11 |
| 0.01 | −0.34 | −5.72 | −3.10 |
| 0.03 | −3.18 | −9.34 | −2.88 |
| 0.05 | 0.87 | −1.78 | −4.33 |
| 0.10 | 3.82 | −1.78 | −0.90 |
| 0.21 | 10.10 | 2.74 | 6.41 |
| 0.42 | 18.01 | 11.06 | 10.41 |
| 0.83 | 39.39 | 28.24 | 20.38 |
| 1.67 | 40.51 | 39.05 | 34.20 |
| 3.34 | 54.59 | 56.00 | 49.82 |
| 6.67 | 69.59 | 76.34 | 63.30 |

"nM Ab" indicates the concentration (nanomolar) of antibody used in each assay.

19D12 corresponds to signal generated using the 19D12 antibody. pAIG1FRLCb2V1 and pAIG1FRLCb2V3 correspond to data generated using the antibody expressed and purified from these two plasmid (light chain F/heavy chain A).

These data demonstrated that the pAIG1FRLCb2V1 and pAIG1FRLCb2V3 plasmids generated anti-IGF1R antibody that was biologically active.

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

I claim:

1. An isolated plasmid vector comprising the nucleotide sequence set forth in SEQ ID NO: 47.

2. An isolated plasmid vector characterized by a plasmid map set forth in FIG. 9.

3. An isolated host cell comprising the plasmid vector of claim 1.

4. The host cell of claim 3 wherein the plasmid vector is integrated into the chromosomal DNA of the host cell.

5. The host cell of claim 4 comprising two or more copies of the plasmid vector.

6. The host cell of claim 3 wherein the plasmid vector is not integrated into the chromosomal DNA of the host cell.

7. The host cell of claim 6 comprising two or more copies of the plasmid vector.

* * * * *

SEQUENCE LISTING

<160> NUMBER OF SEQ ID NOS: 48

<210> SEQ ID NO 1
<211> LENGTH: 13
<212> TYPE: DNA
<213> ORGANISM: Artificial Sequence
<220> FEATURE:
<223> OTHER INFORMATION: Kozak consensus sequence

<400> SEQUENCE: 1

```
gccgccacca tgg                                                         13
```

<210> SEQ ID NO 2
<211> LENGTH: 12
<212> TYPE: DNA
<213> ORGANISM: Artificial Sequence
<220> FEATURE:
<223> OTHER INFORMATION: Kozak consensus sequence

<400> SEQUENCE: 2

```
gccgccacca tg                                                          12
```

<210> SEQ ID NO 3
<211> LENGTH: 194
<212> TYPE: DNA
<213> ORGANISM: Artificial Sequence
<220> FEATURE:
<223> OTHER INFORMATION: Hybrid intron comprising the beta-globin splice
      donor and the Ig. splice acceptor

<400> SEQUENCE: 3

```
attaatacga ctcactatag caattgcacg tgtggccaca ggtaagttta aagctcaggt      60
cgagaccggg cctttgtccg gcgctccctt ggagcctacc tagactcagc cggctctcca    120
cgctttgcct gaccctgctt gctcaactct acgtctttgt ttcgttttct gttcctttct    180
ctccacaggc ttaa                                                      194
```

<210> SEQ ID NO 4
<211> LENGTH: 12
<212> TYPE: DNA
<213> ORGANISM: Artificial Sequence
<220> FEATURE:
<223> OTHER INFORMATION: beta-globin splice donor site

<400> SEQUENCE: 4

```
caggtaagtt ta                                                          12
```

<210> SEQ ID NO 5
<211> LENGTH: 15
<212> TYPE: DNA
<213> ORGANISM: Artificial Sequence
<220> FEATURE:
<223> OTHER INFORMATION: Ig. splice acceptor site

<400> SEQUENCE: 5

```
tttctctcca caggc                                                       15
```

<210> SEQ ID NO 6
<211> LENGTH: 128
<212> TYPE: PRT
<213> ORGANISM: Homo sapiens

<400> SEQUENCE: 6

Met Ser Pro Ser Gln Leu Ile Gly Phe Leu Leu Leu Trp Val Pro Ala
 1               5                  10                  15

Ser Arg Gly Glu Ile Val Leu Thr Gln Val Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Leu Ser Gly Val Pro Ser Arg
65                  70                  75                  80

```
Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Arg
            100                 105                 110

Leu Pro His Thr Phe Gly Gly Gly Thr Lys Val Glu Ile Lys Arg Thr
        115                 120                 125
```

<210> SEQ ID NO 7
<211> LENGTH: 137
<212> TYPE: PRT
<213> ORGANISM: Homo sapiens

<400> SEQUENCE: 7

```
Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val His
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135
```

<210> SEQ ID NO 8
<211> LENGTH: 128
<212> TYPE: PRT
<213> ORGANISM: Homo sapiens

<400> SEQUENCE: 8

```
Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125
```

<210> SEQ ID NO 9
<211> LENGTH: 128
<212> TYPE: PRT

<213> ORGANISM: Homo sapiens

<400> SEQUENCE: 9

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 10
<211> LENGTH: 128
<212> TYPE: PRT
<213> ORGANISM: Homo sapiens

<400> SEQUENCE: 10

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 11
<211> LENGTH: 128
<212> TYPE: PRT
<213> ORGANISM: Homo sapiens

<400> SEQUENCE: 11

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 12
<211> LENGTH: 137
<212> TYPE: PRT
<213> ORGANISM: Homo sapiens

<400> SEQUENCE: 12

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
        130                 135

<210> SEQ ID NO 13
<211> LENGTH: 137
<212> TYPE: PRT
<213> ORGANISM: Homo sapiens

<400> SEQUENCE: 13

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser

<210> SEQ ID NO 14
<211> LENGTH: 144
<212> TYPE: PRT
<213> ORGANISM: Homo sapiens

<400> SEQUENCE: 14

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Gly Ile Ser Trp Asn Ser Gly Ser Lys Gly Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Lys Asp Ile Arg Ile Gly Val Ala Ala Ser Tyr Tyr
        115                 120                 125

Phe Gly Met Asp Val Trp Gly His Gly Thr Thr Val Thr Val Ser Ser
    130                 135                 140

<210> SEQ ID NO 15
<211> LENGTH: 10
<212> TYPE: PRT
<213> ORGANISM: Homo sapiens

<400> SEQUENCE: 15

Gly Phe Thr Phe Asp Asp Tyr Ala Met His
1               5                   10

<210> SEQ ID NO 16
<211> LENGTH: 17
<212> TYPE: PRT
<213> ORGANISM: Homo sapiens

<400> SEQUENCE: 16

Gly Ile Ser Trp Asn Ser Gly Ser Lys Gly Tyr Val Asp Ser Val Lys
1               5                   10                  15

Gly

<210> SEQ ID NO 17
<211> LENGTH: 16
<212> TYPE: PRT
<213> ORGANISM: Homo sapiens

<400> SEQUENCE: 17

Asp Ile Arg Ile Gly Val Ala Ala Ser Tyr Tyr Phe Gly Met Asp Val
1               5                   10                  15

<210> SEQ ID NO 18
<211> LENGTH: 129
<212> TYPE: PRT
<213> ORGANISM: Homo sapiens

<400> SEQUENCE: 18

```
Met Asp Met Arg Val Pro Ala Gln Leu Leu Gly Leu Leu Leu Trp
1               5                   10                  15

Leu Pro Gly Ala Arg Cys Ala Ile Gln Leu Thr Gln Ser Pro Ser
            20                  25                  30

Leu Ser Ala Ser Val Gly Asp Arg Val Thr Ile Thr Cys Arg Ala Ser
        35                  40                  45

Gln Gly Ile Ser Ser Val Leu Ala Trp Tyr Gln Gln Lys Pro Gly Lys
    50                  55                  60

Ala Pro Lys Leu Leu Ile Tyr Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Tyr Thr Phe Gly Gln Gly Thr Lys Leu Glu Ile
        115                 120                 125

Lys
```

<210> SEQ ID NO 19
<211> LENGTH: 11
<212> TYPE: PRT
<213> ORGANISM: Homo sapiens

<400> SEQUENCE: 19

```
Arg Ala Ser Gln Gly Ile Ser Ser Val Leu Ala
1               5                   10
```

<210> SEQ ID NO 20
<211> LENGTH: 7
<212> TYPE: PRT
<213> ORGANISM: Homo sapiens

<400> SEQUENCE: 20

```
Asp Ala Ser Ser Leu Glu Ser
1               5
```

<210> SEQ ID NO 21
<211> LENGTH: 9
<212> TYPE: PRT
<213> ORGANISM: Homo sapiens

<400> SEQUENCE: 21

```
Gln Gln Phe Asn Ser Tyr Pro Tyr Thr
1               5
```

<210> SEQ ID NO 22
<211> LENGTH: 146
<212> TYPE: PRT
<213> ORGANISM: Homo sapiens

<400> SEQUENCE: 22

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Val Met His Trp Val Arg Gln Ala Pro Gly Gln Arg Leu
    50                  55                  60

Glu Trp Met Gly Trp Ile Asn Ala Gly Asn Gly Asn Thr Lys Tyr Ser
```

```
                65                  70                  75                  80
Gln Lys Phe Gln Gly Arg Val Thr Ile Thr Arg Asp Thr Ser Ala Ser
                    85                  90                  95

Thr Val Tyr Met Glu Leu Ser Ser Leu Arg Ser Glu Asp Thr Ala Val
                100                 105                 110

Tyr Tyr Cys Ala Arg Gly Gly Met Pro Val Ala Gly Pro Gly Tyr Phe
                115                 120                 125

Tyr Tyr Tyr Gly Met Asp Val Trp Gly Gln Gly Thr Thr Val Thr Val
            130                 135                 140

Ser Ser
145

<210> SEQ ID NO 23
<211> LENGTH: 10
<212> TYPE: PRT
<213> ORGANISM: Homo sapiens

<400> SEQUENCE: 23

Gly Tyr Thr Phe Thr Ser Tyr Val Met His
1               5                   10

<210> SEQ ID NO 24
<211> LENGTH: 17
<212> TYPE: PRT
<213> ORGANISM: Homo sapiens

<400> SEQUENCE: 24

Trp Ile Asn Ala Gly Asn Gly Asn Thr Lys Tyr Ser Gln Lys Phe Gln
1               5                   10                  15

Gly

<210> SEQ ID NO 25
<211> LENGTH: 18
<212> TYPE: PRT
<213> ORGANISM: Homo sapiens

<400> SEQUENCE: 25

Gly Gly Met Pro Val Ala Gly Pro Gly Tyr Phe Tyr Tyr Tyr Gly Met
1               5                   10                  15

Asp Val

<210> SEQ ID NO 26
<211> LENGTH: 130
<212> TYPE: PRT
<213> ORGANISM: Homo sapiens

<400> SEQUENCE: 26

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Ser Arg Ser Tyr Leu Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95
```

Ser Arg Leu Glu Pro Glu Asp Phe Ala Val Tyr Cys Cys Gln Gln Tyr
            100                 105                 110

Gly Ser Ser Pro Trp Thr Phe Gly Gln Gly Thr Lys Val Glu Ile Lys
        115                 120                 125

Arg Thr
    130

<210> SEQ ID NO 27
<211> LENGTH: 12
<212> TYPE: PRT
<213> ORGANISM: Homo sapiens

<400> SEQUENCE: 27

Arg Ala Ser Gln Ser Val Ser Arg Ser Tyr Leu Ala
1               5                   10

<210> SEQ ID NO 28
<211> LENGTH: 7
<212> TYPE: PRT
<213> ORGANISM: Homo sapiens

<400> SEQUENCE: 28

Gly Ala Ser Ser Arg Ala Thr
1               5

<210> SEQ ID NO 29
<211> LENGTH: 9
<212> TYPE: PRT
<213> ORGANISM: Homo sapiens

<400> SEQUENCE: 29

Gln Gln Tyr Gly Ser Ser Pro Trp Thr
1               5

<210> SEQ ID NO 30
<211> LENGTH: 125
<212> TYPE: PRT
<213> ORGANISM: Homo sapiens

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Thr Thr Phe Tyr Ala Asp Ser Val
    50                  55                  60

Lys Gly Arg Phe Thr Ile Ser Arg Asp Asn Ser Arg Thr Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Trp Ser Asp Ser Tyr Tyr Tyr Tyr Gly Met
            100                 105                 110

Asp Val Trp Gly Gln Gly Thr Thr Val Thr Val Ser Ser
        115                 120                 125

<210> SEQ ID NO 31
<211> LENGTH: 108
<212> TYPE: PRT
<213> ORGANISM: Homo sapiens

```
<400> SEQUENCE: 31

Asp Ile Gln Met Thr Gln Phe Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu His Arg Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Cys
                85                  90                  95

Ser Phe Gly Gln Gly Thr Lys Leu Glu Ile Lys Arg
                100                 105

<210> SEQ ID NO 32
<211> LENGTH: 4699
<212> TYPE: DNA
<213> ORGANISM: Artificial Sequence
<220> FEATURE:
<223> OTHER INFORMATION: pUIGFRLCB2 plasmid sequence

<400> SEQUENCE: 32
ctaaattgta agcgttaata ttttgttaaa attcgcgtta aattttgtt aaatcagctc      60
atttttaac caataggccg aaatcggcaa atcccttat aaatcaaaag aatagaccga     120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt ttttttgggt cgaggtgccg taaagcacta atcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgccaccgg tggcccgggc cggtccgact agttaccgat    660
gtacgggcca gatatacgcg ttgacattga ttattgacta gttattaata gtaatcaatt    720
acggggtcat tagttcatag cccatatatg gagttccgcg ttacataact tacggtaaat    780
ggcccgcctg gctgaccgcc caacgacccc cgcccattga cgtcaataat gacgtatgtt    840
cccatagtaa cgccaatagg gactttccat tgacgtcaat gggtggagta tttacggtaa    900
actgcccact tggcagtaca tcaagtgtat catatgccaa gtacgcccc tattgacgtc    960
aatgacggta aatggcccgc ctggcattat gcccagtaca tgaccttatg gactttcct   1020
acttggcagt acatctacgt attagtcatc gctattacca tggtgatgcg gttttggcag   1080
tacatcaatg ggcgtggata gcggtttgac tcacggggat ttccaagtct ccaccccatt   1140
gacgtcaatg ggagtttgtt ttggcaccaa aatcaacggg actttccaaa atgtcgtaac   1200
aactccgccc cattgacgca aatgggcggt aggcgtgtac ggtgggaggt ctatataagc   1260
agagctctct ggctaactag agaacccact gcttactggc ttatcgaaat taatacgact   1320
cactatagca attgcacgtg tggccacagg taagtttaaa gctcaggtcg agaccgggcc   1380
tttgtccggc gctcccttgg agcctaccta gactcagccg gctctccacg ctttgcctga   1440
```

```
ccctgcttgc tcaactctac gtctttgttt cgttttctgt tcctttctct ccacaggctt    1500
aagaattcta gcgtttaaca tgtcgccatc acaactcatt gggtttctgc tgctctgggt    1560
tccagcctcc aggggtgaaa ttgtgctgac tcagagccca ggtaccctgt ctgtgtctcc    1620
aggcgagaga gccaccctct cctgccgggc cagtcagagc attggtagta gcttacactg    1680
gtaccagcag aaaccaggtc aggctccaag gcttctcatc aagtatgcat cccagtccct    1740
ctcagggatc cccgataggt tcagtggcag tggatctggg acagatttca ccctcaccat    1800
cagtagactg gagcctgaag atttcgcagt gtattactgt catcagagta gtcgtttacc    1860
tcacactttc ggccaaggga ccaaggtgga gatcaaacgt acagtggctg caccatctgt    1920
cttcatcttc ccgccatctg atgagcagtt gaaatctgga actgcctctg ttgtgtgcct    1980
gctgaataac ttctatccca gagaggccaa agtacagtgg aaggtggata acgccctcca    2040
atcgggtaac tcccaggaga gtgtcacaga gcaggacagc aaggacagca cctacagcct    2100
cagcagcacc ctgacgctga gcaaagcaga ctacgagaaa cacaaagtct acgcctgcga    2160
agtcacccat cagggcctga gctcgcccgt cacaaagagc ttcaacaggg gagagtgtta    2220
gagggagaag gggcctccg gaggatccag atcccctcg ctttcttgct gtccaatttc    2280
tattaaaggt tcctttgttc cctaagtcca actactaaac tggggatat tatgaagggc    2340 cttgagcatc tggattctgc ctaataaaaa acatttattt tcattgcaat gatgtattta    2400
aattatttct gaatatttta ctaaaaaggg aatgtgggag gtcagtgcat ttaaaacata    2460
aagaaatgaa gaggggatc tgtcgacaag ctctagagag ctccatatgt ggccatcgcg    2520
attaattaag cgcgcttggc gtaatcatgg tcatagctgt ttcctgtgtg aaattgttat    2580
ccgctcacaa ttccacacaa catacgagcc ggaagcataa agtgtaaagc ctggggtgcc    2640
taatgagtga gctaactcac attaattgcg ttgcgctcac tgcccgcttt ccagtcggga    2700
aacctgtcgt gccagctgca ttaatgaatc ggccaacgcg cggggagagg cggtttgcgt    2760
attgggcgct cttccgcttc ctcgctcact gactcgctgc gctcggtcgt tcggctgcgg    2820
cgagcggtat cagctcactc aaaggcggta atacggttat ccacagaatc aggggataac    2880
gcaggaaaga acatgtgagc aaaaggccag caaaaggcca ggaaccgtaa aaaggccgcg    2940
ttgctggcgt ttttccatag gctccgcccc cctgacgagc atcacaaaaa tcgacgctca    3000
agtcagaggt ggcgaaaccc gacaggacta taaagatacc aggcgtttcc ccctggaagc    3060
tccctcgtgc gctctcctgt tccgaccctg ccgcttaccg gatacctgtc cgcctttctc    3120
ccttcgggaa gcgtggcgct ttctcatagc tcacgctgta ggtatctcag ttcggtgtag    3180
gtcgttcgct ccaagctggg ctgtgtgcac gaaccccccg ttcagcccga ccgctgcgcc    3240
ttatccggta actatcgtct tgagtccaac ccggtaagac acgacttatc gccactggca    3300
gcagccactg gtaacaggat tagcagagcg aggtatgtag gcggtgctac agagttcttg    3360
aagtggtggc ctaactacgg ctacactaga aggacagtat ttggtatctg cgctctgctg    3420
aagccagtta ccttcggaaa aagagttggt agctcttgat ccggcaaaca aaccaccgct    3480
ggtagcggtg gttttttgt ttgcaagcag cagattacgc gcagaaaaaa aggatctcaa    3540
gaagatcctt tgatctttc tacgggtct gacgctcagt ggaacgaaaa ctcacgttaa    3600
gggattttgg tcatgagatt atcaaaaagg atcttcacct agatcctttt aaattaaaaa    3660
tgaagtttta aatcaatcta agtatatat gagtaaactt ggtctgacag ttaccaatgc    3720
ttaatcagtg aggcacctat ctcagcgatc tgtctatttc gttcatccat agttgcctga    3780
ctccccgtcg tgtagataac tacgatacgg gagggcttac catctggccc cagtgctgca    3840
```

```
atgataccgc gagacccacg ctcaccggct ccagatttat cagcaataaa ccagccagcc    3900
ggaagggccg agcgcagaag tggtcctgca actttatccg cctccatcca gtctattaat    3960
tgttgccggg aagctagagt aagtagttcg ccagttaata gtttgcgcaa cgttgttgcc    4020
attgctacag gcatcgtggt gtcacgctcg tcgtttggta tggcttcatt cagctccggt    4080
tcccaacgat caaggcgagt tacatgatcc cccatgttgt gcaaaaaagc ggttagctcc    4140
ttcggtcctc cgatcgttgt cagaagtaag ttggccgcag tgttatcact catggttatg    4200
gcagcactgc ataattctct tactgtcatg ccatccgtaa gatgctttt  tgtgactggt    4260 gagtactcaa ccaagtcatt ctgagaatag tgtatgcggc gaccgagttg ctcttgcccg    4320
gcgtcaatac gggataatac cgcgccacat agcagaactt taaaagtgct catcattgga    4380
aaacgttctt cggggcgaaa actctcaagg atcttaccgc tgttgagatc cagttcgatg    4440
taacccactc gtgcacccaa ctgatcttca gcatctttta ctttcaccag cgttctgggt   4500
tgagcaaaaa caggaaggca aaatgccgca aaaaagggaa taagggcgac acggaaatgt    4560
tgaatactca tactcttcct ttttcaatat tattgaagca tttatcaggg ttattgtctc    4620
atgagcggat acatatttga atgtatttag aaaaataaac aatagggt tccgcgcaca    4680 tttccccgaa aagtgccac                                                  4699
```

<210> SEQ ID NO 33
<211> LENGTH: 7439
<212> TYPE: DNA
<213> ORGANISM: Artificial Sequence
<220> FEATURE:
<223> OTHER INFORMATION: pUIG1FRmodH plasmid sequence

<400> SEQUENCE: 33

```
tataaatcaa agaatagac cgagataggg ttgagtgttg ttccagtttg gaacaagagt       60
ccactattaa agaacgtgga ctccaacgtc aaagggcgaa aaaccgtcta tcagggcgat     120
ggcccactac gtgaaccatc accctaatca agtttttttgg ggtcgaggtg ccgtaaagca    180
ctaaatcgga accctaaagg agcccccga tttagagctt gacggggaaa gccggcgaac     240
gtggcgagaa aggaagggaa gaaagcgaaa ggagcgggcg ctagggcgct ggcaagtgta    300
gcggtcacgc tgcgcgtaac caccacaccc gccgcgctta atgcgccgct acagggcgcg    360
tcccattcgc cattcaggct gcgcaactgt tgggaagggc gatcggtgcg ggcctcttcg    420
ctattacgcc agctggcgaa aggggggatgt gctgcaaggc gattaagttg ggtaacgcca    480
gggttttccc agtcacgacg ttgtaaaacg acggccagtg agcgcgccgt taaacccctc    540
agctaccgat gtacgggcca gatatacgcg ttgacattga ttattgacta gttattaata    600
gtaatcaatt acgggtcat tagttcatag cccatatatg gagttccgcg ttacataact    660
tacggtaaat ggcccgcctg gctgaccgcc caacgacccc cgcccattga cgtcaataat    720
gacgtatgtt cccatagtaa cgccaatagg gactttccat tgacgtcaat gggtggagta    780
tttacggtaa actgcccact ggcagtaca tcaagtgtat catatgccaa gtacgccccc    840
tattgacgtc aatgacggta aatggcccgc ctggcattat gcccagtaca tgaccttatg    900
ggactttcct acttggcagt acatctacgt attagtcatc gctattacca tggtgatgcg    960
gttttggcag tacatcaatg ggcgtggata gcggtttgac tcacggggat ttccaagtct   1020
ccaccccatt gacgtcaatg ggagtttgtt ttggcaccaa aatcaacggg actttccaaa   1080
atgtcgtaac aactccgccc cattgacgca aatgggcggt aggcgtgtac ggtgggaggt   1140
ctatataagc agagctctct ggctaactag agaacccact gcttactggc ttatcgaaat   1200
```

```
taatacgact cactatagca attgcacgtg tggccacagg taagtttaaa gctcaggtcg    1260
agaccgggcc tttgtccggc gctcccttgg agcctaccta gactcagccg gctctccacg    1320
ctttgcctga ccctgcttgc tcaactctac gtctttgttt cgttttctgt tcctttctct    1380
ccacaggctt aagcttggta ccgagctcgg atccactagt ccagtgtggt ggaattcgcc    1440
cttatggagt ttgggctgag ctgggttttc cttgttgcta tattaaaagg tgtccagtgt    1500
gaggttcagc tggtgcagtc tggggaggc ttggtaaagc ctggggggtc cctgagactc     1560
tcctgtgcag cctctggatt cacccttcagt agctttgcta tgcactgggt tcgccaggct   1620
ccaggaaaag gtctggagtg gatatcagtt attgatactc gtggtgccac atactatgca    1680
gactccgtga agggccgatt caccatctcc agagacaatg ccaagaactc cttgtatctt    1740
caaatgaaca gcctgagagc cgaggacact gctgtgtatt actgtgcaag actggggaac    1800
ttctactacg gtatggacgt ctggggccaa gggaccacgg tcaccgtctc ctcagcttcc    1860
accaagggcc catcggtctt ccccctggca ccctcctcca gagcacctc tggggcaca    1920 gcggccctgg gctgcctggt caaggactac ttccccgaac cggtgacggt gtcgtggaac    1980
tcaggcgccc tgaccagcgg cgtgcacacc ttcccggctg tcctacagtc ctcaggactc    2040
tactccctca gcagcgtggt gaccgtgccc tccagcagct gggcaccca gacctacatc     2100 tgcaacgtga atcacaagcc cagcaacacc aaggtggaca gaaagttga gcccaaatct     2160 tgtgacaaaa ctcacacatg cccaccgtgc ccagcacctg aactcctggg gggaccgtca    2220
gtcttcctct tccccccaaa acccaaggac accctcatga tctcccggac ccctgaggtc    2280
acatgcgtgg tggtggacgt gagccacgaa gaccctgagg tcaagttcaa ctggtacgtg    2340
gacggcgtgg aggtgcataa tgccaagaca aagccgcggg aggagcagta caacagcacg    2400
taccgtgtgg tcagcgtcct caccgtcctg caccaggact ggctgaatgg caaggagtac    2460
aagtgcaagg tctccaacaa agccctccca gcccccatcg agaaaaccat ctccaaagcc    2520
aaagggcagc cccgagaacc acaggtgtac accctgcccc catcccggga tgagctgacc    2580
aagaaccagg tcagcctgac ctgcctggtc aaaggcttct atcccagcga catcgccgtg    2640
gagtgggaga gcaatgggca gccggagaac aactacaaga ccacgcctcc cgtgctggac    2700
tccgacggct ccttcttcct ctacagcaag ctcaccgtgg acaagagcag gtggcagcag    2760
gggaacgtct tctcatgctc cgtgatgcat gaggctctgc acaaccacta cacgcagaag    2820
agcctctccc tgtctccggg taaatgaatc gatgattcta gatacgggtc cggaggatcc    2880
agatccccct cgctttcttg ctgtccaatt tctattaaag gttcctttgt tccctaagtc    2940
caactactaa actgggggat attatgaagg gccttgagca tctggattct gcctaataaa    3000
aaacatttat tttcattgca atgatgtatt taaattattt ctgaatattt tactaaaaag    3060
ggaatgtggg aggtcagtgc atttaaaaca taaagaaatg aagaggggga tctgtcgaca    3120
agctctagag agctcacgcg ttgatcatgt acaggccggc caagctttcg actagcttgg    3180
cacgccagaa atccgcgcgg tggttttttgg gggtcggggg tgtttggcag ccacagacgc    3240
ccggtgttcg tgtcgcgcca gtacatgcgg tccatgccca ggccatccaa aaaccatggg    3300
tctgtctgct cagtccagtc gtggacctga cccacgcaa cgcccaaaat aataaccccc    3360
acgaaccata aaccattccc catggggac cccgtcccta ccacgggg ccagtggcta     3420 tggcagggcc tgccgccccg acgttggctg cgagccctgg gccttcaccc gaacttgggg    3480
ggtggggtgg ggaaaaggaa gaaacgcggg cgtattggcc ccaatgggt ctcggtgggg    3540 tatcgacaga gtgccagccc tgggaccgaa ccccgcgttt atgaacaaac gacccaacac    3600
```

```
ccgtgcgttt tattctgtct ttttattgcc gtcatagcgc gggttccttc cggtattgtc   3660
tccttccgtg tttcagttag cctcccccat ctcccgatcc ggacgagtgc tggggcgtcg   3720
gtttccacta tcggcgagta cttctacaca gccatcggtc cagacggccg cgcttctgcg   3780
ggcgatttgt gtacgcccga cagtcccggc tccggatcgg acgattgcgt cgcatcgacc   3840
ctgcgcccaa gctgcatcat cgaaattgcc gtcaaccaag ctctgataga gttggtcaag   3900
accaatgcgg agcatatacg cccggagccg cggcgatcct gcaagctccg gatgcctccg   3960
ctcgaagtag cgcgtctgct gctccataca agccaaccac ggcctccaga agaagatgtt   4020
ggcgacctcg tattgggaat ccccgaacat cgcctcgctc cagtcaatga ccgctgttat   4080
gcggccattg tccgtcagga cattgttgga gccgaaatcc gcgtcacga ggtgccggac    4140 ttcggggcag tcctcggccc aaagcatcag ctcatcgaga gcctgcgcga cggacgcact   4200
gacggtgtcg tccatcacag tttgccagtg atacacatgg ggatcagcaa tcgcgcatat   4260
gaaatcacgc catgtagtgt attgaccgat tccttgcgt ccgaatgggc cgaacccgct    4320
cgtctggcta agatcggccg cagcgatcgc atccatggcc tccgcgaccg gctgcagaac   4380
agcgggcagt tcggtttcag gcaggtcttg caacgtgaca ccctgtgcac ggcgggagat   4440
gcaataggtc aggctctcgc tgaattcccc aatgtcaagc acttccggaa tcgggagcgc   4500
ggccgatgca aagtgccgat aaacataacg atctttgtag aaaccatcgg cgcagctatt   4560 taccccgcagg acatatccac gccctcctac atcgaagctg aaagcacgag attcttcgcc   4620
ctccgagagc tgcatcaggt cggagacgct gtcgaacttt tcgatcagaa acttctcgac   4680
agacgtcgcg gtgagttcag gcttttcat atctcattgc ccccgggat ctgcggcacg     4740 ctgttgacgc tgttaagcgg gtcgctgcag ggtcgctcgg tgttcgaggc cacacgcgtc   4800
accttaatat gcgaagtgga cctcggaccg cgccgccccg actgcatctg cgtgttcgaa   4860
ttcgccaatg acaagacgct gggcgggggtt tgtgtcatca tagaactaaa gacatgcaaa   4920
tatatttctt ccggggacac cgccagcaaa cgcgagcaac gggccacggg gatgaagcag   4980
ggcggcacct cgctaacgga ttcaccactc caagaattgg agccaatcaa ttcttgcgga   5040
gaactgtgaa tgcgcaaacc aaccccttggc agaacatatc catcgcgtcc gccatctcca   5100
gcagccgcac gcggcgcatc tcggggccga cgcgctgggc tacgtcttgc tggcgttcgc   5160
acaggccggc cagcgcgctt ggcgtaatca tggtcatagc tgtttcctgt gtgaaattgt   5220
tatccgctca caattccaca caacatacga gccggaagca taaagtgtaa agcctggggt   5280
gcctaatgag tgagctaact cacattaatt gcgttgcgct cactgcccgc tttccagtcg   5340
ggaaacctgt cgtgccagct gcattaatga atcggccaac gcgcggggag aggcggtttg   5400
cgtattgggc gctcttccgc ttcctcgctc actgactcgc tgcgctcggt cgttcggctg   5460
cggcgagcgg tatcagctca ctcaaaggcg gtaatacggt tatccacaga atcaggggat   5520
aacgcaggaa agaacatgtg agcaaaaggc cagcaaaagg ccaggaaccg taaaaaggcc   5580
gcgttgctgg cgttttttcca taggctccgc cccctgacg agcatcacaa aaatcgacgc    5640
tcaagtcaga ggtggcgaaa cccgacagga ctataaagat accaggcgtt tcccctgga    5700 agctccctcg tgcgctctcc tgttccgacc ctgccgctta ccggatacct gtccgccttt   5760
ctcccttcgg gaagcgtggc gctttctcat agctcacgct gtaggtatct cagttcggtg   5820
taggtcgttc gctccaagct gggctgtgtg cacgaacccc ccgttcagcc cgaccgctgc   5880
gccttatccg gtaactatcg tcttgagtcc aacccggtaa gacacgactt atcgccactg   5940
gcagcagcca ctggtaacag gattagcaga gcgaggtatg taggcggtgc tacagagttc   6000
```

```
ttgaagtggt ggcctaacta cggctacact agaaggacag tatttggtat ctgcgctctg    6060
ctgaagccag ttaccttcgg aaaaagagtt ggtagctctt gatccggcaa acaaaccacc    6120
gctggtagcg gtggttttt tgtttgcaag cagcagatta cgcgcagaaa aaaggatct     6180 caagaagatc ctttgatctt ttctacgggg tctgacgctc agtggaacga aaactcacgt    6240
taagggattt tggtcatgag attatcaaaa aggatcttca cctagatcct tttaaattaa    6300
aaatgaagtt ttaaatcaat ctaaagtata tatgagtaaa cttggtctga cagttaccaa    6360
tgcttaatca gtgaggcacc tatctcagcg atctgtctat ttcgttcatc catagttgcc    6420
tgactccccg tcgtgtagat aactacgata cgggagggct taccatctgg ccccagtgct    6480
gcaatgatac cgcgagaccc acgctcaccg gctccagatt tatcagcaat aaaccagcca    6540
gccggaaggg ccgagcgcag aagtggtcct gcaactttat ccgcctccat ccagtctatt    6600
aattgttgcc gggaagctag agtaagtagt tcgccagtta atagtttgcg caacgttgtt    6660
gccattgcta caggcatcgt ggtgtcacgc tcgtcgtttg gtatggcttc attcagctcc    6720
ggttcccaac gatcaaggcg agttacatga tcccccatgt tgtgcaaaaa agcggttagc    6780
tccttcggtc ctccgatcgt tgtcagaagt aagttggccg cagtgttatc actcatggtt    6840
atggcagcac tgcataattc tcttactgtc atgccatccg taagatgctt ttctgtgact    6900
ggtgagtact caaccaagtc attctgagaa tagtgtatgc ggcgaccgag ttgctcttgc    6960
ccggcgtcaa tacgggataa taccgcgcca catagcagaa ctttaaaagt gctcatcatt    7020
ggaaaacgtt cttcggggcg aaaactctca aggatcttac cgctgttgag atccagttcg    7080
atgtaaccca ctcgtgcacc caactgatct tcagcatctt ttactttcac cagcgtttct    7140
gggtgagcaa aaacaggaag gcaaaatgcc gcaaaaaagg gaataagggc gacacggaaa    7200
tgttgaatac tcatactctt cctttttcaa tattattgaa gcatttatca gggttattgt    7260
ctcatgagcg gatacatatt tgaatgtatt tagaaaaata aacaaatagg ggttccgcgc    7320
acatttcccc gaaaagtgcc acctaaattg taagcgttaa tattttgtta aaattcgcgt    7380 taaattttg ttaaatcagc tcattttta accaataggc cgaaatcggc aaaatccct    7439
```

<210> SEQ ID NO 34
<211> LENGTH: 7318
<212> TYPE: DNA
<213> ORGANISM: Artificial Sequence
<220> FEATURE:
<223> OTHER INFORMATION: pAIGFRLCb2 plasmid sequence

<400> SEQUENCE: 34

```
gcactataca tcaaatattc cttattaacc cctttacaaa ttaaaaagct aaaggtacac      60 aattttttgag catagttatt aatagcagac actctatgcc tgtgtggagt aagaaaaaac     120
agtatgttat gattataact gttatgccta cttataaagg ttacagaata ttttttccata    180 attttcttgt atagcagtgc agcttttttcc tttgtggtgt aaatagcaaa gcaagcaaga    240
gttctattac taaacacagc atgactcaaa aaacttagca attctgaagg aaagtccttg     300
gggtcttcta cctttctctt cttttttgga ggagtagaat gttgagagtc agcagtagcc    360
tcatcatcac tagatggcat ttcttctgag caaaacaggt tttcctcatt aaaggcattc     420
caccactgct cccattcatc agttccatag gttggaatct aaaatacaca acaattaga     480 atcagtagtt taacacatta tacacttaaa aattttatat ttaccttaga gctttaaatc     540
tctgtaggta gtttgtccaa ttatgtcaca ccacagaagt aaggttcctt cacaaagatc    600
gatctaaagc cagcaaaagt cccatggtct tataaaaatg catagcttta ggaggggagc      660
```

```
agagaacttg aaagcatctt cctgttagtc tttcttctcg tagacttcaa acttatactt    720
gatgccttt  tcctcctgga cctcagagag gacgcctggg tattctggga gaagtttata    780
tttccccaaa tcaatttctg ggaaaaacgt gtcacttca  aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt cccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gttttgcag  aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag ggggcatctg   2160
ttggtctgta gatgtaaggt cccctataag tccctggttg ccaccacctg tctcctatt    2220
tgacaaaaac actctttttt cccttttta  cttctaggcc tgtggtcaat agtccttgca   2280
cctgttcttc aattgaggtt gagcgtctct ttctatttc  tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaagagtc  aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caacccctg  gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag cataggctt    2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
```

```
tcgttcggct gcggcgagcg gtatcagctc actcaaaggc ggtaatacgg ttatccacag    3120
aatcagggga taacgcagga agaacatgt  gagcaaaagg ccagcaaaag gccaggaacc    3180
gtaaaaaggc cgcgttgctg gcgttttcc  ataggctccg ccccctgac  gagcatcaca    3240 aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc caacccggta agacacgact    3540
tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt ttgtttgcaa gcagcagatt acgcgcagaa    3780
aaaaaggatc tcaagaagat cctttgatct tttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atccccatg  ttgtgcaaaa    4380 aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca cacgggata  ataccgcgcc acatagcaga actttaaaag    4620
tgctcatcat tggaaaacgt tcttcgggc  gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag gaataagggc    4800 gacacggaa  atgttgaata ctcatactct ccttttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgcc gtttaaaccc tcagctgatc atccggatgt acagcgcgcg gccggccggt    5100
accacgcgtt ggccacatat ggcggccgct cgcgattaat taatcgcgat ggccacatat    5160
ggagctctct agagcttgtc gacagatccc cctcttcatt tctttatgtt ttaaatgcac    5220
tgacctccca cattcccttt ttagtaaaat attcagaaat aatttaaata catcattgca    5280
atgaaaataa atgtttttta ttaggcagaa tccagatgct caaggcccctt cataatatcc    5340 cccagtttag tagttggact tagggaacaa aggaacctt  aatagaaatt ggacagcaag    5400
aaagcgaggg ggatctggat cctccggagg gccccttctc cctctaacac tctcccctgt    5460
```

```
tgaagctctt tgtgacgggc gagctcaggc cctgatgggt gacttcgcag gcgtagactt      5520
tgtgtttctc gtagtctgct tgctcagcg tcagggtgct gctgaggctg taggtgctgt       5580
ccttgctgtc ctgctctgtg acactctcct gggagttacc cgattggagg gcgttatcca     5640
ccttccactg tactttggcc tctctgggat agaagttatt cagcaggcac acaacagagg     5700
cagttccaga tttcaactgc tcatcagatg gcgggaagat gaagacagat ggtgcagcca     5760
ctgtacgttt gatctccacc ttggtccctt ggccgaaagt gtgaggtaaa cgactactct     5820
gatgacagta atacactgcg aaatcttcag gctccagtct actgatggtg agggtgaaat     5880
ctgtcccaga tccactgcca ctgaacctat cggggatccc tgagagggac tgggatgcat     5940
acttgatgag aagccttgga gcctgacctg gtttctgctg gtaccagtgt aagctactac     6000
caatgctctg actggcccgg caggagaggg tggctctctc gcctggagac acagacaggg     6060
tacctgggct ctgagtcagc acaatttcac ccctggaggc tggaacccag agcagcagaa     6120
acccaatgag ttgtgatggc gacatgttaa acgctagaat tcttaagcct gtggagagaa     6180
aggaacagaa aacgaaacaa agacgtagag ttgagcaagc agggtcaggc aaagcgtgga     6240
gagccggctg agtctaggta ggctccaagg gagcgccgga caaaggcccg gtctcgacct     6300
gagctttaaa cttacctgtg gccacacgtg caattgctat agtgagtcgt attaatttcg     6360
ataagccagt aagcagtggg ttctctagtt agccagagag ctctgcttat atagacctcc     6420
caccgtacac gcctaccgcc catttgcgtc aatggggcgg agttgttacg acattttgga     6480
aagtcccgtt gatttggtg ccaaaacaaa ctcccattga cgtcaatggg gtggagactt      6540
ggaaatcccc gtgagtcaaa ccgctatcca cgcccattga tgtactgcca aaaccgcatc     6600
accatggtaa tagcgatgac taatacgtag atgtactgcc aagtaggaaa gtcccataag     6660
gtcatgtact gggcataatg ccaggcgggc catttaccgt cattgacgtc aataggggc      6720 gtacttggca tatgatacac ttgatgtact gccaagtggg cagtttaccg taaatactcc     6780
acccattgac gtcaatggaa agtccctatt ggcgttacta tgggaacata cgtcattatt     6840
gacgtcaatg ggcggggtc gttggcggt cagccaggcg ggccatttac cgtaagttat       6900
gtaacgcgga actccatata tgggctatga actaatgacc ccgtaattga ttactattaa     6960
taactagtca ataatcaatg tcaacgcgta tatctggccc gtacatcggt aactagtcgg     7020
accgccgcgg actagtgccc gggccaccgg tgctcgaagc ttggatcgat ccagacatga     7080
taagatacat tgatgagttt ggacaaacca caactagaat gcagtgaaaa aaatgcttta     7140
tttgtgaaat ttgtgatgct attgctttat tgtaaccat tataagctgc aataaacaag      7200
ttaacaacaa caattgcatt cattttatgt ttcaggttca gggggaggtg tgggaggttt     7260
tttaaagcaa gtaaacctc tacaaatgtg gtatggctga ttatgatctc tagtcaag       7318
```

<210> SEQ ID NO 35
<211> LENGTH: 11928
<212> TYPE: DNA
<213> ORGANISM: Artificial Sequence
<220> FEATURE:
<223> OTHER INFORMATION: pAIG1FRLCb2V1 plasmid sequence

<400> SEQUENCE: 35

```
gcactataca tcaaatattc cttattaacc cctttacaaa ttaaaaagct aaaggtacac       60
aatttttgag catagttatt aatagcagac actctatgcc tgtgtggagt aagaaaaaac     120
agtatgttat gattataact gttatgccta cttataaagg ttacagaata ttttccata      180 atttcttgt atagcagtgc agcttttcc tttgtggtgt aaatagcaaa gcaagcaaga       240
```

```
gttctattac taaacacagc atgactcaaa aaacttagca attctgaagg aaagtccttg    300
gggtcttcta cctttctctt cttttttgga ggagtagaat gttgagagtc agcagtagcc    360
tcatcatcac tagatggcat ttcttctgag caaaacaggt tttcctcatt aaaggcattc    420
caccactgct cccattcatc agttccatag gttggaatct aaaatacaca aacaattaga    480
atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccaggg aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt cccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaaacca cttgtctcac atcctcgttt taagaacagt   1800
ttgtaaccaa aaacttactt aagccctggg aaccgcaagg ttgggccaat aaaggctatt   1860
cataataact catgccatga gttttttgcag aataatgttc tattagtcca gccactgtcc   1920
cctccttggt atggaaaatc tttccccaaa agtgcattcc tgttcctaga taaatataat   1980
catgtacctg ttgtttcatg tcgtctttttt cttcttgaga caacatacac caaggaggtc   2040
tagctctggc gagtctttca cgaaaaggga gggatctata taacactttta tagccattga   2100 ctgtaaccca cctatcccaa tttaagtcat atcttcctgt atatggtaag ggggcatctg   2160
ttggtctgta gatgtaaggt cccctataag tccctggttg ccaccacctg tctcctattt   2220
tgacaaaaac actctttttt ccctttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
```

```
ggcaaagcag agctatgcca agtttgcagc agagaatgaa tatgtctttg tctgatgggc   2700
tcatccgttt gtgcgcagac gggtcgtcct tggtgggaaa caacccctcg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag catagggctt   2940
ggttatgccg gtactgccgg gcctcttgcg ggatatcgtc cattccgaca gcatcgccag   3000
tcactatggc gtgctgctag cgtcttccg cttcctcgct cactgactcg ctgcgctcgg   3060
tcgttcggct gcggcgagcg gtatcagctc actcaaaggc ggtaatacgg ttatccacag   3120
aatcagggga taacgcagga agaacatgt gagcaaaagg ccagcaaaag gccaggaacc   3180
gtaaaaaggc cgcgttgctg gcgttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca acacgggata ataccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct tccttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagaaacc attattatca   4980
tgacattaac ctataaaaat aggcgtatca cgaggccctt tcgtcttcaa gaattgtcta   5040
```

```
gaggcgcgcc gtttaaaccc tcagctaccg atgtacgggc cagatatacg cgttgacatt    5100
gattattgac tagttattaa tagtaatcaa ttacggggtc attagttcat agcccatata    5160
tggagttccg cgttacataa cttacggtaa atggcccgcc tggctgaccg cccaacgacc    5220
cccgcccatt gacgtcaata atgacgtatg ttcccatagt aacgccaata gggactttcc    5280
attgacgtca atgggtggag tatttacggt aaactgccca cttggcagta catcaagtgt    5340
atcatatgcc aagtacgccc cctattgacg tcaatgacgg taaatggccc gcctggcatt    5400
atgcccagta catgacctta tgggactttc ctacttggca gtacatctac gtattagtca    5460
tcgctattac catggtgatg cggttttggc agtacatcaa tgggcgtgga tagcggtttg    5520
actcacgggg atttccaagt ctccacccca ttgacgtcaa tgggagtttg ttttggcacc    5580
aaaatcaacg ggactttcca aaatgtcgta acaactccgc cccattgacg caaatgggcg    5640
gtaggcgtgt acggtgggag gtctatataa gcagagctct ctggctaact agagaaccca    5700
ctgcttactg gcttatcgaa attaatacga ctcactatag caattgcacg tgtggccaca    5760
ggtaagttta aagctcaggt cgagaccggg cctttgtccg gcgctccctt ggagcctacc    5820
tagactcagc cggctctcca cgctttgcct gaccctgctt gctcaactct acgtctttgt    5880
ttcgttttct gttcctttct ctccacaggc ttaagcttgg taccgagctc ggatccacta    5940
gtccagtgtg gtggaattcg cccttatgga gtttgggctg agctgggttt ccttgttgc     6000 tatattaaaa ggtgtccagt gtgaggttca gctggtgcag tctggggag gcttggtaaa    6060 gcctggggg tccctgagac tctcctgtgc agcctctgga ttcaccttca gtagctttgc    6120
tatgcactgg gttcgccagg ctccaggaaa aggtctggag tggatatcag ttattgatac    6180
tcgtggtgcc acatactatg cagactccgt gaagggccga ttcaccatct ccagagacaa    6240
tgccaagaac tccttgtatc ttcaaatgaa cagcctgaga gccgaggaca ctgctgtgta    6300
ttactgtgca agactgggga acttctacta cggtatggac gtctggggcc aagggaccac    6360
ggtcaccgtc tcctcagctt ccaccaaggg cccatcggtc ttccccctgg cacctcctc     6420 caagagcacc tctgggggca gcggccct gggctgcctg gtcaaggact acttccccga    6480
accggtgacg gtgtcgtgga actcaggcgc cctgaccagc ggcgtgcaca ccttcccggc    6540
tgtcctacag tcctcaggac tctactccct cagcagcgtg gtgaccgtgc cctcagcag    6600 cttgggcacc cagacctaca tctgcaacgt gaatcacaag cccagcaaca ccaaggtgga    6660
caagaaagtt gagcccaaat cttgtgacaa aactcacaca tgcccaccgt gcccagcacc    6720
tgaactcctg gggggaccgt cagtcttcct cttccccca aaacccaagg acaccctcat    6780
gatctcccgg acccctgagg tcacatgcgt ggtggtggac gtgagccacg aagaccctga    6840
ggtcaagttc aactggtacg tggacggcgt ggaggtgcat aatgccaaga caaagccgcg    6900
ggaggagcag tacaacagca cgtaccgtgt ggtcagcgtc ctcaccgtcc tgcaccagga    6960
ctggctgaat ggcaaggagt acaagtgcaa ggtctccaac aaagccctcc cagcccccat    7020
cgagaaaacc atctccaaag ccaaagggca gccccgagaa ccacaggtgt acaccctgcc    7080
cccatcccgg gatgagctga ccaagaacca ggtcagcctg acctgcctgg tcaaaggctt    7140
ctatcccagc gacatcgccg tggagtggga gagcaatggg cagccggaga caactacaa     7200 gaccacgcct cccgtgctgg actccgacgg ctccttcttc ctctacagca agctcaccgt    7260
ggacaagagc aggtggcagc aggggaacgt cttctcatgc tccgtgatgc atgaggctct    7320
gcacaaccac tacacgcaga agagcctctc cctgtctccg ggtaaatgaa tcgatgattc    7380
tagatacggg tccggaggat ccagatcccc ctcgctttct tgctgtccaa tttctattaa    7440
```

```
aggttccttt gttccctaag tccaactact aaactggggg atattatgaa gggccttgag   7500
catctggatt ctgcctaata aaaacatttt attttcattg caatgatgta tttaaattat   7560
ttctgaatat tttactaaaa agggaatgtg ggaggtcagt gcatttaaaa cataaagaaa   7620
tgaagagggg gatctgtcga caagctctag agagctcacg cgttgatcat gtacaggccg   7680
gccaagcttt cgactagctt ggcacgccag aaatccgcgc ggtggttttt ggggggtcggg   7740
ggtgtttggc agccacagac gcccggtgtt cgtgtcgcgc cagtacatgc ggtccatgcc   7800
caggccatcc aaaaaccatg ggtctgtctg ctcagtccag tcgtggacct gaccccacgc   7860
aacgcccaaa ataataaccc ccacgaacca taaaccattc cccatggggg accccgtccc   7920
taacccacgg ggccagtggc tatggcaggg cctgccgccc cgacgttggc tgcgagccct   7980
gggccttcac ccgaacttgg ggggtggggt gggaaaagg aagaaacgcg ggcgtattgg   8040
ccccaatggg gtctcggtgg ggtatcgaca gagtgccagc cctgggaccg aaccccgcgt   8100
ttatgaacaa acgacccaac acccgtgcgt tttattctgt ctttttattg ccgtcatagc   8160
gcgggttcct tccggtattg tctccttccg tgtttcagtt agcctccccc atctcccgat   8220
ccggacgagt gctggggcgt cggtttccac tatcggcgag tacttctaca cagccatcgg   8280
tccagacggc cgcgcttctg cgggcgattt gtgtacgccc gacagtcccg gctccggatc   8340
ggacgattgc gtcgcatcga ccctgcgccc aagctgcatc atcgaaattg ccgtcaacca   8400
agctctgata gagttggtca agaccaatgc ggagcatata cgcccggagc cgcggcgatc   8460
ctgcaagctc cggatgcctc cgctcgaagt agcgcgtctg ctgctccata caagccaacc   8520
acggcctcca gaagaagatg ttggcgacct cgtattggga atccccgaac atcgcctcgc   8580
tccagtcaat gaccgctgtt atgcggccat tgtccgtcag gacattgttg gagccgaaat   8640
ccgcgtgcac gaggtgccgg acttcggggc agtcctcggc ccaaagcatc agctcatcga   8700
gagcctgcgc gacggacgca ctgacggtgt cgtccatcac agtttgccag tgatacacat   8760
ggggatcagc aatcgcgcat atgaaatcac gccatgtagt gtattgaccg attccttgcg   8820
gtccgaatgg gccgaacccg ctcgtctggc taagatcggc cgcagcgatc gcatccatgg   8880
cctccgcgac cggctgcaga acagcgggca gttcggtttc aggcaggtct tgcaacgtga   8940
caccctgtgc acgcgggag atgcaatagg tcaggctctc gctgaattcc ccaatgtcaa   9000
gcacttccgg aatcgggagc gcggccgatg caaagtgccg ataaacataa cgatctttgt   9060
agaaaccatc ggcgcagcta tttacccgca ggacatatcc acgccctcct acatcgaagc   9120
tgaaagcacg agattcttcg ccctccgaga gctgcatcag gtcggagacg ctgtcgaact   9180
tttcgatcag aaacttctcg acagacgtcg cggtgagttc aggcttttc atatctcatt   9240
gccccccggg atctgcggca cgctgttgac gctgttaagc gggtcgctgc agggtcgctc   9300
ggtgttcgag gccacacgcg tcaccttaat atgcgaagtg gacctcggac cgcgccgccc   9360
cgactgcatc tgcgtgttcg aattcgccaa tgacaagacg ctgggcgggg tttgtgtcat   9420
catagaacta aagacatgca aatatatttc ttccggggac accgccagca aacgcgagca   9480
acgggccacg gggatgaagc agggcggcac ctcgctaacg gattcaccac tccaagaatt   9540
ggagccaatc aattcttgcg gagaactgtg aatgcgcaaa ccaacccttg cagaacata   9600
tccatcgcgt ccgccatctc cagcagccgc acgcggcgca tctcggggcc gacgcgctgg   9660
gctacgtctt gctggcgttc gcacaggccg gccagcgcgc ggccggccgg taccacgcgt   9720
tggccacata tggcggccgc tcgcgattaa ttaatcgcga tggccacata tggagctctc   9780
tagagcttgt cgacagatcc ccctcttcat ttctttatgt tttaaatgca ctgacctccc   9840
```

```
acattccctt tttagtaaaa tattcagaaa taatttaaat acatcattgc aatgaaaata    9900
aatgtttttt attaggcaga atccagatgc tcaaggccct tcataatatc ccccagttta    9960
gtagttggac ttagggaaca aaggaacctt taatagaaat tggacagcaa gaaagcgagg   10020
gggatctgga tcctccggag ggccccttct ccctctaaca ctctccctg ttgaagctct    10080
ttgtgacggg cgagctcagg ccctgatggg tgacttcgca ggcgtagact ttgtgtttct   10140
cgtagtctgc tttgctcagc gtcagggtgc tgctgaggct gtaggtgctg tccttgctgt   10200
cctgctctgt gacactctcc tgggagttac ccgattggag ggcgttatcc accttccact   10260
gtactttggc ctctctggga tagaagttat tcagcaggca cacaacagag gcagttccag   10320
atttcaactg ctcatcagat ggcgggaaga tgaagacaga tggtgcagcc actgtacgtt   10380
tgatctccac cttggtccct tggccgaaag tgtgaggtaa acgactactc tgatgacagt   10440
aatacactgc gaaatcttca ggctccagtc tactgatggt gagggtgaaa tctgtcccag   10500
atccactgcc actgaaccta tcggggatcc ctgagaggga ctgggatgca tacttgatga   10560
gaagccttgg agcctgacct ggtttctgct ggtaccagtg taagctacta ccaatgctct   10620
gactggcccg gcaggagagg gtggctctct cgcctggaga cacagacagg gtacctgggc   10680
tctgagtcag cacaatttca cccctggagg ctggaaccca gagcagcaga acccaatga   10740
gttgtgatgg cgacatgtta aacgctagaa ttcttaagcc tgtggagaga aaggaacaga   10800
aaacgaaaca aagacgtaga gttgagcaag cagggtcagg caaagcgtgg agagccggct   10860
gagtctaggt aggctccaag ggagcgccgg acaaaggccc ggtctcgacc tgagctttaa   10920
acttacctgt ggccacacgt gcaattgcta tagtgagtcg tattaatttc gataagccag   10980
taagcagtgg gttctctagt tagccagaga gctctgctta tatagacctc ccaccgtaca   11040
cgcctaccgc ccatttgcgt caatggggcg gagttgttac gacattttgg aaagtcccgt   11100
tgattttggt gccaaaacaa actcccattg acgtcaatgg ggtggagact tggaaatccc   11160
cgtgagtcaa accgctatcc acgcccattg atgtactgcc aaaaccgcat caccatggta   11220
atagcgatga ctaatacgta gatgtactgc caagtaggaa agtcccataa ggtcatgtac   11280
tgggcataat gccaggcggg ccatttaccg tcattgacgt caatagggg cgtacttggc    11340
atatgataca cttgatgtac tgccaagtgg gcagtttacc gtaaatactc cacccattga   11400
cgtcaatgga aagtccctat tggcgttact atgggaacat acgtcattat tgacgtcaat   11460
gggcggggt cgttgggcgg tcagccaggc gggccattta ccgtaagtta tgtaacgcgg    11520
aactccatat atgggctatg aactaatgac cccgtaattg attactatta ataactagtc   11580
aataatcaat gtcaacgcgt atatctggcc cgtacatcgt aactagtcgg accgccgcgg   11640
actagtgccc gggccaccgg tgctcgaagc ttggatcgat ccagacatga taagatacat   11700
tgatgagttt ggacaaacca caactagaat gcagtgaaaa aaatgcttta tttgtgaaat   11760
ttgtgatgct attgctttat ttgtaaccat tataagctgc aataaacaag ttaacaacaa   11820
caattgcatt cattttatgt ttcaggttca ggggaggtg tgggaggttt tttaaagcaa    11880
gtaaaacctc tacaaatgtg gtatggctga ttatgatctc tagtcaag               11928
```

<210> SEQ ID NO 36
<211> LENGTH: 11928
<212> TYPE: DNA
<213> ORGANISM: Artificial Sequence
<220> FEATURE:
<223> OTHER INFORMATION: pAIG1FRLCb2V3 plasmid sequence

<400> SEQUENCE: 36

```
gcactataca tcaaatattc cttattaacc cctttacaaa ttaaaaagct aaaggtacac      60
aatttttgag catagttatt aatagcagac actctatgcc tgtgtggagt aagaaaaaac    120
agtatgttat gattataact gttatgccta cttataaagg ttacagaata tttttccata    180
attttcttgt atagcagtgc agcttttcc tttgtggtgt aaatagcaaa gcaagcaaga     240
gttctattac taaacacagc atgactcaaa aaacttagca attctgaagg aaagtccttg    300
gggtcttcta cctttctctt ctttttgga ggagtagaat gttgagagtc agcagtagcc     360
tcatcatcac tagatggcat ttcttctgag caaaacaggt tttcctcatt aaaggcattc    420
caccactgct cccattcatc agttccatag gttggaatct aaaatacaca aacaattaga    480
atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga gaagtttata    780
tttccccaaa tcaatttctg ggaaaaacgt gtcacttca aattcctgca tgatccttgt     840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt cccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gttttgcag aataatgttc tattagtcca gccactgtcc    1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacactta tagccattga    2100 ctgtaaccca cctatcccaa tttaagtcat atcttcctgt atatggtaag ggggcatctg   2160
ttggtctgta gatgtaaggt ccctataag tccctggttg ccaccacctg tctcctattt    2220
tgacaaaaac actctttttt ccctttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
```

```
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca    2640
ggcaaagcag agctatgcca agtttgcagc agagaatgaa tatgtctttg tctgatgggc    2700
tcatccgttt gtgcgcagac gggtcgtcct tggtgggaaa caacccttg gctgcttctc     2760 ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag cataggctt     2940 ggttatgccg gtactgccgg gctcttgcg ggatatcgtc cattccgaca gcatcgccag     3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga aagaacatgt gagcaaaagg ccagcaaaag gccaggaacc    3180
gtaaaaaggc cgcgttgctg gcgttttttcc ataggctccg ccccctgac gagcatcaca    3240 aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca gctcacgc tgtaggtatc      3420 tcagttcggt gtaggtcgtt cgctccaagc tgggctgtgt gcacgaaccc cccgttcagc    3480
ccgaccgctg cgccttatcc ggtaactatc gtcttgagtc aacccggta agacacgact     3540 tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt tgtttgcaa gcagcagatt acgcgcagaa     3780
aaaaaggatc tcaagaagat cctttgatct tttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca cacgggata ataccgcgcc acatagcaga actttaaaag     4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag gaataagggg    4800
```

```
cgacacggaa atgttgaata ctcatactct tccttttca  atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagaaacc attattatca   4980
tgacattaac ctataaaaat aggcgtatca cgaggcccct tcgtcttcaa gaattgtcta   5040
gaggcgcgct ggccggcctg tgcgaacgcc agcaagacgt agcccagcgc gtcggcccccg  5100
agatgcgccg cgtgcggctg ctggagatgg cggacgcgat ggatatgttc tgccaagggt   5160
tggtttgcgc attcacagtt ctccgcaaga attgattggc tccaattctt ggagtggtga   5220
atccgttagc gaggtgccgc cctgcttcat ccccgtggcc cgttgctcgc gtttgctggc   5280
ggtgtcccg  gaagaaatat atttgcatgt ctttagttct atgatgacac aaaccccgcc   5340
cagcgtcttg tcattggcga attcgaacac gcagatgcag tcgggcggc  gcggtccgag   5400
gtccacttcg catattaagg tgacgcgtgt ggcctcgaac accgagcgac cctgcagcga   5460
cccgcttaac agcgtcaaca gcgtgccgca gatcccgggg ggcaatgaga tatgaaaaag   5520
cctgaactca ccgcgacgtc tgtcgagaag tttctgatcg aaaagttcga cagcgtctcc   5580
gacctgatgc agctctcgga gggcgaagaa tctcgtgctt tcagcttcga gtaggaggg   5640
cgtggatatg tcctgcgggt aaatagctgc gccgatggtt tctacaaaga tcgttatgtt   5700
tatcggcact ttgcatcggc cgcgctcccg attccgaaag tgcttgacat tggggaattc   5760
agcgagagcc tgacctattg catctcccgc cgtgcacagg gtgtcacgtt gcaagacctg   5820
cctgaaaccg aactgcccgc tgttctgcag ccggtcgcgg aggccatgga tgcgatcgct   5880
gcggccgatc ttagccagac gagcgggttc ggcccattcg gaccgcaagg aatcggtcaa   5940
tacactacat ggcgtgattt catatgcgcg attgctgatc cccatgtgta tcactggcaa   6000
actgtgatgg acgacaccgt cagtgcgtcc gtcgcgcagg ctctcgatga gctgatgctt   6060
tgggccgagg actgccccga agtccggcac ctcgtgcacg cggatttcgg ctccaacaat   6120
gtcctgacgg acaatggccg cataacagcg gtcattgact ggagcgaggc gatgttcggg   6180
gattcccaat acgaggtcgc caacatcttc ttctggaggc cgtggttggc ttgtatggag   6240
cagcagacgc gctacttcga gcggaggcat ccggagcttg caggatcgcc gcggctccgg   6300
gcgtatatgc tccgcattgg tcttgaccaa ctctatcaga gcttggttga cggcaatttc   6360
gatgatgcag cttgggcgca gggtcgatgc gacgcaatcg tccgatccgg agccgggact   6420
gtcgggcgta cacaaatcgc ccgcagaagc gcggccgtct ggaccgatgg ctgtgtagaa   6480
gtactcgccg atagtggaaa ccgacgcccc agcactcgtc cggatcggga gatgggggag   6540
gctaactgaa acacggaagg agacaatacc ggaaggaacc cgcgctatga cggcaataaa   6600
aagacagaat aaaacgcacg ggtgttgggt cgtttgttca taaacgcggg gttcggtccc   6660
agggctggca ctctgtcgat accccaccga gaccccattg gggccaatac gcccgcgttt   6720
cttccttttc cccaccccac cccccaagtt cgggtgaagg cccagggctc gcagccaacg   6780
tcggggcggc aggccctgcc atagccactg gcccgtggg  ttaggacgg  ggtcccccat   6840
ggggaatggt ttatggttcg tgggggttat tattttgggc gttgcgtggg gtcaggtcca   6900
cgactggact gagcagacag acccatggtt tttggatggc ctgggcatgg accgcatgta   6960
ctggcgcgac acgaacaccg ggcgtctgtg gctgccaaac accccgacc  cccaaaaacc   7020
accgcgcgga tttctggcgt gccaagctag tcgaaagctt ggccggcctg tacatgatca   7080
acgcgtgagc tctctagagc ttgtcgacag atcccctct  tcatttcttt atgttttaaa   7140
tgcactgacc tcccacattc ccttttttagt aaaatattca gaaataattt aaatacatca   7200
```

```
ttgcaatgaa ataaatgtt ttttattagg cagaatccag atgctcaagg cccttcataa    7260
tatcccccag tttagtagtt ggacttaggg aacaaaggaa cctttaatag aaattggaca    7320
gcaagaaagc gagggggatc tggatcctcc ggacccgtat ctagaatcat cgattcattt    7380
acccggagac agggagaggc tcttctgcgt gtagtggttg tgcagagcct catgcatcac    7440
ggagcatgag aagacgttcc cctgctgcca cctgctcttg tccacggtga gcttgctgta    7500
gaggaagaag gagccgtcgg agtccagcac gggaggcgtg gtcttgtagt tgttctccgg    7560
ctgcccattg ctctcccact ccacggcgat gtcgctggga tagaagcctt tgaccaggca    7620
ggtcaggctg acctggttct tggtcagctc atcccgggat gggggcaggg tgtacacctg    7680
tggttctcgg ggctgccctt tggctttgga gatggttttc tcgatggggg ctgggagggc    7740
tttgttggag accttgcact tgtactcctt gccattcagc cagtcctggt gcaggacggt    7800
gaggacgctg accacacggt acgtgctgtt gtactgctcc tcccgcggct ttgtcttggc    7860
attatgcacc tccacgccgt ccacgtacca gttgaacttg acctcaggt cttcgtggct     7920 cacgtccacc accacgcatg tgacctcagg ggtccgggag atcatgaggg tgtccttggg    7980
ttttgggggg aagaggaaga ctgacggtcc ccccaggagt tcaggtgctg ggcacggtgg    8040
gcatgtgtga gttttgtcac aagatttggg ctcaactttc ttgtccacct tggtgttgct    8100
gggcttgtga ttcacgttgc agatgtaggt ctgggtgccc aagctgctgg agggcacggt    8160
caccacgctg ctgagggagt agagtcctga ggactgtagg acagccggga aggtgtgcac    8220
gccgctggtc agggcgcctg agttccacga caccgtcacc ggttcgggga agtagtcctt    8280
gaccaggcag cccagggccg ctgtgccccc agaggtgctc ttggaggagg gtgccagggg    8340
gaagaccgat gggcccttgg tggaagctga ggagacggtg accgtggtcc cttggcccca    8400
gacgtccata ccgtagtaga agttccccag tcttgcacag taatacacag cagtgtcctc    8460
ggctctcagg ctgttcattt gaagatacaa ggagttcttg gcattgtctc tggagatggt    8520
gaatcggccc ttcacggagt ctgcatagta tgtggcacca cgagtatcaa taactgatat    8580
ccactccaga ccttttcctg gagcctggcg aacccagtgc atagcaaagc tactgaaggt    8640
gaatccagag gctgcacagg agagtctcag ggaccccca ggctttacca agcctccccc      8700
agactgcacc agctgaacct cacactggac accttttaat atagcaacaa ggaaaaccca    8760
gctcagccca aactccataa gggcgaattc caccacactg gactagtgga tccgagctcg    8820
gtaccaagct taagcctgtg gagagaaagg aacagaaaac gaaacaaaga cgtagagttg    8880
agcaagcagg gtcaggcaaa gcgtggagag ccggctgagt ctaggtaggc tccaagggag    8940
cgccggacaa aggcccggtc tcgacctgag ctttaaactt acctgtggcc acacgtgcaa    9000
ttgctatagt gagtcgtatt aatttcgata agccagtaag cagtgggttc tctagttagc    9060
cagagagctc tgcttatata gacctcccac cgtacacgcc taccgcccat ttgcgtcaat    9120
ggggcggagt tgttacgaca ttttggaaag tcccgttgat tttggtgcca aaacaaactc    9180
ccattgacgt caatgggtg gagacttgga aatccccgtg agtcaaaccg ctatccacgc     9240
ccattgatgt actgccaaaa ccgcatcacc atggtaatag cgatgactaa tacgtagatg    9300
tactgccaag taggaaagtc ccataaggtc atgtactggg cataatgcca ggcgggccat    9360
ttaccgtcat tgacgtcaat aggggggcgta cttggcatat gatacacttg atgtactgcc    9420
aagtgggcag tttaccgtaa atactccacc cattgacgtc aatggaaagt ccctattggc    9480
gttactatgg gaacatacgt cattattgac gtcaatgggc gggggtcgtt gggcggtcag    9540
ccaggcgggc catttaccgt aagttatgta acgcggaact ccatatatgg gctatgaact    9600
```

```
aatgacccccg taattgatta ctattaataa ctagtcaata atcaatgtca acgcgtatat    9660
ctggcccgta catcggtagc tgagggttta aacggcgcgc ggccggccgg taccacgcgt    9720
tggccacata tggcggccgc tcgcgattaa ttaatcgcga tggccacata tggagctctc    9780
tagagcttgt cgacagatcc ccctcttcat ttctttatgt tttaaatgca ctgacctccc    9840
acattccctt tttagtaaaa tattcagaaa taatttaaat acatcattgc aatgaaaata    9900
aatgtttttt attaggcaga atccagatgc tcaaggccct tcataatatc ccccagttta    9960
gtagttggac ttagggaaca aaggaaccit taatagaaat tggacagcaa gaaagcgagg   10020
gggatctgga tcctccggag ggccccttct ccctctaaca ctctcccctg ttgaagctct   10080
ttgtgacggg cgagctcagg ccctgatggg tgacttcgca ggcgtagact ttgtgtttct   10140
cgtagtctgc tttgctcagc gtcagggtgc tgctgaggct gtaggtgctg tccttgctgt   10200
cctgctctgt gacactctcc tgggagttac ccgattggag ggcgttatcc accttccact   10260
gtactttggc ctctctggga tagaagttat tcagcaggca cacaacagag gcagttccag   10320
atttcaactg ctcatcagat ggcgggaaga tgaagacaga tggtgcagcc actgtacgtt   10380
tgatctccac cttggtccct tggccgaaag tgtgaggtaa acgactactc tgatgacagt   10440
aatacactgc gaaatcttca ggctccagtc tactgatggt gagggtgaaa tctgtcccag   10500
atccactgcc actgaaccta tcggggatcc ctgagaggga ctgggatgca tacttgatga   10560
gaagccttgg agcctgacct ggtttctgct ggtaccagtg taagctacta ccaatgctct   10620
gactggcccg gcaggagagg gtggctctct cgcctggaga cacagacagg gtacctgggc   10680
tctgagtcag cacaatttca cccctggagg ctggaaccca gagcagcaga acccaatga   10740
gttgtgatgg cgacatgtta aacgctagaa ttcttaagcc tgtggagaga aaggaacaga   10800
aaacgaaaca aagacgtaga gttgagcaag cagggtcagg caaagcgtgg agagccggct   10860
gagtctaggt aggctccaag ggagcgccgg acaaaggccc ggtctcgacc tgagctttaa   10920
acttacctgt ggccacacgt gcaattgcta tagtgagtcg tattaatttc gataagccag   10980
taagcagtgg gttctctagt tagccagaga gctctgctta tatagacctc ccaccgtaca   11040
cgcctaccgc ccatttgcgt caatggggcg gagttgttac gacattttgg aaagtcccgt   11100
tgattttggt gccaaaacaa actcccattg acgtcaatgg ggtggagact tggaaatccc   11160
cgtgagtcaa accgctatcc acgccccattg atgtactgcc aaaaccgcat caccatggta   11220
atagcgatga ctaatacgta gatgtactgc caagtaggaa agtcccataa ggtcatgtac   11280
tgggcataat gccaggcggg ccatttaccg tcattgacgt caatagggggg cgtacttggc   11340
atatgataca cttgatgtac tgccaagtgg gcagtttacc gtaaatactc cacccattga   11400
cgtcaatgga aagtccctat tggcgttact atgggaacat acgtcattat tgacgtcaat   11460
gggcgggggt cgttgggcgg tcagccaggc gggccattta ccgtaagtta tgtaacgcgg   11520
aactccatat atgggctatg aactaatgac cccgtaattg attactatta ataactagtc   11580
aataatcaat gtcaacgcgt atatctggcc cgtacatcgt aactagtcgg accgccgcgg   11640
actagtgccc gggccaccgg tgctcgaagc ttggatcgat ccagacatga taagatacat   11700
tgatgagttt ggacaaacca caactagaat gcagtgaaaa aaatgcttta tttgtgaaat   11760
ttgtgatgct attgctttat ttgtaaccat tataagctgc aataaacaag ttaacaacaa   11820
caattgcatt catttatgt ttcaggttca gggggaggtg tgggaggttt tttaaagcaa   11880
gtaaaacctc tacaaatgtg gtatggctga ttatgatctc tagtcaag              11928
```

```
<210> SEQ ID NO 37
<211> LENGTH: 45
<212> TYPE: DNA
<213> ORGANISM: Artificial Sequence
<220> FEATURE:
<223> OTHER INFORMATION: 5' primer

<400> SEQUENCE: 37
gcttggtacc gccgccacca tggagtttgg gctgagctgg gtttt            45

<210> SEQ ID NO 38
<211> LENGTH: 30
<212> TYPE: DNA
<213> ORGANISM: Artificial Sequence
<220> FEATURE:
<223> OTHER INFORMATION: 3' primer

<400> SEQUENCE: 38
agaccgatgg gcccttggtg gaagctgagg                             30

<210> SEQ ID NO 39
<211> LENGTH: 48
<212> TYPE: DNA
<213> ORGANISM: Artificial Sequence
<220> FEATURE:
<223> OTHER INFORMATION: 5' primer

<400> SEQUENCE: 39
gaattcgttt aaacgccgcc accatgtcgc catcacaact cattgggt         48

<210> SEQ ID NO 40
<211> LENGTH: 33
<212> TYPE: DNA
<213> ORGANISM: Artificial Sequence
<220> FEATURE:
<223> OTHER INFORMATION: 3' primer

<400> SEQUENCE: 40
ccaccgtacg tttgatctcc accttggtcc ctt                         33

<210> SEQ ID NO 41
<211> LENGTH: 8376
<212> TYPE: DNA
<213> ORGANISM: Artificial Sequence
<220> FEATURE:
<223> OTHER INFORMATION: pAIG1FRH-K plasmid sequence

<400> SEQUENCE: 41
tataaatcaa agaatagac  cgagataggg ttgagtgttg ttccagtttg gaacaagagt    60
ccactattaa agaacgtgga ctccaacgtc aaagggcgaa aaaccgtcta tcagggcgat   120
ggcccactac gtgaaccatc accctaatca agttttttgg ggtcgaggtg ccgtaaagca   180
ctaaatcgga accctaaagg gagcccccga tttagagctt gacggggaaa gccggcgaac   240
gtggcgagaa aggaagggaa gaaagcgaaa ggagcgggcg ctagggcgct ggcaagtgta   300
gcggtcacgc tgcgcgtaac caccacaccc gccgcgctta atgcgccgct acagggcgcg   360
tcccattcgc cattcaggct gcgcaactgt tgggaagggc gatcggtgcg ggcctcttcg   420
ctattacgcc agctggcgaa agggggatgt gctgcaaggc gattaagttg gtaacgcca   480 gggttttccc agtcacgacg ttgtaaaacg acggccagtg agcgcgctgg ccggcctgtg   540
cgaacgccag caagacgtag cccagcgcgt cggccccgag atgcgccgcg tgcggctgct   600
ggagatggcg gacgcgatgg atatgttctg ccaaggggttg gtttgcgcat tcacagttct   660
ccgcaagaat tgattggctc caattcttgg agtggtgaat ccgttagcga ggtgccgccc   720
```

```
tgcttcatcc ccgtggcccg ttgctcgcgt ttgctggcgg tgtccccgga agaaatatat    780
ttgcatgtct ttagttctat gatgacacaa accccgccca gcgtcttgtc attggcgaat    840
tcgaacacgc agatgcagtc ggggcggcgc ggtccgaggt ccacttcgca tattaaggtg    900
acgcgtgtgg cctcgaacac cgagcgaccc tgcagcgacc cgcttaacag cgtcaacagc    960
gtgccgcaga tcccgggggg caatgagata tgaaaaagcc tgaactcacc gcgacgtctg   1020
tcgagaagtt tctgatcgaa aagttcgaca gcgtctccga cctgatgcag ctctcggagg   1080
gcgaagaatc tcgtgctttc agcttcgatg taggagggcg tggatatgtc ctgcgggtaa   1140
atagctgcgc cgatggtttc tacaaagatc gttatgttta tcggcacttt gcatcggccg   1200
cgctcccgat tccggaagtg cttgacattg ggaattcag cgagagcctg acctattgca    1260
tctcccgccg tgcacagggt gtcacgttgc aagacctgcc tgaaaccgaa ctgcccgctg   1320
ttctgcagcc ggtcgcggag gccatggatg cgatcgctgc ggccgatctt agccagacga   1380
gcgggttcgg cccattcgga ccgcaaggaa tcggtcaata cactacatgg cgtgatttca   1440
tatgcgcgat tgctgatccc catgtgtatc actggcaaac tgtgatggac gacaccgtca   1500
gtgcgtccgt cgcgcaggct ctcgatgagc tgatgctttg ggccgaggac tgccccgaag   1560
tccggcacct cgtgcacgcg gatttcggct ccaacaatgt cctgacggac aatggccgca   1620
taacagcggt cattgactgg agcgaggcga tgttcgggga ttcccaatac gaggtcgcca   1680
acatcttctt ctggaggccg tggttggctt gtatggagca gcagacgcgc tacttcgagc   1740
ggaggcatcc ggagcttgca ggatcgccgc ggctccgggc gtatatgctc cgcattggtc   1800
ttgaccaact ctatcagagc ttggttgacg gcaatttcga tgatgcagct gggcgcagg    1860 gtcgatgcga cgcaatcgtc cgatccggag ccgggactgt cgggcgtaca caaatcgccc   1920
gcagaagcgc ggccgtctgg accgatggct gtgtagaagt actcgccgat agtggaaacc   1980
gacgccccag cactcgtccg gatcgggaga tgggggaggc taactgaaac acggaaggag   2040
acaataccgg aaggaacccg cgctatgacg gcaataaaaa gacagaataa aacgcacggg   2100
tgttgggtcg tttgttcata aacgcggggt tcggtcccag ggctggcact ctgtcgatac   2160
cccaccgaga ccccattggg gccaatacgc ccgcgtttct tccttttccc caccccaccc   2220
cccaagttcg ggtgaaggcc cagggctcgc agccaacgtc ggggcggcag gcccctgccat   2280 agccactggc cccgtgggtt agggacgggg tcccccatgg ggaatggttt atggttcgtg   2340
ggggttatta ttttgggcgt tgcgtggggt caggtccacg actggactga gcagacagac   2400
ccatggtttt tggatggcct gggcatggac cgcatgtact ggcgcgacac gaacaccggg   2460
cgtctgtggc tgccaaacac ccccgacccc caaaaaccac cgcgcggatt tctggcgtgc   2520
caagctagtc gaaagcttgg ccggcctgta catgatcaac gcgtgagctc tctagagctt   2580
gtcgacagat cccctcttc atttctttat gttttaaatg cactgacctc ccacattccc    2640
tttttagtaa aatattcaga aataatttaa atacatcatt gcaatgaaaa taaatgtttt   2700
ttattaggca gaatccagat gctcaaggcc cttcataata tccccagtt tagtagttgg    2760 acttagggaa caaaggaacc tttaatagaa attggacagc aagaaagcga gggggatctg   2820
gatcctccgg acccgtatct agaatcatcg attcatttac ccggagacag ggagaggctc   2880
ttctgcgtgt agtggttgtg cagagcctca tgcatcacgg agcatgagaa gacgttcccc   2940
tgctgccacc tgctcttgtc cacggtgagc ttgctgtaga ggaagaagga gccgtcggag   3000
tccagcacgg gaggcgtggt cttgtagttg ttctccggct gcccattgct ctcccactcc   3060
acggcgatgt cgctgggata gaagcctttg accaggcagg tcaggctgac ctggttcttg   3120
```

```
gtcagctcat cccgggatgg gggcagggtg tacacctgtg gttctcgggg ctgccctttg    3180
gctttggaga tggttttctc gatgggggct gggagggctt tgttggagac cttgcacttg    3240
tactccttgc cattcagcca gtcctggtgc aggacggtga ggacgctgac cacacggtac    3300
gtgctgttgt actgctcctc ccgcggcttt gtcttggcat tatgcacctc cacgccgtcc    3360
acgtaccagt tgaacttgac ctcagggtct tcgtggctca cgtccaccac cacgcatgtg    3420
acctcagggg tccgggagat catgagggtg tccttgggtt ttgggggaa gaggaagact     3480 gacggtcccc ccaggagttc aggtgctggg cacggtgggc atgtgtgagt tttgtcacaa    3540
gatttgggct caactttctt gtccaccttg gtgttgctgg gcttgtgatt cacgttgcag    3600
atgtaggtct gggtgcccaa gctgctggag ggcacggtca ccacgctgct gagggagtag    3660
agtcctgagg actgtaggac agccgggaag gtgtgcacgc cgctggtcag ggcgcctgag    3720
ttccacgaca ccgtcaccgg ttcggggaag tagtccttga ccaggcagcc cagggccgct    3780 gtgccccag aggtgctctt ggaggagggt gccaggggga agaccgatgg gcccttggtg     3840
gaagctgagg agacggtgac cgtggtccct tggccccaga cgtccatacc gtagtagaag    3900
ttccccagtc ttgcacagta atacacagca gtgtcctcgg ctctcaggct gttcatttga    3960
agatacaagg agttcttggc attgtctctg gagatggtga atcggcccctt cacggagtct   4020 gcatagtatg tggcaccacg agtatcaata actgatatcc actccagacc ttttcctgga    4080
gcctggcgaa cccagtgcat agcaaagcta ctgaaggtga atccagaggc tgcacaggag    4140
agtctcaggg accccccagg ctttaccaag cctcccccag actgcaccag ctgaacctca    4200
cactggacac cttttaatat agcaacaagg aaaacccagc tcagcccaaa ctccatggtg    4260
gcggcggtac caagcttaag cctgtggaga gaaaggaaca gaaaacgaaa caaagacgta    4320
gagttgagca agcagggtca ggcaaagcgt ggagagccgg ctgagtctag gtaggctcca    4380
agggagcgcc ggacaaaggc ccggtctcga cctgagcttt aaacttacct gtggccacac    4440
gtgcaattgc tatagtgagt cgtattaatt tcgataagcc agtaagcagt gggttctcta    4500
gttagccaga gagctctgct tatatagacc tcccaccgta cacgcctacc gcccatttgc    4560
gtcaatgggg cggagttgtt acgacatttt ggaaagtccc gttgattttg gtgccaaaac    4620
aaactcccat tgacgtcaat ggggtggaga cttggaaatc cccgtgagtc aaaccgctat    4680
ccacgcccat tgatgtactg ccaaaaccgc atcaccatgg taatagcgat gactaatacg    4740
tagatgtact gccaagtagg aaagtcccat aaggtcatgt actgggcata atgccaggcg    4800
ggccatttac cgtcattgac gtcaataggg ggcgtacttg gcatatgata cacttgatgt    4860
actgccaagt gggcagttta ccgtaaatag tccacccatt gacgtcaatg gaaagtccct    4920
attggcgtta ctatgggaac atacgtcatt attgacgtca atgggcgggg tcgttgggc    4980 ggtcagccag gcgggccatt taccgtaagt tatgtaacgc ggaactccat atatgggcta    5040
tgaactaatg accccgtaat tgattactat taataactag tcaataatca atgtcaacgc    5100
gtatatctgg cccgtacatc ggtagctgag ggtttaaacg gcgcgcttgg cgtaatcatg    5160
gtcatagctg tttcctgtgt gaaattgtta tccgctcaca attccacaca atatacgagc    5220
cggaagcata aagtgtaaag cctggggtgc ctaatgagtg agctaactca cattaattgc    5280
gttgcgctca ctgcccgctt tccagtcggg aaacctgtcg tgccagctgc attaatgaat    5340
cggccaacgc gcggggagag gcggtttgcg tattgggcgc tcttccgctt cctcgctcac    5400
tgactcgctg cgctcggtcg ttcggctgcg gcgagcggta tcagctcact caaaggcggt    5460
aatacggtta tccacagaat caggggataa cgcaggaaag aacatgtgag caaaaggcca    5520
```

-continued

```
gcaaaaggcc aggaaccgta aaaaggccgc gttgctggcg ttttttccata ggctccgccc    5580 ccctgacgag catcacaaaa atcgacgctc aagtcagagg tggcgaaacc cgacaggact    5640
ataaagatac caggcgtttc ccctggaag ctccctcgtg cgctctcctg ttccgaccct    5700
gccgcttacc ggatacctgt ccgcctttct cccttcggga agcgtggcgc tttctcatag    5760
ctcacgctgt aggtatctca gttcggtgta ggtcgttcgc tccaagctgg gctgtgtgca    5820 cgaaccccc gttcagcccg accgctgcgc cttatccggt aactatcgtc ttgagtccaa    5880
cccggtaaga cacgacttat cgccactggc agcagccact ggtaacagga ttagcagagc    5940
gaggtatgta ggcggtgcta cagagttctt gaagtggtgg cctaactacg gctacactag    6000
aaggacagta tttggtatct gcgctctgct gaagccagtt accttcggaa aaagagttgg    6060
tagctcttga tccggcaaac aaaccaccgc tggtagcggt ggttttttg tttgcaagca    6120 gcagattacg cgcagaaaaa aaggatctca agaagatcct ttgatctttt ctacggggtc    6180
tgacgctcag tggaacgaaa actcacgtta agggattttg gtcatgagat tatcaaaaag    6240
gatcttcacc tagatccttt taaattaaaa atgaagtttt aaatcaatct aaagtatata    6300
tgagtaaact tggtctgaca gttaccaatg cttaatcagt gaggcaccta tctcagcgat    6360
ctgtctattt cgttcatcca tagttgcctg actccccgtc gtgtagataa ctacgatacg    6420
ggagggctta ccatctggcc ccagtgctgc aatgataccg cgagacccac gctcaccggc    6480
tccagattta tcagcaataa accagccagc cggaagggcc gagcgcagaa gtggtcctgc    6540
aactttatcc gcctccatcc agtctattaa ttgttgccgg gaagctagag taagtagttc    6600
gccagttaat agtttgcgca acgctgaat cgccccatca tccagccaga aagtgaggga    6660
gccacggttg atgagagctt tgttgtaggt ggaccagttg gtgattttga acttttgctt    6720
tgccacggaa cggtctgcgt tgtcgggaag atgcgtgatc tgatccttca actcagcaaa    6780
agttcgattt attcaacaaa gccgccgtcc cgtcaagtca cgtaatgct ctgccagtgt    6840 tacaaccaat taaccaattc tgattagaaa aactcatcga gcatcaaatg aaactgcaat    6900
ttattcatat caggattatc aataccatat ttttgaaaaa gccgtttctg taatgaagga    6960
gaaaactcac cgaggcagtt ccataggatg caagatcct ggtatcggtc tgcgattccg    7020
actcgtccaa catcaataca acctattaat ttcccctcgt caaaaataag gttatcaagt    7080
gagaaatcac catgagtgac gactgaatcc ggtgagaatg gcaaaagctt atgcatttct    7140
ttccagactt gttcaacagg ccagccatta cgctcgtcat caaaatcact cgcatcaacc    7200
aaaccgttat tcattcgtga ttgcgcctga gcgagacgaa atacgcgatc gctgttaaaa    7260
ggacaattac aaacaggaat cgaatgcaac cggcgcagga acactgccag cgcatcaaca    7320
atattttcac ctgaatcagg atattcttct aatacctgga atgctgtttt cccggggatc    7380
gcagtggtga gtaaccatgc atcatcagga gtacggataa aatgcttgat ggtcggaaga    7440
ggcataaatt ccgtcagcca gtttagtctg accatctcat ctgtaacatc attggcaacg    7500
ctacctttgc catgtttcag aaacaactct ggcgcatcgg gcttcccata caatcgatag    7560
attgtcgcac ctgattgccc gacattatcg cgagcccatt tatacccata taaatcagca    7620
tccatgttgg aatttaatcg cggcctcgag caagacgttt cccgttgaat atggctcata    7680
acaccccttg tattactgtt tatgtaagca gacagtttta ttgttcatga tgatatattt    7740
ttatcttgtg caatgtaaca tcagagattt tgagacacaa cgtggctttg ttgaataaat    7800
cgaacttttg ctgagttgaa ggatcagatc acgcatcttc ccgacaacgc agaccgttcc    7860
gtggcaaagc aaaagttcaa aatcaccaac tggtccacct acaacaaagc tctcatcaac    7920
```

| | |
|---|---|
| cgtggctccc tcactttctg gctggatgat ggggcgattc aggcgttctt cggggcgaaa | 7980 |
| actctcaagg atcttaccgc tgttgagatc cagttcgatg taacccactc gtgcacccaa | 8040 |
| ctgatcttca gcatctttta ctttcaccag cgtttctggg tgagcaaaaa caggaaggca | 8100 |
| aaatgccgca aaaaagggaa taagggcgac acggaaatgt tgaatactca tactcttcct | 8160 |
| ttttcaatat tattgaagca tttatcaggg ttattgtctc atgagcggat acatatttga | 8220 |
| atgtatttag aaaaataaac aaatagggt tccgcgcaca tttccccgaa aagtgccacc | 8280 |
| taaattgtaa gcgttaatat tttgttaaaa ttcgcgttaa attttgtta atcagctca | 8340 |
| tttttaacc aataggccga atcggcaaa atccct | 8376 |

<210> SEQ ID NO 42
<211> LENGTH: 7333
<212> TYPE: DNA
<213> ORGANISM: Artificial Sequence
<220> FEATURE:
<223> OTHER INFORMATION: pAIGFRLCb2(-)L-K plasmid sequence

<400> SEQUENCE: 42

| | |
|---|---|
| gcactataca tcaaatattc cttattaacc cctttacaaa ttaaaaagct aaaggtacac | 60 |
| aatttttgag catagttatt aatagcagac actctatgcc tgtgtggagt aagaaaaaac | 120 |
| agtatgttat gattataact gttatgccta cttataaagg ttacagaata tttttccata | 180 |
| attttcttgt atagcagtgc agcttttcc tttgtggtgt aaatagcaaa gcaagcaaga | 240 |
| gttctattac taaacacagc atgactcaaa aaacttagca attctgaagg aaagtccttg | 300 |
| gggtcttcta cctttctctt ctttttgga ggagtagaat gttgagagtc agcagtagcc | 360 |
| tcatcatcac tagatggcat ttcttctgag caaaacaggt tttcctcatt aaaggcattc | 420 |
| caccactgct cccattcatc agttccatag gttggaatct aaaatacaca aacaattaga | 480 |
| atcagtagtt taacacatta tacacttaaa aatttatat ttaccttaga gctttaaatc | 540 |
| tctgtaggta gtttgtccaa ttatgtcaca ccacagaagt aaggttcctt cacaaagatc | 600 |
| gatctaaagc cagcaaaagt cccatggtct tataaaaatg catagcttta ggaggggagc | 660 |
| agagaacttg aaagcatctt cctgttagtc tttcttctcg tagacttcaa acttatactt | 720 |
| gatgcctttt tcctcctgga cctcagagag gacgcctggg tattctggga gaagtttata | 780 |
| ttttccccaaa tcaatttctg ggaaaaacgt gtcactttca aattcctgca tgatccttgt | 840 |
| cacaaagagt ctgaggtggc ctggttgatt catggcttcc tggtaaacag aactgcctcc | 900 |
| gactatccaa accatgtcta ctttacttgc caattccggt tgttcaataa gtcttaaggc | 960 |
| atcatccaaa cttttggcaa gaaaatgagc tcctcgtggt ggttctttga gttctctact | 1020 |
| gagaactata ttaattctgt cctttaaagg tcgattcttc tcaggaatgg agaaccaggt | 1080 |
| tttcctaccc ataatcacca gattctgttt accttccact gaagaggttg tggtcattct | 1140 |
| ttggaagtac ttgaactcgt tcctgagcgg aggccagggt aggtctccgt tcttgccaat | 1200 |
| ccccatattt tgggacacgg cgacgatgca gttcaatggt cgaaccatga tggcagcggg | 1260 |
| gataaaatcc taccagcctt cacgctagga ttgccgtcaa gtttggcgcg aaatcgcagc | 1320 |
| cctgagctgt ccccccccc aagctcagat ctgagcttgg tccctatggt gagtccgttc | 1380 |
| cgctcttgtg atgatagcca gacaagaaag agacaataca agacaaacac caaatagtag | 1440 |
| aaatagagac aagggtcact tatccgaggg tccctgttcg ggcgccagct gccgcagtcg | 1500 |
| gccgacctga gggtcgccgg ggtctgcggg ggaccctct ggaaagtgaa ggataagtga | 1560 |
| cgagcggaga cgggatggcg aacagacaca aacacacaag aggtgaatgt taggactgtt | 1620 |

```
gcaagtttac tcaaaaaatc agcactcttt tatatcttgg tttacataag catttacata    1680
agatttggat aaattccaaa agaacatagg aaaatagaac actcagagct cagatcagaa    1740
cctttgatac caaaccaagt caggaaacca cttgtctcac atcctcgttt taagaacagt    1800
ttgtaaccaa aaacttactt aagccctggg aaccgcaagg ttgggccaat aaaggctatt    1860
cataataact catgccatga gttttttgcag aataatgttc tattagtcca gccactgtcc   1920
cctccttggt atggaaaatc tttccccaaa agtgcattcc tgttcctaga taaatataat    1980
catgtacctg ttgtttcatg tcgtcttttt cttcttgaga caacatacac caaggaggtc    2040
tagctctggc gagtctttca cgaaaaggga gggatctata taacactttta tagccattga   2100 ctgtaaccca cctatcccaa tttaagtcat atcttcctgt atatggtaag ggggcatctg    2160
ttggtctgta gatgtaaggt cccctataag tccctggttg ccaccacctg tctcctattt    2220
tgacaaaaac actctttttt ccctttttta cttctaggcc tgtggtcaat agtccttgca    2280
cctgttcttc aattgaggtt gagcgtctct ttctattttc tattcccatt tctaacttct    2340
gaatttgagt aaaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca gtttgcagc agagaatgaa tatgtctttg tctgatgggc     2700
tcatccgttt gtgcgcagac gggtcgtcct tggtgggaaa caacccctttg gctgcttctc   2760 ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag cataggcttt    2940
ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga aagaacatgt gagcaaaagg ccagcaaaag gccaggaacc    3180
gtaaaaaggc cgcgttgctg gcgtttttcc ataggctccg ccccccctgac gagcatcaca   3240 aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc aacccggta agacacgact     3540 tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt tgtttgcaa gcagcagatt acgcgcagaa     3780
aaaaaggatc tcaagaagat cctttgatct ttttctacggg gtctgacgct cagtggaacg   3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
```

```
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca acgcgggata ataccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag gaataagggg   4800
cgacacggaa atgttgaata ctcatactct tccttttta atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgcc gtttaaaccc tcagctgatc atccggatgc acagcgcgcg gccggccggt   5100
accacgcgtt ggccacatat ggcggccgct cgcgattaat taatcgcgat ggccacatat   5160
ggagctctct agagcttgtc gacagatccc cctcttcatt tctttatgtt ttaaatgcac   5220
tgacctccca cattcccttt ttagtaaaat attcagaaat aatttaaata catcattgca   5280
atgaaaataa atgttttta ttaggcagaa tccagatgct caaggccctt cataatatcc   5340
cccagtttag tagttggact tagggaacaa aggaaccttt aatagaaatt ggacagcaag   5400
aaagcgaggg ggatctggat cctccggagg gccctggatc ctcctacgta tctagaatca   5460
tcgattaaca ctctcccctg ttgaagctct ttgtgacggg cgagctcagg ccctgatggg   5520
tgacttcgca ggcgtagact ttgtgttct cgtagtctgc tttgctcagc gtcagggtgc   5580
tgctgaggct gtaggtgctg tccttgctgt cctgctctgt gacactctcc tgggagttac   5640
ccgattggag ggcgttatcc accttccact gtactttggc ctctctggga tagaagttat   5700
tcagcaggca cacaacagag gcagttccag atttcaactg ctcatcagat ggcgggaaga   5760
tgaagacaga tggtgcagcc accgtacgtt tgatctccac cttggtccct tggccgaaag   5820
tgtgaggtaa acgactactc tgatgacagt aatacactgc gaaatcttca ggctccagtc   5880
tactgatggt gagggtgaaa tctgtcccag atccactgcc actgaaccta tcggggatcc   5940
ctgagaggga ctgggatgca tacttgatga aagccttgg agcctgacct ggtttctgct   6000
ggtaccagtg taagctacta ccaatgctct gactggcccg gcaggagagg gtggctctct   6060
cgcctggaga cacagacagg gtacctgggc tctgagtcag cacaatttca ccctggagg   6120 ctggaaccca gagcagcaga aacccaatga gttgtgatgg cgacatggtg gcggcgttta   6180
aacgaattct taagcctgtg gagagaaagg aacagaaaac gaaacaaaga cgtagagttg   6240
agcaagcagg gtcaggcaaa gcgtggagag ccggctgagt ctaggtaggc tccaagggag   6300
cgccggacaa aggcccggtc tcgacctgag ctttaaactt acctgtggcc acacgtgcaa   6360
ttgctatagt gagtcgtatt aatttcgata agccagtaag cagtgggttc tctagttagc   6420
```

-continued

```
cagagagctc tgcttatata gacctcccac cgtacacgcc taccgcccat ttgcgtcaat    6480
ggggcggagt tgttacgaca ttttggaaag tcccgttgat tttggtgcca aaacaaactc    6540
ccattgacgt caatggggtg gagacttgga atccccgtg agtcaaaccg ctatccacgc     6600
ccattgatgt actgccaaaa ccgcatcacc atggtaatag cgatgactaa tacgtagatg    6660
tactgccaag taggaaagtc ccataaggtc atgtactggg cataatgcca ggcgggccat    6720
ttaccgtcat tgacgtcaat aggggcgta cttggcatat gatacacttg atgtactgcc     6780
aagtgggcag tttaccgtaa atagtccacc cattgacgtc aatggaaagt ccctattggc    6840
gttactatgg gaacatacgt cattattgac gtcaatgggc ggggtcgtt gggcggtcag     6900 ccaggcgggc catttaccgt aagttatgta acgcggaact ccatatatgg gctatgaact    6960
aatgaccccg taattgatta ctattaataa ctagtcaata atcaatgtca acgcgtatat    7020
ctggcccgta catcggtaac tagtcggacc ggcccgggcc accggtgctc gaagcttgga    7080
tcgatccaga catgataaga tacattgatg agtttggaca aaccacaact agaatgcagt    7140
gaaaaaaatg ctttatttgt gaaatttgtg atgctattgc tttatttgta accattataa     7200
gctgcaataa acaagttaac aacaacaatt gcattcattt tatgtttcag gttcaggggg    7260
aggtgtggga ggttttttaa agcaagtaaa acctctacaa atgtggtatg gctgattatg    7320
atctctagtc aag                                                       7333

<210> SEQ ID NO 43
<211> LENGTH: 11912
<212> TYPE: DNA
<213> ORGANISM: Artificial Sequence
<220> FEATURE:
<223> OTHER INFORMATION: pAIG1FRLCb2V1-K plasmid sequence

<400> SEQUENCE: 43
gcactataca tcaaatattc cttattaacc cctttacaaa ttaaaaagct aaaggtacac       60 aattttttgag catagttatt aatagcagac actctatgcc tgtgtggagt aagaaaaaac     120
agtatgttat gattataact gttatgccta cttataaagg ttacagaata ttttttccata    180 attttcttgt atagcagtgc agcttttttcc tttgtggtgt aaatagcaaa gcaagcaaga    240
gttctattac taaacacagc atgactcaaa aaacttagca attctgaagg aaagtccttg     300
gggtcttcta ccttcctctt cttttttgga ggagtagaat gttgagagtc agcagtagcc     360
tcatcatcac tagatggcat ttcttctgag caaaacaggt tttcctcatt aaaggcattc     420
caccactgct cccattcatc agttccatag gttggaatct aaaatacaca aacaattaga     480
atcagtagtt taacacatta tacacttaaa aattttatat ttaccttaga gctttaaatc     540
tctgtaggta gtttgtccaa ttatgtcaca ccacagaagt aaggttcctt cacaaagatc     600
gatctaaagc cagcaaaagt cccatggtct tataaaaatg catagcttta ggaggggagc     660
agagaacttg aaagcatctt cctgttagtc tttcttctcg tagacttcaa acttatactt     720
gatgcctttt tcctcctgga cctcagagag gacgcctggg tattctggga gaagtttata    780
tttccccaaa tcaattttctg ggaaaaacgt gtcactttca aattcctgca tgatccttgt    840
cacaaagagt ctgaggtggc ctggttgatt catggcttcc tggtaaacag aactgcctcc     900
gactatccaa accatgtcta ctttacttgc caattccggt tgttcaataa gtcttaaggc    960
atcatccaaa cttttggcaa gaaaatgagc tcctcgtggt ggttctttga gttctctact    1020
gagaactata ttaattctgt cctttaaagg tcgattcttc tcaggaatgg agaaccaggt    1080 ttcctaccc ataatcacca gattctgttt accttccact gaagaggttg tggtcattct    1140
```

```
ttggaagtac ttgaactcgt tcctgagcgg aggccagggt aggtctccgt tcttgccaat    1200
ccccatattt tgggacacgg cgacgatgca gttcaatggt cgaaccatga tggcagcggg    1260
gataaaatcc taccagcctt cacgctagga ttgccgtcaa gtttggcgcg aaatcgcagc    1320
cctgagctgt cccccccccc aagctcagat ctgagcttgg tccctatggt gagtccgttc    1380
cgctcttgtg atgatagcca gacaagaaag agacaataca agacaaacac caaatagtag    1440
aaatagagac aagggtcact tatccgaggg tccctgttcg ggcgccagct gccgcagtcg    1500
gccgacctga gggtcgccgg ggtctgcggg gggaccctct ggaaagtgaa ggataagtga    1560
cgagcggaga cgggatggcg aacagacaca aacacacaag aggtgaatgt taggactgtt    1620
gcaagtttac tcaaaaaatc agcactcttt tatatcttgg tttacataag catttacata    1680
agatttggat aaattccaaa agaacatagg aaaatagaac actcagagct cagatcagaa    1740
cctttgatac caaaccaagt caggaaacca cttgtctcac atcctcgttt taagaacagt    1800
ttgtaaccaa aaacttactt aagccctggg aaccgcaagg ttgggccaat aaaggctatt    1860
cataataact catgccatga gttttttgcag aataatgttc tattagtcca gccactgtcc    1920
cctccttggt atggaaaatc tttccccaaa agtgcattcc tgttcctaga taaatataat    1980
catgtacctg ttgtttcatg tcgtcttttt cttcttgaga caacatacac caaggaggtc    2040
tagctctggc gagtctttca cgaaaaggga gggatctata taacactta tagccattga    2100 ctgtaaccca cctatcccaa tttaagtcat atcttcctgt atatggtaag ggggcatctg    2160
ttggtctgta gatgtaaggt cccctataag tccctggttg ccaccacctg tctcctattt    2220
tgacaaaaac actctttttt ccctttttta cttctaggcc tgtggtcaat agtccttgca    2280
cctgttcttc aattgaggtt gagcgtctct ttctattttc tattcccatt tctaacttct    2340
gaatttgagt aaaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca agtttgcagc agagaatgaa tatgtctttg tctgatgggc    2700
tcatccgttt gtgcgcagac gggtcgtcct tggtgggaaa caacccctttg gctgcttctc    2760 ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcacctg gatgctgtag gcataggctt    2940
ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga agaacatgt gagcaaaagg ccagcaaaag gccaggaacc    3180
gtaaaaaggc cgcgttgctg gcgttttcc ataggctccg cccccctgac gagcatcaca    3240
aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc caacccggta agacacgact    3540
```

```
tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg aaaaagagt tggtagctct tgatccggca     3720
aacaaaccac cgctggtagc ggtggttttt ttgtttgcaa gcagcagatt acgcgcagaa    3780
aaaaaggatc tcaagaagat cctttgatct tttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca cacgggata ataccgcgcc acatagcaga actttaaaag    4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag ggaataaggg    4800
cgacacggaa atgttgaata ctcatactct tccttttca atattattga agcatttatc     4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgcc gtttaaaccc tcagctaccg atgtacgggc cagatatacg cgttgacatt    5100
gattattgac tagttattaa tagtaatcaa ttacggggtc attagttcat agcccatata    5160
tggagttccg cgttacataa cttacggtaa atggcccgcc tggctgaccg cccaacgacc    5220
cccgcccatt gacgtcaata atgacgtatg ttcccatagt aacgccaata gggactttcc    5280
attgacgtca atgggtggac tatttacggt aaactgccca cttggcagta catcaagtgt    5340
atcatatgcc aagtacgccc cctattgacg tcaatgacgg taaatggccc gcctggcatt    5400
atgcccagta catgacctta tgggactttc ctacttggca gtacatctac gtattagtca    5460
tcgctattac catggtgatg cggttttggc agtacatcaa tgggcgtgga tagcggtttg    5520
actcacgggg atttccaagt ctccacccca ttgacgtcaa tgggagtttg ttttggcacc    5580
aaaatcaacg ggactttcca aaatgtcgta acaactccgc cccattgacg caaatgggcg    5640
gtaggcgtgt acggtgggag gtctatataa gcagagctct ctggctaact agagaaccca    5700
ctgcttactg gcttatcgaa attaatacga ctcactatag caattgcacg tgtggccaca    5760
ggtaagttta agctcaggt cgagaccggg cctttgtccg gcgctccctt ggagcctacc    5820
tagactcagc cggctctcca cgctttgcct gaccctgctt gctcaactct acgtctttgt    5880
ttcgttttct gttcctttct ctccacaggc ttaagcttgg taccgccgcc accatggagt    5940
```

```
ttgggctgag ctgggttttc cttgttgcta tattaaaagg tgtccagtgt gaggttcagc    6000
tggtgcagtc tgggggaggc ttggtaaagc ctggggggtc cctgagactc tcctgtgcag    6060
cctctggatt caccttcagt agctttgcta tgcactgggt tcgccaggct ccaggaaaag    6120
gtctggagtg gatatcagtt attgatactc gtggtgccac atactatgca gactccgtga    6180
agggccgatt caccatctcc agagacaatg ccaagaactc cttgtatctt caaatgaaca    6240
gcctgagagc cgaggacact gctgtgtatt actgtgcaag actggggaac ttctactacg    6300
gtatggacgt ctggggccaa gggaccacgg tcaccgtctc ctcagcttcc accaagggcc    6360
catcggtctt ccccctggca ccctcctcca agagcacctc tgggggcaca gcggccctgg    6420
gctgcctggt caaggactac ttccccgaac cggtgacggt gtcgtggaac tcaggcgccc    6480
tgaccagcgg cgtgcacacc ttcccggctg tcctacagtc ctcaggactc tactccctca    6540
gcagcgtggt gaccgtgccc tccagcagct tgggcaccca gacctacatc tgcaacgtga    6600
atcacaagcc cagcaacacc aaggtggaca agaaagttga gcccaaatct tgtgacaaaa    6660
ctcacacatg cccaccgtgc ccagcacctg aactcctggg gggaccgtca gtcttcctct    6720
tccccccaaa acccaaggac accctcatga tctcccggac ccctgaggtc acatgcgtgg    6780
tggtggacgt gagccacgaa gaccctgagg tcaagttcaa ctggtacgtg gacggcgtgg    6840
aggtgcataa tgccaagaca aagccgcggg aggagcagta caacagcacg taccgtgtgg    6900
tcagcgtcct caccgtcctg caccaggact ggctgaatgg caaggagtac aagtgcaagg    6960
tctccaacaa agccctccca gccccatcg agaaaaccat ctccaaagcc aaagggcagc    7020
cccgagaacc acaggtgtac accctgcccc catcccggga tgagctgacc aagaaccagg    7080
tcagcctgac ctgcctggtc aaaggcttct atcccagcga catcgccgtg gagtgggaga    7140
gcaatgggca gccggagaac aactacaaga ccacgcctcc cgtgctggac tccgacggct    7200
ccttcttcct ctacagcaag ctcaccgtgg acaagagcag gtggcagcag gggaacgtct    7260
tctcatgctc cgtgatgcat gaggctctgc acaaccacta cacgcagaag agcctctccc    7320
tgtctccggg taaatgaatc gatgattcta gatacgggtc cggaggatcc agatccccct    7380
cgctttcttg ctgtccaatt tctattaaag gttcctttgt tccctaagtc caactactaa    7440
actgggggat attatgaagg gccttgagca tctggattct gcctaataaa aaacatttat    7500
tttcattgca atgatgtatt taaattattt ctgaatattt tactaaaaag ggaatgtggg    7560
aggtcagtgc atttaaaaca taagaaatg aagaggggga tctgtcgaca agctctagag    7620
agctcacgcg ttgatcatgt acaggccggc caagctttcg actagcttgg cacgccagaa    7680
atccgcgcgg tggtttttgg gggtcggggg tgtttggcag ccacagacgc ccggtgttcg    7740
tgtcgcgcca gtacatgcgg tccatgccca ggccatccaa aaaccatggg tctgtctgct    7800
cagtccagtc gtggacctga ccccacgcaa cgcccaaaat aataaccccc acgaaccata    7860
aaccattccc catgggggac cccgtcccta acccacgggg ccagtggcta tggcagggcc    7920
tgccgccccg acgttggctg cgagccctgg gccttcaccc gaacttgggg ggtgggtgg    7980 ggaaaaggaa gaaacgcggg cgtattggcc ccaatggggt ctcggtgggg tatcgacaga    8040
gtgccagccc tgggaccgaa ccccgcgttt atgaacaaac gacccaacac ccgtgcgttt    8100
tattctgtct ttttattgcc gtcatagcgc gggttccttc cggtattgtc tccttccgtg    8160
tttcagttag cctcccccat ctcccgatcc ggacgagtgc tggggcgtcg gtttccacta    8220
tcggcgagta cttctacaca gccatcggtc cagacgccg cgcttctgcg ggcgatttgt    8280
gtacgcccga cagtcccggc tccggatcgg acgattgcgt cgcatcgacc ctgcgcccaa    8340
```

```
gctgcatcat cgaaattgcc gtcaaccaag ctctgataga gttggtcaag accaatgcgg    8400
agcatatacg cccggagccg cggcgatcct gcaagctccg gatgcctccg ctcgaagtag    8460
cgcgtctgct gctccataca agccaaccac ggcctccaga agaagatgtt ggcgacctcg    8520
tattgggaat ccccgaacat cgcctcgctc cagtcaatga ccgctgttat gcggccattg    8580
tccgtcagga cattgttgga gccgaaatcc gcgtgcacga ggtgccggac ttcggggcag    8640
tcctcggccc aaagcatcag ctcatcgaga gcctgcgcga cggacgcact gacggtgtcg    8700
tccatcacag tttgccagtg atacacatgg ggatcagcaa tcgcgcatat gaaatcacgc    8760
catgtagtgt attgaccgat tccttgcggt ccgaatgggc cgaacccgct cgtctggcta    8820
agatcggccg cagcgatcgc atccatggcc tccgcgaccg gctgcagaac agcgggcagt    8880
tcggtttcag gcaggtcttg caacgtgaca ccctgtgcac ggcgggagat gcaataggtc    8940
aggctctcgc tgaattcccc aatgtcaagc acttccggaa tcgggagcgc ggccgatgca    9000
aagtgccgat aaacataacg atctttgtag aaaccatcgg cgcagctatt tacccgcagg    9060
acatatccac gccctcctac atcgaagctg aaagcacgag attcttcgcc ctccgagagc    9120
tgcatcaggt cggagacgct gtcgaacttt tcgatcagaa acttctcgac agacgtcgcg    9180
gtgagttcag gcttttttcat atctcattgc cccccgggat ctgcggcacg ctgttgacgc    9240
tgttaagcgg gtcgctgcag ggtcgctcgg tgttcgaggc cacacgcgtc accttaatat    9300
gcgaagtgga cctcggaccg cgccgccccg actgcatctg cgtgttcgaa ttcgccaatg    9360
acaagacgct gggcggggtt tgtgtcatca tagaactaaa gacatgcaaa tatatttctt    9420
ccggggacac cgccagcaaa cgcgagcaac gggccacggg gatgaagcag ggcggcacct    9480
cgctaacgga ttcaccactc caagaattgg agccaatcaa ttcttgcgga gaactgtgaa    9540
tgcgcaaacc aacccttggc agaacatatc catcgcgtcc gccatctcca gcagccgcac    9600
gcggcgcatc tcggggccga cgcgctgggc tacgtcttgc tggcgttcgc acaggccggc    9660
cagcgcgcgg ccggccggta ccacgcgttg gccacatatg gcggccgctc gcgattaatt    9720
aatcgcgatg ccacatatg gagctctcta gagcttgtcg acagatcccc ctcttcattt    9780
ctttatgttt taaatgcact gacctcccac attccctttt tagtaaaata ttcagaaata    9840
atttaaatac atcattgcaa tgaaaataaa tgttttttat taggcagaat ccagatgctc    9900
aaggcccttc ataatatccc ccagtttagt agttggactt agggaacaaa ggaacccttta   9960 atagaaattg gacagcaaga aagcgagggg gatctggatc ctccggaggg ccctggatcc   10020
tcctacgtat ctagaatcat cgattaacac tctcccctgt tgaagctctt tgtgacgggc   10080
gagctcaggc cctgatgggt gacttcgcag gcgtagactt tgtgtttctc gtagtctgct   10140
ttgctcagcg tcagggtgct gctgaggctg taggtgctgt ccttgctgtc ctgctctgtg   10200
acactctcct gggagttacc cgattggagg gcgttatcca ccttccactg tactttggcc   10260
tctctgggat agaagttatt cagcaggcac acaacagagg cagttccaga tttcaactgc   10320
tcatcagatg gcgggaagat gaagacagat ggtgcagcca ccgtacgttt gatctccacc   10380
ttggtccctt ggccgaaagt gtgaggtaaa cgactactct gatgacagta atacactgcg   10440
aaatcttcag gctccagtct actgatggtg agggtgaaat ctgtcccaga tccactgcca   10500
ctgaacctat cggggatccc tgagagggac tgggatgcat acttgatgag aagccttgga   10560
gcctgacctg gtttctgctg gtaccagtgt aagctactac caatgctctg actggcccgg   10620
caggagaggg tggctctctc gcctggagac acagacaggg tacctgggct ctgagtcagc   10680
acaatttcac ccctggaggc tggaacccag agcagcagaa acccaatgag ttgtgatggc   10740
```

```
gacatggtgg cggcgtttaa acgaattctt aagcctgtgg agagaaagga acagaaaacg    10800
aaacaaagac gtagagttga gcaagcaggg tcaggcaaag cgtggagagc cggctgagtc    10860
taggtaggct ccaagggagc gccggacaaa ggcccggtct cgacctgagc tttaaactta    10920
cctgtggcca cacgtgcaat tgctatagtg agtcgtatta atttcgataa gccagtaagc    10980
agtgggttct ctagttagcc agagagctct gcttatatag acctcccacc gtacacgcct    11040
accgcccatt tgcgtcaatg gggcggagtt gttacgacat tttggaaagt cccgttgatt    11100
ttggtgccaa acaaactcc cattgacgtc aatggggtgg agacttggaa atccccgtga     11160
gtcaaaccgc tatccacgcc cattgatgta ctgccaaaac cgcatcacca tggtaatagc    11220
gatgactaat acgtagatgt actgccaagt aggaaagtcc cataaggtca tgtactgggc    11280
ataatgccag gcgggccatt taccgtcatt gacgtcaata ggggcgtac ttggcatatg     11340 atacacttga tgtactgcca agtgggcagt ttaccgtaaa tagtccaccc attgacgtca    11400
atggaaagtc cctattggcg ttactatggg aacatacgtc attattgacg tcaatgggcg    11460
ggggtcgttg gcggtcagc caggcgggcc atttaccgta agttatgtaa cgcggaactc     11520
catatatggg ctatgaacta tgacccccgt aattgattac tattaataac tagtcaataa    11580
tcaatgtcaa cgcgtatatc tggcccgtac atcggtaact agtcggaccg gcccgggcca    11640
ccggtgctcg aagcttggat cgatccagac atgataagat acattgatga gtttggacaa    11700
accacaacta gaatgcagtg aaaaaaatgc tttatttgtg aaatttgtga tgctattgct    11760
ttatttgtaa ccattataag ctgcaataaa caagttaaca acaacaattg cattcatttt    11820
atgtttcagg ttcaggggga ggtgtgggag gttttttaaa gcaagtaaaa cctctacaaa    11880
tgtggtatgg ctgattatga ctctagtca ag                                   11912
```

<210> SEQ ID NO 44
<211> LENGTH: 11893
<212> TYPE: DNA
<213> ORGANISM: Artificial Sequence
<220> FEATURE:
<223> OTHER INFORMATION: pAIL23V1-K plasmid sequence

<400> SEQUENCE: 44

```
ggcactatac atcaaatatt ccttattaac ccctttacaa attaaaaagc taaaggtaca       60
caatttttga gcatagttat taatagcaga cactctatgc ctgtgtggag taagaaaaaa      120
cagtatgtta tgattataac tgttatgcct acttataaag gttacagaat attttttccat    180 aattttcttg tatagcagtg cagcttttc ctttgtggtg taaatagcaa agcaagcaag       240
agttctatta ctaaacacag catgactcaa aaaacttagc aattctgaag gaaagtcctt      300
ggggtcttct accttcctct tctttttgg aggagtagaa tgttgagagt cagcagtagc       360
ctcatcatca ctagatggca tttcttctga gcaaaacagg ttttcctcat taaaggcatt     420
ccaccactgc tcccattcat cagttccata ggttggaatc taaaatacac aaacaattag     480
aatcagtagt ttaacacatt atacacttaa aaatttata tttaccttag agctttaaat      540
ctctgtaggt agtttgtcca attatgtcac accacagaag taaggttcct tcacaaagat     600
cgatctaaag ccagcaaaag tcccatggtc ttataaaaat gcatagcttt aggaggggag     660
cagagaactt gaaagcatct tcctgttagt ctttcttctc gtagacttca aacttatact     720
tgatgccttt ttcctcctgg acctcagaga ggacgcctgg gtattctggg agaagtttat    780
atttccccaa atcaatttct gggaaaaacg tgtcactttc aaattcctgc atgatccttg    840
tcacaaagag tctgaggtgg cctggttgat tcatggcttc ctggtaaaca gaactgcctc    900
```

```
cgactatcca aaccatgtct actttacttg ccaattccgg ttgttcaata agtcttaagg    960
catcatccaa acttttggca agaaaatgag ctcctcgtgg tggttctttg agttctctac   1020
tgagaactat attaattctg tcctttaaag gtcgattctt ctcaggaatg gagaaccagg   1080
ttttcctacc cataatcacc agattctgtt taccttccac tgaagaggtt gtggtcattc   1140
tttggaagta cttgaactcg ttcctgagcg gaggccaggg taggtctccg ttcttgccaa   1200
tccccatatt ttgggacacg gcgacgatgc agttcaatgg tcgaaccatg atggcagcgg   1260
ggataaaatc ctaccagcct tcacgctagg attgccgtca agtttggcgc gaaatcgcag   1320
ccctgagctg tcccccccc caagctcaga tctgagcttg gtccctatgg tgagtccgtt    1380
ccgctcttgt gatgatagcc agacaagaaa gagacaatac aagacaaaca ccaaatagta   1440
gaaatagaga caagggtcac ttatccgagg gtccctgttc gggcgccagc tgccgcagtc   1500
ggccgacctg agggtcgccg gggtctgcgg ggggaccctc tggaaagtga aggataagtg   1560
acgagcggag acgggatggc gaacagacac aaacacacaa gaggtgaatg ttaggactgt   1620
tgcaagttta ctcaaaaaat cagcactctt ttatatcttg gtttacataa gcatttacat   1680
aagatttgga taaattccaa aagaacatag gaaaatagaa cactcagagc tcagatcaga   1740
acctttgata ccaaaccaag tcaggaaacc acttgtctca catcctcgtt ttaagaacag   1800
tttgtaacca aaaacttact taagccctgg gaaccgcaag gttgggccaa taaggctat    1860
tcataataac tcatgccatg agtttttgca gaataatgtt ctattagtcc agccactgtc   1920
ccctccttgg tatggaaaat ctttcccccaa aagtgcattc ctgttcctag ataaatataa   1980
tcatgtacct gttgtttcat gtcgtctttt tcttcttgag acaacataca ccaaggaggt   2040
ctagctctgg cgagtctttc acgaaaaggg agggatctat ataacacttt atagccattg   2100
actgtaaccc acctatccca atttaagtca tatcttcctg tatatggtaa gggggcatct   2160
gttggtctgt agatgtaagg tccccctataa gtccctggtt gccaccacct gtctcctatt   2220
ttgacaaaaa cactcttttt tcccttttt acttctaggc ctgtggtcaa tagtccttgc   2280
acctgttctt caattgaggt tgagcgtctc tttctatttt ctattcccat ttctaacttc   2340
tgaatttgag taaaaatagt actaaaagat aatgattcat ttcttaacat agtaactaat   2400
aatctaccta ttggattggt cttattggta aaaatataat ttttagcaag cattcttatt   2460
tctatttctg aaggacaaaa tcgatgcggc ttgtaagagg aagttggctg tggtccttgc   2520
ctcaggagga aggtcgagtt ctccgaattg tttagattgt aatcttgcac agaagagcta   2580
ttaaaagagt caagggtgag agccctgcga gcacgaaccg caacttcccc caatagcccc   2640
aggcaaagca gagctatgcc aagtttgcag cagagaatga atatgtcttt gtctgatggg   2700
ctcatccgtt tgtgcgcaga cgggtcgtcc ttggtgggaa acaacccctt ggctgcttct   2760
cccctaggtg taggacactc tcgggagttc aaccatttct gcccaagctc agatctgagc   2820
tttaatgcgg tagtttatca cagttaaatt gctaacgcag tcaggcaccg tgtatgaaat   2880
ctaacaatgc gctcatcgtc atcctcggca ccgtcaccct ggatgctgta ggcataggct   2940
tggttatgcc ggtactgccg ggcctcttgc gggatatcgt ccattccgac agcatcgcca   3000
gtcactatgg cgtgctgcta gcgctcttcc gcttcctcgc tcactgactc gctgcgctcg   3060
gtcgttcggc tgcggcgagc ggtatcagct cactcaaagg cggtaatacg gttatccaca   3120
gaatcagggg ataacgcagg aaagaacatg tgagcaaaag gccagcaaaa ggccaggaac   3180
cgtaaaaagg ccgcgttgct ggcgtttttc cataggctcc gcccccctga cgagcatcac   3240
aaaaatcgac gctcaagtca gaggtggcga aacccgacag gactataaag ataccaggcg   3300
```

```
tttcccctg gaagctccct cgtgcgctct cctgttccga ccctgccgct taccggatac   3360
ctgtccgcct ttctcccttc gggaagcgtg gcgctttctc atagctcacg ctgtaggtat   3420
ctcagttcgg tgtaggtcgt tcgctccaag ctgggctgtg tgcacgaacc ccccgttcag   3480
cccgaccgct gcgccttatc cggtaactat cgtcttgagt ccaacccggt aagacacgac   3540
ttatcgccac tggcagcagc cactggtaac aggattagca gagcgaggta tgtaggcggt   3600
gctacagagt tcttgaagtg gtggcctaac tacggctaca ctagaaggac agtatttggt   3660
atctgcgctc tgctgaagcc agttaccttc ggaaaaagag ttggtagctc ttgatccggc   3720
aaacaaacca ccgctggtag cggtggtttt tttgtttgca agcagcagat tacgcgcaga   3780
aaaaaaggat ctcaagaaga tcctttgatc ttttctacgg gtctgacgc tcagtggaac   3840 gaaaactcac gttaagggat tttggtcatg agattatcaa aaaggatctt cacctagatc   3900
cttttaaatt aaaaatgaag ttttaaatca atctaaagta tatatgagta aacttggtct   3960
gacagttacc aatgcttaat cagtgaggca cctatctcag cgatctgtct atttcgttca   4020
tccatagttg cctgactccc cgtcgtgtag ataactacga tacgggaggg cttaccatct   4080
ggccccagtg ctgcaatgat accgcgagac ccacgctcac cggctccaga tttatcagca   4140
ataaaccagc cagccggaag ggccgagcgc agaagtggtc ctgcaacttt atccgcctcc   4200
atccagtcta ttaattgttg ccgggaagct agagtaagta gttcgccagt taatagtttg   4260
cgcaacgttg ttgccattgc tacaggcatc gtggtgtcac gctcgtcgtt tggtatggct   4320
tcattcagct ccggttccca acgatcaagg cgagttacat gatcccccat gttgtgcaaa   4380
aaagcggtta gctccttcgg tcctccgatc gttgtcagaa gtaagttggc cgcagtgtta   4440
tcactcatgg ttatggcagc actgcataat tctcttactg tcatgccatc cgtaagatgc   4500
ttttctgtga ctggtgagta ctcaaccaag tcattctgag aatagtgtat gcggcgaccg   4560
agttgctctt gcccggcgtc aacacggat aataccgcgc cacatagcag aactttaaaa   4620
gtgctcatca ttggaaaacg ttcttcgggg cgaaaactct caaggatctt accgctgttg   4680
agatccagtt cgatgtaacc cactcgtgca cccaactgat cttcagcatc ttttactttc   4740
accagcgttt ctgggtgagc aaaaacagga aggcaaaatg ccgcaaaaaa gggaataagg   4800
gcgacacgga aatgttgaat actcatactc ttcctttttc aatattattg aagcatttat   4860
cagggttatt gtctcatgag cggatacata tttgaatgta tttagaaaaa taaacaaata   4920
ggggttccgc gcacatttcc ccgaaaagtg ccacctgacg tctaagagac cattattatc   4980
atgacattaa cctataaaaa taggcgtatc acgaggccct ttcgtcttca agaattgtct   5040
agaggcgcgc cgtttaaacc ctcagctacc gatgtacggg ccagatatac gcgttgacat   5100
tgattattga ctagttatta atagtaatca attacggggt cattagttca tagcccatat   5160
atggagttcc gcgttacata acttacggta atggcccgc ctggctgacc gcccaacgac   5220
ccccgcccat tgacgtcaat aatgacgtat gttcccatag taacgccaat agggactttc   5280
cattgacgtc aatgggtgga ctatttacgg taaactgccc acttggcagt acatcaagtg   5340
tatcatatgc caagtacgcc ccctattgac gtcaatgacg gtaaatggcc cgcctggcat   5400
tatgcccagt acatgacctt atgggacttt cctacttggc agtacatcta cgtattagtc   5460
atcgctatta ccatggtgat gcggttttgg cagtacatca atgggcgtgg atagcggttt   5520
gactcacggg gatttccaag tctccacccc attgacgtca atgggagttt gttttggcac   5580
caaaatcaac gggactttcc aaaatgtcgt aacaactccg ccccattgac gcaaatgggc   5640
ggtaggcgtg tacggtggga ggtctatata agcagagctc tctggctaac tagagaaccc   5700
```

```
actgcttact ggcttatcga aattaatacg actcactata gcaattgcac gtgtggccac   5760
aggtaagttt aaagctcagg tcgagaccgg gcctttgtcc ggcgctccct tggagcctac   5820
ctagactcag ccggctctcc acgctttgcc tgaccctgct tgctcaactc tacgtctttg   5880
tttcgttttc tgttcctttc tctccacagg cttaagctcg aggccgccac catggctgtg   5940
ctggggctgc tgttctgcct ggtgacattc ccaagctgtg tgctgtccca ggtgcagctg   6000
gtgcagtctg gcgctgaggt gaagaagcct ggcgcctccg tgaaggtctc ctgcaaggct   6060
tctggctaca tcttcatcac ctactggatg acctgggtgc ggcaggcccc tggccagggg   6120
ctggagtgga tgggccagat cttccctgcc agcggctctg cagactacaa cgagaagttc   6180
gaaggcagag tcaccatgac cacagacaca tccaccagca cagcctacat ggagctgagg   6240
agcctgagat ctgacgacac cgccgtgtat tactgtgcca gaggcggtgg cggattcgct   6300
tactggggcc agggcaccct ggtcaccgtc tccagcgcta gcaccaaggg cccatcggtc   6360
ttccccctgg cacctcctc caagagcacc tctgggggca gcggccct gggctgcctg   6420 gtcaaggact acttccccga accggtgacg gtgtcgtgga actcaggcgc cctgaccagc   6480
ggcgtgcaca ccttcccggc tgtcctacag tcctcaggac tctactccct cagcagcgtg   6540
gtgaccgtgc cctccagcag cttgggcacc cagacctaca tctgcaacgt gaatcacaag   6600
cccagcaaca ccaaggtgga caagaaagtt gagcccaaat cttgtgacaa aactcacaca   6660
tgcccaccgt gcccagcacc tgaactcctg ggggaccgt cagtcttcct cttccccca   6720 aaacccaagg acaccctcat gatctcccgg acccctgagg tcacatgcgt ggtggtggac   6780
gtgagccacg aagaccctga ggtcaagttc aactggtacg tggacggcgt ggaggtgcat   6840
aatgccaaga caaagccgcg ggaggagcag tacaacagca cgtaccgtgt ggtcagcgtc   6900
ctcaccgtcc tgcaccagga ctggctgaat ggcaaggagt acaagtgcaa ggtctccaac   6960
aaagccctcc cagcccccat cgagaaaacc atctccaaag ccaaaggca gccccgagaa   7020 ccacaggtgt acaccctgcc cccatcccgg gatgagctga ccaagaacca ggtcagcctg   7080
acctgcctgg tcaaaggctt ctatcccagc gacatcgccg tggagtggga gagcaatggg   7140
cagccggaga caactacaa gaccacgcct cccgtgctgg actccgacgg ctccttcttc   7200
ctctacagca agctcaccgt ggacaagagc aggtggcagc aggggaacgt cttctcatgc   7260
tccgtgatgc atgaggctct gcacaaccac tacacgcaga agagcctctc cctgtctccg   7320
ggtaaatgaa tcgatgattc tagatacggg tccggaggat ccagatcccc ctcgctttct   7380
tgctgtccaa tttctattaa aggttccttt gttccctaag tccaactact aaactggggg   7440
atattatgaa gggccttgag catctggatt ctgcctaata aaaaacattt attttcattg   7500
caatgatgta tttaaattat ttctgaatat tttactaaaa agggaatgtg ggaggtcagt   7560
gcatttaaaa cataaagaaa tgaagagggg gatctgtcga caagctctag agagctcacg   7620
cgttgatcat gtacaggccg gccaagcttt cgactagctt ggcacgccag aaatccgcgc   7680
ggtggttttt gggggtcggg ggtgtttggc agccacagac gcccggtgtt cgtgtcgcgc   7740
cagtacatgc ggtccatgcc caggccatcc aaaaaccatg ggtctgtctg ctcagtccag   7800
tcgtggacct gacccacgc aacgcccaaa ataataaccc ccacgaacca taaaccattc   7860
cccatggggg acccgtccc taaccacgg ggccagtggc tatggcaggg cctgccgccc   7920
cgacgttggc tgcgagccct gggccttcac ccgaacttgg ggggtggggt gggaaaagg   7980 aagaaacgcg gccgtattgg ccccaatggg gtctcggtgg ggtatcgaca gagtgccagc   8040
cctgggaccg aaccccgcgt ttatgaacaa acgacccaac acccgtgcgt tttattctgt   8100
```

```
cttttttattg ccgtcatagc gcgggttcct tccggtattg tctccttccg tgtttcagtt    8160
agcctccccc atctcccgat ccggacgagt gctggggcgt cggtttccac tatcggcgag    8220
tacttctaca cagccatcgg tccagacggc cgcgcttctg cgggcgattt gtgtacgccc    8280
gacagtcccg gctccggatc ggacgattgc gtcgcatcga ccctgcgccc aagctgcatc    8340
atcgaaattg ccgtcaacca agctctgata gagttggtca agaccaatgc ggagcatata    8400
cgcccggagc cgcggcgatc ctgcaagctc cggatgcctc cgctcgaagt agcgcgtctg    8460
ctgctccata caagccaacc acggcctcca gaagaagatg ttggcgacct cgtattggga    8520
atccccgaac atcgcctcgc tccagtcaat gaccgctgtt atgcggccat tgtccgtcag    8580
gacattgttg gagccgaaat ccgcgtgcac gaggtgccgg acttcggggc agtcctcggc    8640
ccaaagcatc agctcatcga gagcctgcgc gacgacgcga ctgacggtgt cgtccatcac    8700
agtttgccag tgatacacat ggggatcagc aatcgcgcat atgaaatcac gccatgtagt    8760
gtattgaccg attccttgcg gtccgaatgg gccgaacccg ctcgtctggc taagatcggc    8820
cgcagcgatc gcatccatgg cctccgcgac cggctgcaga acagcgggca gttcggtttc    8880
aggcaggtct tgcaacgtga caccctgtgc acggcgggga atgcaatagg tcaggctctc    8940
gctgaattcc ccaatgtcaa gcacttccgg aatcgggagc gcggccgatg caaagtgccg    9000
ataaacataa cgatctttgt agaaaccatc ggcgcagcta tttacccgca ggacatatcc    9060
acgccctcct acatcgaagc tgaaagcacg agattcttcg ccctccgaga gctgcatcag    9120
gtcggagacg ctgtcgaact tttcgatcag aaacttctcg acagacgtcg cggtgagttc    9180
aggctttttc atatctcatt gccccccggg atctgcggca cgctgttgac gctgttaagc    9240
gggtcgctgc agggtcgctc ggtgttcgag gccacacgcg tcaccttaat atgcgaagtg    9300
gacctcggac cgcgccgccc cgactgcatc tgcgtgttcg aattcgccaa tgacaagacg    9360
ctgggcgggg tttgtgtcat catagaacta aagacatgca aatatatttc ttccggggac    9420
accgccagca aacgcgagca acgggccacg gggatgaagc agggcggcac ctcgctaacg    9480
gattcaccac tccaagaatt ggagccaatc aattcttgcg gagaactgtg aatgcgcaaa    9540
ccaacccttg gcagaacata tccatcgcgt ccgccatctc cagcagccgc acgcggcgca    9600
tctcggggcc gacgcgctgg gctacgtctt gctggcgttc gcacaggccg gccagcgcgc    9660
ggccggccgg taccacgcgt tggccacata tggcggccgc tcgcgattaa ttaatcgcga    9720
tggccacata tggagctctc tagagcttgt cgacagatcc ccctcttcat ttctttatgt    9780
tttaaatgca ctgacctccc acattccctt tttagtaaaa tattcagaaa taatttaaat    9840
acatcattgc aatgaaaata aatgtttttt attaggcaga atccagatgc tcaaggccct    9900
tcataatatc ccccagttta gtagttggac ttagggaaca aaggaacctt taatagaaat    9960
tggacagcaa gaaagcgagg gggatctgga tcctcctacg tatctagaat catcgattaa   10020
cactctcccc tgttgaagct ctttgtcacg gggctgctca ggccctgatg ggtcacctcg   10080
caggcgtaca cctttgtgttt ctcgtagtct gctttgctca gggtcagggt gctgctcagg   10140
ctgtaggtgc tgtccttgct gtcctgctct gtcacgctct cctgggagtt gccgctctgg   10200
agggcgttat ccaccttcca ctgcaccttg gcctctctgg gatagaagtt attcagcagg   10260
cacaccacgg aggcagttcc agacttcagc tgctcatcga atggagggaa gatgaacaca   10320
gatggtgcag ccaccgtacg cttgatctcc accttggtgc cctggccgaa ggtgaatgga   10380
attccgtagt ggtgctgaca gtagtaggtg gcgaagtcct caggctgcag gctgctgatg   10440
gtcagggtga agtctgtccc agagccgctg ccgctgaacc tggatggcac cccttcagcc   10500
```

| | | |
|---|---|---|
| agggtcttgg cgttatagat cagcagctta ggggccttcc ctggcttctg ctgataccag | 10560 |
| gccaggtagc tgtagatgtt ctcgctggtc ctgcaggtga tggtcactct gtcgcccaca | 10620 |
| gaggcagaca gggaggatgg agactgggtc atctggatat cacatctcat ggctggcagg | 10680 |
| aacagcacca gcagccccag cagctgcact ggagccatgg tggcggcctc gagaagctta | 10740 |
| agtttaattc ttaagcctgt ggagagaaag aacagaaaa cgaaacaaag acgtagagtt | 10800 |
| gagcaagcag ggtcaggcaa agcgtggaga gccggctgag tctaggtagg ctccaaggga | 10860 |
| gcgccggaca aaggcccggt ctcgacctga gctttaaact tacctgtggc cacacgtgca | 10920 |
| attgctatag tgagtcgtat taatttcgat aagccagtaa gcagtgggtt ctctagttag | 10980 |
| ccagagagct ctgcttatat agacctccca ccgtacacgc ctaccgccca tttgcgtcaa | 11040 |
| tggggcggag ttgttacgac attttggaaa gtcccgttga ttttggtgcc aaaacaaact | 11100 |
| cccattgacg tcaatggggt ggagacttgg aaatccccgt gagtcaaacc gctatccacg | 11160 |
| cccattgatg tactgccaaa accgcatcac catggtaata gcgatgacta atacgtagat | 11220 |
| gtactgccaa gtaggaaagt cccataaggt catgtactgg gcataatgcc aggcgggcca | 11280 |
| tttaccgtca ttgacgtcaa taggggggcgt acttggcata tgatacactt gatgtactgc | 11340 |
| caagtgggca gtttaccgta aatagtccac ccattgacgt caatggaaag tccctattgg | 11400 |
| cgttactatg ggaacatacg tcattattga cgtcaatggg cggggtcgt tgggcggtca | 11460 |
| gccaggcggg ccatttaccg taagttatgt aacgcggaac tccatatatg gctatgaac | 11520 |
| taatgacccc gtaattgatt actattaata actagtcaat aatcaatgtc aacgcgtata | 11580 |
| tctggcccgt acatcggtaa ctagtcggac cggcccgggc caccggtgct cgaagcttgg | 11640 |
| atcgatccag acatgataag atacattgat gagtttggac aaaccacaac tagaatgcag | 11700 |
| tgaaaaaaat gctttatttg tgaaatttgt gatgctattg ctttatttgt aaccattata | 11760 |
| agctgcaata aacaagttaa caacaacaat tgcattcatt ttatgtttca ggttcagggg | 11820 |
| gaggtgtggg aggtttttta aagcaagtaa aacctctaca aatgtggtat ggctgattat | 11880 |
| gatctctagt caa | 11893 |

<210> SEQ ID NO 45
<211> LENGTH: 11901
<212> TYPE: DNA
<213> ORGANISM: Artificial Sequence
<220> FEATURE:
<223> OTHER INFORMATION: pAIL23RV1 plasmid sequence

<400> SEQUENCE: 45

| | | |
|---|---|---|
| ggcactatac atcaaatatt ccttattaac ccctttacaa attaaaaagc taaaggtaca | 60 |
| caatttttga gcatagttat taatagcaga cactctatgc ctgtgtggag taagaaaaaa | 120 |
| cagtatgtta tgattataac tgttatgcct acttataaag gttacagaat attttttccat | 180 |
| aattttcttg tatagcagtg cagcttttc ctttgtggtg taaatagcaa agcaagcaag | 240 |
| agttctatta ctaaacacag catgactcaa aaaacttagc aattctgaag gaaagtcctt | 300 |
| ggggtcttct accttttctct tctttttttgg aggagtagaa tgttgagagt cagcagtagc | 360 |
| ctcatcatca ctagatggca tttcttctga gcaaaacagg ttttcctcat taaaggcatt | 420 |
| ccaccactgc tcccattcat cagttccata ggttggaatc taaatacac aaacaattag | 480 |
| aatcagtagt ttaacacatt atacacttaa aaatttata tttaccttag agctttaaat | 540 |
| ctctgtaggt agtttgtcca attatgtcac accacagaag taaggttcct tcacaaagat | 600 |
| cgatctaaag ccagcaaaag tcccatggtc ttataaaaat gcatagcttt aggagggag | 660 |

```
cagagaactt gaaagcatct tcctgttagt ctttcttctc gtagacttca aacttatact    720
tgatgccttt ttcctcctgg acctcagaga ggacgcctgg gtattctggg agaagtttat    780
atttccccaa atcaatttct gggaaaaacg tgtcactttc aaattcctgc atgatccttg    840
tcacaaagag tctgaggtgg cctggttgat tcatggcttc ctggtaaaca gaactgcctc    900
cgactatcca aaccatgtct actttacttg ccaattccgg ttgttcaata agtcttaagg    960
catcatccaa acttttggca agaaaatgag ctcctcgtgg tggttctttg agttctctac   1020
tgagaactat attaattctg tcctttaaag gtcgattctt ctcaggaatg gagaaccagg   1080
ttttcctacc cataatcacc agattctgtt taccttccac tgaagaggtt gtggtcattc   1140
tttggaagta cttgaactcg ttcctgagcg gaggccaggg taggtctccg ttcttgccaa   1200
tccccatatt ttgggacacg gcgacgatgc agttcaatgg tcgaaccatg atggcagcgg   1260
ggataaaatc ctaccagcct tcacgctagg attgccgtca agtttggcgc gaaatcgcag   1320
ccctgagctg tcccccccccc caagctcaga tctgagcttg gtccctatgg tgagtccgtt   1380
ccgctcttgt gatgatagcc agacaagaaa gagacaatac aagacaaaca ccaaatagta   1440
gaaatagaga caagggtcac ttatccgagg gtccctgttc gggcgccagc tgccgcagtc   1500
ggccgacctg agggtcgccg gggtctgcgg ggggacccctc tggaaagtga aggataagtg   1560
acgagcggag acgggatggc gaacagacac aaacacacaa gaggtgaatg ttaggactgt   1620
tgcaagttta ctcaaaaaat cagcactctt ttatatcttg gtttacataa gcatttacat   1680
aagatttgga taaattccaa aagaacatag gaaaatagaa cactcagagc tcagatcaga   1740
acctttgata ccaaaccaag tcaggaaacc acttgtctca catcctcgtt ttaagaacag   1800
tttgtaacca aaaacttact taagccctgg gaaccgcaag gttgggccaa taaaggctat   1860
tcataataac tcatgccatg agttttgca gaataatgtt ctattagtcc agccactgtc   1920
ccctccttgg tatggaaaat cttccccaa aagtgcattc ctgttcctag ataaatataa   1980
tcatgtacct gttgtttcat gtcgtctttt tcttcttgag acaacataca ccaaggaggt   2040
ctagctctgg cgagtctttc acgaaaaggg agggatctat ataacacttt atagccattg   2100
actgtaaccc acctatccca atttaagtca tatcttcctg tatatggtaa gggggcatct   2160
gttggtctgt agatgtaagg tcccctataa gtccctggtt gccaccacct gtctcctatt   2220
ttgacaaaaa cactctttt tccctttttt acttctaggc ctgtggtcaa tagtccttgc   2280
acctgttctt caattgaggt tgagcgtctc tttctatttt ctattcccat ttctaacttc   2340
tgaatttgag taaaaatagt actaaaagat aatgattcat ttcttaacat agtaactaat   2400
aatctaccta ttggattggt cttattggta aaaatataat ttttagcaag cattcttatt   2460
tctatttctg aaggacaaaa tcgatgcggc ttgtaagagg aagttggctg tggtccttgc   2520
ctcaggagga aggtcgagtt ctccgaattg tttagattgt aatcttgcac agaagagcta   2580
ttaaaagagt caagggtgag agccctgcga gcacgaaccg caacttcccc caatagcccc   2640
aggcaaagca gagctatgcc aagtttgcag cagagaatga atatgtcttt gtctgatggg   2700
ctcatccgtt tgtgcgcaga cgggtcgtcc ttggtgggaa acaaccccctt ggctgcttct   2760 cccctaggtg taggacactc tcgggagttc aaccatttct gcccaagctc agatctgagc   2820
tttaatgcgg tagtttatca cagttaaatt gctaacgcag tcaggcaccg tgtatgaaat   2880
ctaacaatgc gctcatcgtc atcctcggca ccgtcaccct ggatgctgta ggcataggct   2940
tggttatgcc ggtactgccg ggcctcttgc gggatatcgt ccattccgac agcatcgcca   3000
gtcactatgg cgtgctgcta gcgctcttcc gcttcctcgc tcactgactc gctgcgctcg   3060
```

```
gtcgttcggc tgcggcgagc ggtatcagct cactcaaagg cggtaatacg gttatccaca   3120
gaatcagggg ataacgcagg aaagaacatg tgagcaaaag gccagcaaaa ggccaggaac   3180
cgtaaaaagg ccgcgttgct ggcgtttttc cataggctcc gcccccctga cgagcatcac   3240
aaaaatcgac gctcaagtca gaggtggcga acccgacag gactataaag ataccaggcg    3300
tttccccctg gaagctccct cgtgcgctct cctgttccga ccctgccgct taccggatac   3360
ctgtccgcct ttctcccttc gggaagcgtg gcgctttctc atagctcacg ctgtaggtat   3420
ctcagttcgg tgtaggtcgt tcgctccaag ctgggctgtg tgcacgaacc ccccgttcag   3480
cccgaccgct gcgccttatc cggtaactat cgtcttgagt ccaacccggt aagacacgac   3540
ttatcgccac tggcagcagc cactggtaac aggattagca gagcgaggta tgtaggcggt   3600
gctacagagt tcttgaagtg gtggcctaac tacggctaca ctagaaggac agtatttggt   3660
atctgcgctc tgctgaagcc agttaccttc ggaaaaagag ttggtagctc ttgatccggc   3720
aaacaaacca ccgctggtag cggtggtttt tttgtttgca agcagcagat tacgcgcaga   3780
aaaaaaggat ctcaagaaga tcctttgatc ttttctacgg ggtctgacgc tcagtggaac   3840
gaaaactcac gttaagggat tttggtcatg agattatcaa aaaggatctt cacctagatc   3900
cttttaaatt aaaaatgaag ttttaaatca atctaaagta tatatgagta aacttggtct   3960
gacagttacc aatgcttaat cagtgaggca cctatctcag cgatctgtct atttcgttca   4020
tccatagttg cctgactccc cgtcgtgtag ataactacga tacgggaggg cttaccatct   4080
ggccccagtg ctgcaatgat accgcgagac ccacgctcac cggctccaga tttatcagca   4140
ataaaccagc cagccggaag ggccgagcgc agaagtggtc ctgcaacttt atccgcctcc   4200
atccagtcta ttaattgttg ccgggaagct agagtaagta gttcgccagt taatagtttg   4260
cgcaacgttg ttgccattgc tacaggcatc gtggtgtcac gctcgtcgtt tggtatggct   4320
tcattcagct ccggttccca acgatcaagg cgagttacat gatcccccat gttgtgcaaa   4380
aaagcggtta gctccttcgg tcctccgatc gttgtcagaa gtaagttggc cgcagtgtta   4440
tcactcatgg ttatggcagc actgcataat tctcttactg tcatgccatc cgtaagatgc   4500
ttttctgtga ctggtgagta ctcaaccaag tcattctgag aatagtgtat gcggcgaccg   4560
agttgctctt gcccggcgtc aacacgggat aataccgcgc cacatagcag aactttaaaa   4620
gtgctcatca ttggaaaacg ttcttcgggg cgaaaactct caaggatctt accgctgttg   4680
agatccagtt cgatgtaacc cactcgtgca cccaactgat cttcagcatc ttttactttc   4740
accagcgttt ctgggtgagc aaaaacagga aggcaaaatg ccgcaaaaaa gggaataagg   4800
gcgacacgga aatgttgaat actcatactc ttcctttttc aatattattg aagcatttat   4860
cagggttatt gtctcatgag cggatacata tttgaatgta tttagaaaaa taaacaaata   4920
ggggttccgc gcacatttcc ccgaaaagtg ccacctgacg tctaagagac cattattatc   4980
atgacattaa cctataaaaa taggcgtatc acgaggccct ttcgtcttca agaattgtct   5040
agaggcgcgc cgtttaaacc ctcagctacc gatgtacggg ccagatatac gcgttgacat   5100
tgattattga ctagttatta atagtaatca attacgggt cattagttca tagcccatat    5160
atggagttcc gcgttacata acttacggta aatggcccgc ctggctgacc gcccaacgac   5220
ccccgcccat tgacgtcaat aatgacgtat gttcccatag taacgccaat agggactttc   5280
cattgacgtc aatgggtgga ctatttacgg taaactgccc acttggcagt acatcaagtg   5340
tatcatatgc caagtacgcc ccctattgac gtcaatgacg gtaaatggcc cgcctggcat   5400
tatgcccagt acatgacctt atgggacttt cctacttggc agtacatcta cgtattagtc   5460
```

```
atcgctatta ccatggtgat gcggttttgg cagtacatca atgggcgtgg atagcggttt    5520
gactcacggg gatttccaag tctccacccc attgacgtca atgggagttt gttttggcac    5580
caaaatcaac gggactttcc aaaatgtcgt aacaactccg ccccattgac gcaaatgggc    5640
ggtaggcgtg tacggtggga ggtctatata agcagagctc tctggctaac tagagaaccc    5700
actgcttact ggcttatcga aattaatacg actcactata gcaattgcac gtgtggccac    5760
aggtaagttt aaagctcagg tcgagaccgg gcctttgtcc ggcgctccct tggagcctac    5820
ctagactcag ccggctctcc acgctttgcc tgaccctgct tgctcaactc tacgtctttg    5880
tttcgttttc tgttcctttc tctccacagg cttaagctcg aggccgccac catggctgtg    5940
ctggggctgc tgttctgcct ggtgacattc ccaagctgtg tgctgtccca ggtgcagctg    6000
gtgcagtctg gcgctgaggt gaagaagcct ggcgcctccg tgaaggtctc ctgcaaggct    6060
tctggctaca cattcaccaa ctacgctatg aactgggtgc ggcaggcccc tggccagggg    6120
ctggagtgga tgggctggat caacacttac accggtgagc aacctacag cgacgacttc     6180 aagggcagag tcaccttcac cctggacaca tccaccagca cagcctacat ggagctgagg    6240
agcctgagat ctgacgacac cgccgtgtat tactgtgcca gaggtggagg ctacgatgag    6300
gactacttcg actactgggg ccagggcacc ctggtcaccg tctccagcgc tagcaccaag    6360
ggcccatcgg tcttccccct ggcaccctcc tccaagagca cctctggggg cacagcggcc    6420
ctgggctgcc tggtcaagga ctacttcccc gaaccggtga cggtgtcgtg gaactcaggc    6480
gccctgacca gcggcgtgca caccttcccg gctgtcctac agtcctcagg actctactcc    6540
ctcagcagcg tggtgaccgt gccctccagc agcttgggca cccagaccta catctgcaac    6600
gtgaatcaca agcccagcaa caccaaggtg gacaagaaag ttgagcccaa atcttgtgac    6660
aaaactcaca catgcccacc gtgcccagca cctgaactcc tggggggacc gtcagtcttc    6720
ctcttccccc caaaacccaa ggacaccctc atgatctccc ggacccctga ggtcacatgc    6780
gtggtggtgg acgtgagcca cgaagaccct gaggtcaagt tcaactggta cgtggacggc    6840
gtggaggtgc ataatgccaa gacaaagccg cgggaggagc agtacaacag cacgtaccgt    6900
gtggtcagcg tcctcaccgt cctgcaccag gactggctga atggcaagga gtacaagtgc    6960
aaggtctcca acaaagccct cccagccccc atcgagaaaa ccatctccaa agccaaaggg    7020
cagccccgag aaccacaggt gtacaccctg cccccatccc gggatgagct gaccaagaac    7080
caggtcagcc tgacctgcct ggtcaaaggc ttctatccca gcgacatcgc cgtggagtgg    7140
gagagcaatg ggcagccgga gaacaactac aagaccacgc ctcccgtgct ggactccgac    7200
ggctccttct tcctctacag caagctcacc gtggacaaga gcaggtggca gcagggggaac    7260 gtcttctcat gctccgtgat gcatgaggct ctgcacaacc actacacgca gaagagcctc    7320
tccctgtctc cgggtaaata aatcgatgat tctagatacg ggtccggagg atccagatcc    7380
ccctcgcttt cttgctgtcc aatttctatt aaaggttcct tgttcccta agtccaacta     7440 ctaaactggg ggatattatg aagggccttg agcatctgga ttctgcctaa taaaaaacat    7500
ttattttcat tgcaatgatg tatttaaatt atttctgaat attttactaa aagggaatg    7560 tgggaggtca gtgcatttaa acataaaga aatgaagagg gggatctgtc gacaagctct     7620
agagagctca cgcgttgatc atgtacaggc cggccaagct ttcgactagc ttggcacgcc    7680
agaaatccgc gcggtggttt ttgggggtcg ggggtgtttg gcagccacag acgcccggtg    7740
ttcgtgtcgc gccagtacat gcggtccatg cccaggccat ccaaaaacca tgggtctgtc    7800
tgctcagtcc agtcgtggac ctgaccccac gcaacgccca aataataac ccccacgaac    7860
```

```
cataaaccat tccccatggg ggaccccgtc cctaacccac ggggccagtg gctatggcag      7920
ggcctgccgc cccgacgttg gctgcgagcc ctgggccttc acccgaactt gggggtggg       7980 gtggggaaaa ggaagaaacg cgggcgtatt ggccccaatg gggtctcggt ggggtatcga      8040
cagagtgcca gccctgggac cgaacccgc gtttatgaac aaacgaccca acacccgtgc       8100
gttttattct gtcttttat tgccgtcata gcgcgggttc cttccggtat tgtctccttc       8160
cgtgtttcag ttagcctccc ccatctcccg atccggacga gtgctggggc gtcggtttcc      8220
actatcggcg agtacttcta cacagccatc ggtccagacg gccgcgcttc tgcgggcgat      8280
ttgtgtacgc ccgacagtcc cggctccgga tcggacgatt gcgtcgcatc gaccctgcgc      8340
ccaagctgca tcatcgaaat tgccgtcaac caagctctga tagagttggt caagaccaat      8400
gcggagcata tacgcccgga gccgcggcga tcctgcaagc tccggatgcc tccgctcgaa      8460
gtagcgcgtc tgctgctcca tacaagccaa ccacggcctc cagaagaaga tgttggcgac      8520
ctcgtattgg gaatccccga acatcgcctc gctccagtca atgaccgctg ttatgcggcc      8580
attgtccgtc aggacattgt tggagccgaa atccgcgtgc acgaggtgcc ggacttcggg      8640
gcagtcctcg gcccaaagca tcagctcatc gagagcctgc gcgacggacg cactgacggt      8700
gtcgtccatc acagtttgcc agtgatacac atggggatca gcaatcgcgc atatgaaatc      8760
acgccatgta gtgtattgac cgattccttg cggtccgaat gggccgaacc cgctcgtctg      8820
gctaagatcg gccgcagcga tcgcatccat ggcctccgcg accggctgca gaacagcggg      8880
cagttcggtt tcaggcaggt cttgcaacgt gacaccctgt gcacggcggg agatgcaata      8940
ggtcaggctc tcgctgaatt ccccaatgtc aagcacttcc ggaatcggga gcgcggccga      9000
tgcaaagtgc cgataaacat aacgatcttt gtagaaacca tcggcgcagc tatttacccg      9060
caggacatat ccacgccctc ctacatcgaa gctgaaagca cgagattctt cgccctccga      9120
gagctgcatc aggtcggaga cgctgtcgaa cttttcgatc agaaacttct cgacagacgt      9180
cgcggtgagt tcaggctttt tcatatctca ttgcccccg ggatctgcgg cacgctgttg       9240
acgctgttaa gcgggtcgct gcagggtcgc tcggtgttcg aggccacacg cgtcacctta      9300
atatgcgaag tggacctcgg accgcgccgc cccgactgca tctgcgtgtt cgaattcgcc      9360
aatgacaaga cgctgggcgg ggtttgtgtc atcatagaac taaagacatg caaatatatt      9420
tcttccgggg acaccgccag caaacgcgag caacgggcca cggggatgaa gcagggcggc      9480
acctcgctaa cggattcacc actccaagaa ttggagccaa tcaattcttg cggagaactg      9540
tgaatgcgca aaccaaccct tggcagaaca tatccatcgc gtccgccatc tccagcagcc      9600
gcacgcggcg catctcgggg ccgacgcgct gggctacgtc ttgctggcgt tcgcacaggc      9660
cggccagcgc gcggccggcc ggtaccacgc gttggccaca tatggcggcc gctcgcgatt      9720
aattaatcgc gatggccaca tatgagctc tctagagctt gtcgacagat cccctcttc       9780 atttctttat gttttaaatg cactgacctc ccacattccc tttttagtaa aatattcaga     9840
aataatttaa atacatcatt gcaatgaaaa taaatgtttt ttattaggca gaatccagat     9900
gctcaaggcc cttcataata tcccccagtt tagtagttgg acttagggaa caaaggaacc     9960
tttaatagaa attggacagc aagaaagcga gggggatctg gatcctttaa cactctcccc     10020
tgttgaagct ctttgtgacg ggcgagctca ggccctgatg ggtgacttcg caggcgtaga    10080
ctttgtgttt ctcgtagtct gctttgctca gcgtcagggt gctgctgagg ctgtaggtgc    10140
tgtccttgct gtcctgctct gtgacactct cctgggagtt acccgattgg agggcgttat    10200
ccaccttcca ctgtactttg gcctctctgg gatagaagtt attcagcagg cacacaacag    10260
```

```
aggcagttcc agatttcaac tgctcatcag atggcgggaa gatgaagaca gatggtgcag      10320
ccaccgtacg tttgatttcc accttggtcc cctgtccaaa ggtccatggt gtgtcatagt      10380
gctgctgaca gtagtacacg cccacatctt cggcctccac ccggctgatc ttcagagtga      10440
aatctgtccc agatccgctg ccgctgaacc tgtctggcac cccgctctcg cgagtgctgg      10500
cgaaatagat cagcagctga gggctctgcc ctggtttctg cagataccag gccaggtagg      10560
tcttctggtt gatggtgttg aacaggctct ggctgctctt gcagctgatg ctggctggct      10620 ctccggggtgt cacaggcagg gacagtggag actgggtcat cacgatatca catctcatgg     10680
ctggcaggaa cagcaccagc agcccagca gctgcactgg agccatggtg gcggcctcga       10740
gaagcttaag tttaattctt aagcctgtgg agagaaagga acagaaacg aaacaaagac       10800 gtagagttga gcaagcaggg tcaggcaaag cgtggagagc cggctgagtc taggtaggct      10860
ccaagggagc gccggacaaa ggcccggtct cgacctgagc tttaaactta cctgtggcca     10920
cacgtgcaat tgctatagtg agtcgtatta atttcgataa gccagtaagc agtgggttct     10980
ctagttagcc agagagctct gcttatatag acctcccacc gtacacgcct accgccatt     11040 tgcgtcaatg gggcggagtt gttacgacat tttggaaagt cccgttgatt ttggtgccaa     11100
aacaaactcc cattgacgtc aatggggtgg agacttggaa atccccgtga gtcaaaccgc      11160
tatccacgcc cattgatgta ctgccaaaac cgcatcacca tggtaatagc gatgactaat      11220
acgtagatgt actgccaagt aggaaagtcc cataaggtca tgtactgggc ataatgccag      11280
gcgggccatt taccgtcatt gacgtcaata ggggcgtac ttggcatatg atacacttga       11340
tgtactgcca agtgggcagt ttaccgtaaa tagtccaccc attgacgtca atggaaagtc      11400
cctattggcg ttactatggg aacatacgtc attattgacg tcaatgggcg ggggtcgttg      11460
ggcggtcagc caggcgggcc atttaccgta agttatgtaa cgcggaactc catatatggg      11520
ctatgaacta atgaccccgt aattgattac tattaataac tagtcaataa tcaatgtcaa      11580
cgcgtatatc tggcccgtac atcggtaact agtcggaccg gcccgggcca ccggtgctcg      11640
aagcttggat cgatccagac atgataagat acattgatga gtttggacaa accacaacta      11700
gaatgcagtg aaaaaaatgc tttatttgtg aaatttgtga tgctattgct ttatttgtaa      11760
ccattataag ctgcaataaa caagttaaca acaacaattg cattcatttt atgtttcagg      11820
ttcaggggga ggtgtgggag gttttttaaa gcaagtaaaa cctctacaaa tgtggtatgg      11880
ctgattatga tctctagtca a                                                11901
```

<210> SEQ ID NO 46
<211> LENGTH: 11922
<212> TYPE: DNA
<213> ORGANISM: Artificial Sequence
<220> FEATURE:
<223> OTHER INFORMATION: pAIL17AV1 plasmid sequence

<400> SEQUENCE: 46

```
gcactataca tcaaatattc cttattaacc cctttacaaa ttaaaaagct aaaggtacac        60 aattttttgag catagttatt aatagcagac actctatgcc tgtgtggagt aagaaaaaac      120
agtatgttat gattataact gttatgccta cttataaagg ttacagaata tttttccata       180
attttcttgt atagcagtgc agcttttttcc tttgtggtgt aaatagcaaa gcaagcaaga     240
gttctattac taaacacagc atgactcaaa aaacttagca attctgaagg aaagtccttg      300
gggtcttcta cctttctctt ctttttttgga ggagtagaat gttgagagtc agcagtagcc      360
tcatcatcac tagatggcat ttcttctgag caaaacaggt tttcctcatt aaaggcattc      420
```

```
caccactgct cccattcatc agttccatag gttggaatct aaaatacaca aacaattaga    480
atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt ccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gttttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag ggggcatctg   2160
ttggtctgta gatgtaaggt cccctataag tccctggttg ccaccacctg tctcctattt   2220
tgacaaaaac actcttttt ccctttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caacccctg gctgcttctc    2760
ccctaggtgt aggacactct cgggagttca accatttctg cccaagctca gatctgagct   2820
```

```
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
aatcagggga taacgcagga agaacatgt gagcaaaagg ccagcaaaag gccaggaacc    3180
gtaaaaaggc cgcgttgctg gcgttttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca cacgggata ataccgcgcc acatagcaga actttaaaag   4620
tgctcatcat tggaaaacgt tcttcgggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct cctttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgcc gtttaaaccc tcagctaccg atgtacgggc cagatatacg cgttgacatt   5100
gattattgac tagttattaa tagtaatcaa ttacggggtc attagttcat agcccatata   5160
tggagttccg cgttacataa cttacggtaa atggcccgcc tggctgaccg cccaacgacc   5220
```

```
cccgcccatt gacgtcaata atgacgtatg ttcccatagt aacgccaata gggactttcc    5280
attgacgtca atgggtggac tatttacggt aaactgccca cttggcagta catcaagtgt    5340
atcatatgcc aagtacgccc cctattgacg tcaatgacgg taaatggccc gcctggcatt    5400
atgcccagta catgacctta tgggactttc ctacttggca gtacatctac gtattagtca    5460
tcgctattac catggtgatg cggttttggc agtacatcaa tgggcgtgga tagcggtttg    5520
actcacgggg atttccaagt ctccacccca ttgacgtcaa tgggagtttg ttttggcacc    5580
aaaatcaacg ggactttcca aaatgtcgta caactccgc cccattgacg caaatgggcg    5640
gtaggcgtgt acggtgggag gtctatataa gcagagctct ctggctaact agagaaccca    5700
ctgcttactg gcttatcgaa attaatacga ctcactatag caattgcacg tgtggccaca    5760
ggtaagttta aagctcaggt cgagaccggg cctttgtccg gcgctccctt ggagcctacc    5820
tagactcagc cggctctcca cgctttgcct gaccctgctt gctcaactct acgtctttgt    5880
ttcgttttct gttcctttct ctccacaggc ttaagagtac tgccgccacc atggctgtgc    5940
tggggctgct gttctgcctg gtgacattcc caagctgtgt gctgtcccag gtgcagctgc    6000
aggagtctgg accaggcctg gtgaagccta gcgagaccct gagcctgacc tgtaccgtgt    6060
ctggattcag cctgcccagc cacagcgtga gctggatcag acagcctcca ggcaagggac    6120
tggagtggat cggcatcatt tggaatcaag gcggcactga ctataacagc gccttcaaga    6180
gccgcgtgac catctccgtg gacacctcca agaaccagtt cagcctgaag ctgagcagcg    6240
tgaccgctgc cgacaccgct gtgtattact gtgccagaaa tgcatacatc accgactact    6300
attacgagaa ctacttcatg gatgcctggg gacagggcac cctggtgacc gtgagctccg    6360
ctagcaccaa gggcccatcg gtcttccccc tggcaccctc ctccaagagc acctctgggg    6420
gcacagcggc cctgggctgc ctggtcaagg actacttccc cgaaccggtg acggtgtcgt    6480
ggaactcagg cgccctgacc agcggcgtgc acaccttccc ggctgtccta cagtcctcag    6540
gactctactc cctcagcagc gtggtgaccg tgccctccag cagcttgggc acccagacct    6600
acatctgcaa cgtgaatcac aagcccagca caccaaggt ggacaagaaa gttgagccca    6660
aatcttgtga caaaactcac acatgcccac cgtgcccagc acctgaactc ctgggggac    6720 cgtcagtctt cctcttcccc ccaaaaccca aggacaccct catgatctcc cggacccctg    6780
aggtcacatg cgtggtggtg gacgtgagcc acgaagaccc tgaggtcaag ttcaactggt    6840
acgtggacgg cgtggaggtg cataatgcca agacaaagcc gcgggaggag cagtacaaca    6900
gcacgtaccg tgtggtcagc gtcctcaccg tcctgcacca ggactggctg aatggcaagg    6960
agtacaagtg caaggtctcc aacaaagccc tcccagcccc catcgagaaa accatctcca    7020
aagccaaagg gcagccccga gaaccacagg tgtacaccct gcccccatcc cgggatgagc    7080
tgaccaagaa ccaggtcagc ctgacctgcc tggtcaaagg cttctatccc agcgacatcg    7140
ccgtggagtg ggagagcaat gggcagccgg agaacaacta caagaccacg cctcccgtgc    7200
tggactccga cggctccttc ttcctctaca gcaagctcac cgtggacaag agcaggtggc    7260 agcagggaa cgtcttctca tgctccgtga tgcatgaggc tctgcacaac cactacacgc    7320
agaagagcct ctccctgtct ccgggtaaat gaatcgatga ttctagatac gggtccggag    7380
gatccagatc cccctcgctt tcttgctgtc caatttctat taaaggttcc tttgttccct    7440
aagtccaact actaaactgg gggatattat gaagggcctt gagcatctgg attctgccta    7500
ataaaaaaca tttattttca ttgcaatgat gtatttaaat tatttctgaa tattttacta    7560
aaaagggaat gtgggaggtc agtgcattta aaacataaag aaatgaagag gggatctgt    7620
```

```
cgacaagctc tagagagctc acgcgttgat catgtacagg ccggccaagc tttcgactag    7680
cttggcacgc cagaaatccg cgcggtggtt tttggggggtc gggggtgttt ggcagccaca    7740
gacgcccggt gttcgtgtcg cgccagtaca tgcggtccat gcccaggcca tccaaaaacc    7800
atgggtctgt ctgctcagtc cagtcgtgga cctgacccca cgcaacgccc aaaataataa    7860
cccccacgaa ccataaacca ttccccatgg ggaccccgt ccctaaccca cggggccagt     7920
ggctatggca gggcctgccg ccccgacgtt ggctgcgagc cctgggcctt cacccgaact    7980 tgggggggtgg ggtggggaaa aggaagaaac gcgggcgtat tggccccaat ggggtctcgg   8040
tggggtatcg acagagtgcc agccctggga ccgaaccccg cgtttatgaa caaacgaccc    8100
aacacccgtg cgttttattc tgtctttta ttgccgtcat agcgcgggtt ccttccggta     8160
ttgtctcctt ccgtgtttca gttagcctcc cccatctccc gatccggacg agtgctgggg   8220
cgtcggtttc cactatcggc gagtacttct acacagccat cggtccagac ggccgcgctt    8280
ctgcgggcga tttgtgtacg cccgacagtc ccggctccgg atcggacgat tgcgtcgcat    8340
cgaccctgcg cccaagctgc atcatcgaaa ttgccgtcaa ccaagctctg atagagttgg    8400
tcaagaccaa tgcggagcat atacgcccgg agccgcggcg atcctgcaag ctccggatgc    8460
ctccgctcga agtagcgcgt ctgctgctcc atacaagcca accacggcct ccagaagaag    8520
atgttggcga cctcgtattg ggaatccccg aacatcgcct cgctccagtc aatgaccgct    8580
gttatgcggc cattgtccgt caggacattg ttggagccga atccgcgtg cacgaggtgc     8640 cggacttcgg ggcagtcctc ggcccaaagc atcagctcat cgagagcctg cgcgacggac   8700
gcactgacgg tgtcgtccat cacagtttgc cagtgataca catgggatc agcaatcgcg     8760 catatgaaat cacgccatgt agtgtattga ccgattcctt gcggtccgaa tgggccgaac    8820
ccgctcgtct ggctaagatc ggccgcagcg atcgcatcca tggcctccgc gaccggctgc    8880
agaacagcgg gcagttcggt ttcaggcagg tcttgcaacg tgacccctg tgcacggcgg     8940 gagatgcaat aggtcaggct ctcgctgaat tccccaatgt caagcacttc cggaatcggg    9000 agcgcggcc atgcaaagtg ccgataaaca taacgatctt tgtagaaacc atcggcgcag    9060
ctatttaccc gcaggacata tccacgccct cctacatcga agctgaaagc acgagattct    9120
tcgccctccg agagctgcat caggtcggag acgctgtcga acttttcgat cagaaacttc    9180
tcgacagacg tcgcggtgag ttcaggcttt ttcatatctc attgccccc gggatctgcg     9240 gcacgctgtt gacgctgtta agcgggtcgc tgcaggtcg ctcggtgttc gaggccacac     9300
gcgtcacctt aatatgcgaa gtggacctcg gaccgcgccg ccccgactgc atctgcgtgt    9360
tcgaattcgc caatgacaag acgctgggcg gggtttgtgt catcatagaa ctaaagacat    9420
gcaaatatat ttcttccggg gacaccgcca gcaaacgcga gcaacgggcc acggggatga   9480
agcagggcgg cacctcgcta acggattcac cactccaaga attggagcca atcaattctt    9540
gcggagaact gtgaatgcgc aaaccaaccc ttggcagaac atatccatcg cgtccgccat    9600
ctccagcagc cgcacgcggc gcatctcggg gccgacgcgc tggctacgt cttgctggcg     9660 ttcgcacagg ccgccagcg cgcggccggc cggtaccacg cgttggccac atatggcggc    9720
cgctcgcgat taattaatcg cgatggccac atatggagct ctctagagct tgtcgacaga   9780
tccccctctt catttcttta tgttttaaat gcactgacct cccacattcc cttttttagta   9840 aaatattcag aaataattta aatacatcat tgcaatgaaa ataaatgttt tttattaggc    9900
agaatccaga tgctcaaggc ccttcataat atccccagt ttagtagttg gacttaggga     9960
acaaaggaac ctttaataga aattggacag caagaaagcg agggggatct ggatcctccg   10020
```

```
gagggcccct tctccctcta acactctccc ctgttgaagc tctttgtgac gggcgagctc    10080
aggccctgat gggtgacttc gcaggcgtag actttgtgtt tctcgtagtc tgctttgctc    10140
agcgtcaggg tgctgctgag gctgtaggtg ctgtccttgc tgtcctgctc tgtgacactc    10200
tcctgggagt tacccgattg gagggcgtta tccaccttcc actgtacttt ggcctctctg    10260
ggatagaagt tattcagcag gcacacaaca gaggcagttc cagatttcaa ctgctcatca    10320
gatggcggga agatgaagac agatggtgca gccaccgtac gtttgatttc caccttggtc    10380
ccctgtccaa aggtgtaggg tgtgtaatag ctctgctgac agtagtacac gcccacatct    10440
tcggcctcca cccggctgat cttcagagtg aaatctgtcc cagatccgct gccgctgaac    10500
ctgtctggca ccccgctctg ccgggtgctg gtccaataga tcagcagctg agggctctgc    10560
cctggtttct gcagatacca ggccaggtag ttcttctggt tctcgctgaa cagcaggctc    10620
tggctgctct tgcagctgat gctggctggc tctccgggtg tcacaggcag ggacagtgga    10680
gactgggtca tcacgatatc acatctcatg gctggcagga acagcaccag cagccccagc    10740
agctgcactg gagccatggt ggcggcgcta gcgaattctt aagcctgtgg agagaaagga    10800
acagaaaacg aaacaaagac gtagagttga gcaagcaggg tcaggcaaag cgtggagagc    10860
cggctgagtc taggtaggct ccaagggagc gccggacaaa ggcccggtct cgacctgagc    10920
tttaaactta cctgtggcca cacgtgcaat tgctatagtg agtcgtatta atttcgataa    10980
gccagtaagc agtgggttct ctagttagcc agagagctct gcttatatag acctcccacc    11040
gtacacgcct accgcccatt tgcgtcaatg ggcggagtg gttacgacat tttggaaagt    11100
cccgttgatt ttggtgccaa acaaactcc cattgacgtc aatgggtgg agacttggaa     11160 atccccgtga gtcaaaccgc tatccacgcc cattgatgta ctgccaaaac cgcatcacca    11220
tggtaatagc gatgactaat acgtagatgt actgccaagt aggaaagtcc cataaggtca    11280
tgtactgggc ataatgccag gcgggccatt taccgtcatt gacgtcaata ggggcgtac     11340 ttggcatatg atacacttga tgtactgcca agtgggcagt ttaccgtaaa tagtccaccc    11400
attgacgtca atggaaagtc cctattggcg ttactatggg aacatacgtc attattgacg    11460
tcaatgggcg ggggtcgttg ggcggtcagc caggcgggcc atttaccgta agttatgtaa    11520
cgcggaactc catatatggg ctatgaacta atgaccccgt aattgattac tattaataac    11580
tagtcaataa tcaatgtcaa cgcgtatatc tggcccgtac atcggtaact agtcggaccg    11640
gcccgggcca ccggtgctcg aagcttggat cgatccagac atgataagat acattgatga    11700
gtttggacaa accacaacta gaatgcagtg aaaaaaatgc tttatttgtg aaatttgtga    11760
tgctattgct ttatttgtaa ccattataag ctgcaataaa caagttaaca acaacaattg    11820
cattcatttt atgtttcagg ttcagggggga ggtgtgggag gttttttaaa gcaagtaaaa    11880
cctctacaaa tgtggtatgg ctgattatga tctctagtca ag                      11922
```

<210> SEQ ID NO 47
<211> LENGTH: 11859
<212> TYPE: DNA
<213> ORGANISM: Artificial Sequence
<220> FEATURE:
<223> OTHER INFORMATION: pAPD16V1-GA plasmid sequence

<400> SEQUENCE: 47

```
gcactataca tcaaatattc cttattaacc cctttacaaa ttaaaaagct aaaggtacac       60 aattttttgag catagttatt aatagcagac actctatgcc tgtgtggagt aagaaaaaac     120
agtatgttat gattataact gttatgccta cttataaagg ttacagaata ttttttccata    180
```

```
attttcttgt atagcagtgc agcttttcc tttgtggtgt aaatagcaaa gcaagcaaga     240
gttctattac taaacacagc atgactcaaa aaacttagca attctgaagg aaagtccttg     300
gggtcttcta cctttctctt cttttttgga ggagtagaat gttgagagtc agcagtagcc     360
tcatcatcac tagatggcat tcttctgag caaaacaggt tttcctcatt aaaggcattc      420
caccactgct cccattcatc agttccatag gttggaatct aaaatacaca acaattaga      480 atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagctttta ggaggggagc   660 agagaacttg aaagcatctt cctgttagtc tttcttctcg tagacttcaa acttatactt    720
gatgcctttt tcctcctgga cctcagagag gacgcctggg tattctggga aagtttata    780 tttccccaaa tcaatttctg ggaaaaacgt gtcactttca aattcctgca tgatccttgt     840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt    1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt ccccccccc aagctcagat ctgagcttgg tccctatggt gagtccgttc    1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata    1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gttttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc    2040
tagctctggc gagtctttca cgaaaaggga gggatctata taacacttta tagccattga   2100
ctgtaaccca cctatcccaa tttaagtcat atcttcctgt atatggtaag ggggcatctg   2160
ttggtctgta gatgtaaggt cccctataag tccctggttg ccaccacctg tctcctattt   2220
tgacaaaaac actctttttt cccttttta cttctaggcc tgtggtcaat agtccttgca     2280
cctgttcttc aattgaggtt gagcgtctct ttctattttc tattcccatt ctaacttct    2340 gaatttgagt aaaaatagta ctaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga gttggctgt ggtccttgcc     2520 tcaggaggaa ggtcgagttc tccgaattgt ttagattgta atcttgcaca aagagctat    2580
```

```
taaaagagtc aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caaccccttg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
aatcagggga taacgcagga agaacatgt gagcaaaagg ccagcaaaag gccaggaacc   3180
gtaaaaaggc cgcgttgctg gcgttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc aacccggta agacacgact   3540 tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca cacgggata ataccgcgcc acatagcaga actttaaaag   4620
tgctcatcat tggaaaacgt tcttcgggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag gaataagggc   4800 gacacggaa atgttgaata ctcatactct tcctttttca atattattga gcatttatc    4860 agggttattg tctcatgagc ggatacatat ttgaatgtat ttagaaaaat aaacaaatag   4920
gggttccgcg cacatttccc cgaaaagtgc cacctgacgt ctaagagacc attattatca   4980
```

```
tgacattaac ctataaaaat aggcgtatca cgaggcccct tcgtcttcaa gaattgtcta   5040
gaggcgcgcc gtttaaaccc tcagctaccg atgtacgggc cagatatacg cgttgacatt   5100
gattattgac tagttattaa tagtaatcaa ttacggggtc attagttcat agcccatata   5160
tggagttccg cgttacataa cttacggtaa atggcccgcc tggctgaccg cccaacgacc   5220
cccgcccatt gacgtcaata atgacgtatg ttcccatagt aacgccaata gggactttcc   5280
attgacgtca atgggtggac tatttacggt aaactgccca cttggcagta catcaagtgt   5340
atcatatgcc aagtacgccc cctattgacg tcaatgacgg taaatggccc gcctggcatt   5400
atgcccagta catgacctta tgggactttc ctacttggca gtacatctac gtattagtca   5460
tcgctattac catggtgatg cggttttggc agtacatcaa tgggcgtgga tagcggtttg   5520
actcacgggg atttccaagt ctccacccca ttgacgtcaa tgggagtttg ttttggcacc   5580
aaaatcaacg ggactttcca aaatgtcgta acaactccgc cccattgacg caaatgggcg   5640
gtaggcgtgt acggtgggag gtctatataa gcagagctct ctggctaact agagaaccca   5700
ctgcttactg gcttatcgaa attaatacga ctcactatag caattgcacg tgtggccaca   5760
ggtaagttta aagctcaggt cgagaccggg cctttgtccg cgctcccttg gagcctacc    5820 tagactcagc cggctctcca cgctttgcct gaccctgctt gctcaactct acgtctttgt   5880
ttcgttttct gttcctttct ctccacaggc ttaagctcga ggccgccacc atggccgtgc   5940
tgggcctgct gttctgcctg gtgaccttcc cttcctgcgt gctgtcccag gtgcagctgg   6000
tgcagtccgg cgtggaggtg aagaagcctg gcgcctccgt caaggtgtcc tgtaaggcct   6060
ccggctacac cttcaccaac tactacatgt actgggtgcg gcaggcccca ggccagggac   6120
tggagtggat gggcggcatc aacccttcca acggcggcac caacttcaac gagaagttca   6180
agaaccgggt gaccctgacc accgactcct ccaccacaac cgcctacatg gaactgaagt   6240
ccctgcagtt cgacgacacc gccgtgtact actgcgccag gcgggactac cggttcgaca   6300
tgggcttcga ctactggggc cagggcacca ccgtgaccgt gtcctccgct agcaccaagg   6360
gcccttccgt gttccctctg gcccttgct ccggtccac ctccgagtcc accgccgctc    6420
tgggctgtct ggtgaaggac tacttccctg agcctgtgac cgtgagctgg aactctggcg   6480
ccctgacctc cggcgtgcac accttccctg ccgtgctgca gtcctccggc ctgtactccc   6540
tgtcctccgt ggtgaccgtg ccttcctcct ccctgggcac caagacctac acctgcaacg   6600
tggaccacaa gccttccaac accaaggtgg acaagcgggt ggagtccaag tacggccctc   6660
cttgccctcc ctgccctgcc cctgagttcc tgggcggacc ctccgtgttc ctgttccctc   6720
ctaagcctaa ggacaccctg atgatctccc ggacccctga ggtgacctgc gtggtggtgg   6780
acgtgtccca ggaagatcct gaggtccagt tcaattggta cgtggatggc gtggaggtgc   6840
acaacgccaa gaccaagcct cgggaggaac agttcaactc cacctaccgg gtggtgtctg   6900
tgctgaccgt gctgcaccag gactggctga acggcaagga atacaagtgc aaggtcagca   6960
acaagggcct gccctcctcc atcgagaaaa ccatctccaa ggccaagggc agcctcgcg    7020 agcctcaggt gtacaccctg cctccctagcc aggaagagat gaccaagaat caggtgtccc   7080
tgacatgcct ggtgaagggc ttctacccct tcgatatcgc cgtggagtgg gagagcaacg   7140
gccagccaga gaacaactac aagaccaccc ctcctgtgct ggactccgac ggctccttct   7200
tcctgtactc caggctgacc gtggacaagt cccggtggca ggaaggcaac gtcttttcct   7260
gctccgtgat gcacgaggcc ctgcacaacc actacaccca gaagtccctg tccctgtctc   7320
tgggcaagtg aatcgatgga tccagatccc cctcgctttc ttgctgtcca atttctatta   7380
```

```
aaggttcctt tgttccctaa gtccaactac taaactgggg gatattatga agggccttga   7440
gcatctggat tctgcctaat aaaaaacatt tattttcatt gcaatgatgt atttaaatta   7500
tttctgaata ttttactaaa aagggaatgt gggaggtcag tgcatttaaa acataaagaa   7560
atgaagaggg ggatctgtcg acaagctcta gagagctcac gcgttgatca tgtacaggcc   7620
ggccaagctt tcgactagct tggcacgcca gaaatccgcg cggtggtttt tggggggtcgg   7680 gggtgtttgg cagccacaga cgcccggtgt tcgtgtcgcg ccagtacatg cggtccatgc   7740
ccaggccatc caaaaaccat gggtctgtct gctcagtcca gtcgtggacc tgaccccacg   7800
caacgcccaa aataataacc cccacgaacc ataaaccatt ccccatgggg gaccccgtcc   7860
ctaacccacg gggccagtgg ctatggcagg gcctgccgcc ccgacgttgg ctgcgagccc   7920
tgggccttca cccgaacttg gggggtgggg tgggaaaag gaagaaacgc gggcgtattg   7980
gccccaatgg ggtctcggtg gggtatcgac agagtgccag ccctgggacc gaaccccgcg   8040
tttatgaaca aacgacccaa cacccgtgcg ttttattctg tctttttatt gccgtcatag   8100
cgcgggttcc ttccggtatt gtctccttcc gtgtttcagt tagcctcccc catctcccga   8160 tccgacgag tgctggggcg tcggtttcca ctatcggcga gtacttctac acagccatcg   8220
gtccagacgg ccgcgcttct gcgggcgatt tgtgtacgcc cgacagtccc ggctccggat   8280
cggacgattg cgtcgcatcg accctgcgcc caagctgcat catcgaaatt gccgtcaacc   8340
aagctctgat agagttggtc aagaccaatg cggagcatat acgcccggag ccgcggcgat   8400
cctgcaagct ccgatgcct ccgctcgaag tagcgcgtct gctgctccat acaagccaac   8460
cacggcctcc agaagaagat gttggcgacc tcgtattggg aatccccgaa catcgcctcg   8520
ctccagtcaa tgaccgctgt tatgcggcca ttgtccgtca ggacattgtt ggagccgaaa   8580
tccgcgtgca cgaggtgccg gacttcgggg cagtcctcgg cccaaagcat cagctcatcg   8640
agagcctgcg cgacggacgc actgacggtg tcgtccatca cagtttgcca gtgatacaca   8700
tggggatcag caatcgcgca tatgaaatca cgccatgtag tgtattgacc gattccttgc   8760
ggtccgaatg ggccgaaccc gctcgtctgg ctaagatcgg ccgcagcgat cgcatccatg   8820
gcctccgcga ccggctgcag aacagcgggc agttcggttt caggcaggtc ttgcaacgtg   8880
acaccctgtg cacggcggga gatgcaatag gtcaggctct cgctgaattc cccaatgtca   8940
agcacttccg gaatcgggag cgcggccgat gcaaagtgcc gataaacata acgatctttg   9000
tagaaaccat cggcgcagct atttacccgc aggacatatc cacgccctcc tacatcgaag   9060
ctgaaagcac gagattcttc gccctccgag agctgcatca ggtcggagac gctgtcgaac   9120
ttttcgatca gaaacttctc gacagacgtc gcggtgagtt caggcttttt catatctcat   9180 tgcccccgg gatctgcggc acgctgttga cgctgttaag cgggtcgctg cagggtcgct   9240
cggtgttcga ggccacacgc gtcaccttaa tatgcgaagt ggacctcgga ccgcgccgcc   9300
ccgactgcat ctgcgtgttc gaattcgcca atgacaagac gctgggcggg gtttgtgtca   9360
tcatagaact aaagacatgc aaatatattt cttccgggga caccgccagc aaacgcgagc   9420
aacgggccac ggggatgaag cagggcggca cctcgctaac ggattcacca ctccaagaat   9480
tggagccaat caattcttgc ggagaactgt gaatgcgcaa accaaccctt ggcagaacat   9540
atccatcgcg tccgccatct ccagcagccg cacgcggcgc atctcgggc cgacgcgctg   9600 ggctacgtct tgctggcgtt cgcacaggcc ggccagcgcg cggccggccg gtaccacgcg   9660
ttggccacat atggcggccg ctcgcgatta attaatcgcg atggcacat atggagctct   9720 ctagagcttg tcgacagatc cccctcttca tttctttatg ttttaaatgc actgacctcc   9780
```

```
cacattccct ttttagtaaa atattcagaa ataatttaaa tacatcattg caatgaaaat   9840
aaatgttttt tattaggcag aatccagatg ctcaaggccc ttcataatat cccccagttt   9900
agtagttgga cttagggaac aaaggaacct ttaatagaaa ttggacagca agaaagcgag   9960
ggggatctgg atccctccct tcagcactcg ccccggttga aggacttggt cacagggctg  10020
gacaggccct ggtgggtcac ctcgcaggcg tacaccttgt gcttctcgta gtcggcttg   10080 gacagggtca gggtggagga cagggagtag gtgctgtcct tggagtcctg ctcggtgacg  10140
gattcctggg agttgccgga ctgcaggca ttgtccacct tccactgcac cttggcctcc   10200
cgagggtaga agttgttcag caggcacacc acggaggcgg tgccggactt cagctgctcg   10260
tcggagggag ggaagatgaa cacgaagga gcggccaccg tacgcttgat ctccagcttg    10320
gtgccctggc cgaaggtcag aggcaggtcc cgggagtgct ggcagtagta cacgcccacg   10380
tcctcggcct ccacccggga gatcttcagg gtgaagtcgg tgccgctgcc ggagccggag   10440
aaccggtcag gcacgccgga ctccaggtag gaggccaggt agatcagcag ctgggggggac  10500 tggccaggct tctgcagata ccagtgcagg taggagtagc cggaggtgga cacgcccttg   10560
gaggcccggc aggagatgga ggcaggctcg ccaggggtca caggcaggga cagaggggac   10620
tgggtcagca cgatctcgca ccgcatggca ggcaggaaca gcaccagcag gcccagcagc   10680
tgcacagggg ccatggtggc ggcctcgagg aattcttaag cctgtggaga gaaggaaca    10740 gaaaacgaaa caaagacgta gagttgagca agcagggtca ggcaaagcgt ggagagccgg   10800
ctgagtctag gtaggctcca agggagcgcc ggacaaaggc ccggtctcga cctgagcttt   10860
aaacttacct gtggccacac gtgcaattgc tatagtgagt cgtattaatt tcgataagcc   10920
agtaagcagt gggttctcta gttagccaga gagctctgct tatatagacc tcccaccgta   10980
cacgcctacc gcccatttgc gtcaatgggg cggagttgtt acgacattt ggaaagtccc    11040 gttgattttg gtgccaaaac aaactcccat tgacgtcaat ggggtggaga cttggaaatc   11100
cccgtgagtc aaaccgctat ccacgcccat tgatgtactg ccaaaaccgc atcaccatgg   11160
taatagcgat gactaatacg tagatgtact gccaagtagg aaagtcccat aaggtcatgt   11220
actgggcata atgccaggcg ggccatttac cgtcattgac gtcaataggg ggcgtacttg   11280
gcatatgata cacttgatgt actgccaagt gggcagttta ccgtaaatag tccacccatt   11340
gacgtcaatg gaaagtccct attggcgtta ctatgggaac atacgtcatt attgacgtca   11400
atgggcgggg tcgttgggc ggtcagccag gcgggccatt taccgtaagt tatgtaacgc    11460
ggaactccat atatgggcta tgaactaatg accccgtaat tgattactat taataactag   11520
tcaataatca atgtcaacgc gtatatctgg cccgtacatc ggtaactagt cggaccggcc   11580
cgggccaccg gtgctcgaag cttggatcga tccagacatg ataagataca ttgatgagtt   11640
tggacaaacc acaactagaa tgcagtgaaa aaaatgcttt atttgtgaaa tttgtgatgc   11700
tattgcttta tttgtaacca ttataagctg caataaacaa gttaacaaca acaattgcat   11760
tcattttatg tttcaggttc agggggaggt gtgggaggtt ttttaaagca agtaaaacct   11820
ctacaaatgt ggtatggctg attatgatct ctagtcaag                         11859
```

<210> SEQ ID NO 48
<211> LENGTH: 11909
<212> TYPE: DNA
<213> ORGANISM: Artificial Sequence
<220> FEATURE:
<223> OTHER INFORMATION: pAHGFV1 plasmid sequence

<400> SEQUENCE: 48

```
ggcactatac atcaaatatt ccttattaac ccctttacaa attaaaaagc taaaggtaca      60 caattttga gcatagttat taatagcaga cactctatgc ctgtgtggag taagaaaaaa     120
cagtatgtta tgattataac tgttatgcct acttataaag gttacagaat attttttccat    180 aattttcttg tatagcagtg cagcttttc ctttgtggtg taaatagcaa agcaagcaag     240
agttctatta ctaaacacag catgactcaa aaaacttagc aattctgaag gaaagtcctt     300
ggggtcttct acctttctct tcttttttgg aggagtagaa tgttgagagt cagcagtagc    360
ctcatcatca ctagatggca tttcttctga gcaaaacagg ttttcctcat taaaggcatt    420
ccaccactgc tcccattcat cagttccata ggttggaatc taaaatacac aaacaattag    480
aatcagtagt ttaacacatt atacacttaa aaattttata tttaccttag agctttaaat    540
ctctgtaggt agtttgtcca attatgtcac accacagaag taaggttcct tcacaaagat    600
cgatctaaag ccagcaaaag tcccatggtc ttataaaaat gcatagcttt aggaggggag    660
cagagaactt gaaagcatct tcctgttagt cttctttctc gtagacttca aacttatact    720
tgatgccttt ttcctcctgg acctcagaga ggacgcctgg gtattctggg agaagtttat    780
atttccccaa atcaatttct gggaaaaacg tgtcactttc aaattcctgc atgatccttg    840
tcacaaagag tctgaggtgg cctggttgat tcatggcttc ctggtaaaca gaactgcctc    900
cgactatcca aaccatgtct actttacttg ccaattccgg ttgttcaata agtcttaagg    960
catcatccaa acttttggca agaaaatgag ctcctcgtgg tggttctttg agttctctac    1020
tgagaactat attaattctg tcctttaaag gtcgattctt ctcaggaatg gagaaccagg    1080
ttttcctacc cataatcacc agattctgtt taccttccac tgaagaggtt gtggtcattc    1140
tttggaagta cttgaactcg ttcctgagcg gaggccaggg taggtctccg ttcttgccaa    1200
tccccatatt ttgggacacg gcgacgatgc agttcaatgg tcgaaccatg atggcagcgg    1260
ggataaaatc ctaccagcct tcacgctagg attgccgtca agtttggcgc gaaatcgcag    1320
ccctgagctg tcccccccc caagctcaga tctgagcttg gtccctatgg tgagtccgtt    1380
ccgctcttgt gatgatagcc agacaagaaa gagacaatac aagacaaaca ccaaatagta    1440
gaaatagaga caagggtcac ttatccgagg gtccctgttc gggcgccagc tgccgcagtc    1500
ggccgacctg agggtcgccg gggtctgcgg ggggaccctc tggaaagtga aggataagtg    1560
acgagcggag acgggatggc gaacagacac aaacacacaa gaggtgaatg ttaggactgt    1620
tgcaagttta ctcaaaaaat cagcactctt ttatatcttg gtttacataa gcatttacat    1680
aagatttgga taaattccaa aagaacatag gaaaatagaa cactcagagc tcagatcaga    1740
acctttgata ccaaaccaag tcaggaaacc acttgtctca catcctcgtt ttaagaacag    1800
tttgtaacca aaaacttact taagccctgg gaaccgcaag gttgggccaa taaaggctat    1860
tcataataac tcatgccatg agttttttgca gaataatgtt ctattagtcc agccactgtc    1920
ccctccttgg tatggaaaat cttccccaa aagtgcattc ctgttcctag ataaatataa    1980
tcatgtacct gttgtttcat gtcgtctttt tcttcttgag acaacataca ccaaggaggt    2040
ctagctctgg cgagtctttc acgaaaaggg agggatctat ataacacttt atagccattg    2100
actgtaaccc acctatccca atttaagtca tatcttcctg tatatggtaa gggggcatct    2160
gttggtctgt agatgtaagg tcccctataa gtccctggtt gccaccacct gtctcctatt    2220
ttgacaaaaa cactctttt tccctttttt acttctaggc ctgtggtcaa tagtccttgc     2280
acctgttctt caattgaggt tgagcgtctc tttctatttt ctattcccat ttctaacttc    2340
tgaatttgag taaaaatagt actaaaagat aatgattcat ttcttaacat agtaactaat    2400
```

```
aatctaccta ttggattggt cttattggta aaaatataat ttttagcaag cattcttatt    2460
tctatttctg aaggacaaaa tcgatgcggc ttgtaagagg aagttggctg tggtccttgc    2520
ctcaggagga aggtcgagtt ctccgaattg tttagattgt aatcttgcac agaagagcta    2580
ttaaaagagt caagggtgag agccctgcga gcacgaaccg caacttcccc caatagcccc    2640
aggcaaagca gagctatgcc aagtttgcag cagagaatga atatgtcttt gtctgatggg    2700
ctcatccgtt tgtgcgcaga cgggtcgtcc ttggtgggaa acaacccctt ggctgcttct    2760
cccctaggtg taggacactc tcgggagttc aaccatttct gcccaagctc agatctgagc    2820
tttaatgcgg tagtttatca cagttaaatt gctaacgcag tcaggcaccg tgtatgaaat    2880
ctaacaatgc gctcatcgtc atcctcggca ccgtcaccct ggatgctgta ggcataggct    2940
tggttatgcc ggtactgccg ggcctcttgc gggatatcgt ccattccgac agcatcgcca    3000
gtcactatgg cgtgctgcta gcgctcttcc gcttcctcgc tcactgactc gctgcgctcg    3060
gtcgttcggc tgcggcgagc ggtatcagct cactcaaagg cggtaatacg ttatccaca    3120
gaatcagggg ataacgcagg aaagaacatg tgagcaaaag gccagcaaaa ggccaggaac    3180
cgtaaaaagg ccgcgttgct ggcgtttttc cataggctcc gcccccctga cgagcatcac    3240
aaaaatcgac gctcaagtca gaggtggcga aacccgacag gactataaag ataccaggcg    3300
tttccccctg gaagctccct cgtgcgctct cctgttccga ccctgccgct taccggatac    3360
ctgtccgcct ttctcccttc gggaagcgtg gcgctttctc atagctcacg ctgtaggtat    3420
ctcagttcgg tgtaggtcgt tcgctccaag ctgggctgtg tgcacgaacc cccgttcag    3480
cccgaccgct gcgccttatc cggtaactat cgtcttgagt ccaacccggt aagacacgac    3540
ttatcgccac tggcagcagc cactggtaac aggattagca gagcgaggta tgtaggcggt    3600
gctacagagt tcttgaagtg gtggcctaac tacggctaca ctagaaggac agtatttggt    3660
atctgcgctc tgctgaagcc agttaccttc ggaaaaagag ttggtagctc ttgatccggc    3720
aaacaaacca ccgctggtag cggtggtttt tttgtttgca agcagcagat tacgcgcaga    3780
aaaaaaggat ctcaagaaga tcctttgatc ttttctacgg ggtctgacgc tcagtggaac    3840
gaaaactcac gttaagggat tttggtcatg agattatcaa aaaggatctt cacctagatc    3900
cttttaaatt aaaaatgaag ttttaaatca atctaaagta tatatgagta aacttggtct    3960
gacagttacc aatgcttaat cagtgaggca cctatctcag cgatctgtct atttcgttca    4020
tccatagttg cctgactccc cgtcgtgtag ataactacga tacgggaggg cttaccatct    4080
ggccccagtg ctgcaatgat accgcgagac ccacgctcac cggctccaga tttatcagca    4140
ataaaccagc cagccggaag ggccgagcgc agaagtggtc ctgcaacttt atccgcctcc    4200
atccagtcta ttaattgttg ccgggaagct agagtaagta gttcgccagt taatagtttg    4260
cgcaacgttg ttgccattgc tacaggcatc gtggtgtcac gctcgtcgtt tggtatggct    4320
tcattcagct ccggttccca acgatcaagg cgagttacat gatccccccat gttgtgcaaa    4380
aaagcggtta gctccttcgg tcctccgatc gttgtcagaa gtaagttggc cgcagtgtta    4440
tcactcatgg ttatggcagc actgcataat tctcttactg tcatgccatc cgtaagatgc    4500
ttttctgtga ctggtgagta ctcaaccaag tcattctgag aatagtgtat gcggcgaccg    4560
agttgctctt gcccggcgtc aacacgggat aataccgcgc cacatagcag aactttaaaa    4620
gtgctcatca ttggaaaacg ttcttcgggg cgaaaactct caaggatctt accgctgttg    4680
agatccagtt cgatgtaacc cactcgtgca cccaactgat cttcagcatc ttttactttc    4740
accagcgttt ctgggtgagc aaaaacagga aggcaaaatg ccgcaaaaaa gggaataagg    4800
```

```
gcgacacgga aatgttgaat actcatactc ttccttttc  aatattattg aagcatttat   4860
cagggttatt gtctcatgag cggatacata tttgaatgta tttagaaaaa taaacaaata   4920
ggggttccgc gcacatttcc ccgaaaagtg ccacctgacg tctaagagac cattattatc   4980
atgacattaa cctataaaaa taggcgtatc acgaggccct ttcgtcttca agaattgtct   5040
agaggcgcgc cgtttaaacc ctcagctacc gatgtacggg ccagatatac gcgttgacat   5100
tgattattga ctagttatta atagtaatca attacggggt cattagttca tagcccatat   5160
atggagttcc gcgttacata acttacggta atggcccgc  ctggctgacc gcccaacgac   5220
ccccgcccat tgacgtcaat aatgacgtat gttcccatag taacgccaat agggactttc   5280
cattgacgtc aatgggtgga ctatttacgg taaactgccc acttggcagt acatcaagtg   5340
tatcatatgc caagtacgcc ccctattgac gtcaatgacg gtaaatggcc cgcctggcat   5400
tatgcccagt acatgacctt atgggacttt cctacttggc agtacatcta cgtattagtc   5460
atcgctatta ccatggtgat gcggttttgg cagtacatca atgggcgtgg atagcggttt   5520
gactcacggg gatttccaag tctccacccc attgacgtca atgggagttt gttttggcac   5580
caaaatcaac gggactttcc aaaatgtcgt aacaactccg ccccattgac gcaaatgggc   5640
ggtaggcgtg tacggtggga ggtctatata agcagagctc tctggctaac tagagaaccc   5700
actgcttact ggcttatcga aattaatacg actcactata gcaattgcac gtgtggccac   5760
aggtaagttt aaagctcagg tcgagaccgg gcctttgtcc ggcgctccct tggagcctac   5820
ctagactcag ccggctctcc acgctttgcc tgaccctgct tgctcaactc tacgtctttg   5880
tttcgttttc tgttcctttc tctccacagg cttaaaacgc cgccaccatg gggtcaaccg   5940
ccatcctcgc cctcctcctg gctgttctcc aaggagtctg tgccgaagtg cagctggtgc   6000
agtctggagc agaggtgaaa aagcccgggg agtctctgaa gatctcctgt aagggttctg   6060
gatacagctt taccacctac tggatgcact gggtgcgcca gatgcccggg aaaggcctgg   6120
agtggatggg ggagattaat cctaccaacg gtcatactaa ctacaatccg tccttccaag   6180
gccaggtcac catctcagct gacaagtcca tcagcactgc ctacctgcag tggagcagcc   6240
tgaaggcctc ggacaccgcc atgtattact gtgcgagaaa ctatgttggt agcatctttg   6300
actactgggg ccaaggaacc ctggtcaccg tctcctcagc tagcaccaag ggcccatcgg   6360
tcttccccct ggcaccctcc tccaagagca cctctggggg cacagcggcc ctgggctgcc   6420
tggtcaagga ctacttcccc gaaccggtga cggtgtcgtg gaactcaggc gccctgacca   6480
gcggcgtgca caccttcccg gctgtcctac agtcctcagg actctactcc ctcagcagcg   6540
tggtgaccgt gccctccagc agcttgggca cccagaccta catctgcaac gtgaatcaca   6600
agcccagcaa caccaaggtg gacaagaaag ttgagcccaa atcttgtgac aaaactcaca   6660
catgcccacc gtgcccagca cctgaactcc tggggggacc gtcagtcttc ctcttccccc   6720
caaaacccaa ggacaccctc atgatctccc ggacccctga ggtcacatgc gtggtggtgg   6780
acgtgagcca cgaagaccct gaggtcaagt tcaactggta cgtggacggc gtggaggtgc   6840
ataatgccaa gacaaagccg cgggaggagc agtacaacag cacgtaccgt gtggtcagcg   6900
tcctcaccgt cctgcaccag gactggctga atggcaagga gtacaagtgc aaggtctcca   6960
acaaagccct cccagccccc atcgagaaaa ccatctccaa agccaagggg cagccccgag   7020
aaccacaggt gtacaccctg cccccatccc gggatgagct gaccaagaac caggtcagcc   7080
tgacctgcct ggtcaaaggc ttctatccca gcgacatcgc cgtggagtgg gagagcaatg   7140
ggcagccgga gaacaactac aagaccacgc ctcccgtgct ggactccgac ggctccttct   7200
```

```
tcctctacag caagctcacc gtggacaaga gcaggtggca gcagggggaac gtcttctcat    7260 gctccgtgat gcatgaggct ctgcacaacc actacacgca gaagagcctc tccctgtctc    7320
cgggtaaatg aatcgatgat tctagatacg ggtccggagg atccagatcc ccctcgcttt    7380
cttgctgtcc aatttctatt aaaggttcct tgttcccta agtccaacta ctaaactggg    7440
ggatattatg aagggccttg agcatctgga ttctgcctaa taaaaaacat ttattttcat    7500
tgcaatgatg tatttaaatt atttctgaat attttactaa aaagggaatg tgggaggtca    7560
gtgcatttaa aacataaaga aatgaagagg gggatctgtc gacaagctct agagagctca    7620
cgcgttgatc atgtacaggc cggccaagct ttcgactagc ttggcacgcc agaaatccgc    7680
gcggtggttt ttgggggtcg ggggtgtttg gcagccacag acgcccgtgt tcgtgtcgc    7740 gccagtacat gcggtccatg cccaggccat ccaaaaacca tgggtctgtc tgctcagtcc    7800
agtcgtggac ctgaccccac gcaacgccca aaataataac ccccacgaac cataaaccat    7860
tccccatggg ggaccccgtc cctaacccac ggggccagtg gctatggcag ggcctgccgc    7920
cccgacgttg gctgcgagcc ctgggccttc acccgaactt gggggtggg gtgggaaaa    7980 ggaagaaacg cgggcgtatt ggccccaatg gggtctcggt ggggtatcga cagagtgcca    8040
gccctgggac cgaaccccgc gtttatgaac aaacgaccca acaccgtgc gttttattct    8100 gtcttttat tgccgtcata gcgcgggttc cttccggtat tgtctccttc cgtgtttcag    8160
ttagcctccc ccatctcccg atccggacga gtgctggggc gtcggtttcc actatcggcg    8220
agtacttcta cacagccatc ggtccagacg gccgcgcttc tgcgggcgat ttgtgtacgc    8280
ccgacagtcc cggctccgga tcggacgatt gcgtcgcatc gaccctgcgc ccaagctgca    8340
tcatcgaaat tgccgtcaac caagctctga tagagttggt caagaccaat gcggagcata    8400
tacgcccgga gccgcggcga tcctgcaagc tccggatgcc tccgctcgaa gtagcgcgtc    8460
tgctgctcca tacaagccaa ccacggcctc cagaagaaga tgttggcgac ctcgtattgg    8520
gaatccccga acatcgcctc gctccagtca atgaccgctg ttatgcggcc attgtccgtc    8580
aggacattgt tggagccgaa atccgcgtgc acgaggtgcc ggacttcggg gcagtcctcg    8640
gcccaaagca tcagctcatc gagagcctgc gcgacggacg cactgacggt gtcgtccatc    8700
acagtttgcc agtgatacac atggggatca gcaatcgcgc atatgaaatc acgccatgta    8760
gtgtattgac cgattccttg cggtccgaat gggccgaacc cgctcgtctg gctaagatcg    8820
gccgcagcga tcgcatccat ggcctccgcg accggctgca gaacagcggg cagttcggtt    8880
tcaggcaggt cttgcaacgt gacaccctgt gcacggcggg agatgcaata ggtcaggctc    8940
tcgctgaatt ccccaatgtc aagcacttcc ggaatcggga gcgcggccga tgcaaagtgc    9000
cgataaacat aacgatcttt gtagaaacca tcggcgcagc tatttacccg caggacatat    9060
ccacgccctc ctacatcgaa gctgaaagca cgagattctt cgccctccga gagctgcatc    9120
aggtcggaga cgctgtcgaa cttttcgatc agaaacttct cgacagacgt cgcggtgagt    9180
tcaggctttt tcatatctca ttgccccccg ggatctgcgg cacgctgttg acgctgttaa    9240
gcgggtcgct gcagggtcgc tcggtgttcg aggccacacg cgtcaccta atatgcgaag    9300 tggacctcgg accgcgccgc cccgactgca tctgcgtgtt cgaattcgcc aatgacaaga    9360
cgctgggcgg ggtttgtgtc atcatagaac taaagacatg caaatatatt tcttccgggg    9420
acaccgccag caaacgcgag caacgggcca cggggatgaa gcaggcggc acctcgctaa    9480 cggattcacc actccaagaa ttggagccaa tcaattcttg cggagaactg tgaatgcgca    9540
aaccaaccct tggcagaaca tatccatcgc gtccgccatc tccagcagcc gcacgcggcg    9600
```

```
catctcgggg ccgacgcgct gggctacgtc ttgctggcgt tcgcacaggc cggccagcgc    9660
gcggccggcc ggtaccacgc gttggccaca tatggcggcc gctcgcgatt aattaatcgc    9720
gatggccaca tatggagctc tctagagctt gtcgacagat cccctcttc atttctttat    9780 gttttaaatg cactgacctc ccacattccc tttttagtaa aatattcaga aataatttaa    9840
atacatcatt gcaatgaaaa taaatgtttt ttattaggca gaatccagat gctcaaggcc    9900
cttcataata tcccccagtt tagtagttgg acttagggaa caaaggaacc tttaatagaa    9960
attggacagc aagaaagcga gggggatctg gatcctccta cgtatctaga atcatcgatt   10020
aacactctcc cctgttgaag ctctttgtca cggggctgct caggccctga tgggtcacct   10080
cgcaggcgta caccttgtgt ttctcgtagt ctgctttgct cagggtcagg gtgctgctca   10140
ggctgtaggt gctgtccttg ctgtcctgct ctgtcacgct ctcctgggag ttgccgctct   10200
ggagggcgtt atccaccttc cactgcacct tggcctctct gggatagaag ttattcagca   10260
ggcacaccac ggaggcagtt ccagacttca gctgctcatc agatggaggg aagatgaaca   10320
cagatggtgc agccaccgta cgtttgatct ccagcttggt cccctggcca acgtgtacg   10380 gatagttgta actctgccca cagtagtaag ttgcaaaatc ttcaggttgc agactgctga   10440
tggtgagagt gaaatctgtc ccagatccac tgccactgaa ccttgatggg accccagtgt   10500
tccggttgga tgcccatag atcaggagct tagggctttt ccctggtttc tgctgatacc   10560
aggatacata agaaaccaca ttctcactgg ccttgcaagt gatggtgact ctgtctccta   10620
cagatgcaga cagggaggat ggagactggg tcatctggat gtcacatctg gcacctcgga   10680
gccagagtag caggagcccc aggagctgag cggggaccct catgtccatg gtggcggcga   10740
attctcgaga agcttaagtt taattcttaa gcctgtggag agaaaggaac agaaaacgaa   10800
acaaagacgt agagttgagc aagcagggtc aggcaaagcg tggagagccg gctgagtcta   10860
ggtaggctcc aagggagcgc cggacaaagg cccggtctcg acctgagctt taaacttacc   10920
tgtggccaca cgtgcaattg ctatagtgag tcgtattaat ttcgataagc cagtaagcag   10980
tgggttctct agttagccag agagctctgc ttatatagac ctcccaccgt acacgcctac   11040
cgcccatttg cgtcaatggg gcggagttgt tacgacattt tggaaagtcc cgttgatttt   11100
ggtgccaaaa caaactccca ttgacgtcaa tggggtggag acttggaaat ccccgtgagt   11160
caaaccgcta tccacgccca ttgatgtact gccaaaaccg catcaccatg gtaatagcga   11220
tgactaatac gtagatgtac tgccaagtag gaaagtccca taaggtcatg tactgggcat   11280
aatgccaggc gggccattta ccgtcattga cgtcaatagg gggcgtactt ggcatatgat   11340
acacttgatg tactgccaag tgggcagttt accgtaaata gtccaccat tgacgtcaat   11400 ggaaagtccc tattggcgtt actatgggaa catacgtcat tattgacgtc aatgggcggg   11460
ggtcgttggg cggtcagcca ggcgggccat ttaccgtaag ttatgtaacg cggaactcca   11520
tatatgggct atgaactaat gaccccgtaa ttgattacta ttaataacta gtcaataatc   11580
aatgtcaacg cgtatatctg gcccgtacat cggtaactag tcggaccggc ccgggccacc   11640
ggtgctcgaa gcttggatcg atccagacat gataagatac attgatgagt ttggacaaac   11700
cacaactaga atgcagtgaa aaaaatgctt tatttgtgaa atttgtgatg ctattgcttt   11760
atttgtaacc attataagct gcaataaaca agttaacaac aacaattgca ttcattttat   11820
gtttcaggtt caggggggagg tgtgggaggt tttttaaagc aagtaaaacc tctacaaatg   11880
tggtatggct gattatgatc tctagtcaa                                     11909
```